US008299221B2

(12) United States Patent
Walmsley et al.

(10) Patent No.: US 8,299,221 B2
(45) Date of Patent: Oct. 30, 2012

(54) LINGO BINDING MOLECULES AND PHARMACEUTICAL USE THEREOF

(75) Inventors: Adrian Walmsley, Well am Rheim (DE); William Leonard Wishart, Allschwil (CH); Marta Cortes-Cros, Basel (CH); Josef Prassler, Germering (DE); Ingo Klagge, Neuried (DE)

(73) Assignee: Novartis AG, Basel (CH)

( * ) Notice: Subject to any disclaimer, the term of this patent is extended or adjusted under 35 U.S.C. 154(b) by 266 days.

(21) Appl. No.: 12/514,542

(22) PCT Filed: Nov. 15, 2007

(86) PCT No.: PCT/EP2007/009880

§ 371 (c)(1), (2), (4) Date: May 12, 2009

(87) PCT Pub. No.: WO2008/058736

PCT Pub. Date: May 22, 2008

(65) Prior Publication Data

US 2010/0143362 A1 Jun. 10, 2010

(30) Foreign Application Priority Data

Nov. 17, 2006 (EP) .................................... 06124350

(51) Int. Cl.
*A61K 39/00* (2006.01)

(52) U.S. Cl. ............... 530/388.1; 424/133.1; 424/139.1; 530/387.9

(58) Field of Classification Search ........................ None
See application file for complete search history.

(56) References Cited

U.S. PATENT DOCUMENTS

2005/0214288 A1 9/2005 Bell et al.
2006/0009388 A1 * 1/2006 Mi et al. .......................... 514/12

FOREIGN PATENT DOCUMENTS

WO 2004/085648 A2 10/2004
WO 2006/002437 A2 1/2006
WO 2007/008547 A2 1/2007

OTHER PUBLICATIONS

Ji et al., "LINGO-1 antagonist promotes functional recovery and axonal sprouting after spinal cord injury," Mol. Cell. Neurosci. 33(3):311-320 (Nov. 7, 2006).
Mi et al., "LINGO-1 Negatively Regulates Myelination by Oligodendrocytes," Nature Neuroscience 8(6)145-751 (Jun. 2005).
Mi et al., "LINGO-1 is a Component of the NOGO-66 Receptor/P75 Signaling Complex," Nature Neuroscience 7(3):221-228 (Mar. 2004).
Stangel et al., "Remyelination Strategies: New Advancements Toward a Regenerative Treatment in Multiple Sclerosis." Current Neurology and Neuroscience Reports 6(3):229-235 (May 2006).

* cited by examiner

*Primary Examiner* — John Ulm
(74) *Attorney, Agent, or Firm* — Karen A. Lacourse

(57) ABSTRACT

The present invention provides a binding molecule which is capable of binding to the rat, cynomolgus monkey and human LINGO polypeptide, and a polynucleotide encoding the binding molecule. The invention also provides an expression vector comprising the polynucleotide, an expression system comprising a polynucleotide capable of producing a binding molecule, as well as an isolated host cell comprising the expression system for producing the binding molecule. The invention also provides for compositions comprising the LINGO binding molecules and the use of binding molecule compositions as a pharmaceutical, especially in the treatment to promote axonal regeneration/plasticity. The invention further provides for a method of treatment of diseases associated with axonal degeneration and demyelination.

6 Claims, 8 Drawing Sheets

LINGO BINDING MOLECULES AND PHARMACEUTICAL USE THEREOF

Figure 1:
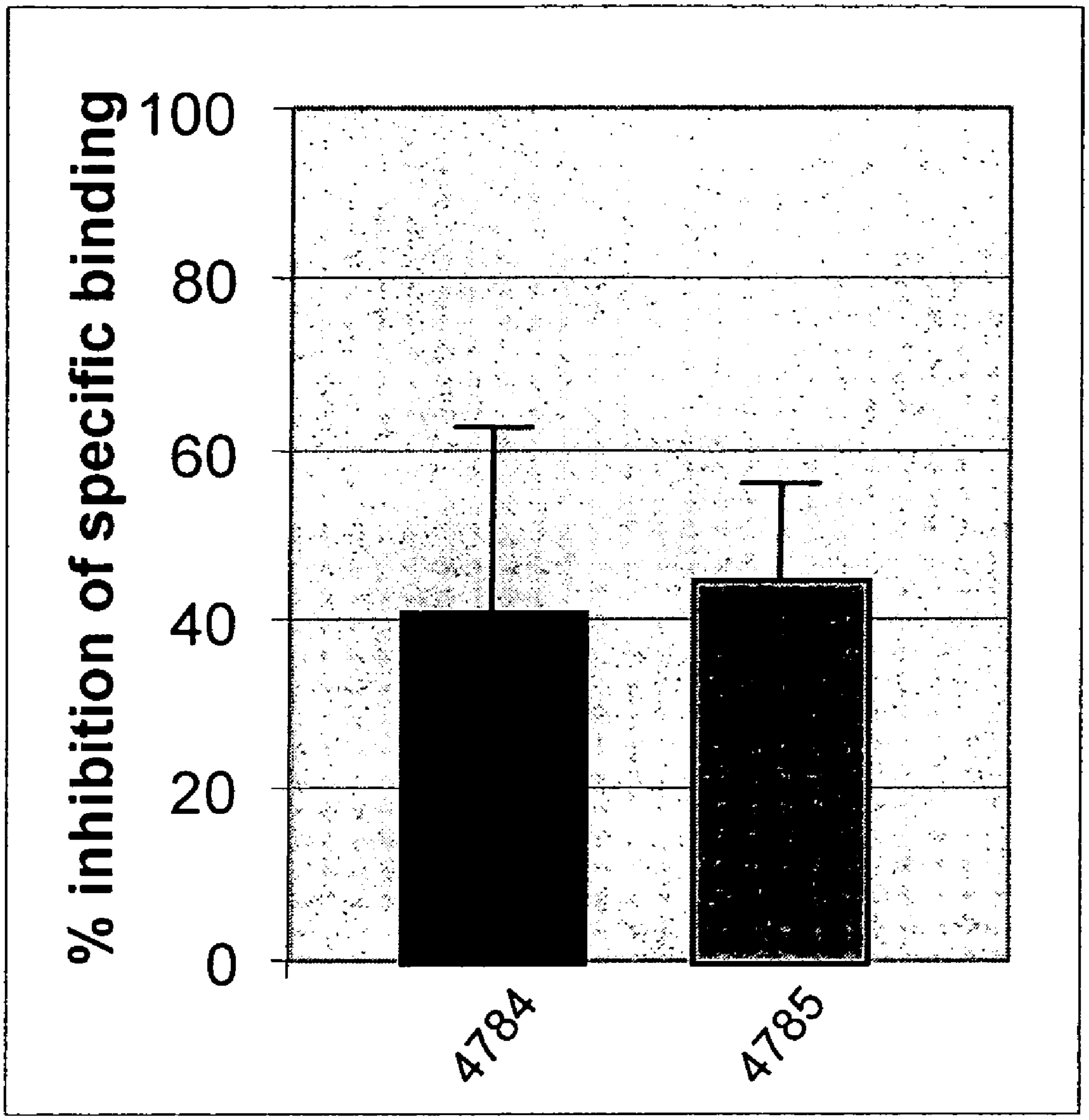

This application is the National Stage of Application No. PCT/EP2007/009880, filed on Nov. 15, 2007, which claims benefit under 35 U.S.C. §119(a)-(d) or (f) or 365(b) of EP Application No. 06124350.7, filed Nov. 17, 2006, the contents of which are incorporated herein by reference in their entirety.

The present invention relates to LINGO binding molecules, such as for example monoclonal antibodies or Fab fragments thereof, and the use of such binding molecules for treating patients with injuries to their central nervous system.

BACKGROUND OF THE INVENTION

Functional recovery following injury to the central nervous system (CNS) of adult higher vertebrates is exceptionally limited, resulting in persistent neurological deficits such as loss of limb movement and sensation. As yet, there is a lack of an effective therapy to treat humans with CNS injuries such as spinal cord injury (SCI) and brain cortical injury. Although adult CNS neurons generally survive axotomy, axonal regeneration is transitory and only occurs over a confined area, hence retarding the re-formation of functionally-relevant synaptic contacts. Furthermore, the plastic capacity of the adult CNS is also restricted, thus hindering the re-organisation of uninjured pathways to functionally compensate for those ablated by the injury. Paradoxically, axotomised axons in the peripheral nervous system (PNS) have a high capacity to regenerate over long distances and frequently establish functionally-meaningful connections (Schwab (2004) Curr Opin Neurobiol 14, 118-124). This restriction in axonal regeneration/plasticity is in part due to the expression on myelinating oligodendrocytes of several proteins that have been shown to be potent inhibitors of neurite outgrowth, namely Nogo-A (Chen et al. (2000) Nature 403, 434-439; GrandPre et al. (2000) Nature 403, 439-444; Prinjha et al. (2000) Nature 403, 383-384), myelin-associated glycoprotein (MAG), and oligodendrocyte myelin glycoprotein (OMgp) (McKerracher et al. (1994) Neuron 13, 805-811; Wang et al. (2002) Nature 417:941-944) (FIG. 1A).

Nogo-A contains multiple neurite outgrowth inhibitory domains exposed on the surface of oligodendrocytes: two are located within the amino-terminal region (amino-Nogo-A) and one in the C-terminal region (Nogo-66) (Oertle et al. (2003) J Neurosci 23, 5393-5406). Nogo-66 binds and signals through a glycosyl-phosphatidylinositol (GPI)-anchored leucine-rich repeat (LRR)-containing receptor on the neuronal surface known as the Nogo-66 receptor (NgR) (Fournier et al. (2001) Nature 409, 341-346). Although structurally unrelated, MAG and OMgp also bind and signal through NgR (Domeniconi et al. (2002) Neuron 35, 283-290; Liu et al. (2002) Science 297, 1190-1193; Wang et al. (2002) Nature 417:941-944). Signaling through NgR leads to the activation of the small GTPase RhoA which in turn activates Rho-associated kinase (ROCK) leading to a rigidification of the actin cytoskeleton and inhibition of axonal extension (Niederöst et al. (2002) J Neurosci 22, 10368-10376; Schweigreiter et al. (2004) Mol Cell Neurosci 27:163-174). All three ligands bind within the LRR region of NgR and have partially overlapping binding sites (Fournier et al. (2002) J Neurosci 22, 8876-8883; Liu et al. (2002) Science 297, 1190-1193; Wang et al. (2002) Nature 417:941-944; Barton et al. (2003) EMBO J 22, 3291-3302). The receptor(s) for the inhibitory domains within amino-Nogo-A are unknown but have been shown to be distinct from NgR (Schweigreiter et al. (2004) Mol Cell Neurosci 27:163-174). MAG has also been found to signal through a close homologue of NgR known as NgR2 (Pignot et al. (2003) J Neurochem 85, 717-728; Venkatesh et al. (2005) J Neurosci 25, 808-822).

As NgR lacks a cytoplasmic domain, it utilizes several transmembrane proteins for signal transduction, namely the low affinity neurotrophin receptor $p75^{NTR}$, TROY (a.k.a. TAJ) and LINGO-1 (LRR and Ig domain-containing, Nogo receptor-interacting protein a.k.a LRRN6A or LERN1) (Wang et al. (2002) Nature 420, 74-78; Carim-Todd et al. (2003) Eur J Neurosci 18, 3167-3182; Mi et al. (2004) Nat Neurosci 7, 221-228; Park et al. (2005) Neuron 45:345-351; Shao et al. (2005) Neuron 45, 353-359). TROY and $p75^{NTR}$ can functionally replace each other in the NgR receptor complex, whereas the presence of LINGO-1 is an absolute prerequisite for signaling to occur. The NgR receptor complex is therefore seen as a ternary complex comprising NgR as the ligand binding subunit and LINGO-1 as the common signal transducing subunit acting in concert with either $p75^{NTR}$ or TROY.

LINGO-1 is a single transmembrane protein expressed exclusively within the CNS predominantly on neurons and oligodendrocytes. The expression of LINGO-1 peaks in the early postnatal period and is up-regulated in the adult spinal cord upon injury. The ectodomain of LINGO-1 contains twelve tandem LRRs flanked by N- and C-terminal subdomains followed by a basic region and an Ig domain (FIG. 1B). Given that an AP fusion of the LINGO-1 ectodomain bound to COS-7 cells expressing NgR or $p75^{NTR}$ or both and, similarly, LINGO-1 co-precipitated with NgR or $p75^{NTR}$ in cells expressing all three proteins, LINGO-1 most likely forms a ternary complex with NgR and $p75^{NTR}$ by interacting with both simultaneously.

In addition to being expressed on neurons, LINGO-1 is also expressed in oligodendrocytes in the adult CNS (Mi et al. (2005) Nat Neurosci 8, 745-751). Inhibiting LINGO -1 signaling in oligodendrocyte cultures by either treatment with LINGO-1-Fc, down-regulation of the protein with RNAi or over-expression of DN-LINGO-1 augmented the differentiation of OPCs to myelinating oligodendrocytes. Furthermore, genetic ablation of LINGO-1 in mice increased the number of mature oligodendrocytes and, correspondingly, myelinated axons in the spinal cord. Inhibition of LINGO-1 signaling reduced the activation of RhoA and increased the activity of Fyn kinase, both of which are reported to promote oligodendrocyte differentiation, although the actual ligands/interactions responsible for activating LINGO-1 signaling have yet to be exemplified. This has led to the conclusion the LINGO-1 is a negative regulator of myelination.

Multiple Sclerosis (MS) is a chronic inflammatory disease of the CNS characterised by demyelination and axonal degeneration leading to multiple neurological deficits. Although remyelination of axons can occur early in the disease, at some point remyelination fails completely leading to accelerated axonal degeneration and irreversible damage. Remyelination most likely arises from the differentiation of adult oligodendrocyte precursor cells (OPCs) which migrate to the margins of active lesions. As LINGO-1 negatively regulates myelination, blockade of LINGO-1 may augment remyelination, attenuate axonal degeneration, promote axonal regeneration and thus attenuate, halt or even reverse the progress of demyelinating diseases such as MS.

Blockade of LINGO-1 has also been shown to improve the survival of dopaminergic neurons and reduce behavioural abnormalities in rodent models of Parkinson's disease (Inoue et al. (2007) Proc Natl Acad Sci USA 104, 14430-14435).

SUMMARY OF THE INVENTION

It has now surprisingly been found that novel monoclonal human antibodies against LINGO-1 (known as antibody 4784, and antibody 4785 hereafter) significantly inhibit the association of LINGO-1 with NgR and significantly attenuate the neurite outgrowth inhibitory activity of adult rat spinal cord myelin at sub-nM concentrations in vitro. In addition, the said antibodies significantly increase the differentiation of primary oligodendrocytes in vitro and have been shown to significantly downregulate cell surface LINGO-1 in living cells. Treatment with these antibodies is expected to increase axonal regeneration/plasticity and improve functional recovery following acute CNS injuries such as SCI and brain cortical injury. Furthermore, blocking LINGO-1 signaling using the said antibodies in oligodendroglial cells has the potential to augment the remyelination of axons in demyelinating diseases such as MS leading to an attenuation of disease progression. In concert, inhibiting LINGO-1 signaling in neurons with the said antibodies can be expected to improve axonal regeneration and neuroplasticity and promote the recovery of neurological function lost during the course of the disease. Finally, blockade of LINGO-1 with the said antibodies can be expected to attenuate the pathogenesis of Parkinson's disease.

Furthermore, the invention provides binding molecules which bind to specific epitopes on LINGO-1.

The antibodies have sub-nM $K_D$s against the rat, cynomolgus monkey and human LINGO-1 ectodomain, significantly attenuate the neurite outgrowth inhibitory activity of adult rat spinal cord myelin at sub-nM concentrations and significantly increase oligodendrocyte differentiation in vitro. Moreover, it is now possible to construct other LINGO-1 binding molecules having the same variable regions as said antibodies.

DETAILED DESCRIPTION OF THE INVENTION

Accordingly, the invention provides binding molecules to a particular region or epitope of LINGO-1 (hereinafter referred to as "the binding molecules of the invention" or simply "binding molecules").

The binding molecules of the invention bind the mature ectodomain (residues 34-550) of rat LINGO-1 (SEQ ID NO: 1), cynomolgus monkey LINGO-1 (SEQ ID NO: 2) and human LINGO-1 (SEQ ID NO: 3) with a dissociation constant ($K_D$)<1000 nM, more preferably with a $K_D$<100 nM, most preferably with a $K_D$<10 nM. The binding reaction may be shown by standard methods (qualitative assays) including, for example, the FACS method described in Examples. In addition, the binding to rat, cynomolgus monkey and human LINGO-1, and also the efficiency, may be shown in a neurite outgrowth assay and oligodendrocyte assay as described below.

Thus, in a further preferred embodiment the binding molecules (at a concentration of 100 nM, preferably 10 nM, more preferably at 1 nM even more preferably at 0.1 nM) increase the mean neurite length per cell of rat cerebellar granule cells grown on a substrate of adult rat spinal cord myelin by at least 20%, preferably 50%, most preferred 60% compared to the mean neurite length per cell of rat cerebellar granule cells which are treated with a control antibody that does not bind to the rat, cynomolgous monkey and human LINGO-1 ectodomain.

By using peptide microarrays, the specific epitope to which the binding molecules of the invention bind is determined according to methods well known in the art. Consequently, in another embodiment the invention provides binding molecules which bind to at least one of the LINGO-1 epitopes as defined by SEQ ID NO: 46-51. SEQ ID NO: 46: KIVILLDYMFQD, SEQ ID NO: 47: AIRDYSFKRLYR, SEQ ID NO: 48: LKVLEISHWPYL, SEQ ID NO: 49: NLTAVPYLAVRHLVY, SEQ ID NO: 50: YFTCRRARI, or SEQ ID NO: 51: DVLLPNYFTCRRARI.

In another embodiment, the binding molecules of the invention comprises one or more, of the following CDR sequences, e.g. all of the Antibody 4784 or all of the Antibody 4785 sequences mentioned there:

SEQ ID NO: 12
(Antibody 4784 Cdr-H1)
SSGVGVG
SEQ ID NO: 13
(Antibody 4784 CDR-H2)
HIGSDDDKYYSTSLKT
SEQ ID NO: 14
(Antibody 4784 CDR-H3)
NQQYGDGYPGYFDY
SEQ ID NO: 15
(Antibody 4784 Cdr-L1)
SGDNIGNYYVY
SEQ ID NO: 16
(Antibody 4784 Cdr-L2)
EDTNRPS
SEQ ID NO: 17
(Antibody 4784 Cdr-L3)
QSYDNLHEQV
SEQ ID NO: 18
(Antibody 4785 Cdr'-H1)
DNSAAWS
SEQ ID NO: 19
(Antibody 4785 Cdr'-H2)
LIYLRSKWDNDYAVSVKS
SEQ ID NO: 20
(Antibody 4785 Cdr'-H3)
TGRADEFDV
SEQ ID NO: 21
(Antibody 4785 Cdr'-L1)
SGSSSNIGNNYVS
SEQ ID NO: 22
(Antibody 4785 Cdr'-L2)
RNSKRPS
SEQ ID NO: 23
(Antibody 4785 Cdr'-L3)
STYDTFSIV More preferably, the binding molecules comprise one or more of the sequences given above for Antibody 4784 with the SEQ ID NO: 12, 13, 14, 15, 16 and/or 17; or for Antibody 4785 with the SEQ ID NO: 18, 19, 20, 21, 22 and/or 23.

Those skilled in the art understand that changes can be made to 4784 or 4785 which, though they change several, more preferably one or more amino acids, preferably up to three, e.g. one or two, of the SDRs given above, especially in one or more or all of them, e.g. one or two of them, or provide alternative post-translational modification of product formats, result in a therapeutic agent demonstrating the same or substantially similar anti-Lingo-1 binding behaviour.

In another embodiment the binding molecules of the invention comprises at least one antigen binding site chosen from the group consisting of; a sequence which is at least 50%, at least 60%, at least 70%, at least 80%, at least 90%, at least 95%, at least 97%, or at least 99% homologous to SEQ ID NO: 5 or SEQ ID NO: 7, and;

a sequence which is at least 50%, at least 60%, at least 70%, at least 80%, at least 90%, at least 95%, at least 97%, or at least 99% homologous to SEQ ID NO: 4 or SEQ ID NO: 6, or a direct equivalent thereof.

In one embodiment, the binding molecule comprises at least one binding site chosen from the group consisting of SEQ ID NO: 5 or SEQ ID NO: 7, and; SEQ ID NO: 4 or SEQ ID NO: 6.

The invention further provides a binding molecule which comprises a first sequence which is at least 50%, at least 60%, at least 70%, at least 80%, at least 90%, at least 95%, at least 97%, or at least 99% homologous to SEQ ID NO: 5, and a second sequence which is at least 50% at least 60%, at least 70%, at least 80%, at least 90%, at least 95%, at least 97%, or at least 99% homologous to SEQ ID NO: 4, or a direct equivalent thereof.

The invention further provides a binding molecule which comprises a first sequence which is at least 50%, at least 60%, at least 70%, at least 80%, at least 90%, at least 95%, at least 97%, or at least 99% homologous to SEQ ID NO: 7, and a second sequence which is at least 50% at least 60%, at least 70%, at least 80%, at least 90%, at least 95%, at least 97%, or at least 99% homologous to SEQ ID NO: 6, or a direct equivalent thereof.

In one embodiment, the invention provides a binding molecule according to claims 1 to 7 which comprises at least a) one immunoglobulin heavy chain or fragment thereof which comprises (i) a variable domain comprising SEQ ID NO: 5 or SEQ ID NO: 7, and (ii) the constant part or fragment thereof of a human heavy chain; and b) one immunoglobulin light chain or fragment thereof which comprises (i) a variable domain comprising SEQ ID NO: 4 or SEQ ID NO: 6, and (ii) the constant part or fragment thereof of a human light chain; or direct equivalents thereof; e.g. two or three of each of the chains given under a) or b).

The sequences may be at least 50%, at least 60%, at least 70%, at least 80%, at least 90%, at least 95%, at least 97%, or at least 99% homologous to SEQ ID NO: 4-7. The important factor is that such variants retain the binding capabilities to LINGO-1, the disinhibitory effect (especially the ability to attenuate the neurite outgrowth inhibitory activity of adult rat spinal cord myelin at sub-nM concentrations), and/or to improve the funcrtional recovery of SCI (especially in a rat model), in each case preferably as described in the Examples or the remaining description.

In one embodiment, the invention provides a binding molecule which is an antibody comprising one or more of the sequences according to SEQ ID NO: 4-7 or SEQ ID NO: 12-23, or a fragment thereof, or a direct equivalent thereof.

In a further embodiment, the binding molecule, as an antibody, has a constant part or fragment thereof of the human heavy chain of the γ4 type and the constant part or fragment thereof of the human light chain is of the λ type.

In a further embodiment, the binding molecule, as an antibody, has a constant part or fragment thereof of the human heavy chain of the γ4 type and the constant part or fragment thereof of the human light chain is of the κ type.

In a further embodiment, the binding molecule is a human or chimeric or humanized monoclonal antibody.

In a further embodiment, the binding molecule is a humaneered antibody.

The invention also provides a polynucleotide encoding a binding molecule as defined above.

The polynucleotide may be chosen from the group consisting of SEQ ID NO: 8 and SEQ ID NO: 9; or from the group consisting of SEQ ID NO: 10 and SEQ ID NO: 11.

The invention also provides an expression vector comprising one or more polynucleotides according to SEQ ID NO:8-11.

Furthermore, the invention provides an expression system comprising a polynucleotide according to SEQ ID NO:8-11, wherein said expression system or part thereof is capable of producing a binding molecule as set out above, when said expression system or part thereof is present in a compatible host cell. The invention also provides an isolated host cell which comprises such an expression system.

The invention also provides the use of a binding molecule as set out above, as a medicament.

The invention also provides the use of a binding molecule as set out above in the preparation of a medicament for the treatment of a CNS injury.

The invention also provides a pharmaceutical composition comprising a binding molecule as set out above together with at least one pharmaceutically acceptable carrier or diluent.

Furthermore, the invention provides a method of treatment of diseases associated with the promotion of axonal regeneration/plasticity comprising administering to a subject in need of such treatment an effective amount of a binding molecule as set out above.

The invention also provides a method of treatment of diseases associated with the promotion of axonal regeneration/plasticity comprising administering to a subject in need of such treatment an effective amount of a binding molecule according to any one of claims 1 to 10.

When the antigen binding site comprises both the first and second domains, these may be located on the same polypeptide molecule or, preferably, each domain may be on a different chain, the first domain being part of an immunoglobulin heavy chain or fragment thereof and the second domain being part of an immunoglobulin light chain or fragment thereof.

Examples of binding molecules of the invention include antibodies as produced by phage display and human or chimeric humanized antibodies, or further humaneered antibodies, or any fragment thereof, e.g. F(ab')2; and Fab fragments, as well as single chain or single domain antibodies. The term "antibody" is meant to include such binding molecules.

A single chain antibody consists of the variable domains of an antibody heavy and light chains covalently bound by a peptide linker usually consisting of from 10 to 30 amino acids, preferably from 15 to 25 amino acids. Therefore, such a structure does not include the constant part of the heavy and light chains and it is believed that the small peptide spacer should be less antigenic than a whole constant part. By "chimeric antibody" is meant an antibody in which the constant regions of heavy or light chains or both are of human origin while the variable domains of both heavy and light chains are of non-human (e.g. murine) origin. By "humanized antibody" is meant an antibody in which the hypervariable regions (CDRs) are of non-human (e.g. murine) origin, while all or substantially all the other parts of the immunoglobulin e.g. the constant regions and the highly conserved parts of the variable domains, i.e. the framework regions, are of human origin. A humanized antibody may however retain a few amino acids of the murine sequence in the parts of the framework regions adjacent to the hypervariable regions.

Hypervariable regions may be associated with any kind of framework regions, preferably of murine or human origin. Suitable framework regions are described in "Sequences of proteins of immunological interest" (Kabat E. A. et al, US department of health and human services, Public health service, National Institute of Health, preferably incorporated herein, especially with regard to the framework regions, by reference). Preferably the constant part of a human heavy chain of the binding molecules may be of the γ4 type, including subtypes, preferably the constant part of a human light chain may be of the κ or λ type, more preferably of the λ type.

A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antigen portion"), as used herein, refers to full length or one or more fragments of an antibody that retain the ability to specifically bind to an antigen (e.g., LINGO-1 and/or LINGO-2). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and CH1 domains; a $F(ab)_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

The terms "monoclonal antibody" or "monoclonal antibody composition" as used herein refer to a preparation of antibody molecules of single molecular composition (that is, that are identical because they are produced by one type of immune cell that are all clones of a single parent cell). A monoclonal antibody composition displays an (essentially) single binding specificity and affinity for a particular epitope.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying an (essentially) single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM, IgE, IgG such as IgG1 or IgG4) that is provided by the heavy chain constant region genes.

As used herein, the term "Affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "$K_D$", as used herein, is intended to refer to the dissociation constant, which is obtained from the ratio of $K_d$ to $K_a$ (association rate to dissociation rate) (i.e. $K_d/K_a$) and is expressed as a molar concentration (M). $K_D$) values for antibodies can be determined using methods well established in the art. A method for determining the $K_D$ of an antibody is by using surface plasmon resonance, or using a biosensor system such as a Biacore® system.

A binding molecule according to the invention is preferably an "isolated antibody", which, as used herein, refers to an antibody that is substantially free of other antibodies having different antigenic specificities (e.g., an isolated antibody that specifically binds LINGO-1, LINGO-2 or LINGO-1 and LINGO-2 is substantially free of antibodies that specifically bind antigens other than those mentioned). An isolated antibody that specifically binds may, however, have cross-reactivity to other antigens, such as LINGO-1 or LINGO-2 molecules from other species. Moreover, an isolated antibody is preferably substantially free of other cellular material and/or chemicals.

The invention also provides a binding molecule of the invention which may be selected from a single chain binding molecule which comprises an antigen binding site (especially with the CDRs described above for Antibody 4784) of antibody 4784 comprising a) a first domain comprising the variable sequence of the heavy chain having the amino acid sequence (SEQ ID NO: 5)
b) a second domain comprising the variable sequence of the light chain having the amino acid sequence (SEQ ID NO: 4)
c) a peptide linker which is bound either to the N-terminal extremity of the first domain and to the C-terminal extremity of the second domain or to the C-terminal extremity of the first domain and to the N-terminal extremity of second domain;

or direct equivalents thereof.

A binding molecule of the invention may be selected from a single chain binding molecule which comprises an antigen binding site (especially with the CDRs described above for Antibody 4785) of antibody 4785 comprising a) a first domain comprising the variable sequence of the heavy chain having the amino acid sequence (SEQ ID NO: 7)
b) a second domain comprising the variable sequence of the light chain having the amino acid sequence (SEQ ID NO: 6)
c) a peptide linker which is bound either to the N-terminal extremity of the first domain and to the C-terminal extremity of the second domain or to the C-terminal extremity of the first domain and to the N-terminal extremity of second domain;

or direct equivalents thereof.

As it is well known, minor changes in an amino acid sequence such as deletion, addition or substitution of one or several amino acids may lead to an allelic form of the original protein which has substantially identical properties. Thus, by the term "direct equivalents thereof" is meant either any single domain binding molecule of the invention (molecule X)

(i) in which the variable region of the binding molecule (e.g. SEQ ID NO: 4, 5, 6 or 7) is at least 50 or 80% homologous, preferably at least 90% homologous, more preferably at least 95, 96, 97, 98, 99% homologous to the equivalent variable regions of the light and heavy chains comprising the direct equivalents of SEQ ID NO: 4 and SEQ ID NO: 5, respectively or light and heavy chains comprising the direct equivalents of SEQ ID NO: 6 and SEQ ID NO: 7, respectively).
(ii) which is capable of binding to the ectodomain (residues 34-550) of rat LINGO-1 (SEQ ID NO: 1), cynomolgus monkey LINGO-1 (SEQ ID NO: 2) and human LINGO-1 (SEQ ID NO: 3), preferably with a dissociation constant ($K_D$)<1000 nM, more preferably with a $K_D$<100 nM, most preferably with a $K_D$<10 nM, or any binding molecule of the invention having at least two domains per binding site (molecule X').

Thus further embodiments of the inventions are for example a binding molecule which is capable of binding to the ectodomain of rat, cynomolgus monkey and/or human LINGO-1 with a dissociation constant <1000 nM and comprises at least one antigen binding site, said antigen binding site comprising in sequence the variable region which is at least 50%, preferably 80, 90, 95, 96, 97, 98, 99% homologous to the equivalent variable regions of the light and heavy chains of 4784 (SEQ ID NO: 4 and SEQ ID NO: 5, respectively) or light and heavy chains of 4785 (SEQ ID NO: 6 and SEQ ID NO: 7, respectively).

In another embodiment, the binding molecule comprises at least one amino acid sequence chosen from the group consisting of SEQ ID NO: 12-23, or a sequence which is at least 50%, preferably 80, 90, 95, 96, 97, 98, 99% homologous to these sequences.

This dissociation constant may be conveniently tested in various assays including, for example, the FACS method described in the examples. In addition, the binding and functional effect of the binding molecules may be shown in a bioassay, e.g. the neurite outgrowth assay as described below.

The constant part of a human heavy chain may be of the γ1; γ2; γ3; γ4; α1; α2; δ or ϵ type, preferably of the γ type, more preferably of the γ4 type, whereas the constant part of a human light chain may be of the κ or λ type (which includes the λ1; λ2; and λ3 subtypes) but is preferably of the λ type. The amino acid sequence of all these constant parts are given in Kabat et al (Supra).

Conjugates of the binding molecules of the invention, e.g. enzyme or toxin or radioisotope conjugates, are also included within the scope of the invention.

"Polypeptide", if not otherwise specified herein, includes any peptide or protein comprising amino acids joined to each other by peptide bonds, having an amino acid sequence starting at the N-terminal extremity and ending at the C-terminal extremity. Preferably, the polypeptide of the present invention is a monoclonal antibody, more preferred is a chimeric (also called V-grafted) or humanised (also called CDR-grafted) monoclonal antibody. The humanised (CDR-grafted) monoclonal antibody may or may not include further mutations introduced into the framework (FR) sequences of the acceptor antibody.

A functional derivative of a polypeptide as used herein includes a molecule having a qualitative biological activity in common with a polypeptide to the present invention, i.e. having the ability to bind to the ectodomain of rat, cynomolgus monkey and human LINGO-1.

A functional derivative includes fragments and peptide analogs of a polypeptide according to the present invention. It also includes the term "direct derivatives".

Fragments comprise regions within the sequence of a polypeptide according to the present invention, e.g. of a specified sequence. Fragments of binding molecules, especially of antibodies, are functional fragments, i.e. they comprise at least one portion capable of binding to LINGO-1 and/or LINGO-2, especially to at least one of the epitopes given by SEQ ID NO: 46, 47, 48, 49, 50 and 51, preferably with the binding affinities ($K_D$) mentioned above or in the Examples, especially as being preferred.

The term "derivative" is used to define amino acid sequence variants, and covalent modifications of a polypeptide according to the present invention. e.g. of a specified sequence. The functional derivatives of a polypeptide according to the present invention, e.g. of a specified sequence, e.g. of the hypervariable region of the light and the heavy chain, preferably have at least about 65%, more preferably at least about 75%, even more preferably at least about 85%, most preferably at least about 95, 96, 97, 98, 99% overall sequence homology with the amino acid sequence of a polypeptide according to the present invention, e.g. of a specified sequence, and substantially retain the ability to bind the ectodomain of rat, cynomolgus monkey and human LINGO-1 (and optionally in addition to LINGO-2).

The term "covalent modification" includes modifications of a polypeptide according to the present invention, e.g. of a specified sequence; or a fragment thereof with an organic proteinaceous or non-proteinaceous derivatizing agent, fusions to heterologous polypeptide sequences, and post-translational modifications. Covalent modified polypeptides, e.g. of a specified sequence, still have the ability to bind to the ectodomain of rat, cynomolgus monkey and human LINGO-1. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deaminated under mildly acidic conditions. Other post-translational modifications include hydroxylation of proline and lysine, phosphorylation of hydroxyl groups of seryl, tyrosine or threonyl residues, methylation of the α-amino groups of lysine, arginine, and histidine side chains, see e.g. T. E. Creighton, Proteins: Structure and Molecular Properties, W. H. Freeman & Co., San Francisco, pp. 79-86 (1983). Covalent modifications e.g. include fusion proteins comprising a polypeptide according to the present invention, e.g. of a specified sequence and their amino acid sequence variants, such as immunoadhesins, and N-terminal fusions to heterologous signal sequences.

"Homology" (or "identity) with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N- or C-terminal extensions nor insertions shall be construed as reducing identity or homology. Methods and computer programs for the alignment are well known.

Preferably, as used herein, the percent homology between two amino acid sequences or two nucleotide sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below:

The percent identity between two amino acid sequences can be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available on the world wide web at gcg.com), using either a Blossom 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al., 1990 J. Mol. Biol. 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., 1997 Nucleic Acids Res. 25(17):3389-3402. When utilizing BLAST and Gapped BLAST programs, the default parameters of the respective programs (e.g., XBLAST and NBLAST) can be used. See ncbi.nhn.nih.gov on the world wide web.

"Amino acid(s)" refer to all naturally occurring L-α-amino acids, e.g. and including D-amino acids. The amino acids are identified by either the well known single-letter or three-letter designations.

The term "amino acid sequence variant" refers to molecules with some differences in their amino acid sequences as compared to a polypeptide according to the present invention, e.g. of a specified sequence. Amino acid sequence variants of a polypeptide according to the present invention, e.g. of a specified sequence, still have the ability to bind to the ectodomain of rat, cynomolgus monkey and human LINGO-1. Substitutional variants are those that have at least one amino acid residue removed and a different amino acid inserted in its place at the same position in a polypeptide according to the present invention, e.g. of a specified sequence. These substitutions may be single, where only one amino acid in the molecule has been substituted, or they may be multiple, where two or more, e.g. 1 to 10, preferably 1 to 5, more preferably 1 to 3, amino acids have been substituted in the same molecule. Insertional variants are those with one or more, e.g. 1 to 100, such as 1 to 10, amino acids inserted immediately adjacent to an amino acid at a particular position in a polypeptide according to the present invention, e.g. of a specified sequence. Immediately adjacent to an amino acid means connected to either the α-carboxy or α-amino functional group of the amino acid. Deletional variants are those with one or more, e.g. 1 to 100, such as 1 to 10 or 1 to 5, amino acids in a polypeptide according to the present invention, e.g. of a specified sequence, removed. Ordinarily, deletional variants will have one or two amino acids deleted in a particular region of the molecule.

A binding molecule of the invention may be produced by recombinant DNA techniques. In view of this, one or more DNA molecules encoding the binding molecule must be constructed, placed under appropriate control sequences and transferred into a suitable host organism for expression.

In a very general manner, there are accordingly provided (i) DNA molecules encoding a single domain binding molecule of the invention, a single chain binding molecule of the invention, a heavy or light chain or fragments thereof of a binding molecule of the invention; and (ii) the use of the DNA molecules of the invention for the production of a binding molecule of the invention by recombinant means.

The present state of the art is such that the skilled person will be able to synthesize the DNA molecules of the invention given the information provided herein i.e. the amino acid sequences of the hypervariable regions and the DNA sequences coding for them. A method for constructing a variable domain gene is for example described in EP 239 400 (preferably incorporated herein by reference, especially regarding the methods for constructing a variable domain gene) and may be briefly summarized as follows: A gene encoding a variable domain of a monoclonal antibody of whatever specificity is cloned. The DNA segments encoding the framework and hypervariable regions are determined and the DNA segments encoding the hypervariable regions are removed so that the DNA segments encoding the framework regions are fused together with suitable restriction sites at the junctions. The restriction sites may be generated at the appropriate positions by mutagenesis of the DNA molecule by standard procedures. Double stranded synthetic variable region cassettes are prepared by DNA synthesis according to the sequences given above. These cassettes are provided with sticky ends so that they can be ligated at the junctions to the framework by standard protocol for achieving a DNA molecule encoding an immunoglobulin variable domain.

Furthermore, it is not necessary to have access to the mRNA from a producing hybridoma cell line in order to obtain a DNA construct coding for the monoclonal antibodies of the invention. Thus, PCT application WO 90/07861 (preferably incorporated herein by reference, especially with regard to the production of monoclonal antibodies) gives full instructions for the production of a monoclonal antibody by recombinant DNA techniques given only written information as to the nucleotide sequence of the gene.

The method comprises the synthesis of a number of oligonucleotides, their amplification by the PCR method, and their splicing to give the desired DNA sequence.

Expression vectors comprising a suitable promoter or genes encoding heavy and light chain constant parts are publicly available. Thus, once a DNA molecule of the invention is prepared it may be conveniently transferred in an appropriate expression vector.

DNA molecules encoding single chain antibodies may also be prepared by standard methods, for example, as described in WO 88/1649 (preferably incorporated herein by reference, especially with regard to the DNA molecules encoding single chain antibodies).

In a particular embodiment of the invention, the recombinant means for the production of some of the binding molecules of the invention includes first and second DNA constructs as described below:

The first DNA construct encodes a heavy chain or fragment thereof and comprises a) a first part which encodes the variable domain of the heavy chain of either antibody 4784, DNA-4784 $V_H$ (SEQ ID NO: 8), or antibody 4785, DNA-4785 $V_H$ (SEQ ID NO: 9); this first part starting with a codon encoding the first amino acid of the variable domain and ending with a codon encoding the last amino acid of the variable domain, and b) a second part encoding a heavy chain constant part or fragment thereof which starts with a codon encoding the first amino acid of the constant part of the heavy chain and ends with a codon encoding the last amino acid of the constant part or fragment thereof, followed by a non-sense codon.

Preferably, the second part encodes the constant part of a human heavy chain, more preferably the constant part of the human γ4 chain. This second part may be a DNA fragment of genomic origin (comprising introns) or a cDNA fragment (without introns).

The second DNA construct encodes a light chain or fragment thereof and comprises a) a first part which encodes the variable domain of the light chain of either antibody 4784, DNA-4784 $V_L$ (SEQ ID NO: 10), or antibody 4785, DNA-4785 $V_L$ (SEQ ID NO: 11); this first part starting with a codon encoding the first amino acid of the variable domain and ending with a codon encoding the last amino acid of the variable domain, and b) a second part encoding a light chain constant part or fragment thereof which starts with a codon encoding the first amino acid of the constant part of the light chain and ends with a codon encoding the last amino acid of the constant part or fragment thereof followed by a non-sense codon.

Preferably, the second part encodes the constant part of a human light chain, more preferably the constant part of the human κ chain.

Each of the DNA constructs are placed under the control of suitable control sequences, in particular under the control of a suitable promoter. Any kind of promoter may be used, provided that it is adapted to the host organism in which the DNA constructs will be transferred for expression. However, if expression is to take place in a mammalian cell, it is particularly preferred to use the promoter of an immunoglobulin gene.

The desired antibody may be produced in a cell culture or in a transgenic animal: A suitable transgenic animal may be obtained according to standard methods which include micro injecting into eggs the first and second DNA constructs placed under suitable control sequences transferring the so prepared eggs into appropriate pseudo-pregnant females and selecting a descendant expressing the desired antibody.

When the antibody chains have to be produced in a cell culture, the DNA constructs must first be inserted into either a single expression vector or into two separate but compatible expression vectors, the latter possibility being preferred.

Accordingly, the invention also provides an expression vector able to replicate in a prokaryotic or eukaryotic cell line which comprises at least one of the DNA constructs above described.

Each expression vector containing a DNA construct is then transferred into a suitable host organism. When the DNA constructs are separately inserted on two expression vectors, they may be transferred separately, i.e. one type of vector per cell, or co-transferred, this latter possibility being preferred. A suitable host organism may be a bacterium, a yeast or a mammalian cell line, this latter being preferred. More preferably, the mammalian cell line is of lymphoid origin e.g. a myeloma, hybridoma or a normal immortalized B-cell, but does not express any endogeneous antibody heavy or light chain.

It is also preferred that the host organism contains a large number of copies of the vectors per cell. If the host organism is a mammalian cell line, this desirable goal may be reached by amplifying the number of copies according to standard methods. Amplification methods usually consist of selecting for increased resistance to a drug, said resistance being encoded by the expression vector.

In another aspect of the invention, there is provided a process for producing a multi-chain binding molecule of the invention, which comprises (i) culturing an organism which is transformed with the first and second DNA constructs of the invention and (ii) recovering an active binding molecule of the invention from the culture.

Alternatively, the heavy and light chains may be separately recovered and reconstituted into an active binding molecule after in vitro refolding. Reconstitution methods are well-known in the art; Examples of methods are in particular provided in EP 120 674 or in EP 125 023. Therefore a process may also comprise (i) culturing a first organism which is transformed with a first DNA construct of the invention and recovering said heavy chain or fragment thereof from the culture and (ii) culturing a second organism which is transformed with a second DNA construct of the invention and recovering said light chain or fragment thereof from the culture and (iii) reconstituting in vitro an active binding molecule of the invention from the heavy chain or fragment thereof obtained in (i) and the light chain or fragment thereof obtained in (ii).

In a similar manner, there is also provided a process for producing a single chain or single domain binding molecule of the invention which comprises (i) culturing an organism which is transformed with a DNA construct respectively encoding a single chain or single domain binding molecule of the invention and (ii) recovering said molecule from the culture.

The binding molecules of the invention significantly inhibit the binding of LINGO-1 to NgR, significantly attenuate the neurite outgrowth inhibitory activity of adult rat spinal cord myelin at sub-nM concentrations and significantly increase oligodendrocyte differentiation in vitro as exemplified below:

FIGURE LEGENDS

FIG. 1. Effect of Fabs 4784 and 4785 on AP-LINGO-1 binding to NgR:SH-SY5Y cells NgR:SH-SY5Y cells in suspension are incubated with either 1 nM AP or AP-LINGO-1 in the absence or presence of 2 μM of the indicated anti-LINGO-1 Fab or anti-hen lysozyme Fab 3207. Bound AP activity on the cells is measured as absorbance at 405 nm after a 30 min incubation with 1-Step™ PNPP. The specific binding of AP-LINGO-1 is calculated as the difference between the total amount of AP-LINGO-1 binding and the amount of binding with AP alone. The mean percentage inhibition of specific binding (n=3, ±STD) is calculated as the percentile difference between the amount of specific binding of AP-LINGO-1 in the presence of Fab 3207 and the presence of an anti-LINGO-1 Fab.

Figure 2:
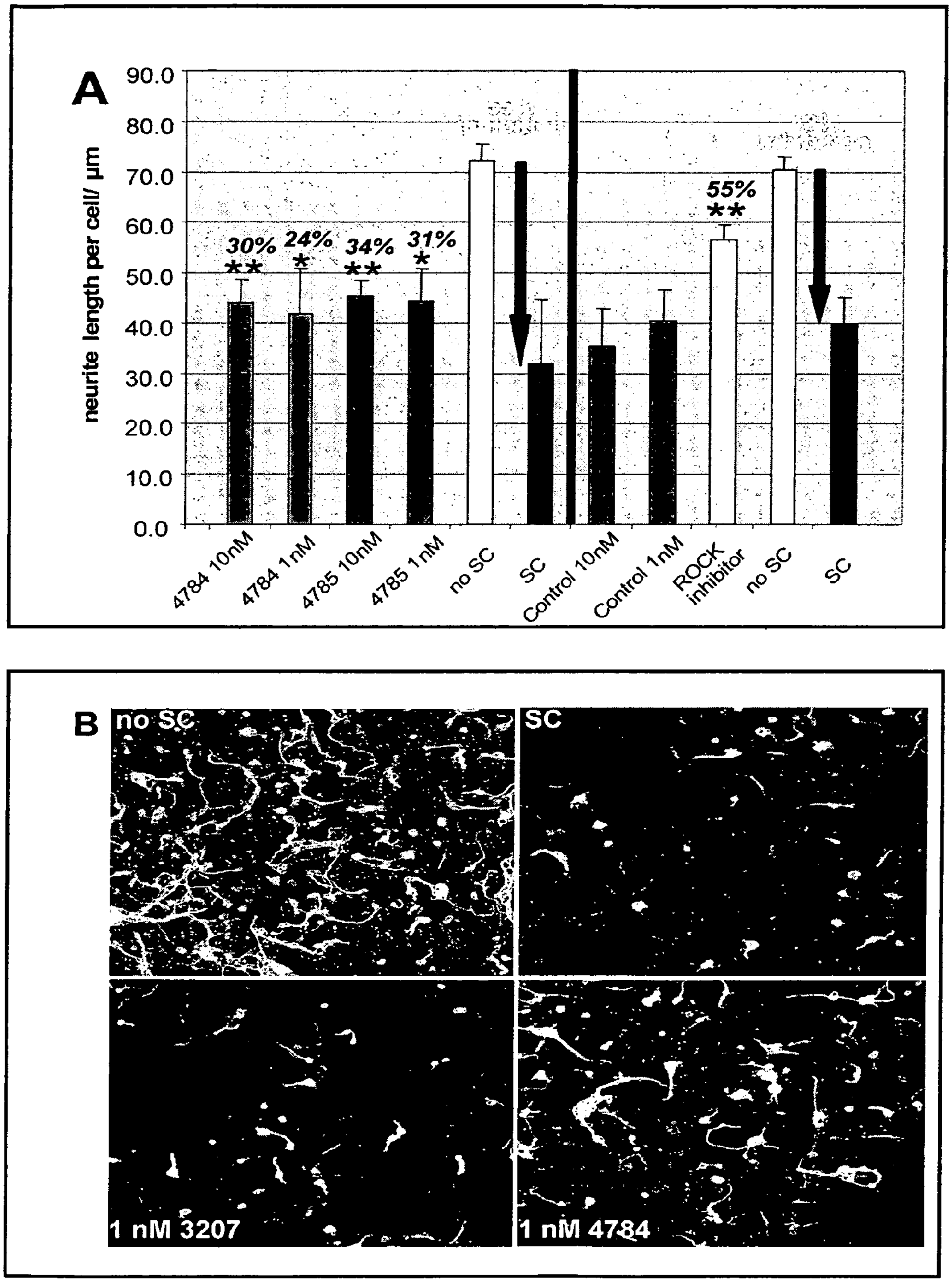

FIG. 2. Disinhibition of spinal cord myelin by anti-LINGO-1 IgG4 antibodies 4784 and 4785

A) P7 CGN cells are incubated for 16 hr on wells coated without spinal cord myelin (no SC, white bars) or wells coated with spinal cord myelin in the absence (SC, red bars) or presence of anti-LINGO-1 IgG4 antibodies, a control anti-lysozyme IgG4 antibody 3207 (green bars) or 1 μm of the ROCK inhibitor Y27632 (yellow bar). ROCK is the secondary messenger in the signaling pathway of most, it not all, myelin-associated neurite outgrowth inhibitors, including those which do not signal through the NgR receptor complex and as such Y27632 treatment is used as a positive control for the attenuation of the neurite outgrowth inhibitory activity of spinal cord myelin (FIG. 1). The experiment is performed in three 96 well plates with an SC and no SC condition per plate to which the effects of the antibodies on that plate are compared and mean neurite length per neuron (μm) is calculated for 500 neurons per well in replicates of 10. The percentage inhibition (white text) is calculated as the percentile difference in mean neurite length/neuron between cells plated on wells coated with and without SC. The percentage disinhibition (black italic text) is calculated as the difference in mean neurite length between cells plated on SC in the presence and absence of anti-LINGO-1 antibody as a percentile of the difference between cells plated on wells coated with and without SC. *$p<0.05$, **$p<0.01$ (one way ANOVA, Holm-Sidak comparison to mean neurite length/neuron for cells plated on spinal cord myelin in the absence of antibody).

B) Fluorescent images of a representative field of view of cells incubated on wells coated without spinal cord myelin (no SC) and on wells coated with spinal cord myelin in the absence (SC) or presence of 1 nM control IgG4 3207 or anti-LINGO-1 IgG4 4784. Cells grown on spinal cord myelin in the presence of 4784 have visibly longer neurites and more neurites per cell than those grown in the absence of antibody or presence of the control antibody 3207.

Figure 3:
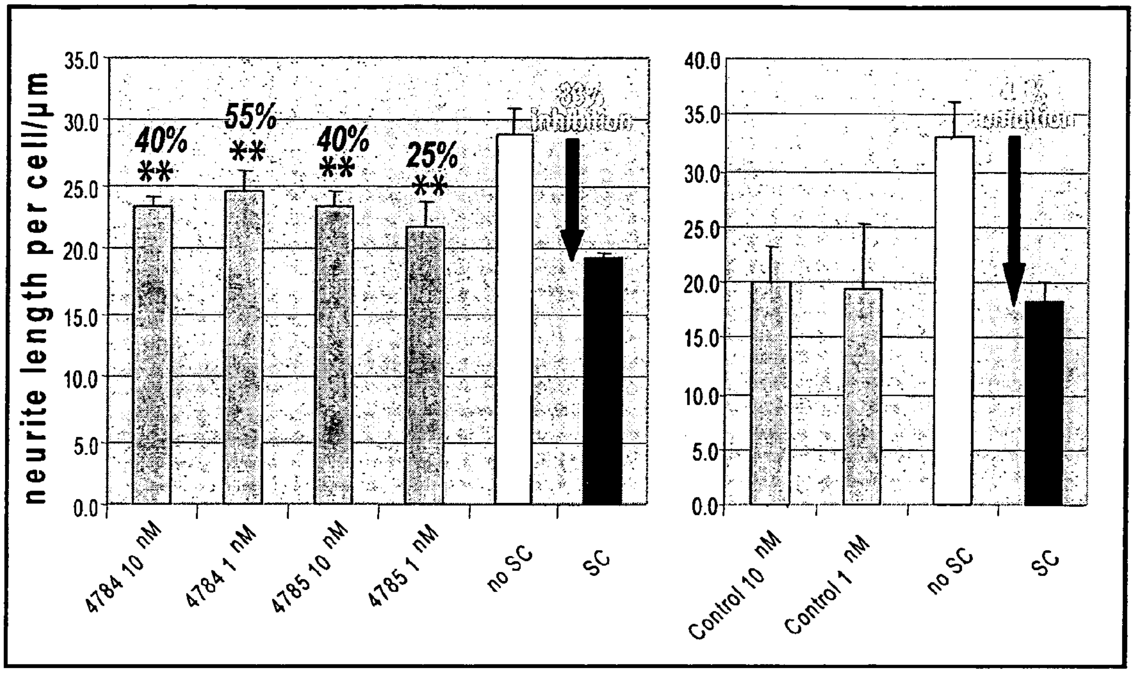

FIG. 3. Disinhibition of spinal cord myelin by anti-LINGO-1 IgG4 antibodies II A) P7 CGN cells are incubated for 8 hr on wells coated without spinal cord myelin (no SC, white bars) or wells coated with spinal cord myelin in the absence (SC, red bars) or presence of anti-LINGO-1 IgG4 antibodies or a control anti-lysozyme IgG4 antibody 3207. The experiment is performed in three 96 well plates with an SC and no SC condition per plate to which the effects of the antibodies on that plate are compared and mean neurite length per neuron (μm) is calculated for 500 neurons per well in replicates of 10. The percentage inhibition (white text) and disinhibition (black italic text) is calculated as above. **$p<0.01$ (one way ANOVA, Holm-Sidak comparison to mean neurite length/neuron for cells plated on spinal cord myelin in the absence of antibody).

Figure 4:
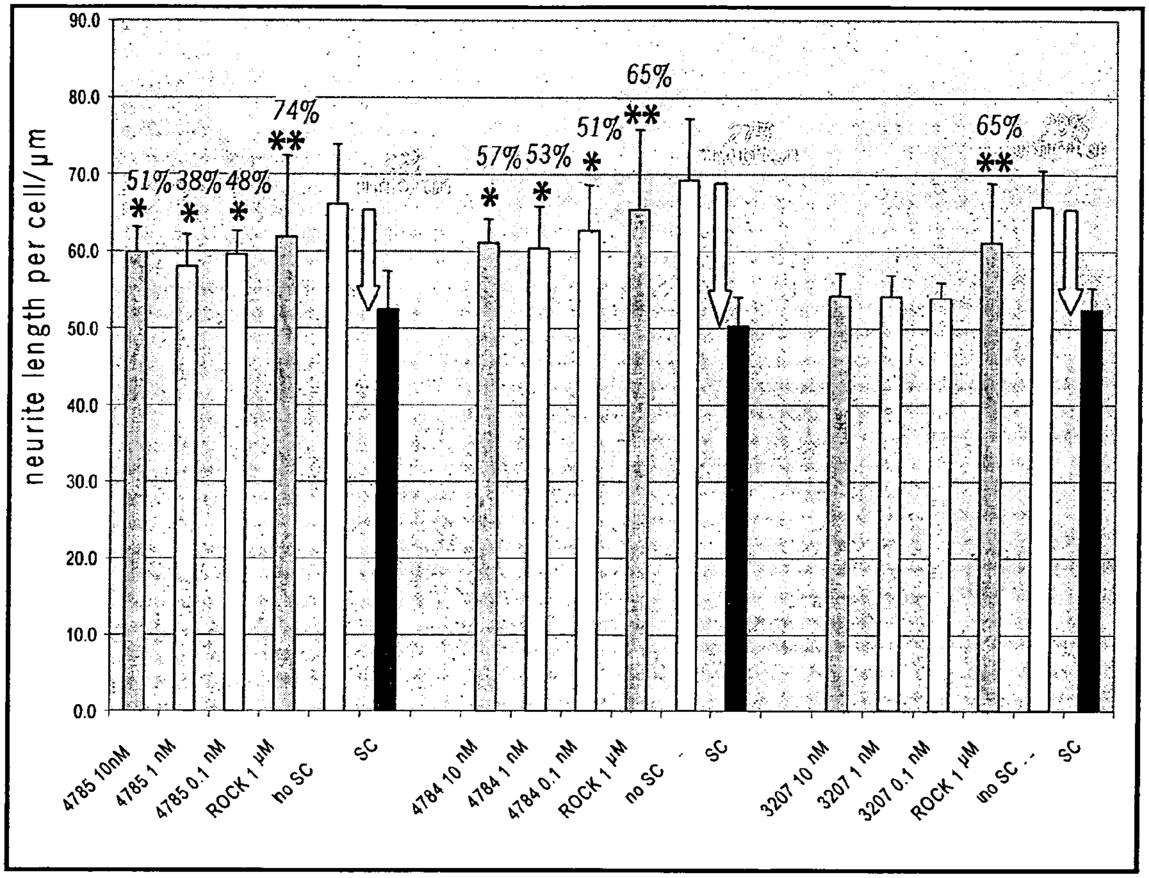

FIG. 4. Disinhibition of spinal cord myelin by anti-LINGO-1 IgG4 antibodies III P7 CGN cells are incubated for 8 hr on wells coated without spinal cord myelin (no SC) or wells coated with spinal cord myelin in the absence (SC) or presence of the indicated concentrations of anti-LINGO-1 IgG4 antibodies 4784 or 4785, a control anti-lysozyme IgG4 antibody 3207 or 1 μM Y27632 (ROCK). The experiment is performed in three 96 well plates with an SC and no SC condition per plate to which the effects of the antibodies on that plate are compared and mean neurite length per neuron (μm) is calculated for 500 neurons per well in replicates of 10. The percentage inhibition (white text) and disinhibition (black italic text) is calculated as above. *$p<0.05$, **$p<0.01$ (one way ANOVA, Holm-Sidak comparison to mean neurite length/neuron for cells plated on spinal cord myelin in the absence of antibody).

Figure 5:
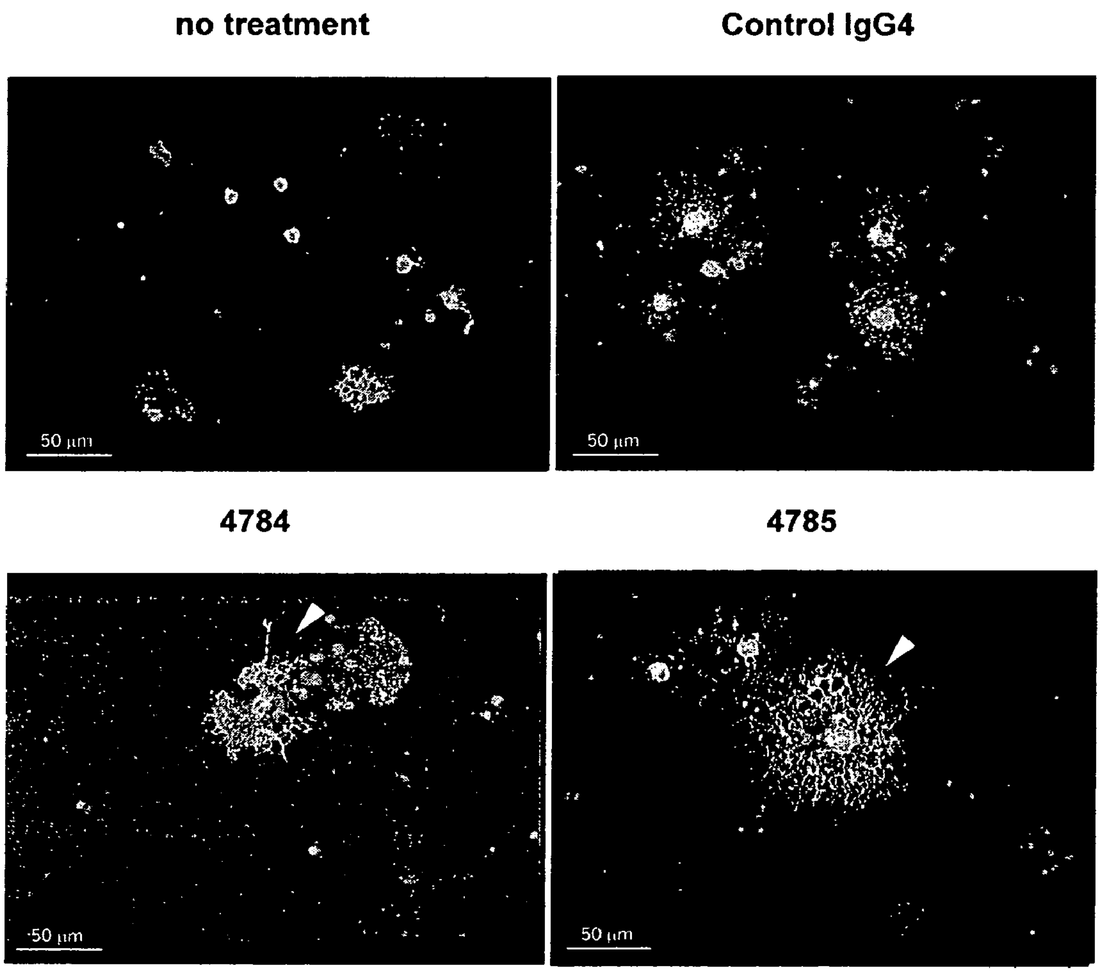
Figure 5:
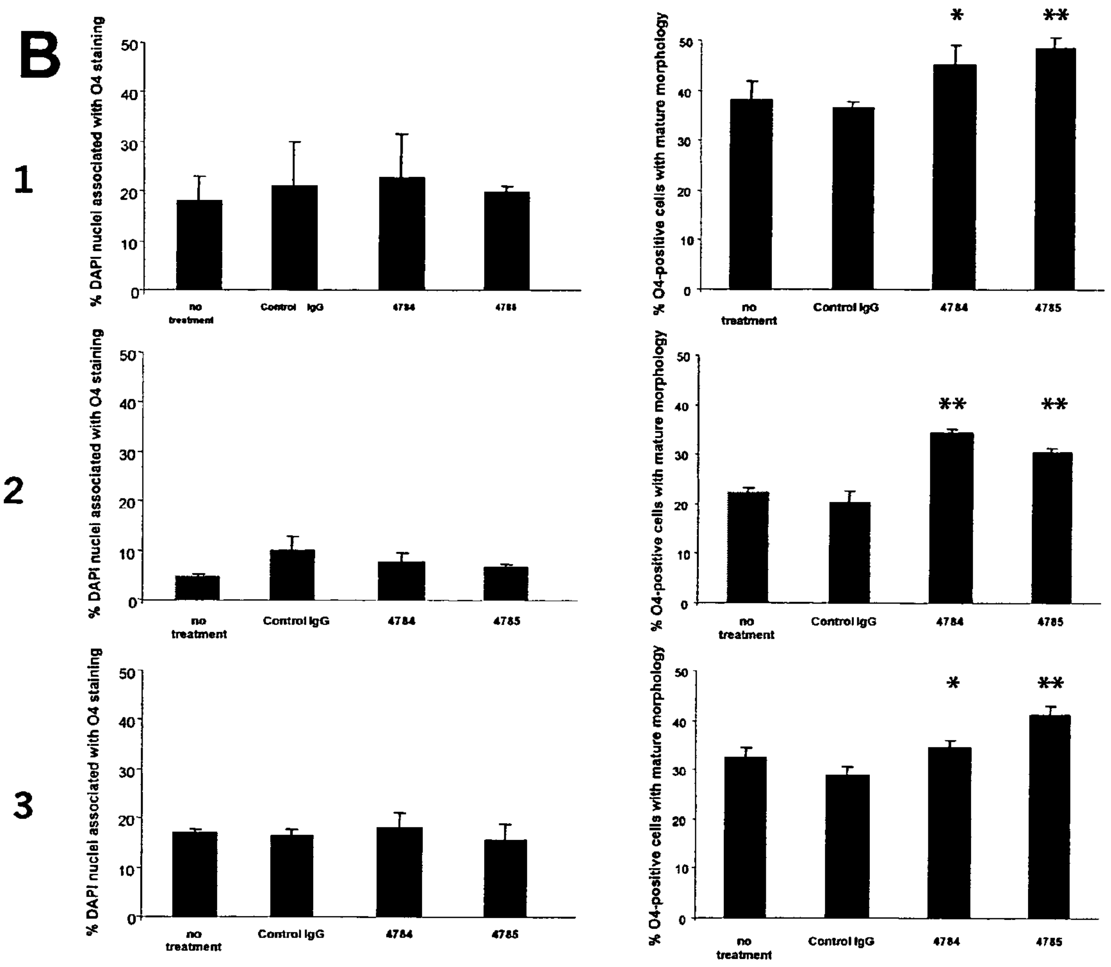

FIG. 5. Anti-LINGO-1 antibodies significantly increase the differentiation of immature oligodendrocytes A) Freshly isolated OPCs are treated with 100 nM 4784, 4785 or control IgG4 3207 for 3 days in DMEM/CNTF/T3 medium followed by staining with the anti-04 antibody to visualise immature and mature oligodendrocytes (larger, more diffuse labeling) and the nucleic acid dye DAPI (4', 6-diamidin-2'-phenyl-indol-dihydrochloride) to visualise cell nuclei (smaller circular dots). Oligodendrocytes bearing highly arborised and extended processes and myelin sheet-like structures are considered to have a mature morphology and are indicated with white arrows. Anti-LINGO-1 antibody treatment results in an increase in the proportion of O4-postive cells with a mature morphology whereas treatment with control IgG4 3207 has no effect.

B) The proportion of total (left graph) and mature (right graph) oligodendrocytes is quantified in three independent experiments (1,2,3). The left bar graph depicts the percentage of DAPI-stained nuclei associated with O4-staining and the right bar graph depicts the percentage of O4-positive cells with a mature morphology (mean of triplicates +STD). In each bar graph, the leftmost bar is with no treatment, the second to left bar Control with Control IgG, the next represents treatment with 4784 and the rightmost treatment with 4785. Anti-LINGO-1 antibodies have no effect on the proportion of cells that are oligodendrocytes but significantly increase the proportion of oligodendrocytes with a mature morphology. * $p<0.05$, ** $p<0.01$, one-way ANOVA with a Holm-Sidak comparison to the proportion of mature oligodendrocytes in the presence of the control IgG4 3207.

Figure 6:
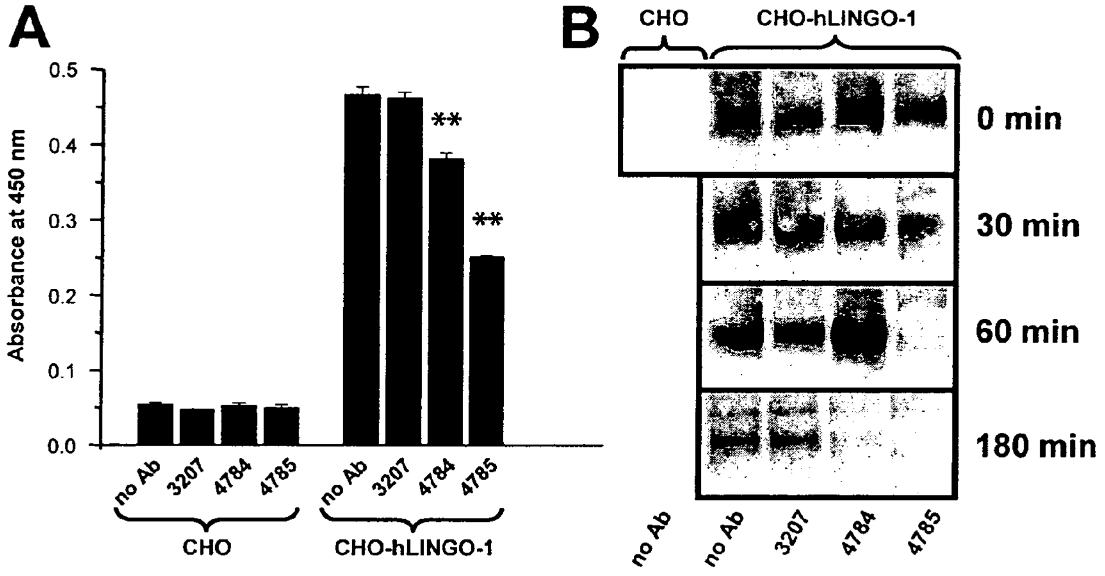

FIG. 6. Anti-LINGO-1 antibodies downregulate cell surface LINGO-1

A) Untransfected CHO-K1 or CHO-K1-hLINGO-1 cells are incubated at 37° C. for 24 hrs with 100 nM 4784, 4785 and 3207 and LINGO-1 detected at the cell surface by a further incubation at room temperature for 30 min with the anti-V5 antibody. The cells are fixed with 4% PFA, blocked with BSA and bound anti-V5 antibody detected using an anti-mouse-IgG (Fc specific)-POD conjugate that is subsequently developed using a 1-Step™ Turbo TMB ELISA kit. The absorbance at 450 nm is taken as a measure of the amount of LINGO-1 at the cell surface (mean of triplicates±STD). A very low level of anti-V5 antibody binding is observed to untransfected CHO-K1 cells. Incubation of CHO-K1-hLINGO-1 cells with anti-LINGO-1 antibodies but not the control IgG4 3207 result in a significant reduction in the amount of LINGO-1 at the cell surface ** $p<0.01$, one-way ANOVA with a Holm-Sidak comparison to the absorbance following incubation with the control IgG4 3207.

B) Cell surface proteins on untransfected CHO-K1 or CHO-K1-hLINGO-1 cells are biotinylated at 4° C. and the cells are incubated at 37° C. for the indicated times with or without 100 nM 4784, 4785 and 3207. At the end of the incubation period, LINGO-1 is precipitated from the cell lysate using the anti-V5 antibody coupled to agarose beads and biotinylated (cell surface) LINGO-1 detected by Western blot analysis using an anti-biotin antibody. No signal is detected for biotinylated LINGO-1 in untransfected CHO-K1 cells. Incubation of CHO-K1-hLINGO-1 cells with anti-LINGO-1 antibodies increases the rate of degradation of cell surface LINGO-1.

Figure 7:
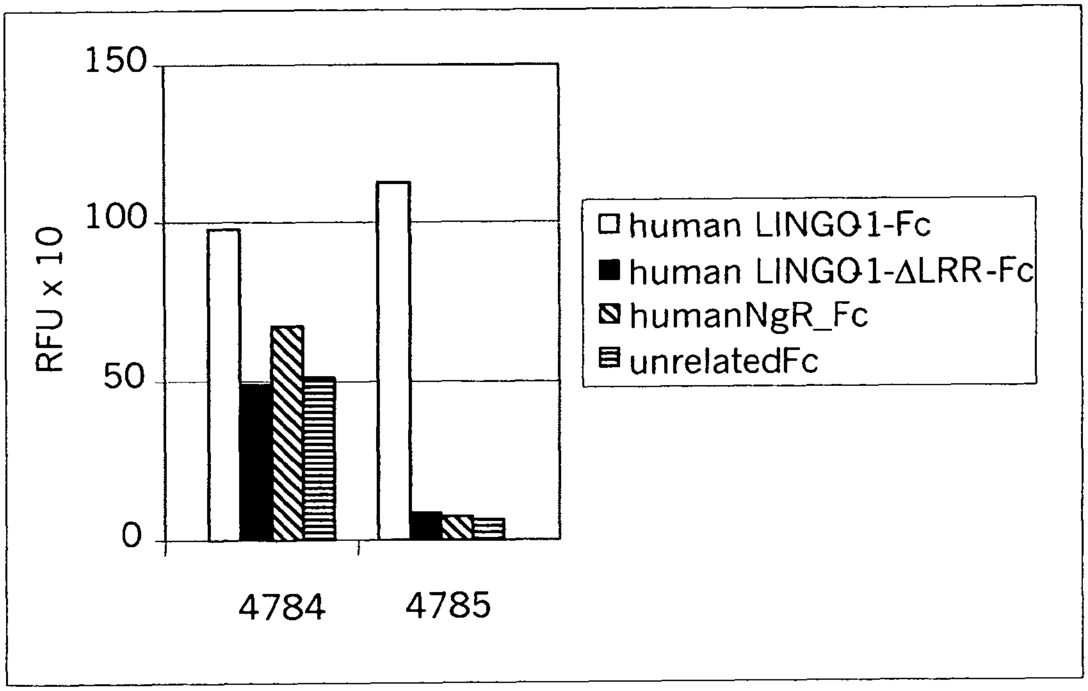

FIG. 7. Characterization of anti-LINGO-1 Fabs by ELISA Values for ELISA analyses are given as mean values of relative fluorescence units (RFU). The binding affinities of these clones are characterized by FACS saturation assays.

The present invention also provides the use of the binding molecules of the invention in the promotion of axonal regeneration/plasticity of a mammalian nervous system, in particular the human nervous system.

The invention also provides a method of promoting axonal regeneration/plasticity of a mammalian nervous system, in particular human nervous system which comprises administering an effective amount of the binding molecules of the invention to a patient in need of such treatment.

The invention also provides a pharmaceutical composition for promoting axonal regeneration/plasticity of a mammalian nervous system, in particular human nervous system which comprises the binding molecules of the invention and a pharmaceutically acceptable carrier or diluent.

In particular, the binding molecules of the invention are useful for promoting axonal regeneration and plasticity after CNS injury (the term injury, in the present application, refers especially to injury caused by mechanical or chemical effects or due to diseases or disorders that e.g. lead to degeneration of neurons, especially their structure or form, e.g. in neurological diseases such as Alzheimer's or Parkinson's Disease or other disorders or dieseases mentioned below). Thus the molecules of the invention have a wide utility in particular for human subjects. For example the binding molecule of the invention are useful in the treatment of various diseases of the peripheral (PNS) and central (CNS) nervous system, i.e. more particularly in neurodegenerative diseases such as Alzheimer's disease, Parkinson's disease, Amyotrophic lateral sclerosis (ALS), Lewy like pathologies or other dementia in general, diseases following cranial, cerebral or spinal trauma and stroke. Furthermore, given that LINGO-1 is a negative regulator of myelination, the binding molecules of the invention are useful for promoting remyelination in concert with promoting axonal regeneration/plasticity in demyelinating diseases that include, but are not limited to, multiple sclerosis, monophasic demyelination, encephalomyelitis, multifocal leukoencephalopathy, panencephalitis, Marchiafava-Bignami disease, pontine myelmolysis, adrenoleukodystrophy, Pelizaeus-Merzbacher disease, Spongy degeneration, Alexander's disease, Canavan's disease, metachromatic leukodystrophy and Krabbe's disease. In one example, cells which express the binding molecules of the invention may be transplanted to a site spinal cord injury to facilitate axonal growth throughout the injured site. Such transplanted cells would provide a means for restoring spinal cord function following injury or trauma. Such cells could include olfactory ensheathing cells and stem cells of different lineages of fetal nerve or tissue grafts.

In addition, the binding molecules of the invention are useful for the treatment of degenerative ocular disorders which may directly or indirectly involve the degeneration of retinal or corneal cells including ischemic retinopathies in general, anterior ischemic optic neuropathy, all forms of optic neuritis, age-related macular degeneration, diabetic retinopathy, cystoid macular edema (CME), retinitis pigmentosa, Stargardt's disease, Best's vitelliform retinal degeneration, Leber's congenital amaurosis and other hereditary retinal degenerations, pathologic myopia, retinopathy of prematurity, and Leber's hereditary optic neuropathy, the after effects of corneal transplantation or of refractive corneal surgery, and herpes keratitis.

Furthermore, the binding molecules of the invention are useful for the treatment of psychiatric conditions, particularly schizophrenia and depression.

For these indications, the appropriate dosage will, of course, vary depending upon, for example, the particular molecule of the invention to be employed, the mode of administration and the nature and severity of the condition being treated. In general, the dosage preferably will be in the range of 1 μg/kg/day to 1 mg/kg/day. The binding molecules of the invention are conveniently administered by pumps or injected as therapeutics at the lesioned site or near it, e.g. they can be administered directly into the CNS intracranially or into the spine intrathecally to the lesioned site. However, systemic administration is not excluded here. The binding molecules of the invention can be provided alone, or in combination, or in sequential combination with other agents. For example, the binding molecules of the invention can be administered in combination with anti-Nogo-A antibodies or anti-inflammatory agents such as but not limited to corticosteroids following stroke or spinal cord injury as a means for blocking further neuronal damage and inhibition of axonal regeneration, neurotrophic factors such as NGF, BDNF or other drugs for neurodegenerative diseases such as Exelon™ or Levodopa. Other suitable combination partners for the treatment of stroke are Alteplase and Desmoteplase (DSPA, e.g. disclosed in WO90/09438). In one embodiment, the present invention provides a combination comprising a binding molecule of the invention and Desmoteplase, in particular for the treatment of stroke as well as pharmaceutical compositions comprising said combination. As used herein, two agents are said to be administered in combination when the two agents are administered simultaneously or are administered independently in a fashion such that the agents will act at the same time.

The structure of the active ingredients identified by code nos., generic or trade names may be taken from the actual edition of the standard compendium "The Merck Index" or from databases, e.g. Patents International (e.g. IMS World Publications) or other databases provided by IMS Health. The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

Pharmaceutical compositions of the invention may be manufactured in conventional manner. E.g. a composition according to the invention comprising the molecules of the invention is preferably provided in lyophilized form. For immediate administration it is dissolved in a suitable aqueous carrier, for example sterile water for injection or sterile buffered physiological saline.

To aid in making up suitable compositions, the binding molecules of the invention and optionally a second drug enhancing the effect of the binding molecules of the invention, may be packaged separately within the same container, with instructions for mixing or concomitant administration. Optional second drug candidates are provided above.

The synergistic effect of a combination of the binding molecules of the invention and growth factors such as NGF may be demonstrated in vivo by the spinal cord injury models.

The invention will be more fully understood by reference to the following examples. They should not, however, be construed as limiting the scope of the invention.

The monoclonal antibodies of attention in the Examples are binding molecules according to the present invention containing for antibody 4784 the variable part of the light chain (SEQ ID NO: 4) and the variable part of the heavy chain (SEQ ID NO: 5) and comprising for 4785 the variable part of the light chain (SEQ ID NO: 6) and the variable part of the heavy chain (SEQ ID NO: 7).

The following abbreviations are used:

| | |
|---|---|
| AP | human placental alkaline phosphatase |
| CDR | complementarity determining region |
| cDNA | complementary DNA |
| ELISA | enzyme linked immuno-sorbant assay |
| FACS | fluorescence activated cell sorting |
| FBS | foetal bovine serum |
| HCMV | human cytomegalovirus promoter |
| IgG | immunoglobulin isotype G |
| PBS | phosphate-buffered saline |
| PCR | polymerase chain reaction |
| PFA | paraformaldehyde |
| PNPP | para-nitrophenyl phosphate |

EXAMPLE 1

Generation of CHO-K1 Cells Expressing Full Length Rat, Cynomolgus Monkey or Human LINGO-1 and Human LINGO-2

A human cDNA library is generated by RT-PCR of universal human reference RNA (Stratagene) using random and oligo dT primers. A cynomolgus monkey brain cDNA library is generated by RT-PCR of polyA RNA isolated from frozen cynomolgus monkey brain using random and oligo dT primers. A Marathon-ready rat brain cDNA library is obtained from Clontech. cDNA encoding the mature sequence (residues 34-614) of human LINGO-1 (SEQ ID NO: 27), cynomolgus monkey LINGO-1 (SEQ ID NO: 28) and rat LINGO-1 (SEQ ID NO: 29) flanked by 5"-XbaI and 3"-XhoI sites is PCR amplified from the respective library using the forward primer DM14, 5"-CTACGICTAGAACGGGCTGC-CCGCCCCGCT-3' (SEQ ID NO: 30), and reverse primer DM15, 5"-GGTTTCTCGAGTCATATCATCTTCATGT-TGAACTTGCGG-3' (SEQ ID NO: 31). The PCR product is cleaved with XbaI and XhoI and inserted into the respective sites of the vector pSecTag2-V5 (SEQ ID NO: 32) to generate hLINGO-1-pSecTag2-V5, cmLINGO-1-pSecTag2-V5 and rLINGO-1-pSecTag2-V5, respectively. The predicted protein product is the mature sequence of LINGO-1 fused at the N-terminus to a 14 amino acid residue V5 epitope tag via a 2 amino acid residue linker. cDNA encoding the mature sequence (residues 26-606) of human LINGO-2 (SEQ ID NO: 33) flanked by 5"-XbaI and 3"-XhoI sites is PCR amplified from a Marathon-ready human brain cDNA library (Clontech) using the forward primer DM16, 5"-CTACGTCTAGAATTGGCTGCCCCGCTCGCT-3" (SEQ ID NO: 34), and reverse primer DM17, 5"-GGTTTCTCGAGTCAAATCATTTTCATGTTGAAC CTCCTG-3" (SEQ ID NO: 35). The PCR product is cleaved with XbaI and XhoI and inserted into the respective sites of the vector pSecTag2-V5 to generate hLINGO-2-pSecTag2-V5. The predicted protein product is the mature sequence of LINGO-2 fused at the N-terminus to a 14 amino acid residue V5 epitope tag via a 2 amino acid residue linker. CHO-K1 cells stably expressing human LINGO-1 (CHO-K1-hLINGO-1), cynomolgous LINGO-1 (CHO-K1-cmLINGO-1), rat LINGO-1 (CHO-K1-rLINGO-1) and human LINGO-2 (CHO-K1-hLINGO-2) are generated by transfection of cells with hLINGO-1-pSecTag2-V5, cmLINGO-1-pSecTag2-V5, rLINGO-1-pSecTag2-V5 and hLINGO-2-pSecTag2-V5, respectively, using lipofectamine-2000 (Invitrogen) according to the manufacturer's instructions. Stably expressing transfectants are selected with 1 mg/ml zeocin (Invivogen) and single clones isolated either by serial dilution into 96-well plates or by using clonal rings. Expression of the constructs on the cell surface is confirmed by immunofluorescent analysis using an anti-V5 antibody (InvitroGen).

EXAMPLE 2

Generation and Expression of Human LINGO-1-Fc and Human LINGO-1ΔLRR-Fc

A MGC mRNA coding for human LINGO-1 (clone MGC: 17422 IMAGE:421-4343) is used as template for PCR amplification. The extracellular domain (ECD) preceded by the natural signal sequence (aa1-550) of human LINGO-1 is amplified by PCR with the Pwo1 polymerase (Roche Diagnostics) and with primers which added a HindIII restriction site and a Kozak consensus sequence at the 5' end of the target sequence and an XhoI restriction site immediately after the last codon of the target sequence at the 3' end. The PCR product is digested with HindIII and XhoI, gel purified and inserted into plasmid pRS5a-IgG (SEQ ID NO: 36) previously digested with the same enzymes. The accuracy of the inserted sequence, complete Fc and flanking regions in the resulting expression clone (natleader-hsLINGO-1-Fc/pRS5a, SEQ ID NO: 37) is confirmed by DNA sequencing.

The same MGC clone serves as template for the construction by gene SOEing of the expression plasmid for human LINGO-1 lacking the LRR domain (aa34-65+aa354-550). The N-terminal region of human ECD LINGO-1 (aa34-65) is amplified by PCR with primers extending the 5' end with a partial sequence coding for an heterologous secretion signal fused to mature LINGO-1 and adding, at the 3' end, a sequence coding for the first seven amino acids of the C-terminal fragment. The C-terminal region of human ECD LINGO-1 (aa354-550) is amplified by PCR with primers extending the 5' end with a sequence coding for the last seven amino acids of the N-terminal fragment and adding, at the 3' end, an XhoI site immediately after the last codon of the target sequence. The two PCR products are gel purified, mixed and serves as template for a second PCR amplification using at the 5' end a primer which adds a HindIII restriction site, a Kozak consensus sequence and completes the herologous secretion signal sequence and, at the 3' end, the external primer previously used to amplify the C-terminal fragment. The PCR product is digested with HindIII and XhoI, gel purified and inserted into plasmid pRS5a-IgG previously digested with the same enzymes. The accuracy of the inserted sequence, complete Fc and flanking regions in the resulting expression clone (Igleader-hsLINGO-1-ΔLRR-Fc/pRS5a, SEQ ID NO: 38) is confirmed by DNA sequencing.

As an initial expression evaluation both constructs are tested in small scale experiments. HEK.EBNA cells (Invitrogen, previous cat.no. R620-07) are cultivated in attached mode on tissue culture flasks in Dulbecco's Modified Eagle Medium (DMEM) buffered with 25 mM Hepes (Gibco/Life Technologies cat.no. 42430-025) and additionally enriched with 10% fetal calf serum; the cultures are maintained at 37° C. and 5% $CO_2$ in humidified atmosphere. For small scale transfection experiments, $4\times10^5$ cells are seeded one day prior to transfection into poly-D-lysine-coated 6-wells (plates). Transfections are performed using 3 μg of plasmid DNA and 6 μl of Lipofectamine$^{2000}$ reagent (Invitrogen cat.no. 11668-019) per well, essentially as described by the vendor. Three days post-transfection the cell supernatants are harvested and the cell-free supernatant is subjected to protein analysis, i.e. to immunoaffinity HPLC analysis on Protein G columns. Titers ranging between 8 mg/l for construct natleader-hsLINGO-1-Fc/pRS5a and 40 mg/l for construct Igleader-hsLINGO-1-ΔLRR-Fc/pRS5a are determined. Subsequently, for both plasmids large-scale plasmid preps are prepared to enable transient transfections on the multi-liter scale in HEK.EBNA suspension cultures.

For production of natleader-hsLINGO-1-Fc on enlarged scale, 2.9 L of HEK.EBNA cell culture at a density of $1.4\times10^6$ cells/ml is mixed with 1.1 L DNA:PEI solution (1 μg DNA:2 μg PEI per ml). Following incubation of cells for 4 hrs, the culture is fed with 4 L of ExCell VPRO medium (SAFC, previously JRH, Lenexa, Kans.). The cell culture supernatant is harvested after 6 days of cultivation and concentrated by diafiltration down to 1-L using a disposable Hemoflow F10HPS filter with a 10 kDa cut-off (Fresenius Medical Care, Germany).

The second relevant protein production run to generate Igleader-hsLINGO-1-ΔLRR-Fc protein is done in a similar fashion. Details on large-scale transfection, DNA:PEI ratio, cell densities, feeding and harvest are exactly the same as described above.

a) Natleader-hsLINGO-1-Fc

1 L concentrate (from 8 L culture supernatant) is chromatographed on 20 ml Protein A Sepharose. After base-line washing with 100 mM NaPi, pH 7.3, bound material is eluted with 50 mM citrate, 140 mM NaCl, pH 2.7, neutralized and sterile filtered. The eluted fraction is further concentrated and gel filtered on Superdex 75 in PBS yielding 8.2 mg product at a concentration of 1.2 mg/ml.

b) Igleader-hsLINGO-1-ΔLRR-Fc

1 L concentrate (from 8 L culture supernatant) is chromatographed on 20 ml Protein A Sepharose. After base-line washing with 100 mM NaPi, pH 7.3, bound material is eluted with 50 mM citrate, 140 mM NaCl, pH 2.7, neutralized and sterile filtered yielding 52.5 mg product at a concentration of 1.5 mg/ml.

The purified proteins are extensively characterized by N-terminal sequencing and by MALDI peptide mass analysis after reduction/alkylation and trypsin digestion.

EXAMPLE 3

AP-LINGO-1 Binding Assay

Blocking the binding of LINGO-1 to NgR is expected to prevent the signaling of three myelin-associated inhibitors of neurite outgrowth, namely Nogo-66, MAG and OMgp, and hence attenuate the neurite outgrowth inhibitory activity of CNS myelin thus leading to increased axonal regeneration/plasticity and improved functional recovery following acute CNS injury. To demonstrate that an anti-LINGO-1 antibody blocks the binding of LINGO-1 to NgR, an assay can be used which measures the binding of human placental alkaline phosphatase (AP)-tagged rat LINGO-1 ectodomain (AP-LINGO-1) to SH-SY5Y cells stably expressing NgR (NgR-SH-SY5Y, Walmsley et. al. (2004) J Cell Sci 117, 4591-4602). cDNA encoding the majority of the rat LINGO-1 ectodomain (residues 34-532) flanked by 5"-Xho I and 3'-Xba I sites is PCR amplified from rLINGO-1-pSecTag2-V5 using the forward primer DM22, 5"-GGTTATCTCGAGACCGGCTGCCCGCCCC-3" (SEQ ID NO: 24), and reverse primer DM23, 5"-GGCCCTTCTAGATCACTCGCCTGGCTGGTTGGAGATG-3" (SEQ ID NO: 25). The PCR product is cleaved with XhoI and XbaI and inserted into the respective sites of the vector APtag-5-NHIS (SEQ ID NO: 26) to generate APtag-5-NHIS-solrLINGO-1. The predicted protein product is the majority of the rat LINGO-1 ectodomain fused at the N-terminus to residues 23-511 of human placental alkaline phosphatase via a 3 amino acid residue linker. HEK293T cells are transfected with APtag-5-NHIS-solrLINGO-1 using lipofectamine$^{200°}$ according to the manufacturer's instructions. The transfection medium is removed 4 hrs after transfection and replaced with OptiMEM I without phenol red (Invitrogen). Medium is harvested after 24 hrs, replaced and harvested again after another 24 hrs. The medium is clarified by centrifugation at 13000×g for 5 min and the supernatant concentrated around 15-fold using a Centriprep filter device (Millipore) according to the manufacturer's instructions. AP activity of the concentrated supernatant is measured using 1-Step™ PNPP (Pierce) as change in absorbance at 405 nm over time and transformed to a concentration using the following equation (applies for a 96 well plate format with 200 μl PNPP/well):

$$\text{Concentration of } AP\text{-fusion (nM)} = \frac{\text{Change in absorbance (mAU/min)}}{7.945 \times \text{volume of sample added to } PNPP(\mu l)}$$

Concentrated supernatant is subjected to SDS-PAGE gel electrophoresis and Western blotted as described (Walmsley et. al. (2004) J Cell Sci 117, 4591-4602). AP-LINGO-1 is detected with 0.1% (v/v) anti-penta-histidine antibody (Qiagen) followed by 0.02% (v/v) peroxidase-conjugated anti-mouse IgG antibody (Sigma) using the ECL™ system (GE Healthcare). AP-LINGO-1 is visualised as a band of approximately 110 kDa, similar to its predicted molecular weight of 112 kDa. No N-terminal degradation products are observed. NgR:SH-SY5Y cells at 50% confluency are harvested with enzyme-free dissociation buffer (Invitrogen) to preserve cell surface proteins such as NgR. 1 nM AP, 1 nM AP-LINGO-1 or 1 nM AP-LINGO-1 in the presence of 2 μM anti-LINGO-1 Fab or a control Fab 3207 against lysozyme from hen egg white is pre-incubated for 30 min in OptiMEM (Invitrogen) and subsequently incubated with constant agitation for 1.5 hr with NgR:SH-SY5Y cells in suspension. Cells are washed 6 times in HBH (20 mM HEPES pH 7.4/1% bovine serum albumin in Hanks balanced saline) and fixed in 4% paraformaldehyde (PFA)/5% sucrose in PBS for 15 min. Following inactivation of endogenous AP activity by incubation at 65° C. for 1 hr in 20 mM HEPES pH 7.4 in Hanks balanced saline, cell-bound AP activity is quantified as absorbance at 405 nm after a 30 min incubation with 1-Step™ PNPP (Pierce) according to the manufacturer's instructions.

The Fabs are used at a concentration of 2 μM in order to saturate AP-LINGO-1 with bound Fab and thus minimise the influence of their affinities on their ability to inhibit binding. The reason for this is to exclude the possibility of prematurely discarding Fabs from further studies which fail to inhibit binding due to their low affinity rather than the position of their binding site as the affinity of such Fabs could be increased at later stages by affinity maturation and IgG4 conversion. 1 nM AP-LINGO-1 is pre-incubated with either the control Fab 3207 or anti-LINGO-1 Fabs 4784 and 4785 and then allowed to bind in the presence of the Fab to NgR: SH-SY5Y cells in suspension (FIG. 1). The percentage inhibition in specific AP-LINGO-1 binding in the presence of the anti-LINGO-1 Fabs is normalized to that for Fab 3207. 4784 and 4785 give a significant inhibition ($p<0.01$, one way ANOVA, Holm-Sidak comparison to specific binding of AP-LINGO-1 in presence of control Fab 3207) of AP-LINGO-1 binding to the cells.

Blocking the binding of LINGO-1 to NgR is predicted to prevent the signaling of the myelin-associated inhibitors Nogo-66, MAG and OMgp leading to a reduction in the neurite outgrowth inhibitory activity of CNS myelin. In that regard, 4784 and 4785 Fabs are converted to the final IgG4 format (see Example 8) and assessed for their ability to attenuate the inhibition of neurite outgrowth from postnatal day 7 rat cerebellar granule neurons grown on adult rat spinal cord myelin.

EXAMPLE 4

Neurite Outgrowth Inhibition Assay

The most relevant in vitro assay to predict the effect of anti-LINGO-1 antibodies on axonal regeneration/plasticity in vivo is their ability to attenuate the neurite outgrowth inhibitory activity of CNS myelin. In this assay, postnatal day 7 rat cerebellar granule neurons (CGN) are grown in wells coated with whole spinal cord myelin extracted from adult rats and neurite outgrowth quantified by an automated ArrayScan® HCS Reader (Cellomics).

The disinhibitory activity of anti-LINGO-1 IgG4 antibodies 4784 and 4785 is assessed in the said neurite outgrowth assay (FIG. 2).

Fresh rat spinal cord tissue from adult rats is homogenized in 3 volumes (w/v) extraction buffer (60 mM Chaps, 20 mM Tris pH 8.0, 1 mM EDTA, protease inhibitor cocktail), incubated for 30 min at 4° C. and clarified by centrifugation at 170000×g for 30 min at 4° C. Each well in a 96 well plate is coated with 5 μl nitrocellulose in MeOH (5 $cm^2$ nitrocellulose in 12 ml MeOH), air dried and coated with 100 μl 5 μg/ml poly-D-lysine by incubation for 4 hr at 37° C. Following three washes in water, the plates are air dried for 1 hr and then coated with 60 μg/$cm^2$ spinal cord extract by incubation overnight at 37° C. CGN cells are freshly purified from trypsin dissociates of postnatal day 7 rat cerebellar tissue as described previously (Schweigreiter et al., 2004). Western blot analysis to detect LINGO-1 is performed on lysates from CHO-K1 cells expressing V5-tagged rat LINGO-1 or P7 CGN cells using 2 μg/ml (or 13.3 nM) anti-LINGO-1 polyclonal antibody (Upstate) followed by 0.02% (v/v) peroxidase-conjugated anti-rabbit IgG antibody (Sigma). CGN cells (35000 cells/well) are incubated for 30 min at 37° C. on wells coated without or with spinal cord myelin prior to the addition of either 0-100 nM anti-LINGO-1 IgG4 antibody or the control 3207 IgG4 antibody. Following an 8-16 hr incubation at 37° C., cells are fixed with 4% PFA and stained with Hoechst 3342 (Invitrogen) for visualisation of the nucleus and anti-β-tubulin III antibody (R&D Systems) followed by an Alexa Fluor 546-conjugated anti-mouse IgG antibody (Invitrogen) to specifically visualize neurons. Parameters of neurite outgrowth are determined using an ArrayScan® HCS Reader (Cellomics). ArrayScan® II automatically locates, focuses and exposes fields of cells within a 96-well microtiter plate. ArrayScan® consists of a high-resolution optical system, a multiple bandpass emission filter with matched single band excitation filter (XF100), a CCD camera with frame grabber, and proprietary applications software. In this assay, the Extended Neurite Outgrowth Bioapplication is used. An excitation filter wheel and multiple bandpass emission filters are used to enable multichannel imaging of fluorescence from two fluorophores in the same cells. Bandpass images of Hoechst 33342-labelled nuclei are acquired to identify discrete cells, and bandpass images of Alexa Fluor 488 are then acquired to indentify the extent of cells labeled with anti-tubulin antibody (using a secondary conjugated to Alexa Fluor 488). Inappropriate bodies within cells are automatically excluded from the analysis, so that only overlapping Hoechst and beta-tubulin cell bodies are analyzed. Dual emission images are acquired for 5 discrete 350 $\mu m^2$ fields in each well of the plate. Using a 10-x objective, this results in 400-500 cells per well analyzed. The Extended Neurite Outgrowth Bioapplication then reports several quantitative measures of neuronal morphology for single cells, including neurite length number of neurites per cell, cell body area, and branch and cross points. The mean neurite length per neuron (μm) is calculated for 500 neurons per well in replicates of 10.

In the above neurite outgrowth assay, the anti-LINGO-1 IgG4 antibodies 4784 and 4785 are disinhibitory at 1 and 10 nM, whereas the control IgG4 against lysozyme gives no disinhibition at both concentrations (FIG. 2). The mean length of neurites per neuron on spinal cord myelin in the presence of 4784 and 4785 at both concentrations is statistically higher than that in the absence of antibody. The greater level of disinhibition achieved with the ROCK inhibitor Y27632 compared to the anti-LINGO-1 antibodies 4784 and 4785 is expected as this compound inhibits the signaling pathways of additional myelin-associated neurite outgrowth inhibitors other than those that signal through the NgR receptor complex.

To confirm the above results, the neurite outgrowth assay is repeated (FIG. 3). Again, the anti-LINGO-1 antibodies 4784 and 4785 are disinhibitory at 1 nM and 10 nM, whereas the control IgG4 against lysozyme gives no disinhibition at both concentrations. The mean length of neurites per neuron on spinal cord myelin in the presence of 4784 and 4785 at both concentrations is statistically higher than that in the absence of antibody.

To further establish the potency of the anti-LINGO-1 antibodies 4784 and 4785, the effect on neurite outgrowth inhibition of sub-nM concentrations of the antibody is assessed (FIG. 4). 4784 and 4785 give a significant disinhibition (38-51% and 51-57%, respectively) of spinal cord myelin at concentrations as low as 0.1 nM, whereas the control anti-lysozyme antibody has no effect. Again, the ROCK inhibitor Y27632 gives a higher degree of disinhibition (65-74%) than the anti-LINGO-1 IgG4 antibodies as expected.

EXAMPLE 5

Primary Oligodendrocyte Differentiation Assay

Blockade of LINGO-1 function by genetic means or by treatment with a receptor-body antagonist has been reported to increase the proportion of mature oligodendrocytes arising from purified OPC cultures (Mi et al. (2005) Nat Neurosci 8, 745-751). To assess the ability of anti-LINGO-1 antibodies to block LINGO-1 function in OPC cultures and promote oligodendrocyte maturation, freshly isolated rat OPCs are incubated with 4784, 4785 or control IgG4 3207 for 3 days in DMEM/CNTF/T3 medium followed by staining with the anti-04 antibody to label both immature and mature oligodendrocytes (FIG. 5). The degree of oligodendrocyte maturation is measured as the proportion of O4-positive cells exhibiting a mature morphology.

Enriched populations of OPCs are isolated from OFA P3 rats: Briefly, the brain is dissected and the telencephalons are placed in ice-cold Hank's buffered saline solution (HBSS, Invitrogen) containing 0.15% $MgSO_4$. The tissue is incubated with 1:1 HBBS/trypsin-EDTA (Invitrogen) and 100 μg/ml DNAse I (Roche) for 10 min at 37° C. and the trypsin inactivated by addition of FCS (Invitrogen) to a final concentration of 10%. The tissue suspension is centrifuged at 890 rpm for 10 min and the pellet resuspended in Basal Medium Eagle (BME, Invitrogen) with 10% horse serum (Invitrogen). The suspension is filtered through a 40 μm cell strainer (BD Falcon) and the cells plated on poly-D-lysine pre-coated 80 $cm^2$ tissue culture flasks (BD Falcon) at 1 brain per flask. Cells are cultivated at 37° C. for 11 days in BME/10% horse serum. Microglial cells are killed by adding 5 mM L-leucine-methyl esther and the flasks are agitated by shaking at 140 rpm for 2 hrs. OPCs are harvested by shaking the flasks overnight at 200 rpm at 37° C. and any astrocytes remaining in the supernatant are further separated from the OPCs by pre-attachment for 2 hrs at 37° C. on 10 cm bacterial culture dishes. Non-adherent cells are collected, centrifuged for 10 minutes at 890 rpm and plated at approximately $3\times10^4$ cells/well in poly-D-lysine-coated 8-well chamber slides (BD Falcon). Cultures are maintained for 3 days in either in DMEM/T3/CNTF medium consisting of DMEM (Invitrogen) containing 10 ng/ml Ciliary Neurotrophic Factor (R&D Systems) and 15 nM Triiodothyronine (Sigma) or in SATO medium consisting of DMEM (Invitrogen) containing 10 μg/ml transferrin (Sigma), 10 μg/ml insulin (Sigma), 100 μM putrescine (Sigma), 200 nM progesterone (Sigma), 520 nM thyroxine (Sigma), 500 μM Triiodothyronine (Sigma), 220 nM sodium selenite (Sigma), 25 μg/ml gentamycin (Sigma) and 1% HS (Invitrogen). To assess the purity of the cultures with respect to the oligodendrocyte lineage, the percentage of cells that are stained with the anti-04 antibody is quantified after 7 days of culture in SATO medium. Typically, 80-95% of the cells are stained with the anti-04 antibody demonstrating that the majority of the cells in the culture are of the oligodendrocyte lineage. To assess oligodendrocyte maturation based on oligodendrocyte morphology, freshly isolated OPC cultures are incubated in DMEM/T3/CNTF medium for 3 days in the absence or presence of 100 nM 4784, 4785 or control IgG4 3207 followed by staining with the anti-04 antibody to label both immature and mature oligodendrocytes and DAPI to label cell nuclei. O4-positive cells with clearly defined short processes are considered to represent immature oligodendrocytes whereas O4-positive cells bearing extended and highly arborised processes with myelin sheet-like structures are considered to represent mature oligodendrocytes. The proportion of O4-positive cells with a mature morphology is quantified for around 300-1300 cells in triplicate per treatment and significance determined using one-way ANOVA with a Holm-Sidak comparison to the proportion of mature oligodendrocytes in the presence of the control IgG4 3207. To assess the effect of the antibody treatment on the proportion of total (immature and mature) oligodendrocytes in the culture, the proportion of DAPI nuclei associated with O4-staining is quantified.

In three independent experiments, treatment with the anti-LINGO-1 antibodies 4784 and 4785 significantly increases the proportion of oligodendrocytes with a mature morphology as represented by cells bearing highly arborised processes that extend over a wide area and myelin sheet-like structures (FIG. 5). Treatment with the control IgG4 antibody 3207 has no effect on the proportion of mature oligodendrocytes in the culture. The proportion of DAPI-stained nuclei associated with O4-staining is similar for all treatments, demonstrating that anti-LINGO-1 antibodies have no effect on the proportion of cells corresponding to both immature and mature oligodendrocytes.

As anti-LINGO-1 antibody treatment has no effect on the proportion of total oligodendrocytes, the increase in the proportion of mature oligodendrocytes most likely arises due to an increase in the rate of differentiation of immature oligodendrocytes to mature oligodendrocytes rather than an increase in the rate of differentiation of OPCs to immature oligodendrocytes.

EXAMPLE 6

Anti-LINGO-1 Antibody-mediated Downrequlation of Cell Surface LINGO-1

The binding of multi-valent antibodies to cell surface targets can lead to the internalisation of the antibody:target complex and subsequent degradation of the target within the endocytic pathway (Weinmann et al. (2006) Mol Cell Neurosci 32, 161-173).

To determine the effect of anti-LINGO-1 antibodies on the amount of cell surface LINGO -1, untransfected CHO-K1 or CHO-K1-hLINGO-1 cells (see Example 1) are incubated at 37° C. for 24 hrs with 100 nM 4784, 4785 or 3207 and cell surface LINGO-1 is subsequently detected with an anti-V5 antibody followed by an anti-mouse IgG (Fc specific)-POD conjugate developed with a 1-Step™ Turbo TMB-ELISA kit (Pierce) (FIG. 6A).

The amount of cell surface LINGO-1 in CHO-K1-hLINGO-1 cells is significantly reduced following a 24 hr incubation with anti-LINGO-1 antibodies 4784 and 4785, whereas incubation with the control IgG4 3207 has no effect. In addition, incubation with 4785 reduces cell surface LINGO-1 to a greater extent than 4784.

To assess the effect of anti-LINGO-1 antibodies on the degradation of cell surface LINGO-1, cell surface proteins on untransfected CHO-K1 or CHO-K1-hLINGO-1 cells are biotinylated at 4° C. as described (Walmsley et al. (2004) J Cell Sci 117, 4591-4602) and the cells incubated at 37° C. for various times over a 180 min period with or without 100 nM 4784, 4785 or 3207 (FIG. 6B). At the end of the incubation period, LINGO-1 is immunoprecipitated from the cell lysate using anti-V5 antibody coupled to agarose beads and biotinylated LINGO-1 detected in the precipitate by Western blot analysis using an anti-biotin antibody (Sigma). The intensity of the band corresponding to biotinylated (and hence cell surface) LINGO-1 diminishes more rapidly in CHO-K1-hLINGO-1 cells incubated with the anti-LINGO-1 antibodies 4784 and 4785 than in cells incubated without antibody or with the control IgG4 3207. In addition, incubation with 4785 increases the rate of degradation of cell surface LINGO-1 to a greater extent than 4784.

These results cumulatively show that anti-LINGO-1 antibodies 4784 and 4785 significantly downregulate LINGO-1 at the cell surface most likely by augmenting the internalisation and degradation of the protein. This property is expected to contribute to the efficacy of these antibodies in blocking LINGO-1 function.

EXAMPLE 7

Enzyme Linked Immunosorbent Assay (ELISA) and FACS Techniques

Human recombinant LINGO-1-Fc fusion protein is immobilized onto Maxisorp plates 96 or 384 well for 1 h at RT indirectly by capturing of the Fc part via a directly immobilized goat anti-human IgG Fc antibody (100 μl or 20 μl coated at 10 μg/ml in PBS).

After coating of 20 μl of the antigen at 5 μg/ml in PBS, the wells are blocked with PBS/0.05% Tween (PBS-T)/5% milk powder for 1 h at RT. After washing the wells with PBS-T BEL -extracts, purified Fabs or control IgGs are diluted in PBS, added to the wells and incubated for 1 h at RT. To detect the primary antibodies, the following secondary antibodies are applied: alkaline phospatase (AP)-conjugated AffiniPure goat F(ab')$_2$ fragment anti-human IgG or anti-mouse IgG (Jackson ImmunoResearch). For the detection of AP-conjugates fluorogenic substrates like AttoPhos (Roche) are used according to the manufacturers' instructions. Between all incubation steps, the wells of the microtiter plate are washed with PBS-T five times and five times after the final incubation with secondary antibody. Fluorescence is measured in a TECAN Spectrafluor plate reader.

FACS Analysis of Antibody Binding to LINGO-1 Expressed on the Cell Surface of Transfected CHO-K1 Cells All stainings are performed in round bottom 96-well microtiter plates (NUNC™, Wiesbaden, Germany) with $2\times10^5$ cells per well. Cells of the respective cell line are resuspended in PBS/3% FCS/0.02% $NaN_3$ (FACS buffer) and mixed with a) antibody from periplasmic extracts or BEL lysates or b) purified Fab fragments or c) purified IgG diluted in FACS buffer and incubated at 4° C. for 30-60 min. Cells are then washed once with 150 μl FACS buffer/well and taken up in 100 μl phycoerythrin-labeled secondary antibody (R-PE conjugated goat anti-human IgG (H+L) (Jackson ImmunoResearch) which has been diluted 1:200 in FACS buffer. After incubation for 30-60 min at 4° C. cells are washed once with FACS buffer, resuspended in 100 μl FACS buffer and binding of LINGO-1 specific antibodies is measured via FL2 fluorescence intensity of cells in FACSCalibur™ or FACSArray™ (Becton Dickinson). For identification of LINGO-1 specific antibodies, stainings are done in parallel using CHO-K1-cmLINGO-1 or CHO-K1-rLINGO-1. Untransfected CHO-K1 cells serve as an additional control. Cynomolgus monkey and rat LINGO-1 expressing cells are chosen for screening as these species orthologues differ only in a few amino acids from the human LINGO-1 protein. Only those clones are judged as being LINGO-1 specific which are negative on untransfected CHO-K1 cells and ≧5× above background on LINGO-1 expressing cell lines. Cross-reactivity to human LINGO-1 and other orthologues (cynomolgus LINGO-1, rat LINGO-1) and to the human LINGO-2 paralogue is tested sequentially.

After sequence analysis thirty one (31) unique clones are identified that show strong binding to cell surface expressed human LINGO-1 in FACS analysis. Twelve (12) binders show strong binding to captured human LINGO-1-Fc in ELISA (signal:noise ratio greater than 10:1) and seven (7) show intermediate binding in ELISA (signal:noise ratio greater than 5:1). Four (4) of the binders showed strong binding to captured human NgR-Fc fusion protein (R&D Systems) in ELISA and are discontinued. Another three (3) of the binders do not cross-react to all of the three species of LINGO-1 and are discontinued. The remaining 24 clones that are cross-reactive to human/cynomolgus monkey/rat LINGO-1 but not to human NgR-Fc are expressed, purified and tested for their ability to significantly inhibit the binding of LINGO-1 to NgR (see FIG. 1) and disinhibit the neurite outgrowth inhibitory activity of spinal cord myelin in vitro (see FIGS. 2-4) leading to the selection of Fabs 4784 and 4785 for further analysis. In an ELISA, 4784 and 4785 bind to captured human LINGO-1-Fc but no binding is observed to human LINGO-1-ΔLRR-Fc or human NgR-Fc compared to an unrelated Fc control (see Table 1 and FIG. 7). This indicates that 4784 and 4785 have epitopes that are within the LRR region (residues 66-353) of LINGO-1.

TABLE 1

Characterization of anti-LINGO-1 Fabs by ELISA

| Human LINGO-1 | Human LINGO-1 Fc | Human LINGO-1ΔLRR-Fc | Human NgR-Fc | Unrelated Fc |
|---|---|---|---|---|
| 4784 | 98 | 49 | 68 | 52 |
| 4785 | 113 | 8 | 7 | 6 |

Values for ELISA analyses are given as mean values of relative fluorescence units.

Affinity Determination of Selected Anti-LINGO-1 Fabs Using FACS Saturation Analysis Cell based affinity of anti-LINGO-1 specific antibodies is determined by FACS saturation binding experiments. As the concentration of the antigen present in the sample to stain influences the apparent $K_D$ values, only $1.25\times10^4$ cells/well in contrast to $2\times10^5$ cells/well are used in order to reduce the antigen concentration in FACS saturation experiments. Otherwise the staining procedure is done identical to the FACS staining procedure described above.

In detail, CHO-K1-hLINGO-1, CHO-K1-cmLINGO-1 or CHO-K1-rLINGO-1 are detached from culture flasks by versene, washed with FACS buffer and resuspended in FACS buffer. Purified anti-LINGO-1 Fabs are serially diluted in FACS buffer and spread into round bottom 96-well microtiter plates (NUNC™, Wiesbaden, Germany). For each concentration, duplicate wells are incubated with $1.25\times10^4$ cells for 30-60 min on ice in a total volume of 100 μl. After a washing step by applying 150 μl FACS buffer and centrifugation for 5 min at 400×g, the cell pellets are resuspended in 100 μl phycoerythrin-labeled secondary antibody (R-PE conjugated goat anti-human IgG (H+L) (Jackson ImmunoResearch) which has been diluted 1:200 in FACS buffer. After incubation for 30-60 min at 4° C. cells are washed once with FACS buffer, resuspended in 100 μl FACS buffer and binding of LINGO-1 specific antibodies is measured via FL2 fluorescence intensity of cells in FACSArray™ (Becton Dickinson). Apparent $K_D$ values/EC50 values are determined from the saturation binding curves using GraphPad Prism v3.03 software or GraphPad Prism v4.03 applying a non-linear regression curve fit.

Using this assay the following apparent $K_D$ values can be determined (Table 2). In Fab format the clone 4784 has rather weak affinities to human LINGO-1, cynomolgus monkey LINGO-1 and rat LINGO-1 (14.07 nM, 27.11, and 24.03 nM respectively). However, clone 4784 does not bind to human LINGO-2 in the Fab format. In Fab format the clone 4785 shows subnanomolar binding affinities (i.e. apparent $K_D$ values being less than $1\times10^{-9}$ M) to human LINGO-1, cynomolgus monkey LINGO-1 and rat LINGO-1. Clone 4785 shows cross-reactivity to human LINGO-2 in Fab format with low nanomolar to subnanomolar affinity. The consequence of cross-reactivity to LINGO-2 cannot be assessed at the time of writing as LINGO-2 function and distribution are as yet unknown. However, beneficial effects cannot be excluded.

TABLE 2

Apparent $K_D$ values of anti-LINGO-1 Fabs to LINGO-1 or LINGO-2 expressed by CHO-K1 cells

| | Human LINGO-1 | Human LINGO-2 | Cynomolgus LINGO-1 | Rat LINGO-1 |
|---|---|---|---|---|
| 4784 | 14.07 | nb | 27.11 | 24.03 |
| 4785 | 0.35 | 1.21 | 0.26 | 0.260 |

Values given are mean values of apparent $K_D$s in nM. nb, not binding.

EXAMPLE 8

Cloning, Expression and Purification of HuCAL®IgG4

Conversion into the IqG Format

In order to express full length immunoglobulin (Ig), variable domain fragments of heavy (VH) and light chains (VL) are subcloned from the pMORPH®X9_MH (SEQ ID NO: 39) Fab expression vectors either into the pMORPH®_h_Ig (SEQ ID NOS: 40-42) or the pMORPH®2_h_Ig (SEQ ID NOS: 43-45) vector series for human IgG4.

Restriction enzymes EcoRI, MfeI, and Blpl are used for subcloning of the VH domain fragment into pMORPH®_h_IgG4 (SEQ ID NO: 40): the vector backbone is generated by EcoRI/BlpI digestion and extraction of the 6400 by fragment whereas the VH fragment (350 bp) is produced by digestion with MfeI and BlpI and subsequent purification. Vector and insert are ligated via compatible overhangs generated by the EcoRI and MfeI digests, respectively, and via the BlpI site. Thereby, both the EcoRI and the MfeI restriction site are destroyed.

Restriction enzymes MfeI and BlpI are used for subcloning of the VH domain fragment into pMORPH®2_h_IgG4 (SEQ ID NO: 43). In this new generation of IgG vectors, upon other modifications, the EcoRI site (which allowed only sub-cloning via compatible overhangs) is replaced by the MfeI site thus allowing MfeI/BlpI digestion of both, vector and insert.

Subcloning of the VL domain fragment into pMORPH®_h_Igk (SEQ ID NO: 42) and pMORPH®2_h_Igk (SEQ ID NO: 45) is performed via the EcoRV and BsiWI sites, whereas subcloning into pMORPH®_h_IgA (SEQ ID NO: 41) and pMORPH®2_h_IgA2 (SEQ ID NO: 43) is done using EcoRV and HpaI.

Transient Expression and Purification of Human IqG

HEK293 cells are transfected with an equimolar amount of IgG heavy and light chain expression vectors. On days 4 or 5 post-transfection the cell culture supernatant is harvested. After adjusting the pH of the supernatant to 8.0 and sterile filtration, the solution is subjected to standard protein A column chromatography (Poros 20A, PE Biosystems).

EXAMPLE 9

Affinity Determination of Selected Anti-LINGO-1 IgG4s Using FACS Saturation Analysis Cell based affinity of anti-LINGO-1 specific antibodies is determined by FACS saturation binding experiments. The determination of the apparent $K_D$ values is carried out identical to the procedure described above using anti-LINGO-1 Fab antibodies.

In detail, CHO-K1-hLINGO-1, CHO-K1-cmLINGO-1 or CHO-K1-rLINGO-1 are detached from culture flasks by versene, washed with FACS buffer and resuspended in FACS buffer. Purified anti-LINGO-1 IgG4s are serially diluted in FACS buffer and spread into round bottom 96-well microtiter plates (NUNC™, Wiesbaden, Germany). For each concentration, duplicate wells are incubated with $1.25\times10^4$ cells for 30-60 min on ice in a total volume of 100 μl. After a washing step by applying 150 μl FACS buffer and centrifugation for 5 min at 400×g, the cell pellets are resuspended in 100 μl phycoerythrin-labeled secondary antibody (R-PE conjugated goat anti-human IgG (H+L) (Jackson ImmunoResearch) which has been diluted 1:200 in FACS buffer. After incubation for 30-60 min at 4° C. cells are washed once with FACS buffer, resuspended in 100 μl FACS buffer and binding of LINGO-1 specific antibodies is measured via FL2 fluorescence intensity of cells in FACSArray™ (Becton Dickinson). Apparent $K_D$ values/EC50 values are determined from the saturation binding curves using GraphPad Prism v3.03 software or GraphPad Prism v4.03 applying a non-linear regression curve fit. Using this assay the following apparent $K_D$ values can be determined (Table 3).

The affinity of 4784 and 4785 IgG4 antibodies produced by using the pMORPH®2_h_Ig vector series are shown in Table 3. 4784 and 4785 in the IgG4 format have apparent $K_D$ values clearly below 1 nM to human, cynomolgus and rat LINGO-1. 4784 has a far lower cross-reactivity to human LINGO-2 than 4785.

TABLE 3

Apparent $K_D$ values of anti-LINGO-1 IgG4s to LINGO-1 or LINGO-2 expressed by CHO-K1 cells

| | Human LINGO-1 | Human LINGO-2 | Cynomolgus LINGO-1 | Rat LINGO-1 |
|---|---|---|---|---|
| 4784 | 0.29 | 25.94 | 0.62 | 0.98 |
| 4785 | 0.07 | 0.95 | 0.18 | 0.07 |

Values given are mean values of apparent $K_D$s in nM.

EXAMPLE 10

Influence of Human Cerebro-spinal Fluid on Binding of Selected Anti-LINGO-1 IgG4s to Human LINGO-1 Using FACS Analysis Influence of human cerebro-spinal fluid on binding of anti-LINGO-1 IgG4s to human LINGO-1 is tested by FACS saturation binding experiments. Serial dilutions of the 4784 and 4785 are prepared. Binding to CHO-K1-hLINGO-1 is tested in the presence of 50% human cerebro-spinal fluid. The cells are stained in the presence of human CSF with these IgG4 antibodies according to the FACS stainings described above.

In detail, CHO-K1-hLINGO-1 are detached from culture flasks by versene, washed with FACS buffer and resuspended in FACS buffer. Purified anti-LINGO-1 IgG4s are serially diluted in FACS buffer plus 50% human serum and incubated for 60 min at 4° C. As controls, serial dilutions of the candidate binders in IgG4 format are incubated in FACS buffer with 2.6% BSA resembling protein content of human cerebro-spinal fluid for 60 min at 4° C. After incubation the serial dilutions are spread into round bottom 96-well microtiter plates (NUNC™, Wiesbaden, Germany). For each concentration, duplicate wells are incubated with $1.25\times10^4$ cells for 30-60 min on ice in a total volume of 100 µl. After three washing steps by applying 150 µl FACS buffer and centrifugation for 5 min at 400×g, the cell pellets are resuspended in 100 µl phycoerythrin-labeled secondary antibody (R-PE conjugated goat anti-human IgG (H+L) (Jackson ImmunoResearch) which has been diluted 1:200 in FACS buffer. After incubation for 30-60 min at 4° C. cells are washed once with FACS buffer, resuspended in 100 µl FACS buffer and binding of LINGO-1 specific antibodies is measured via FL2 fluorescence intensity of cells in FACSArray™ (Becton Dickinson). Apparent $K_D$ values/EC50 values are determined from the saturation binding curves using GraphPad Prism v3.03 software or GraphPad Prism v4.03 applying a non-linear regression curve fit.

Using this assay the influence of 50% human cerebrospinal fluid could be compared to the controls (Table 4). Incubation in 50% human cerebro-spinal fluid leads to a decrease in binding affinity with all binders being affected differently. The strongest impact on binding affinity by the presence of human cerebro-spinal fluid is seen for 4784 which shows a reduction in affinity by 73% from 0.43 nM to 1.57 nM.

TABLE 4

Influence of Human Cerebro-spinal Fluid on Apparent $K_D$ values of anti-LINGO-1 IgG4s to LINGO-1 expressed by CHO-K1 cells

| | App. $K_D$ w/o 50% CSF | App. $K_D$ w/CSF | App. $K_D$ ratio w/o CSF:w/CSF |
|---|---|---|---|
| 4784 | 0.43 | 1.57 | 0.27 |
| 4785 | 0.19 | 0.25 | 0.76 |

Values given are mean values of apparent $K_D$s in nM.

EXAMPLE 11

Influence of Human Serum on Binding of Selected Anti-LINGO-1 IgG4s to Human LINGO-1 Using FACS Analysis Influence of human serum on binding of anti-LINGO-1 IgG4s to human LINGO-1 is tested by FACS saturation binding experiments. Serial dilutions of 4784 and 4785 are prepared in the presence of 50% v/v human serum. After incubation for 60 min cells are stained with these preincubated IgG4 antibodies according to the FACS stainings described above.

In detail, CHO-K1-hLINGO-1 are detached from culture flasks by versene, washed with FACS buffer and resuspended in FACS buffer. Purified anti-LINGO-1 IgG4s are serially diluted in FACS buffer plus 50% human serum and incubated for 60 min at 4° C. As controls, serial dilutions of the candidate binders in IgG4 format are incubated in FACS buffer plus 2.6% BSA resembling protein content of human serum or are incubated in FACS buffer alone for 60 min at 4° C. After incubation the serial dilutions are spread into round bottom 96-well microtiter plates (NUNC™, Wiesbaden, Germany). For each concentration, duplicate wells are incubated with $1.25\times10^4$ cells for 30-60 min on ice in a total volume of 100 µl. After three washing steps by applying 150 µl FACS buffer and centrifugation for 5 min at 400×g, the cell pellets are resuspended in 100 µl phycoerythrin-labeled secondary antibody (R-PE conjugated goat anti-human IgG (H+L) (Jackson ImmunoResearch) which has been diluted 1:200 in FACS buffer. After incubation for 30-60 min at 4° C. cells are washed once with FACS buffer, resuspended in 100 µl FACS buffer and binding of LINGO-1 specific antibodies is measured via FL2 fluorescence intensity of cells in FACSArray™ (Becton Dickinson). Apparent $K_D$ values/EC50 values are determined from the saturation binding curves using GraphPad Prism v3.03 software or GraphPad Prism v4.03 applying a non-linear regression curve fit.

Using this assay the influence of preincubation in 50% human serum can be compared to the controls (Table 5). Incubation for 1 hr in the presence of human serum has no effect on the $K_D$ values of 4784 and 4785. These antibodies are therefore stable in human serum over this time period and, furthermore, as their $K_D$ s are unchanged, they do not appear to cross-react with serum components.

TABLE 5

Influence of Human Serum on Apparent $K_D$ values of anti-LINGO-1 IgG4s to LINGO-1 expressed by CHO-K1 cells

| | FACS Buffer (FB) | FB + 2.6% BSA | FB + 50% HS |
|---|---|---|---|
| 4784 | 0.28 | 0.19 | 0.27 |
| 4785 | 0.08 | 0.05 | 0.06 |

Values given are mean values of apparent $K_D$s in nM.

List of Sequences with short description

Rat mature LINGO-1 ectodomain (residues 34-550)

SEQ ID NO: 1

```
TGCPPRCECSAQDRAVLCHRKRFVAVPEGIPTETRLLDLGKNRIKTLNQDEFASFPHLEE

LELNENIVSAVEPGAFNNLFNLRTLGLRSNRLKLIPLGVFTGLSNLTKLDISENKIVILL

DYMFQDLYNLKSLEVGDNDLVYISHRAFSGLNSLEQLTLEKCNLTSIPTEALSHLHGLIV

LRLRHLNINAIRDYSFKRLYRLKVLEISHWPYLDTMTPNCLYGLNLTSLSITHCNLTAVP
```

-continued

| List of Sequences with short description |
|---|

YLAVRHLVYLRFLNLSYNPIGTIEGSMLHELLRLQEIQLVGGQLAVVEPYAFRGLNYLRV

LNVSGNQLTTLEESAFHSVGNLETLILDSNPLACDCRLLWVFRRRWRLNFNRQQPTCATP

EFVQGKEFKDFPDVLLPNYFTCRRAHIRDRKAQQVFVDEGHTVQFVCRADGDPPPAILWL

SPRKHLVSAKSNGRLTVFPDGTLEVRYAQVQDNGTYLCIAANAGGNDSMPAHLHVRSYSP

DWPHQPNKTFAFISNQPGEGEANSTRATVPFPFDIKT

Cynomologus mature LINGO-1 ectodomain (residues 34-550)

SEQ ID NO: 2

TGCPPRCECSAQDRAVLCHRKRFVAVPEGIPTETRLLDLGKNRIKTLNQDEFASFPHLEE

LELNENIVSAVEPGAFNNLFNLRTLGLRSNRLKLIPLGVFTGLSNLTKLDISENKIVILL

DYMFQDLYNLKSLEVGDNDLVYISHRAFSGLNSLEQLTLEKCNLTSIPTEALSHLHGLIV

LRLRHLNINAIRDYSFKRLYRLKVLEISHWPYLDTMTPNCLYGLNLTSLSITHCNLTAVP

YLAVRHLVYLRFLNLSYNPISTIEGSMLHELLRLQEIQLVGGQLAMVEPYAFRGLNYLRV

LNVSGNQLTTLEESVFHSVGNLETLILDSNPLACDCRLLWVFRRRWRLNFNRQQPTCATP

EFVQGKEFKDFPDVLLPNYFTCRRARIRDRKAQQVFVDEGHTVQFVCRADGDPPPAILWL

SPRKHLVSAKSNGRLTVFPDGTLEVRYAQVQDNGTYLCIAANAGGNDSMPAHLHVRSYSP

DWPHQPNKTFAFIPNQPGEGEANSTRATVPFPFDIKT

Human mature LINGO-1 ectodomain (residues 34-550)

SEQ ID NO: 3

TGCPPRCECSAQDRAVLCHRKRFVAVPEGIPTETRLLDLGKNRIKTLNQDEFASFPHLEE

LELNENIVSAVEPGAFNNLFNLRTLGLRSNRLKLIPLGVFTGLSNLTKLDISENKIVILL

DYMFQDLYNLKSLEVGDNDLVYISHRAFSGLNSLEQLTLEKCNLTSIPTEALSHLHGLIV

LRLRHLNINAIRDYSFKRLYRLKVLEISHWPYLDTMTPNCLYGLNLTSLSITHCNLTAVP

YLAVRHLVYLRFLNLSYNPISTIEGSMLHELLRLQEIQLVGGQLAVVEPYAFRGLNYLRV

LNVSGNQLTTLEESVFHSVGNLETLILDSNPLACDCRLLWVFRRRWRLNFNRQQPTCATP

EFVQGKEFKDFPDVLLPNYFTCRRARIRDRKAQQVFVDEGHTVQFVCRADGDPPPAILWL

SPRKHLVSAKSNGRLTVFPDGTLEVRYAQVQDNGTYLCIAANAGGNDSMPAHLHVRSYSP

DWPHQPNKTFAFISNQPGEGEANSTRATVPFPFDIKT

4784 $V_L$

SEQ ID NO: 4

DIELTQPPSVSVAPGQTARISCSGDNIGNYYVYWYQQKPGQAPVLVIYEDTNRPSGIPERFSGSNSGNTATLTIS

GTQAEDEADYYCQSYDNLHEQVFGGGTKLTVLG

4784 $V_H$

SEQ ID NO: 5

QVQLKESGPALVKPTQTLTLTCTFSGFSLSSSGVGVGWIRQPPGKALEWLAHIGSDDDKYYSTSLKTRLTISKDT

SKNQVVLTMTNMDPVDTATYYCARNQQYGDGYPGYFDYWGQGTLVTVSS

4785 $V_L$

SEQ ID NO: 6

DIVLTQPPSVSGAPGQRVTISCSGSSSNIGNNYVSWYQQLPGTAPKLLISRNSKRPSGVPDRFSGSKSGTSASLA

ITGLQSEDEADYYCSTYDTFSIVFGGGTKLTVLG

4785 $V_H$

SEQ ID NO: 7

QVQLQQSGPGLVKPSQTLSLTCAISGDSVSDNSAAWSWIRQSPGRGLEWLGLIYLRSKWDNDYAVSVKSRITINP

DTSKNQFSLQLNSVTPEDTAVYYCARTGRADEFDVWGQGTLVTVSS

DNA-4784 $V_H$

SEQ ID NO: 8

CAGGTGCAATTGAAAGAAAGCGGCCCGGCCCTGGTGAAACCGACCCAAACCCTGACCCTGACCTGTACCTTTTCC

-continued

List of Sequences with short description

GGATTTAGCCTGTCTTCTTCTGGTGTTGGTGTGGGTTGGATTCGCCAGCCGCCTGGGAAAGCCCTCGAGTGGCTG

GCTCATATCGGTTCTGATGATGATAAGTATTATAGCACCAGCCTGAAAACGCGTCTGACCATTAGCAAAGATACT

TCGAAAAATCAGGTGGTGCTGACTATGACCAACATGGACCCGGTGGATACGGCCACCTATTATTGCGCGCGTAAT

CAGCAGTATGGTGATGGTTATCCTGGTTATTTTGATTATTGGGGCCAAGGGACCCTGGTGACGGTTAGCTCA

DNA-4785 $V_H$

SEQ ID NO: 9

CAGGTGCAATTGCAACAGTCTGGTCCGGGCCTGGTGAAACCGAGCCAAACCCTGAGCCTGACCTGTGCGATTTCC

GGAGATAGCGTGAGCGATAATTCTGCTGCTTGGTCTTGGATTCGCCAGTCTCCTGGGCGTGGCCTCGAGTGGCTG

GGCCTTATCTATCTTCGTAGCAAGTGGGATAACGATTATGCGGTGAGCGTGAAAAGCCGGATTACCATCAACCCG

GATACTTCGAAAAACCAGTTTAGCCTGCAACTGAACAGCGTGACCCCGGAAGATACGGCCGTGTATTATTGCGCG

CGTACTGGTCGTGCTGATGAGTTTGATGTTTGGGGCCAAGGCACCCTGGTGACGGTTAGCTCA

DNA-4784 $V_L$

SEQ ID NO: 10

GATATCGAACTGACCCAGCCGCCTTCAGTGAGCGTTGCACCAGGTCAGACCGCGCGTATCTCGTGTAGCGGCGAT

AATATTGGTAATTATTATGTTTATTGGTACCAGCAGAAACCCGGGCAGGCGCCAGTTCTTGTGATTTATGAGGAT

ACTAATCGTCCCTCAGGCATCCCGGAACGCTTTAGCGGATCCAACAGCGGCAACACCGCGACCCTGACCATTAGC

GGCACTCAGGCGGAAGACGAAGCGGATTATTATTGCCAGTCTTATGATAATCTTCATGAGCAGGTGTTTGGCGGC

GGCACGAAGTTAACCGTTCTTGGCCAG

DNA-4785 $V_L$

SEQ ID NO: 11

GATATCGTGCTGACCCAGCCGCCTTCAGTGAGTGGCGCACCAGGTCAGCGTGTGACCATCTCGTGTAGCGGCAGC

AGCAGCAACATTGGTAATAATTATGTGTCTTGGTACCAGCAGTTGCCCGGGACGGCGCCGAAACTTCTGATTTCT

CGTAATTCTAAGCGTCCCTCAGGCGTGCCGGATCGTTTTAGCGGATCCAAAAGCGGCACCAGCGCGAGCCTTGCG

ATTACGGGCCTGCAAAGCGAAGACGAAGCGGATTATTATTGCTCTACTTATGATACTTTTTCTATTGTGTTTGGC

GGCGGCACGAAGTTAACCGTTCTTGGCCAG

Antibody 4784 CDR-H1

SEQ ID NO: 12

SSGVGVG

Antibody 4784 CDR-H2

SEQ ID NO: 13

HIGSDDDKYYSTSLKT

Antibody 4784 CDR-H3

SEQ ID NO: 14

NQQYGDGYPGYFDY

Antibody 4784 CDR-L1

SEQ ID NO: 15

SGDNIGNYYVY

Antibody 4784 CDR-L2

SEQ ID NO: 16

EDTNRPS

Antibody 4784 CDR-L3

SEQ ID NO: 17

QSYDNLHEQV

Antibody 4785 CDR'-H1

SEQ ID NO: 18

DNSAAWS

Antibody 4785 CDR'-H2

SEQ ID NO: 19

LIYLRSKWDNDYAVSVKS

Antibody 4785 CDR'-H3

-continued

| List of Sequences with short description |
|---|

SEQ ID NO: 20

TGRADEFDV

Antibody 4785 CDR'-L1

SEQ ID NO: 21

SGSSSNIGNNYVS

Antibody 4785 CDR'-L2

SEQ ID NO: 22

RNSKRPS

Antibody 4785 CDR'-L3

SEQ ID NO: 23

STYDTFSIV

Forward primer DM22

SEQ ID NO: 24

GGTTATCTCGAGACCGGCTGCCCGCCCC

Reverse primer DM23

SEQ ID NO: 25

GGCCCTTCTAGATCACTCGCCTGGCTGGTTGGAGATG

APtag-5-NHIS vector

SEQ ID NO: 26 gacggatcgggagatctcccgatcccctatggtcgactctcagtacaatctgctctgatgccgcatagttaagcc agtatctgctccctgcttgtgtgttggaggtcgctgagtagtgcgcgagcaaaatttaagctacaacaaggcaag gcttgaccgacaattgcatgaagaatctgcttagggttaggcgttttgcgctgcttcgcgatgtacgggccagat atacgcgttgacattgattattgactagttattaatagtaatcaattacggggtcattagttcatagcccatata tggagttccgcgttacataacttacggtaaatggcccgcctggctgaccgcccaacgacccccgcccattgacgt caataatgacgtatgttcccatagtaacgccaatagggactttccattgacgtcaatgggtggactatttacggt aaactgcccacttggcagtacatcaagtgtatcatatgccaagtacgccccctattgacgtcaatgacggtaaat ggcccgcctggcattatgcccagtacatgaccttatgggactttcctacttggcagtacatctacgtattagtca tcgctattaccatggtgatgcggttttggcagtacatcaatgggcgtggatagcggtttgactcacggggatttc caagtctccaccccattgacgtcaatgggagtttgttttggcaccaaaatcaacgggactttccaaaatgtcgta acaactccgccccattgacgcaaatgggcggtaggcgtgtacggtgggaggtctatataagcagagctctctggc taactagagaacccactgcttactggcttatcgaaattaatacgactcactatagggagacccaagctggctagc caccatggagacagacacactcctgctatgggtactgctgctctgggttccaggttccactggtgacgcggccca gccggcccatcatcatcatcatcatgaagcttacgtaagatcttccggaatcatcccagttgaggaggagaaccc ggacttctggaaccgcgaggcagccgaggccctgggtgccgccaagaagctgcagcctgcacagacagccgccaa gaacctcatcatcttcctgggcgatgggatgggggtgtctacggtgacagctgccaggatcctaaaagggcagaa gaaggacaaactggggcctgagatacccctggccatggaccgcttcccatatgtggctctgtccaagacatacaa tgtagacaaacatgtgccagacagtggagccacagccacggcctacctgtgcggggtcaagggcaacttccagac cattggcttgagtgcagccgcccgctttaaccagtgcaacacgacacgcggcaacgaggtcatctccgtgatgaa tcgggccaagaaagcagggaagtcagtgggagtggtaaccaccacacgagtgcagcacgcctcgccagccggcac ctacgcccacacggtgaaccgcaactggtactcggacgccgacgtgcctgcctcggcccgccaggagggggtgcca ggacatcgctacgcagctcatctccaacatggacattgacgtgatcctaggtggaggccgaaagtacatgtttcg catgggaaccccagaccctgagtacccagatgactacagccaaggtgggaccaggctggacgggaagaatctggt gcaggaatggctggcgaagcgccagggtgcccggtatgtgtggaaccgcactgagctcatgcaggcttccctgga cccgtctgtgacccatctcatgggtctctttgagcctggagacatgaaatacgagatccaccgagactccacact ggacccctccctgatggagatgacagaggctgccctgcgcctgctgagcaggaacccccgcggcttcttcctctt cgtggagggtggtcgcatcgaccatggtcatcatgaaagcagggcttaccgggcactgactgagacgatcatgtt -continued

| List of Sequences with short description |
| --- |

cgacgacgccattgagagggcgggccagctcaccagcgaggaggacacgctgagcctcgtcactgccgaccactc
ccacgtcttctccttcggaggctacccccctgcgagggagctccatcttcgggctggcccctggcaaggcccggga
caggaaggcctacacggtcctcctatacggaaacggtccaggctatgtgctcaaggacggcgcccggccggatgt
taccgagagcgagagcgggagccccgagtatcggcagcagtcagcagtgcccctggacgaagagacccacgcagg
cgaggacgtggcggtgttcgcgcgcggcccgcaggcgcacctggttcacggcgtgcaggagcagaccttcatagc
gcacgtcatggccttcgccgcctgcctggagccctacaccgcctgcgacctggcgccccccgccggcaccaccga
cgccgcgcacccgggttatctcgaggaagcgctctctctagaagggcccgaacaaaaactcatctcagaagagga
tctgaatagcgccgtcgaccatcatcatcatcatcattgagtttaaacccgctgatcagcctcgactgtgccttc
tagttgccagccatctgttgtttgcccctcccccgtgccttccttgaccctggaaggtgccactcccactgtcct
ttcctaataaaatgaggaaattgcatcgcattgtctgagtaggtgtcattctattctggggggtggggtggggca
ggacagcaagggggaggattgggaagacaatagcaggcatgctggggatgcggtgggctctatggcttctgaggc
ggaaagaaccagctggggctctagggggtatccccacgcgccctgtagcggcgcattaagcgcggcgggtgtggt
ggttacgcgcagcgtgaccgctacacttgccagcgccctagcgcccgctcctttcgctttcttcccttcctttct
cgccacgttcgccggctttccccgtcaagctctaaatcggggcatccctttagggttccgatttagtgctttacg
gcacctcgaccccaaaaaacttgattagggtgatggttcacgtagtgggccatcgccctgatagacggtttttcg
ccctttgacgttggagtccacgttctttaatagtggactcttgttccaaactggaacaacactcaaccctatctc
ggtctattcttttgatttataagggattttggggatttcggcctattggttaaaaaatgagctgatttaacaaaa
atttaacgcgaattaattctgtggaatgtgtgtcagttagggtgtggaaagtccccaggctccccagcaggcaga
agtatgcaaagcatgcatctcaattagtcagcaaccaggtgtggaaagtccccaggctccccagcaggcagaagt
atgcaaagcatgcatctcaattagtcagcaaccatagtcccgcccctaactccgcccatcccgcccctaactccg
cccagttccgcccattctccgccccatggctgactaattttttttatttatgcagaggccgaggccgcctctgcc
tctgagctattccagaagtagtgaggaggcttttttggaggcctaggcttttgcaaaaagctcccgggagcttgt
atatccattttcggatctgatcagcacgtgttgacaattaatcatcggcatagtatatcggcatagtataatacg
acaaggtgaggaactaaaccatggccaagttgaccagtgccgttccggtgctcaccgcgcgcgacgtcgccggag
cggtcgagttctggaccgaccggctcgggttctcccgggacttcgtggaggacgacttcgccggtgtggtccggg
acgacgtgaccctgttcatcagcgcggtccaggaccaggtggtgccggacaacaccctggcctgggtgtgggtgc
gcggcctggacgagctgtacgccgagtggtcggaggtcgtgtccacgaacttccgggacgcctccgggccggcca
tgaccgagatcggcgagcagccgtgggggcgggagttcgccctgcgcgacccggccggcaactgcgtgcacttcg
tggccgaggagcaggactgacacgtgctacgagatttcgattccaccgccgccttctatgaaaggttgggcttcg
gaatcgttttccgggacgccggctggatgatcctccagcgcggggatctcatgctggagttcttcgcccacccca
acttgtttattgcagcttataatggttacaaataaagcaatagcatcacaaatttcacaaataaagcattttttt
cactgcattctagttgtggtttgtccaaactcatcaatgtatcttatcatgtctgtataccgtcgacctctagct
agagcttggcgtaatcatggtcatagctgtttcctgtgtgaaattgttatccgctcacaattccacacaacatac
gagccggaagcataaagtgtaaagcctggggtgcctaatgagtgagctaactcacattaattgcgttgcgctcac
tgcccgctttccagtcgggaaacctgtcgtgccagctgcattaatgaatcggccaacgcgcggggagaggcggtt
tgcgtattgggcgctcttccgcttcctcgctcactgactcgctgcgctcggtcgttcggctgcggcgagcggtat
cagctcactcaaaggcggtaatacggttatccacagaatcaggggataacgcaggaaagaacatgtgagcaaaag
gccagcaaaaggccaggaaccgtaaaaaggccgcgttgctggcgtttttccataggctccgcccccctgacgagc
atcacaaaaatcgacgctcaagtcagaggtggcgaaacccgacaggactataaagataccaggcgtttccccctg -continued List of Sequences with short description gaagctccctcgtgcgctctcctgttccgaccctgccgcttaccggatacctgtccgcctttctcccttcgggaa gcgtggcgctttctcaatgctcacgctgtaggtatctcagttcggtgtaggtcgttcgctccaagctgggctgtg tgcacgaaccccccgttcagcccgaccgctgcgccttatccggtaactatcgtcttgagtccaacccggtaagac acgacttatcgccactggcagcagccactggtaacaggattagcagagcgaggtatgtaggcggtgctacagagt tcttgaagtggtggcctaactacggctacactagaaggacagtatttggtatctgcgctctgctgaagccagtta ccttcggaaaaagagttggtagctcttgatccggcaaacaaaccaccgctggtagcggtggtttttttgtttgca agcagcagattacgcgcagaaaaaaaggatctcaagaagatcctttgatcttttctacggggtctgacgctcagt ggaacgaaaactcacgttaagggattttggtcatgagattatcaaaaaggatcttcacctagatccttttaaatt aaaaatgaagttttaaatcaatctaaagtatatatgagtaaacttggtctgacagttaccaatgcttaatcagtg aggcacctatctcagcgatctgtctatttcgttcatccatagttgcctgactccccgtcgtgtagataactacga tacgggagggcttaccatctggccccagtgctgcaatgataccgcgagacccacgctcaccggctccagatttat cagcaataaaccagccagccggaagggccgagcgcagaagtggtcctgcaactttatccgcctccatccagtcta ttaattgttgccgggaagctagagtaagtagttcgccagttaatagtttgcgcaacgttgttgccattgctacag gcatcgtggtgtcacgctcgtcgtttggtatggcttcattcagctccggttcccaacgatcaaggcgagttacat gatcccccatgttgtgcaaaaaagcggttagctccttcggtcctccgatcgttgtcagaagtaagttggccgcag tgttatcactcatggttatggcagcactgcataattctcttactgtcatgccatccgtaagatgcttttctgtga ctggtgagtactcaaccaagtcattctgagaatagtgtatgcggcgaccgagttgctcttgcccggcgtcaatac gggataataccgcgccacatagcagaactttaaaagtgctcatcattggaaaacgttcttcggggcgaaaactct caaggatcttaccgctgttgagatccagttcgatgtaacccactcgtgcacccaactgatcttcagcatcttta ctttcaccagcgtttctgggtgagcaaaaacaggaaggcaaaatgccgcaaaaaagggaataagggcgacacgga aatgttgaatactcatactcttcctttttcaatattattgaagcatttatcagggttattgtctcatgagcggat acatatttgaatgtatttagaaaaataaacaaataggggttccgcgcacatttccccgaaaagtgccacctgacg tc human LINGO-1 mature DNA sequence

SEQ ID NO: 27 acgggctgcccgccccgctgcgagtgctccgcccaggaccgcgctgtgctgtgccaccgcaagcgctttgtggca gtccccgagggcatccccaccgagacgcgcctgctggacctaggcaagaaccgcatcaaaacgctcaaccaggac gagttcgccagcttcccgcacctggaggagctggagctcaacgagaacatcgtgagcgccgtggagcccggcgcc ttcaacaacctcttcaacctccggacgctgggtctccgcagcaaccgcctgaagctcatcccgctaggcgtcttc actggcctcagcaacctgaccaagctggacatcagcgagaacaagattgttatcctgctggactacatgtttcag gacctgtacaacctcaagtcactggaggttggcgacaatgacctcgtctacatctctcaccgcgccttcagcggc ctcaacagcctggagcagctgacgctggagaaatgcaacctgacctccatccccaccgaggcgctgtcccacctg cacggcctcatcgtcctgaggctccggcacctcaacatcaatgccatccgggactactccttcaagaggctctac cgactcaaggtcttggagatctcccactggccctacttggacaccatgacacccaactgcctctacggcctcaac ctgacgtccctgtccatcacacactgcaatctgaccgctgtgccctacctggccgtccgccacctagtctatctc cgcttcctcaacctctcctacaaccccatcagcaccattgagggctccatgttgcatgagctgctccggctgcag gagatccagctggtgggcgggcagctggccgtggtggagccctatgccttccgcggcctcaactacctgcgcgtg ctcaatgtctctggcaaccagctgaccacactggaggaatcagtcttccactcggtgggcaacctggagacactc atcctggactccaacccgctggcctgcgactgtcggctcctgtgggtgttccggcgccgctggcggctcaacttc aaccggcagcagcccacgtgcgccacgcccgagtttgtccagggcaaggagttcaaggacttccctgatgtgcta -continued List of Sequences with short description ctgcccaactacttcacctgccgccgcgcccgcatccgggaccgcaaggcccagcaggtgtttgtggacgagggc cacacggtgcagtttgtgtgccgggccgatggcgacccgccgcccgccatcctctggctctcaccccgaaagcac ctggtctcagccaagagcaatgggcggctcacagtcttccctgatggcacgctggaggtgcgctacgcccaggta caggacaacggcacgtacctgtgcatcgcggccaacgcgggcggcaacgactccatgcccgcccacctgcatgtg cgcagctactcgcccgactggccccatcagcccaacaagaccttcgctttcatctccaaccagccgggcgaggga gaggccaacagcacccgcgccactgtgcctttccccttcgacatcaagaccctcatcatcgccaccaccatgggc ttcatctctttcctgggcgtcgtcctcttctgcctggtgctgctgtttctctggagccggggcaagggcaacaca aagcacaacatcgagatcgagtatgtgccccgaaagtcggacgcaggcatcagctccgccgacgcgccccgcaag ttcaacatgaagatgata Cynomolgus monkey LINGO-1 mature DNA sequence

SEQ ID NO: 28 acgggctgcccgccccgctgcgagtgctccgcccaggaccgggctgtgctctgccaccgcaagcgctttgtggca gtgcctgagggcatccccacggagacgcgcctgctggacctggggaagaaccgcatcaaaacgctcaaccaggac gagttcgccagcttcccgcacctggaggagctggagctcaacgagaacatcgtgagcgccgtggagcctggcgcc ttcaacaaccttttcaacctccggacgctgggtctccgcagcaaccgcctgaagctcatcccgctgggcgtcttc actggcctcagcaacttgaccaagctggacatcagcgagaacaagatcgttatcctgctggactacatgttccag gacctgtacaacctcaagtcactggaggttggcgacaatgacctcgtctacatctcccaccgcgccttcagcggc ctcaacagcctggagcagctgacgctggagaaatgcaacctgacctccatccccaccgaggcgctgtcccacctg cacggcctcatcgtcctgaggctccggcacctcaacatcaatgccatccgggactactccttcaagaggttgtac cgactcaaggtcttggagatctcccactggccctacttggacaccatgacacccaactgcctctacggcctcaac ctgacgtccctgtccatcacgcactgcaatctgaccgctgtgccctacctggccgtccgccacctggtctatctc cgcttcctcaacctctcctacaaccccatcagcaccattgagggctccatgttgcatgagctgctccggctgcag gagatccagctggtgggcgggcagctggccatggtggagccctatgccttccgcggcctcaactacctgcgcgtg ctcaatgtctctggcaaccagctgaccacgctggaagaatcagtcttccactcggtgggcaacctggagacgctc atcctggactccaacccactggcctgcgactgtcggctcctgtgggtgttccggcgccgctggcggctcaacttc aaccggcagcagcccacgtgcgccacgcccgagttcgtccagggcaaggagttcaaggacttccctgatgtgcta ctgcccaactacttcacctgccgccgcgcccgcatccgggatcgcaaggcccagcaggtgtttgtggatgagggc cacacggtgcagtttgtgtgccgggccgatggcgacccgccgcccgccatcctctggctctcaccccgaaagcac ctggtctcagccaagagcaatgggcggctcacagtcttccctgatggcacgctggaggtgcgctacgcccaggta caggacaatggcacgtacctgtgcatcgcggccaatgcaggcggcaacgactccatgcctgcccacctgcatgtg cgcagctactcacccgactggccccatcagcccaacaagaccttcgccttcatccccaaccagccgggcgaggga gaggccaacagcacccgagccactgtgcctttccccttcgacatcaagaccctcatcatcgccaccaccatgggc ttcatctctttcctgggcgtcgtcctcttctgcctggtgctgctgtttctctggagccggggcaagggcaacacg aagcacaacatcgagatcgagtatgtcccccgaaagtcggacgcaggcatcagctccgccgacgcgccccgcaag ttcaacatgaagatgata Rat LINGO-1 mature DNA sequence

SEQ ID NO: 29 accggctgcccgccccgctgcgagtgctcagcgcaggaccgagcagtgctctgtcaccgcaagcgctttgtggcg gtgcccgagggcatccccaccgagactcgcctgctggacctgggcaaaaaccgcatcaagacactcaaccaggac gagtttgccagtttcccacacctggaggagctagaactcaatgagaacattgtgagcgctgtggagccgggcgcc ttcaacaacctcttcaacctgaggacgctggggcttcgcagcaaccgcctgaagctcatcccgctgggcgtcttc -continued

| List of Sequences with short description |
|---|

accggcctcagcaacttgaccaagctggacatcagcgagaacaagatcgtcatcctgctagactacatgttccaa
gacctatacaacctcaagtcgctggaggtcggcgacaatgacctcgtctacatctcccatcgagccttcagcggc
ctcaacagcctggaacagctgacgctggagaaatgcaatctgacctccatccccactgaggcactctcccacctg
catggcctcatcgtcctgcggctacgacacctcaacatcaatgccatacgggactactccttcaagaggctgtac
cgactcaaggtcttagagatctcccactggccctacctggacaccatgacccccaactgcctctacggcctcaac
ctgacatccctatctatcacgcactgcaacctgacagccgtgccctatctggcagtgcgccacctggtctatctc
cgtttcctcaatctttcctacaaccccatcggtacaatcgagggctccatgctgcatgagctgctgcggttgcaa
gagatccaactggtgggcgggcagctggccgtggtggagccctacgcctttcgtgggctcaattacctgcgtgtg
ctcaatgtttctggcaaccagctgaccaccctggaggagtcagccttccactcggtgggcaacctggagacgctc
attctggactccaacccactggcctgtgactgccggctgctgtgggtgttccggcgccgctggcggctcaacttc
aacaggcagcagcctacctgcgccacacctgagttcgtccagggcaaggagttcaaggacttccccgatgtgctc
ctacccaactacttcacctgccgccgggcccacatccgggaccgcaaggcacagcaggtgtttgtagatgagggc
cacacggtgcagttcgtatgccgggcagatggcgaccctccaccagctatcctttggctctcaccccgcaagcac
ttggtctcagccaagagcaatgggcggctcacagtcttccctgatggcacgctggaggtgcgctacgcccaggta
caggacaacggcacgtacctgtgcatcgcagccaatgcaggcggcaacgactccatgcccgcccacttgcatgtg
cgcagctactcgcctgactggccccatcaacccaacaagaccttcgccttcatctccaaccagccaggcgaggga
gaggccaacagcacccgcgccactgtgcctttccccttcgacatcaagacgctcatcatcgccaccaccatgggc
ttcatctccttcctgggcgtggtcctattctgcctggtgctgctgtttctatggagccggggcaaaggcaacaca
aagcacaacatcgaaattgaatatgtgccccggaaatcggacgcaggcatcagctcagctgatgcaccccgcaag
ttcaacatgaagatgata Forward primer DM14

SEQ ID NO: 30

CTACGTCTAGAACGGGCTGCCCGCCCCGCT

Reverse primer DM15

SEQ ID NO: 31

GGTTTCTCGAGTCATATCATCTTCATGTTGAACTTGCGG pSecTag2-V5 vector

SEQ ID NO: 32 gacggatcgggagatctcccgatcccctatggtcgactctcagtacaatctgctctgatgccgcatagttaagcc
agtatctgctccctgcttgtgtgttggaggtcgctgagtagtgcgcgagcaaaatttaagctacaacaaggcaag
gcttgaccgacaattgcatgaagaatctgcttagggttaggcgttttgcgctgcttcgcgatgtacgggccagat
atacgcgttgacattgattattgactagttattaatagtaatcaattacggggtcattagttcatagcccatata
tggagttccgcgttacataacttacggtaaatggcccgcctggctgaccgcccaacgacccccgcccattgacgt
caataatgacgtatgttcccatagtaacgccaatagggactttccattgacgtcaatgggtggactatttacggt
aaactgcccacttggcagtacatcaagtgtatcatatgccaagtacgccccctattgacgtcaatgacggtaaat
ggcccgcctggcattatgcccagtacatgaccttatgggactttcctacttggcagtacatctacgtattagtca
tcgctattaccatggtgatgcggttttggcagtacatcaatgggcgtggatagcggtttgactcacggggatttc
caagtctccaccccattgacgtcaatgggagtttgttttggcaccaaaatcaacgggactttccaaaatgtcgta
acaactccgccccattgacgcaaatgggcggtaggcgtgtacggtgggaggtctatataagcagagctctctggc
taactagagaacccactgcttactggcttatcgaaattaatacgactcactatagggagacccaagctggctagc
caccatggagacagacacactcctgctatgggtactgctgctctgggttccaggttccactggtgacgcggccca
gcccggtaagcctatccctaaccctctcctcggtctcgattctacgtctagatatcctcgagaaacccgctgatc -continued

| List of Sequences with short description |
|---|
| agcctcgactgtgccttctagttgccagccatctgttgtttgcccctcccccgtgccttccttgaccctggaagg<br>tgccactcccactgtcctttcctaataaaatgaggaaattgcatcgcattgtctgagtaggtgtcattctattct<br>ggggggtggggtggggcaggacagcaagggggaggattgggaagacaatagcaggcatgctggggatgcggtggg<br>ctctatggcttctgaggcggaaagaaccagctggggctctagggggtatccccacgcgccctgtagcggcgcatt<br>aagcgcggcgggtgtggtggttacgcgcagcgtgaccgctacacttgccagcgccctagcgcccgctcctttcgc<br>tttcttcccttcctttctcgccacgttcgccggctttccccgtcaagctctaaatcggggcatccctttagggtt<br>ccgatttagtgctttacggcacctcgaccccaaaaaacttgattagggtgatggttcacgtagtgggccatcgcc<br>ctgatagacggtttttcgccctttgacgttggagtccacgttctttaatagtggactcttgttccaaactggaac<br>aacactcaaccctatctcggtctattcttttgatttataagggattttggggatttcggcctattggttaaaaaa<br>tgagctgatttaacaaaaatttaacgcgaattaattctgtggaatgtgtgtcagttagggtgtggaaagtcccca<br>ggctccccagcaggcagaagtatgcaaagcatgcatctcaattagtcagcaaccaggtgtggaaagtccccaggc<br>tccccagcaggcagaagtatgcaaagcatgcatctcaattagtcagcaaccatagtcccgcccctaactccgccc<br>atcccgcccctaactccgcccagttccgcccattctccgccccatggctgactaattttttttatttatgcagag<br>gccgaggccgcctctgcctctgagctattccagaagtagtgaggaggcttttttggaggcctaggcttttgcaaa<br>aagctcccgggagcttgtatatccattttcggatctgatcagcacgtgttgacaattaatcatcggcatagtata<br>tcggcatagtataatacgacaaggtgaggaactaaaccatggccaagttgaccagtgccgttccggtgctcaccg<br>cgcgcgacgtcgccggagcggtcgagttctggaccgaccggctcgggttctcccgggacttcgtggaggacgact<br>tcgccggtgtggtccgggacgacgtgaccctgttcatcagcgcggtccaggaccaggtggtgccggacaacaccc<br>tggcctgggtgtgggtgcgcggcctggacgagctgtacgccgagtggtcggaggtcgtgtccacgaacttccggg<br>acgcctccgggccggccatgaccgagatcggcgagcagccgtgggggcgggagttcgccctgcgcgacccggccg<br>gcaactgcgtgcacttcgtggccgaggagcaggactgacacgtgctacgagatttcgattccaccgccgccttct<br>atgaaaggttgggcttcggaatcgttttccgggacgccggctggatgatcctccagcgcggggatctcatgctgg<br>agttcttcgcccaccccaacttgtttattgcagcttataatggttacaaataaagcaatagcatcacaaatttca<br>caaataaagcatttttttcactgcattctagttgtggtttgtccaaactcatcaatgtatcttatcatgtctgta<br>taccgtcgacctctagctagagcttggcgtaatcatggtcatagctgtttcctgtgtgaaattgttatccgctca<br>caattccacacaacatacgagccggaagcataaagtgtaaagcctggggtgcctaatgagtgagctaactcacat<br>taattgcgttgcgctcactgcccgctttccagtcgggaaacctgtcgtgccagctgcattaatgaatcggccaac<br>gcgcggggagaggcggtttgcgtattgggcgctcttccgcttcctcgctcactgactcgctgcgctcggtcgttc<br>ggctgcggcgagcggtatcagctcactcaaaggcggtaatacggttatccacagaatcaggggataacgcaggaa<br>agaacatgtgagcaaaaggccagcaaaaggccaggaaccgtaaaaaggccgcgttgctggcgtttttccataggc<br>tccgcccccctgacgagcatcacaaaaatcgacgctcaagtcagaggtggcgaaacccgacaggactataaagat<br>accaggcgtttccccctggaagctccctcgtgcgctctcctgttccgaccctgccgcttaccggatacctgtccg<br>cctttctcccttcgggaagcgtggcgctttctcaatgctcacgctgtaggtatctcagttcggtgtaggtcgttc<br>gctccaagctgggctgtgtgcacgaaccccccgttcagcccgaccgctgcgccttatccggtaactatcgtcttg<br>agtccaacccggtaagacacgacttatcgccactggcagcagccactggtaacaggattagcagagcgaggtatg<br>taggcggtgctacagagttcttgaagtggtggcctaactacggctacactagaaggacagtatttggtatctgcg<br>ctctgctgaagccagttaccttcggaaaaagagttggtagctcttgatccggcaaacaaaccaccgctggtagcg<br>gtggtttttttgtttgcaagcagcagattacgcgcagaaaaaaaggatctcaagaagatcctttgatcttttcta<br>cggggtctgacgctcagtggaacgaaaactcacgttaagggattttggtcatgagattatcaaaaaggatcttca |

-continued

List of Sequences with short description cctagatccttttaaattaaaaatgaagttttaaatcaatctaaagtatatatgagtaaacttggtctgacagtt
accaatgcttaatcagtgaggcacctatctcagcgatctgtctatttcgttcatccatagttgcctgactccccg
tcgtgtagataactacgatacgggagggcttaccatctggccccagtgctgcaatgataccgcgagacccacgct
caccggctccagatttatcagcaataaaccagccagccggaagggccgagcgcagaagtggtcctgcaactttat
ccgcctccatccagtctattaattgttgccgggaagctagagtaagtagttcgccagttaatagtttgcgcaacg
ttgttgccattgctacaggcatcgtggtgtcacgctcgtcgtttggtatggcttcattcagctccggttcccaac
gatcaaggcgagttacatgatcccccatgttgtgcaaaaaagcggttagctccttcggtcctccgatcgttgtca
gaagtaagttggccgcagtgttatcactcatggttatggcagcactgcataattctcttactgtcatgccatccg
taagatgcttttctgtgactggtgagtactcaaccaagtcattctgagaatagtgtatgcggcgaccgagttgct
cttgcccggcgtcaatacgggataataccgcgccacatagcagaactttaaaagtgctcatcattggaaaacgtt
cttcggggcgaaaactctcaaggatcttaccgctgttgagatccagttcgatgtaacccactcgtgcacccaact
gatcttcagcatcttttactttcaccagcgtttctgggtgagcaaaaacaggaaggcaaaatgccgcaaaaaagg
gaataagggcgacacggaaatgttgaatactcatactcttcctttttcaatattattgaagcatttatcagggtt
attgtctcatgagcggatacatatttgaatgtatttagaaaaataaacaaataggggttccgcgcacatttcccc
gaaaagtgccacctgacgtc Human LINGO-2 mature DNA sequence

SEQ ID NO: 33 attggctgccccgctcgctgtgagtgctctgcccagaacaaatctgttagctgtcacagaaggcgattgatcgcc
atcccagagggcattcccatcgaaaccaaaatcttggacctcagtaaaaacaggctaaaaagcgtcaaccctgaa
gaattcatatcatatcctctgctggaagagatagacttgagtgacaacatcattgccaatgtggaaccaggagca
ttcaacaatctctttaacctgcgttccctccgcctaaaaggcaatcgtctaaagctggtccctttgggagtattc
acggggctgtccaatctcactaagcttgacattagtgagaataagattgtcattttactagactacatgttccaa
gatctacataacctgaagtctctagaagtgggggacaatgatttggtttatatatcacacagggcattcagtggg
cttcttagcttggagcagctcaccctggagaaatgcaacttaacagcagtaccaacagaagccctctcccacctc
cgcagcctcatcagcctgcatctgaagcatctcaatatcaacaatatgcctgtgtatgcctttaaaagattgttc
cacctgaaacacctagagattgactattggcctttactggatatgatgcctgccaatagcctctacggtctcaac
ctcacatccctttcagtcaccaacaccaatctgtctactgtacccttccttgcctttaaacacctggtatacctg
actcaccttaacctctcctacaatcccatcagcactattgaagcaggcatgttctctgacctgatccgccttcag
gagcttcatatagtgggggcccagcttcgcaccattgagcctcactccttccaagggctccgcttcctacgcgtg
ctcaatgtgtctcagaacctgctggaaactttggaagagaatgtcttctcctcccctagggctctggaggtcttg
agcattaacaacaaccctctggcctgtgactgccgccttctctggatcttgcagcgacagcccaccctgcagttt
ggtggccagcaacctatgtgtgctggcccagacaccatccgtgagaggtctttcaaggatttccatagcactgcc
ctttctttttactttacctgcaaaaaacccaaaatccgtgaaaagaagttgcagcatctgctagtagatgaaggg
cagacagtccagctagaatgcagtgcagatggagacccgcagcctgtgatttcctgggtgacaccccgaaggcgt
ttcatcaccaccaagtccaatggaagagccaccgtgttgggtgatggcaccttggaaatccgctttgcccaggat
caagacagcgggatgtatgtttgcatcgctagcaatgctgctgggaatgataccttcacagcctccttaactgtg
aaaggattcgcttcagatcgttttctttatgcgaacaggacccctatgtacatgaccgactccaatgacaccatt
tccaatggcaccaatgccaatactttttccctggaccttaaaacaatactggtgtctacagctatgggctgcttc
acattcctgggagtggttttattttgttttcttctcctttttgtgtggagccgagggaaaggcaagcacaaaaac
agcattgaccttgagtatgtgcccagaaaaaacaatggtgctgttgtggaaggggaggtagctggacccaggagg -continued List of Sequences with short description ttcaacatgaaaatgatt Forward primer DM16

SEQ ID NO: 34

CTACGTCTAGAATTGGCTGCCCCGCTCGCT

Reverse primer DM17

SEQ ID NO: 35

GGTTTCTCGAGTCAAATCATTTTCATGTTGAACCTCCTG pRS5a-IgG

SEQ ID NO: 36 tcgacggatcgggagatccgggacatgtacctcccaggggcccaggaagactacgggaggctacaccaacgtcaa tcagaggggcctgtgtagctaccgataagcggaccctcaagagggcattagcaatagtgtttataaggcccccttg gttaaccctaaacgggtagcatatgcttcccgggtagtagtatatactatccagactaaccctaattcaatagca tatgttacccaacgggaagcatatgctatcgaattagggttagtaaaagggtcctaaggaacagcgatatctccc accccatgagctgtcacggttttatttacatggggtcaggattccacgagggtagtgaaccattttagtcacaag ggcagtggctgaagatcaaggagcgggcagtgaactctcctgaatcttcgcctgcttcttcattctccttcgttt agctaatagaataactgctgagttgtgaacagtaaggtgtatgtgaggtgctcgaaaacaaggtttcaggtgacg cccccagaataaaatttggacggggggttcagtggtggcattgtgctatgacaccaatataaccctcacaaaccc cttgggcaataaatactagtgtaggaatgaaacattctgaatatctttaacaatagaaatccatggggtggggac aagccgtaaagactggatgtccatctcacacgaatttatggctatgggcaacacataatcctagtgcaatatgat actggggttattaagatgtgtcccaggcagggaccaagacaggtgaaccatgttgttacactctatttgtaacaa ggggaaagagagtggacgccgacagcagcggactccactggttgtctctaacacccccgaaaattaaacggggct ccacgccaatggggcccataaacaaagacaagtggccactcttttttttgaaattgtggagtgggggcacgcgtc agcccccacacgccgccctgcggttttggactgtaaaataagggtgtaataacttggctgattgtaaccccgcta accactgcggtcaaaccacttgcccacaaaaccactaatggcaccccggggaatacctgcataagtaggtgggcg ggccaagataggggcgcgattgctgcgatctggaggacaaattacacacacttgcgcctgagcgccaagcacagg gttgttggtcctcatattcacgaggtcgctgagagcacggtgggctaatgttgccatgggtagcatatactaccc aaatatctggatagcatatgctatcctaatctatatctgggtagcataggctatcctaatctatatctgggtagc atatgctatcctaatctatatctgggtagtatatgctatcctaatttatatctgggtagcataggctatcctaat ctatatctgggtagcatatgctatcctaatctatatctgggtagtatatgctatcctaatctgtatccgggtagc atatgctatcctaatagagattagggtagtatatgctatcctaatttatatctgggtagcatatactacccaaat atctggatagcatatgctatcctaatctatatctgggtagcatatgctatcctaatctatatctgggtagcatag gctatcctaatctatatctgggtagcatatgctatcctaatctatatctgggtagtatatgctatcctaatttat atctgggtagcataggctatcctaatctatatctgggtagcatatgctatcctaatctatatctgggtagtatat gctatcctaatctgtatccgggtagcatatgctatcctcatgcatatacagtcagcatatgatacccagtagtag agtgggagtgctatcctttgcatatgccgccacctcccaagggggcgtgaattttcgctgcttgtccttttcctg catgcggatcttcaatattggccattagccatattattcattggttatatagcataaatcaatattggctattgg ccattgcatacgttgtatctatatcataatatgtacatttatattggctcatgtccaatatgaccgccatgttgg cattgattattgactagttattaatagtaatcaattacggggtcattagttcatagcccatatatggagttccgc gttacataacttacggtaaatggcccgcctggctgaccgcccaacgacccccgcccattgacgtcaataatgacg tatgttcccatagtaacgccaatagggactttccattgacgtcaatgggtggagtatttacggtaaactgcccac ttggcagtacatcaagtgtatcatatgccaagtccgccccctattgacgtcaatgacggtaaatggcccgcctgg cattatgcccagtacatgaccttacgggactttcctacttggcagtacatctacgtattagtcatcgctattacc -continued

| List of Sequences with short description |
|---|
| atggtgatgcggttttggcagtacaccaatgggcgtggatagcggtttgactcacggggatttccaagtctccac<br>cccattgacgtcaatgggagtttgttttggcaccaaaatcaacgggactttccaaaatgtcgtaataaccccgcc<br>ccgttgacgcaaatgggcggtaggcgtgtacggtgggaggtctatataagcagagctcgtttagtgaaccgtcag<br>atcgcctggagacgccatccacgctgttttgacctccatagaagacaccgggaccgatccagcctccgcggccgg<br>gaacggtgcattggaacgcggattccccgtgccaagagtgacgtaagtaccgcctatagagtctataggcccacc<br>cccttggcttcgttagaacgcggctacaattaatacataaccttatgtatcatacacatacgatttaggtgacac<br>tatagaataacatccactttgcctttctctccacaggtgtccactcccaggtccaactgcacggaagcttcaatt<br>gggatccctcgaggttctgttccagggtccgaaatcttgtgacaaaactcacacatgcccaccgtgcccagcacc<br>tgaactcctggggggaccgtcagtcttcctcttccccccaaaacccaaggacaccctcatgatctcccggacccc<br>tgaggtcacatgcgtggtggtggacgtgagccacgaagaccctgaggtcaagttcaactggtacgtggacggcgt<br>ggaggtgcataatgccaagacaaagccgcgggaggagcagtacaacagcacgtaccgtgtggtcagcgtcctcac<br>cgtcctgcaccaggactggctgaatggcaaggagtacaagtgcaaggtctccaacaaagccctcccagcccccat<br>cgagaaaaccatctccaaagccaaagggcagccccgagaaccacaggtgtacaccctgcccccatcccgggatga<br>gctgaccaagaaccaggtcagcctgacctgcctggtcaaaggcttctatcccagcgacatcgccgtggagtggga<br>gagcaatgggcagccggagaacaactacaagaccacgcctcccgtgctggactccgacggctccttcttcctcta<br>cagcaagctcaccgtggacaagagcaggtggcagcaggggaacgtcttctcatgctccgtgatgcatgaggctct<br>gcacaaccactacacgcagaagagcctctccctgtctccgggtaaatgagatctggtacctcgcgatggcggccg<br>ctctagagggcccgtttaaacccgctgatcagcctcgactgtgccttctagttgccagccatctgttgtttgccc<br>ctcccccgtgccttccttgaccctggaaggtgccactcccactgtcctttcctaataaaatgaggaaattgcatc<br>gcattgtctgagtaggtgtcattctattctggggggtggggtggggcaggacagcaagggggaggattgggaaga<br>caatagcaggcatgctggggatgcggtgggctctatggcttctgaggcggaaagaaccagctagctcgatcgagg<br>caggcagaagtatgcaaagcatgcatctcaattagtcagcaaccaggtgtggaaagtccccaggctccccagcag<br>gcagaagtatgcaaagcatgcatctcaattagtcagcaaccatagtcccgcccctaactccgcccatcccgcccc<br>taactccgcccagttccgcccattctccgccccatggctgactaattttttttatttatgcagaggccgaggccg<br>cctctgcctctgagctattccagaagtagtgaggaggcttttttggaggcctaggcttttgcaaaaagctcccgg<br>gagcttgtatatccattttcggatctgatcagcacgtgttgacaattaatcatcggcatagtatatcggcatagt<br>ataatacgacaaggtgaggaactaaaccatggccaagttgaccagtgccgttccggtgctcaccgcgcgcgacgt<br>cgccggagcggtcgagttctggaccgaccggctcgggttctcccgggacttcgtggaggacgacttcgccggtgt<br>ggtccgggacgacgtgaccctgttcatcagcgcggtccaggaccaggtggtgccggacaacaccctggcctgggt<br>gtgggtgcgcggcctggacgagctgtacgccgagtggtcggaggtcgtgtccacgaacttccgggacgcctccgg<br>gccggccatgaccgagatcggcgagcagccgtgggggcgggagttcgccctgcgcgacccggccggcaactgcgt<br>gcacttcgtggccgaggagcaggactgacacgtgctacgagatttcgattccaccgccgccttctatgaaaggtt<br>gggcttcggaatcgttttccgggacgccggctggatgatcctccagcgcggggatctcatgctggagttcttcgc<br>ccaccccaacttgtttattgcagcttataatggttacaaataaagcaatagcatcacaaatttcacaaataaagc<br>atttttttcactgcattctagttgtggtttgtccaaactcatcaatgtatcttatcatgtctgaattttgcatta<br>atgaatcggccaacgcgcggggagaggcggtttgcgtattgggcgctcttccgcttcctcgctcactgactcgct<br>gcgctcggtcgttcggctgcggcgagcggtatcagctcactcaaaggcggtaatacggttatccacagaatcagg<br>ggataacgcaggaaagaacatgtgagcaaaaggccagcaaaaggccaggaaccgtaaaaaggccgcgttgctggc<br>gtttttccataggctccgcccccctgacgagcatcacaaaaatcgacgctcaagtcagaggtggcgaaacccgac |

-continued

| List of Sequences with short description |
|---|

aggactataaagataccaggcgtttccccctggaagctccctcgtgcgctctcctgttccgaccctgccgcttac cggatacctgtccgcctttctcccttcgggaagcgtggcgctttctcaatgctcacgctgtaggtatctcagttc ggtgtaggtcgttcgctccaagctgggctgtgtgcacgaaccccccgttcagcccgaccgctgcgccttatccgg taactatcgtcttgagtccaacccggtaagacacgacttatcgccactggcagcagccactggtaacaggattag cagagcgaggtatgtaggcggtgctacagagttcttgaagtggtggcctaactacggctacactagaaggacagt atttggtatctgcgctctgctgaagccagttaccttcggaaaaagagttggtagctcttgatccggcaaacaaac caccgctggtagcggtggtttttttgtttgcaagcagcagattacgcgcagaaaaaaaggatctcaagaagatcc tttgatcttttctacggggtctgacgctcagtggaacgaaaactcacgttaagggattttggtcatgagattatc aaaaaggatcttcacctagatccttttaaattaaaaatgaagttttaaatcaatctaaagtatatatgagtaaac ttggtctgacagttaccaatgcttaatcagtgaggcacctatctcagcgatctgtctatttcgttcatccatagt tgcctgactccccgtcgtgtagataactacgatacgggagggcttaccatctggccccagtgctgcaatgatacc gcgagacccacgctcaccggctccagatttatcagcaataaaccagccagccggaagggccgagcgcagaagtgg tcctgcaactttatccgcctccatccagtctattaattgttgccgggaagctagagtaagtagttcgccagttaa tagtttgcgcaacgttgttgccattgctacaggcatcgtggtgtcacgctcgtcgtttggtatggcttcattcag ctccggttcccaacgatcaaggcgagttacatgatcccccatgttgtgcaaaaaagcggttagctccttcggtcc tccgatcgttgtcagaagtaagttggccgcagtgttatcactcatggttatggcagcactgcataattctcttac tgtcatgccatccgtaagatgcttttctgtgactggtgagtactcaaccaagtcattctgagaatagtgtatgcg gcgaccgagttgctcttgcccggcgtcaatacgggataataccgcgccacatagcagaactttaaaagtgctcat cattggaaaacgttcttcggggcgaaaactctcaaggatcttaccgctgttgagatccagttcgatgtaacccac tcgtgcacccaactgatcttcagcatcttttactttcaccagcgtttctgggtgagcaaaaacaggaaggcaaaa tgccgcaaaaaagggaataagggcgacacggaaatgttgaatactcatactcttcctttttcaatattattgaag catttatcagggttattgtctcatgagcggatacatatttgaatgtatttagaaaaataaacaaataggggttcc gcgcacatttccccgaaaagtgccacctgacgtcga natleader-hsLINGO-1-Fc/pRS5a

SEQ ID NO: 37 tcgacggatcgggagatccgggacatgtacctcccaggggcccaggaagactacgggaggctacaccaacgtcaa tcagaggggcctgtgtagctaccgataagcggaccctcaagagggcattagcaatagtgtttataaggccccctt gttaaccctaaacgggtagcatatgcttcccgggtagtagtatatactatccagactaaccctaattcaatagca tatgttacccaacgggaagcatatgctatcgaattagggttagtaaaagggtcctaaggaacagcgatatctccc accccatgagctgtcacggttttatttacatggggtcaggattccacgagggtagtgaaccattttagtcacaag ggcagtggctgaagatcaaggagcgggcagtgaactctcctgaatcttcgcctgcttcttcattctccttcgttt agctaatagaataactgctgagttgtgaacagtaaggtgtatgtgaggtgctcgaaaacaaggtttcaggtgacg cccccagaataaaatttggacggggggttcagtggtggcattgtgctatgacaccaatataaccctcacaaaccc cttgggcaataaatactagtgtaggaatgaaacattctgaatatctttaacaatagaaatccatggggtggggac aagccgtaaagactggatgtccatctcacacgaatttatggctatgggcaacacataatcctagtgcaatatgat actggggttattaagatgtgtcccaggcagggaccaagacaggtgaaccatgttgttacactctatttgtaacaa ggggaaagagagtggacgccgacagcagcggactccactggttgtctctaacacccccgaaaattaaacggggct ccacgccaatggggcccataaacaaagacaagtggccactctttttttttgaaattgtggagtgggggcacgcgtc agcccccacacgccgccctgcggttttggactgtaaaataagggtgtaataacttggctgattgtaaccccgcta accactgcggtcaaaccacttgcccacaaaaccactaatggcaccccggggaatacctgcataagtaggtgggcg -continued

| List of Sequences with short description |
|---|

ggccaagataggggcgcgattgctgcgatctggaggacaaattacacacacttgcgcctgagcgccaagcacagg gttgttggtcctcatattcacgaggtcgctgagagcacggtgggctaatgttgccatgggtagcatatactaccc aaatatctggatagcatatgctatcctaatctatatctgggtagcataggctatcctaatctatatctgggtagc atatgctatcctaatctatatctgggtagtatatgctatcctaatttatatctgggtagcataggctatcctaat ctatatctgggtagcatatgctatcctaatctatatctgggtagtatatgctatcctaatctgtatccgggtagc atatgctatcctaatagagattagggtagtatatgctatcctaatttatatctgggtagcatatactacccaaat atctggatagcatatgctatcctaatctatatctgggtagcatatgctatcctaatctatatctgggtagcatag gctatcctaatctatatctgggtagcatatgctatcctaatctatatctgggtagtatatgctatcctaatttat atctgggtagcataggctatcctaatctatatctgggtagcatatgctatcctaatctatatctgggtagtatat gctatcctaatctgtatccgggtagcatatgctatcctcatgcatatacagtcagcatatgatacccagtagtag agtgggagtgctatcctttgcatatgccgccacctcccaagggggcgtgaattttcgctgcttgtccttttcctg catgcggatcttcaatattggccattagccatattattcattggttatatagcataaatcaatattggctattgg ccattgcatacgttgtatctatatcataatatgtacatttatattggctcatgtccaatatgaccgccatgttgg cattgattattgactagttattaatagtaatcaattacggggtcattagttcatagcccatatatggagttccgc gttacataacttacggtaaatggcccgcctggctgaccgcccaacgacccccgcccattgacgtcaataatgacg tatgttcccatagtaacgccaatagggactttccattgacgtcaatgggtggagtatttacggtaaactgcccac ttggcagtacatcaagtgtatcatatgccaagtccgccccctattgacgtcaatgacggtaaatggcccgcctgg cattatgcccagtacatgaccttacgggactttcctacttggcagtacatctacgtattagtcatcgctattacc atggtgatgcggttttggcagtacaccaatgggcgtggatagcggtttgactcacggggatttccaagtctccac cccattgacgtcaatgggagtttgttttggcaccaaaatcaacgggactttccaaaatgtcgtaataaccccgcc ccgttgacgcaaatgggcggtaggcgtgtacggtgggaggtctatataagcagagctcgtttagtgaaccgtcag atcgcctggagacgccatccacgctgttttgacctccatagaagacaccgggaccgatccagcctccgcggccgg gaacggtgcattggaacgcggattccccgtgccaagagtgacgtaagtaccgcctatagagtctataggcccacc cccttggcttcgttagaacgcggctacaattaatacataaccttatgtatcatacacatacgatttaggtgacac tatagaataacatccactttgcctttctctccacaggtgtccactcccaggtccaactgcacggaagcttgccgc caccatgcaggtgagcaagaggatgctggcgggggcgtgaggagcatgcccagcccctcctggcctgctggca gcccatcctcctgctggtgctgggctcagtgctgtcaggctcggccacgggctgcccgccccgctgcgagtgctc cgcccaggaccgcgctgtgctgtgccaccgcaagcgctttgtggcagtccccgagggcatccccaccgagacgcg cctgctggacctaggcaagaaccgcatcaaaacgctcaaccaggacgagttcgccagcttcccgcacctggagga gctggagctcaacgagaacatcgtgagcgccgtggagcccggcgccttcaacaacctcttcaacctccggacgct gggtctccgcagcaaccgcctgaagctcatcccgctaggcgtcttcactggcctcagcaacctgaccaagctgga catcagcgagaacaagatcgttatcctactggactacatgtttcaggacctgtacaacctcaagtcactggaggt tggcgacaatgacctcgtctacatctctcaccgcgccttcagcggcctcaacagcctggagcagctgacgctgga gaaatgcaacctgacctccatccccaccgaggcgctgtcccacctgcacggcctcatcgtcctgaggctccggca cctcaacatcaatgccatccgggactactccttcaagaggctgtaccgactcaaggtcttggagatctcccactg gccctacttggacaccatgacacccaactgcctctacggcctcaacctgacgtccctgtccatcacacactgcaa tctgaccgctgtgccctacctggccgtccgccacctagtctatctccgcttcctcaacctctcctacaaccccat cagcaccattgagggctccatgttgcatgagctgctccggctgcaggagatccagctggtgggcgggcagctggc cgtggtggagccctatgccttccgcggcctcaactacctgcgcgtgctcaatgtctctggcaaccagctgaccac -continued List of Sequences with short description actggaggaatcagtcttccactcggtgggcaacctggagacactcatcctggactccaacccgctggcctgcga
ctgtcggctcctgtgggtgttccggcgccgctggcggctcaacttcaaccggcagcagcccacgtgcgccacgcc
cgagtttgtccagggcaaggagttcaaggacttccctgatgtgctactgcccaactacttcacctgccgccgcgc
ccgcatccgggaccgcaaggcccagcaggtgtttgtggacgagggccacacggtgcagtttgtgtgccgggccga
tggcgacccgccgcccgccatcctctggctctcaccccgaaagcacctggtctcagccaagagcaatgggcggct
cacagtcttccctgatggcacgctggaggtgcgctacgcccaggtacaggacaacggcacgtacctgtgcatcgc
ggccaacgcgggcggcaacgactccatgcccgcccacctgcatgtgcgcagctactcgcccgactggccccatca
gcccaacaagaccttcgctttcatctccaaccagccgggcgagggagaggccaacagcacccgcgccactgtgcc
tttccccttcgacatcaagaccctcgaggttctgttccagggtccgaaatcttgtgacaaaactcacacatgccc
accgtgcccagcacctgaactcctggggggaccgtcagtcttcctcttccccccaaaacccaaggacaccctcat
gatctcccggacccctgaggtcacatgcgtggtggtggacgtgagccacgaagaccctgaggtcaagttcaactg
gtacgtggacggcgtggaggtgcataatgccaagacaaagccgcgggaggagcagtacaacagcacgtaccgtgt
ggtcagcgtcctcaccgtcctgcaccaggactggctgaatggcaaggagtacaagtgcaaggtctccaacaaagc
cctcccagcccccatcgagaaaaccatctccaaagccaaagggcagccccgagaaccacaggtgtacaccctgcc
cccatcccgggatgagctgaccaagaaccaggtcagcctgacctgcctggtcaaaggcttctatcccagcgacat
cgccgtggagtgggagagcaatgggcagccggagaacaactacaagaccacgcctcccgtgctggactccgacgg
ctccttcttcctctacagcaagctcaccgtggacaagagcaggtggcagcaggggaacgtcttctcatgctccgt
gatgcatgaggctctgcacaaccactacacgcagaagagcctctccctgtctccgggtaaatgagatctggtacc
tcgcgatggcggccgctctagagggcccgtttaaacccgctgatcagcctcgactgtgccttctagttgccagcc
atctgttgtttgcccctcccccgtgccttccttgaccctggaaggtgccactcccactgtcctttcctaataaaa
tgaggaaattgcatcgcattgtctgagtaggtgtcattctattctggggggtggggtggggcaggacagcaaggg
ggaggattgggaagacaatagcaggcatgctggggatgcggtgggctctatggcttctgaggcggaaagaaccag
ctagctcgatcgaggcaggcagaagtatgcaaagcatgcatctcaattagtcagcaaccaggtgtggaaagtccc
caggctccccagcaggcagaagtatgcaaagcatgcatctcaattagtcagcaaccatagtcccgcccctaactc
cgcccatcccgcccctaactccgcccagttccgcccattctccgccccatggctgactaattttttttatttatg
cagaggccgaggccgcctctgcctctgagctattccagaagtagtgaggaggcttttttggaggcctaggctttt
gcaaaaagctcccgggagcttgtatatccattttcggatctgatcagcacgtgttgacaattaatcatcggcata
gtatatcggcatagtataatacgacaaggtgaggaactaaaccatggccaagttgaccagtgccgttccggtgct
caccgcgcgcgacgtcgccggagcggtcgagttctggaccgaccggctcgggttctcccgggacttcgtggagga
cgacttcgccggtgtggtccgggacgacgtgaccctgttcatcagcgcggtccaggaccaggtggtgccggacaa
caccctggcctgggtgtgggtgcgcggcctggacgagctgtacgccgagtggtcggaggtcgtgtccacgaactt
ccgggacgcctccgggccggccatgaccgagatcggcgagcagccgtgggggcgggagttcgccctgcgcgaccc
ggccggcaactgcgtgcacttcgtggccgaggagcaggactgacacgtgctacgagatttcgattccaccgccgc
cttctatgaaaggttgggcttcggaatcgttttccgggacgccggctggatgatcctccagcgcggggatctcat
gctggagttcttcgcccaccccaacttgtttattgcagcttataatggttacaaataaagcaatagcatcacaaa
tttcacaaataaagcatttttttcactgcattctagttgtggtttgtccaaactcatcaatgtatcttatcatgt
ctgaattttgcattaatgaatcggccaacgcgcggggagaggcggtttgcgtattgggcgctcttccgcttcctc
gctcactgactcgctgcgctcggtcgttcggctgcggcgagcggtatcagctcactcaaaggcggtaatacggtt
atccacagaatcaggggataacgcaggaaagaacatgtgagcaaaaggccagcaaaaggccaggaaccgtaaaaa -continued

| List of Sequences with short description |
|---|

ggccgcgttgctggcgtttttccataggctccgcccccctgacgagcatcacaaaaatcgacgctcaagtcagag gtggcgaaacccgacaggactataaagataccaggcgtttccccctggaagctccctcgtgcgctctcctgttcc gaccctgccgcttaccggatacctgtccgcctttctcccttcgggaagcgtggcgctttctcaatgctcacgctg taggtatctcagttcggtgtaggtcgttcgctccaagctgggctgtgtgcacgaaccccccgttcagcccgaccg ctgcgccttatccggtaactatcgtcttgagtccaacccggtaagacacgacttatcgccactggcagcagccac tggtaacaggattagcagagcgaggtatgtaggcggtgctacagagttcttgaagtggtggcctaactacggcta cactagaaggacagtatttggtatctgcgctctgctgaagccagttaccttcggaaaaagagttggtagctcttg atccggcaaacaaaccaccgctggtagcggtggtttttttgtttgcaagcagcagattacgcgcagaaaaaaagg atctcaagaagatcctttgatcttttctacggggtctgacgctcagtggaacgaaaactcacgttaagggatttt ggtcatgagattatcaaaaaggatcttcacctagatccttttaaattaaaaatgaagttttaaatcaatctaaag tatatatgagtaaacttggtctgacagttaccaatgcttaatcagtgaggcacctatctcagcgatctgtctatt tcgttcatccatagttgcctgactccccgtcgtgtagataactacgatacgggagggcttaccatctggccccag tgctgcaatgataccgcgagacccacgctcaccggctccagatttatcagcaataaaccagccagccggaagggc cgagcgcagaagtggtcctgcaactttatccgcctccatccagtctattaattgttgccgggaagctagagtaag tagttcgccagttaatagtttgcgcaacgttgttgccattgctacaggcatcgtggtgtcacgctcgtcgtttgg tatggcttcattcagctccggttcccaacgatcaaggcgagttacatgatcccccatgttgtgcaaaaaagcggt tagctccttcggtcctccgatcgttgtcagaagtaagttggccgcagtgttatcactcatggttatggcagcact gcataattctcttactgtcatgccatccgtaagatgcttttctgtgactggtgagtactcaaccaagtcattctg agaatagtgtatgcggcgaccgagttgctcttgcccggcgtcaatacgggataataccgcgccacatagcagaac tttaaaagtgctcatcattggaaaacgttcttcggggcgaaaactctcaaggatcttaccgctgttgagatccag ttcgatgtaacccactcgtgcacccaactgatcttcagcatcttttactttcaccagcgtttctgggtgagcaaa aacaggaaggcaaaatgccgcaaaaaagggaataagggcgacacggaaatgttgaatactcatactcttcctttt tcaatattattgaagcatttatcagggttattgtctcatgagcggatacatatttgaatgtatttagaaaaataa acaaataggggttccgcgcacatttccccgaaaagtgccacctgacgtcga Igleader-hsLINGO-1-ΔLRR-Fc/pRS5a

SEQ ID NO: 38 tcgacggatcgggagatccgggacatgtacctcccaggggcccaggaagactacgggaggctacaccaacgtcaa tcagaggggcctgtgtagctaccgataagcggaccctcaagagggcattagcaatagtgtttataaggcccctt gttaaccctaaacgggtagcatatgcttcccgggtagtagtatatactatccagactaaccctaattcaatagca tatgttacccaacgggaagcatatgctatcgaattagggttagtaaaagggtcctaaggaacagcgatatctccc accccatgagctgtcacggttttatttacatggggtcaggattccacgagggtagtgaaccattttagtcacaag ggcagtggctgaagatcaaggagcgggcagtgaactctcctgaatcttcgcctgcttcttcattctccttcgttt agctaatagaataactgctgagttgtgaacagtaaggtgtatgtgaggtgctcgaaaacaaggtttcaggtgacg cccccagaataaaatttggacgggggttcagtggtggcattgtgctatgacaccaatataaccctcacaaaccc cttgggcaataaatactagtgtaggaatgaaacattctgaatatctttaacaatagaaatccatggggtggggac aagccgtaaagactggatgtccatctcacacgaatttatggctatgggcaacacataatcctagtgcaatatgat actggggttattaagatgtgtcccaggcagggaccaagacaggtgaaccatgttgttacactctatttgtaacaa ggggaaagagagtggacgccgacagcagcggactccactggttgtctctaacacccccgaaaattaaacggggct ccacgccaatggggcccataaacaaagacaagtggccactcttttttttgaaattgtggagtgggggcacgcgtc agcccccacacgccgccctgcggttttggactgtaaaataagggtgtaataacttggctgattgtaaccccgcta -continued

| List of Sequences with short description |
| --- |

accactgcggtcaaaccacttgcccacaaaaccactaatggcaccccggggaatacctgcataagtaggtgggcg
ggccaagataggggcgcgattgctgcgatctggaggacaaattacacacacttgcgcctgagcgccaagcacagg
gttgttggtcctcatattcacgaggtcgctgagagcacggtgggctaatgttgccatgggtagcatatactaccc
aaatatctggatagcatatgctatcctaatctatatctgggtagcataggctatcctaatctatatctgggtagc
atatgctatcctaatctatatctgggtagtatatgctatcctaatttatatctgggtagcataggctatcctaat
ctatatctgggtagcatatgctatcctaatctatatctgggtagtatatgctatcctaatctgtatccgggtagc
atatgctatcctaatagagattagggtagtatatgctatcctaatttatatctgggtagcatatactacccaaat
atctggatagcatatgctatcctaatctatatctgggtagcatatgctatcctaatctatatctgggtagcatag
gctatcctaatctatatctgggtagcatatgctatcctaatctatatctgggtagtatatgctatcctaatttat
atctgggtagcataggctatcctaatctatatctgggtagcatatgctatcctaatctatatctgggtagtatat
gctatcctaatctgtatccgggtagcatatgctatcctcatgcatatacagtcagcatatgatacccagtagtag
agtgggagtgctatcctttgcatatgccgccacctcccaaggggggcgtgaattttcgctgcttgtccttttcctg
catgcggatcttcaatattggccattagccatattattcattggttatatagcataaatcaatattggctattgg
ccattgcatacgttgtatctatatcataatatgtacatttatattggctcatgtccaatatgaccgccatgttgg
cattgattattgactagttattaatagtaatcaattacggggtcattagttcatagcccatatatggagttccgc
gttacataacttacggtaaatggcccgcctggctgaccgcccaacgacccccgcccattgacgtcaataatgacg
tatgttcccatagtaacgccaatagggactttccattgacgtcaatgggtggagtatttacggtaaactgcccac
ttggcagtacatcaagtgtatcatatgccaagtccgccccctattgacgtcaatgacggtaaatggcccgcctgg
cattatgcccagtacatgaccttacgggactttcctacttggcagtacatctacgtattagtcatcgctattacc
atggtgatgcggttttggcagtacaccaatgggcgtggatagcggtttgactcacggggatttccaagtctccac
cccattgacgtcaatgggagtttgttttggcaccaaaatcaacgggactttccaaaatgtcgtaataaccccgcc
ccgttgacgcaaatgggcggtaggcgtgtacggtgggaggtctatataagcagagctcgtttagtgaaccgtcag
atcgcctggagacgccatccacgctgttttgacctccatagaagacaccgggaccgatccagcctccgcggccgg
gaacggtgcattggaacgcggattccccgtgccaagagtgacgtaagtaccgcctatagagtctataggcccacc
cccttggcttcgttagaacgcggctacaattaatacataaccttatgtatcatacacatacgatttaggtgacac
tatagaataacatccactttgcctttctctccacaggtgtccactcccaggtccaactgcacggaagcttgccgc
caccatgagtgtgctcactcaggtcctggcgttgctgctgctgtggcttacaggtacgcgttgtacgggctgccc
gccccgctgcgagtgctccgcccaggaccgcgctgtgctgtgccaccgcaagcgctttgtggcagtccccgaggg
catccccaccaacctggagacactcatcctggactccaacccgctggcctgcgactgtcggctcctgtgggtgtt
ccggcgccgctggcggctcaacttcaaccggcagcagcccacgtgcgccacgcccgagtttgtccagggcaagga
gttcaaggacttccctgatgtgctactgcccaactacttcacctgccgccgcgcccgcatccgggaccgcaaggc
ccagcaggtgtttgtggacgagggccacacggtgcagtttgtgtgccgggccgatggcgacccgccgcccgccat
cctctggctctcaccccgaaagcacctggtctcagccaagagcaatgggcggctcacagtcttccctgatggcac
gctggaggtgcgctacgcccaggtacaggacaacggcacgtacctgtgcatcgcggccaacgcgggcggcaacga
ctccatgcccgcccacctgcatgtgcgcagctactcgcccgactggccccatcagcccaacaagaccttcgcttt
catctccaaccagccgggcgagggagaggccaacagcacccgcgccactgtgcctttccccttcgacatcaagac
cctcgaggttctgttccagggtccgaaatcttgtgacaaaactcacacatgcccaccgtgcccagcacctgaact
cctggggggaccgtcagtcttcctcttccccccaaaacccaaggacaccctcatgatctcccggacccctgaggt
cacatgcgtggtggtggacgtgagccacgaagaccctgaggtcaagttcaactggtacgtggacggcgtggaggt -continued List of Sequences with short description gcataatgccaagacaaagccgcgggaggagcagtacaacagcacgtaccgtgtggtcagcgtcctcaccgtcct
gcaccaggactggctgaatggcaaggagtacaagtgcaaggtctccaacaaagccctcccagcccccatcgagaa
aaccatctccaaagccaaagggcagccccgagaaccacaggtgtacaccctgcccccatcccgggatgagctgac
caagaaccaggtcagcctgacctgcctggtcaaaggcttctatcccagcgacatcgccgtggagtgggagagcaa
tgggcagccggagaacaactacaagaccacgcctcccgtgctggactccgacggctccttcttcctctacagcaa
gctcaccgtggacaagagcaggtggcagcaggggaacgtcttctcatgctccgtgatgcatgaggctctgcacaa
ccactacacgcagaagagcctctccctgtctccgggtaaatgagatctggtacctcgcgatggcggccgctctag
agggcccgtttaaacccgctgatcagcctcgactgtgccttctagttgccagccatctgttgtttgcccctcccc
cgtgccttccttgaccctggaaggtgccactcccactgtcctttcctaataaaatgaggaaattgcatcgcattg
tctgagtaggtgtcattctattctggggggtggggtggggcaggacagcaagggggaggattgggaagacaatag
caggcatgctggggatgcggtgggctctatggcttctgaggcggaaagaaccagctagctcgatcgaggcaggca
gaagtatgcaaagcatgcatctcaattagtcagcaaccaggtgtggaaagtccccaggctccccagcaggcagaa
gtatgcaaagcatgcatctcaattagtcagcaaccatagtcccgcccctaactccgcccatcccgcccctaactc
cgcccagttccgcccattctccgccccatggctgactaattttttttatttatgcagaggccgaggccgcctctg
cctctgagctattccagaagtagtgaggaggcttttttggaggcctaggcttttgcaaaaagctcccgggagctt
gtatatccattttcggatctgatcagcacgtgttgacaattaatcatcggcatagtatatcggcatagtataata
cgacaaggtgaggaactaaaccatggccaagttgaccagtgccgttccggtgctcaccgcgcgcgacgtcgccgg
agcggtcgagttctggaccgaccggctcgggttctcccgggacttcgtggaggacgacttcgccggtgtggtccg
ggacgacgtgaccctgttcatcagcgcggtccaggaccaggtggtgccggacaacaccctggcctgggtgtgggt
gcgcggcctggacgagctgtacgccgagtggtcggaggtcgtgtccacgaacttccgggacgcctccgggccggc
catgaccgagatcggcgagcagccgtgggggcgggagttcgccctgcgcgacccggccggcaactgcgtgcactt
cgtggccgaggagcaggactgacacgtgctacgagatttcgattccaccgccgccttctatgaaaggttgggctt
cggaatcgttttccgggacgccggctggatgatcctccagcgcggggatctcatgctggagttcttcgcccaccc
caacttgtttattgcagcttataatggttacaaataaagcaatagcatcacaaatttcacaaataaagcattttt
ttcactgcattctagttgtggtttgtccaaactcatcaatgtatcttatcatgtctgaattttgcattaatgaat
cggccaacgcgcggggagaggcggtttgcgtattgggcgctcttccgcttcctcgctcactgactcgctgcgctc
ggtcgttcggctgcggcgagcggtatcagctcactcaaaggcggtaatacggttatccacagaatcaggggataa
cgcaggaaagaacatgtgagcaaaaggccagcaaaaggccaggaaccgtaaaaaggccgcgttgctggcgttttt
ccataggctccgcccccctgacgagcatcacaaaaatcgacgctcaagtcagaggtggcgaaacccgacaggact
ataaagataccaggcgtttccccctggaagctccctcgtgcgctctcctgttccgaccctgccgcttaccggata
cctgtccgcctttctcccttcgggaagcgtggcgctttctcaatgctcacgctgtaggtatctcagttcggtgta
ggtcgttcgctccaagctgggctgtgtgcacgaaccccccgttcagcccgaccgctgcgccttatccggtaacta
tcgtcttgagtccaacccggtaagacacgacttatcgccactggcagcagccactggtaacaggattagcagagc
gaggtatgtaggcggtgctacagagttcttgaagtggtggcctaactacggctacactagaaggacagtatttgg
tatctgcgctctgctgaagccagttaccttcggaaaaagagttggtagctcttgatccggcaaacaaaccaccgc
tggtagcggtggtttttttgtttgcaagcagcagattacgcgcagaaaaaaaggatctcaagaagatcctttgat
cttttctacggggtctgacgctcagtggaacgaaaactcacgttaagggattttggtcatgagattatcaaaaag
gatcttcacctagatccttttaaattaaaaatgaagttttaaatcaatctaaagtatatatgagtaaacttggtc
tgacagttaccaatgcttaatcagtgaggcacctatctcagcgatctgtctatttcgttcatccatagttgcctg -continued List of Sequences with short description actccccgtcgtgtagataactacgatacgggagggcttaccatctggccccagtgctgcaatgataccgcgaga
cccacgctcaccggctccagatttatcagcaataaaccagccagccggaagggccgagcgcagaagtggtcctgc
aactttatccgcctccatccagtctattaattgttgccgggaagctagagtaagtagttcgccagttaatagttt
gcgcaacgttgttgccattgctacaggcatcgtggtgtcacgctcgtcgtttggtatggcttcattcagctccgg
ttcccaacgatcaaggcgagttacatgatcccccatgttgtgcaaaaaagcggttagctccttcggtcctccgat
cgttgtcagaagtaagttggccgcagtgttatcactcatggttatggcagcactgcataattctcttactgtcat
gccatccgtaagatgcttttctgtgactggtgagtactcaaccaagtcattctgagaatagtgtatgcggcgacc
gagttgctcttgcccggcgtcaatacgggataataccgcgccacatagcagaactttaaaagtgctcatcattgg
aaaacgttcttcggggcgaaaactctcaaggatcttaccgctgttgagatccagttcgatgtaacccactcgtgc
acccaactgatcttcagcatcttttactttcaccagcgtttctgggtgagcaaaaacaggaaggcaaaatgccgc
aaaaaagggaataagggcgacacggaaatgttgaatactcatactcttcctttttcaatattattgaagcattta
tcagggttattgtctcatgagcggatacatatttgaatgtatttagaaaaataaacaaataggggttccgcgcac
atttccccgaaaagtgccacctgacgtcga Fab Expression Vector pMORPH ® X9_MH

SEQ ID NO: 39

CTAGATAACG AGGCCAAAAA ATGAAAAAGA CAGCTATCGC GATTGCAGTG
GCACTGGCTG GTTTCGCTAC CGTAGCGCAG GCCGATATCG TGCTGACCCA
GCCGCCTTCA GTGAGTGGCG CACCAGGTCA GCGTGTGACC ATCTCGTGTA
GCGGCAGCAG CAGCAACATT GGTAATAATT ATGTGTCTTG GTACCAGCAG
TTGCCCGGGA CGGCGCCGAA ACTTCTGATT TCTCGTAATT CTAAGCGTCC
CTCAGGCGTG CCGGATCGTT TTAGCGGATC CAAAAGCGGC ACCAGCGCGA
GCCTTGCGAT TACGGGCCTG CAAAGCGAAG ACGAAGCGGA TTATTATTGC
TCTACTTATG ATACTTTTTC TATTGTGTTT GGCGGCGGCA CGAAGTTAAC
CGTTCTTGGC CAGCCGAAAG CCGCACCGAG TGTGACGCTG TTTCCGCCGA
GCAGCGAAGA ATTGCAGGCG AACAAAGCGA CCCTGGTGTG CCTGATTAGC
GACTTTTATC CGGGAGCCGT GACAGTGGCC TGGAAGGCAG ATAGCAGCCC
CGTCAAGGCG GGAGTGGAGA CCACCACACC CTCCAAACAA AGCAACAACA
AGTACGCGGC CAGCAGCTAT CTGAGCCTGA CGCCTGAGCA GTGGAAGTCC
CACAGAAGCT ACAGCTGCCA GGTCACGCAT GAGGGGAGCA CCGTGGAAAA
AACCGTTGCG CCGACTGAGG CCTGATAAGC ATGCGTAGGA GAAAATAAAA
TGAAACAAAG CACTATTGCA CTGGCACTCT TACCGTTGCT CTTCACCCCT
GTTACCAAAG CCCAGGTGCA ATTGCAACAG TCTGGTCCGG GCCTGGTGAA
ACCGAGCCAA ACCCTGAGCC TGACCTGTGC GATTTCCGGA GATAGCGTGA
GCGATAATTC TGCTGCTTGG TCTTGGATTC GCCAGTCTCC TGGGCGTGGC
CTCGAGTGGC TGGGCCTTAT CTATCTTCGT AGCAAGTGGG ATAACGATTA
TGCGGTGAGC GTGAAAAGCC GGATTACCAT CAACCCGGAT ACTTCGAAAA
ACCAGTTTAG CCTGCAACTG AACAGCGTGA CCCCGGAAGA TACGGCCGTG
TATTATTGCG CGCGTACTGG TCGTGCTGAT GAGTTTGATG TTTGGGGCCA
AGGCACCCTG GTGACGGTTA GCTCAGCGTC GACCAAAGGT CCAAGCGTGT
TTCCGCTGGC TCCGAGCAGC AAAAGCACCA GCGGCGGCAC GGCTGCCCTG

-continued

List of Sequences with short description

GGCTGCCTGG TTAAAGATTA TTTCCCGGAA CCAGTCACCG TGAGCTGGAA

CAGCGGGGCG CTGACCAGCG GCGTGCATAC CTTTCCGGCG GTGCTGCAAA

GCAGCGGCCT GTATAGCCTG AGCAGCGTTG TGACCGTGCC GAGCAGCAGC

TTAGGCACTC AGACCTATAT TTGCAACGTG AACCATAAAC CGAGCAACAC

CAAAGTGGAT AAAAAAGTGG AACCGAAAAG CGAATTCGAG CAGAAGCTGA

TCTCTGAGGA GGATCTGAAC GGCGCGCCGC ACCATCATCA CCATCACTGA

TAAGCTTGAC CTGTGAAGTG AAAAATGGCG CAGATTGTGC GACATTTTTT

TTGTCTGCCG TTTAATTAAA GGGGGGGGGG GGCCGGCCTG GGGGGGGGTG

TACATGAAAT TGTAAACGTT AATATTTTGT TAAAATTCGC GTTAAATTTT

TGTTAAATCA GCTCATTTTT TAACCAATAG GCCGAAATCG GCAAAATCCC

TTATAAATCA AAAGAATAGA CCGAGATAGG GTTGAGTGTT GTTCCAGTTT

GGAACAAGAG TCCACTATTA AAGAACGTGG ACTCCAACGT CAAAGGGCGA

AAAACCGTCT ATCAGGGCGA TGGCCCACTA CGAGAACCAT CACCCTAATC

AAGTTTTTTG GGGTCGAGGT GCCGTAAAGC ACTAAATCGG AACCCTAAAG

GGAGCCCCCG ATTTAGAGCT TGACGGGGAA AGCCGGCGAA CGTGGCGAGA

AAGGAAGGGA AGAAAGCGAA AGGAGCGGGC GCTAGGGCGC TGGCAAGTGT

AGCGGTCACG CTGCGCGTAA CCACCACACC CGCCGCGCTT AATGCGCCGC

TACAGGGCGC GTGCTAGACT AGTGTTTAAA CCGGACCGGG GGGGGGCTTA

AGTGGGCTGC AAAACAAAAC GGCCTCCTGT CAGGAAGCCG CTTTTATCGG

GTAGCCTCAC TGCCCGCTTT CCAGTCGGGA AACCTGTCGT GCCAGCTGCA

TCAGTGAATC GGCCAACGCG CGGGGAGAGG CGGTTTGCGT ATTGGGAGCC

AGGGTGGTTT TTCTTTTCAC CAGTGAGACG GGCAACAGCT GATTGCCCTT

CACCGCCTGG CCCTGAGAGA GTTGCAGCAA GCGGTCCACG CTGGTTTGCC

CCAGCAGGCG AAAATCCTGT TTGATGGTGG TCAGCGGCGG GATATAACAT

GAGCTGTCCT CGGTATCGTC GTATCCCACT ACCGAGATGT CCGCACCAAC

GCGCAGCCCG GACTCGGTAA TGGCACGCAT TGCGCCCAGC GCCATCTGAT

CGTTGGCAAC CAGCATCGCA GTGGGAACGA TGCCCTCATT CAGCATTTGC

ATGGTTTGTT GAAAACCGGA CATGGCACTC CAGTCGCCTT CCCGTTCCGC

TATCGGCTGA ATTTGATTGC GAGTGAGATA TTTATGCCAG CCAGCCAGAC

GCAGACGCGC CGAGACAGAA CTTAATGGGC CAGCTAACAG CGCGATTTGC

TGGTGGCCCA ATGCGACCAG ATGCTCCACG CCCAGTCGCG TACCGTCCTC

ATGGGAGAAA ATAATACTGT TGATGGGTGT CTGGTCAGAG ACATCAAGAA

ATAACGCCGG AACATTAGTG CAGGCAGCTT CCACAGCAAT AGCATCCTGG

TCATCCAGCG GATAGTTAAT AATCAGCCCA CTGACACGTT GCGCGAGAAG

ATTGTGCACC GCCGCTTTAC AGGCTTCGAC GCCGCTTCGT TCTACCATCG

ACACGACCAC GCTGGCACCC AGTTGATCGG CGCGAGATTT AATCGCCGCG

ACAATTTGCG ACGGCGCGTG CAGGGCCAGA CTGGAGGTGG CAACGCCAAT

CAGCAACGAC TGTTTGCCCG CCAGTTGTTG TGCCACGCGG TTAGGAATGT

AATTCAGCTC CGCCATCGCC GCTTCCACTT TTTCCCGCGT TTTCGCAGAA

-continued

List of Sequences with short description

ACGTGGCTGG CCTGGTTCAC CACGCGGGAA ACGGTCTGAT AAGAGACACC
GGCATACTCT GCGACATCGT ATAACGTTAC TGGTTTCACA TTCACCACCC
TGAATTGACT CTCTTCCGGG CGCTATCATG CCATACCGCG AAAGGTTTTG
CGCCATTCGA TGCTAGCCAT GTGAGCAAAA GGCCAGCAAA AGGCCAGGAA
CCGTAAAAAG GCCGCGTTGC TGGCGTTTTT CCATAGGCTC CGCCCCCCTG
ACGAGCATCA CAAAAATCGA CGCTCAAGTC AGAGGTGGCG AAACCCGACA
GGACTATAAA GATACCAGGC GTTTCCCCCT GGAAGCTCCC TCGTGCGCTC
TCCTGTTCCG ACCCTGCCGC TTACCGGATA CCTGTCCGCC TTTCTCCCTT
CGGGAAGCGT GGCGCTTTCT CATAGCTCAC GCTGTAGGTA TCTCAGTTCG
GTGTAGGTCG TTCGCTCCAA GCTGGGCTGT GTGCACGAAC CCCCCGTTCA
GCCCGACCGC TGCGCCTTAT CCGGTAACTA TCGTCTTGAG TCCAACCCGG
TAAGACACGA CTTATCGCCA CTGGCAGCAG CCACTGGTAA CAGGATTAGC
AGAGCGAGGT ATGTAGGCGG TGCTACAGAG TTCTTGAAGT GGTGGCCTAA
CTACGGCTAC ACTAGAAGAA CAGTATTTGG TATCTGCGCT CTGCTGTAGC
CAGTTACCTT CGGAAAAAGA GTTGGTAGCT CTTGATCCGG CAAACAAACC
ACCGCTGGTA GCGGTGGTTT TTTTGTTTGC AAGCAGCAGA TTACGCGCAG
AAAAAAAGGA TCTCAAGAAG ATCCTTTGAT CTTTTCTACG GGGTCTGACG
CTCAGTGGAA CGAAAACTCA CGTTAAGGGA TTTTGGTCAG ATCTAGCACC
AGGCGTTTAA GGGCACCAAT AACTGCCTTA AAAAAATTAC GCCCCGCCCT
GCCACTCATC GCAGTACTGT TGTAATTCAT TAAGCATTCT GCCGACATGG
AAGCCATCAC AAACGGCATG ATGAACCTGA ATCGCCAGCG GCATCAGCAC
CTTGTCGCCT TGCGTATAAT ATTTGCCCAT AGTGAAAACG GGGGCGAAGA
AGTTGTCCAT ATTGGCTACG TTTAAATCAA AACTGGTGAA ACTCACCCAG
GGATTGGCTG AGACGAAAAA CATATTCTCA ATAAACCCTT TAGGGAAATA
GGCCAGGTTT TCACCGTAAC ACGCCACATC TTGCGAATAT ATGTGTAGAA
ACTGCCGGAA ATCGTCGTGG TATTCACTCC AGAGCGATGA AAACGTTTCA
GTTTGCTCAT GGAAAACGGT GTAACAAGGG TGAACACTAT CCCATATCAC
CAGCTCACCG TCTTTCATTG CCATACGGAA CTCCGGGTGA GCATTCATCA
GGCGGGCAAG AATGTGAATA AAGGCCGGAT AAAACTTGTG CTTATTTTTC
TTTACGGTCT TTAAAAAGGC CGTAATATCC AGCTGAACGG TCTGGTTATA
GGTACATTGA GCAACTGACT GAAATGCCTC AAAATGTTCT TTACGATGCC
ATTGGGATAT ATCAACGGTG GTATATCCAG TGATTTTTTT CTCCATTTTA
GCTTCCTTAG CTCCTGAAAA TCTCGATAAC TCAAAAAATA CGCCCGGTAG
TGATCTTATT TCATTATGGT GAAAGTTGGA ACCTCACCCG ACGTCTAATG
TGAGTTAGCT CACTCATTAG GCACCCCAGG CTTTACACTT TATGCTTCCG
GCTCGTATGT TGTGTGGAAT TGTGAGCGGA TAACAATTTC ACACAGGAAA
CAGCTATGAC CATGATTACG AATTT

-continued

| List of Sequences with short description |
|---|

IgG4 Expression Vector pMORPH ®_h_Igγ4

SEQ ID NO: 40

AATTGCATGA AGAATCTGCT TAGGGTTAGG CGTTTTGCGC TGCTTCGCGA

TGTACGGGCC AGATATACGC GTTGACATTG ATTATTGACT AGTTATTAAT

AGTAATCAAT TACGGGGTCA TTAGTTCATA GCCCATATAT GGAGTTCCGC

GTTACATAAC TTACGGTAAA TGGCCCGCCT GGCTGACCGC CCAACGACCC

CCGCCCATTG ACGTCAATAA TGACGTATGT TCCCATAGTA ACGCCAATAG

GGACTTTCCA TTGACGTCAA TGGGTGGACT ATTTACGGTA AACTGCCCAC

TTGGCAGTAC ATCAAGTGTA TCATATGCCA AGTACGCCCC CTATTGACGT

CAATGACGGT AAATGGCCCG CCTGGCATTA TGCCCAGTAC ATGACCTTAT

GGGACTTTCC TACTTGGCAG TACATCTACG TATTAGTCAT CGCTATTACC

ATGGTGATGC GGTTTTGGCA GTACATCAAT GGGCGTGGAT AGCGGTTTGA

CTCACGGGGA TTTCCAAGTC TCCACCCCAT TGACGTCAAT GGGAGTTTGT

TTTGGCACCA AAATCAACGG GACTTTCCAA AATGTCGTAA CAACTCCGCC

CCATTGACGC AAATGGGCGG TAGGCGTGTA CGGTGGGAGG TCTATATAAG

CAGAGCTCTC TGGCTAACTA GAGAACCCAC TGCTTACTGG CTTATCGAAA

TTAATACGAC TCACTATAGG GAGACCCAAG CTGGCTAGCG CCACCATGAA

ACACCTGTGG TTCTTCCTCC TGCTGGTGGC AGCTCCCAGA TGGGTCCTGT

CCCAGGTGGA ATTGCAACAG TCTGGTCCGG GCCTGGTGAA ACCGAGCCAA

ACCCTGAGCC TGACCTGTGC GATTTCCGGA GATAGCGTGA GCGATAATTC

TGCTGCTTGG TCTTGGATTC GCCAGTCTCC TGGGCGTGGC CTCGAGTGGC

TGGGCCTTAT CTATCTTCGT AGCAAGTGGG ATAACGATTA TGCGGTGAGC

GTGAAAAGCC GGATTACCAT CAACCCGGAT ACTTCGAAAA ACCAGTTTAG

CCTGCAACTG AACAGCGTGA CCCCGGAAGA TACGGCCGTG TATTATTGCG

CGCGTACTGG TCGTGCTGAT GAGTTTGATG TTTGGGGCCA AGGCACCCTG

GTGACGGTTA GCTCAGCTTC CACCAAGGGA CCATCCGTCT TCCCCCTGGC

GCCCTGCTCC AGGAGCACCT CCGAGAGCAC AGCCGCCCTG GGCTGCCTGG

TCAAGGACTA CTTCCCCGAA CCGGTGACGG TGTCGTGGAA CTCAGGCGCC

CTGACCAGCG GCGTGCACAC CTTCCCGGCT GTCCTACAGT CCTCAGGACT

CTACTCCCTC AGCAGCGTGG TGACCGTGCC CTCCAGCAGC TTGGGCACGA

AGACCTACAC CTGCAACGTA GATCACAAGC CCAGCAACAC CAAGGTGGAC

AAGAGAGTTG AGTCCAAATA TGGTCCCCCA TGCCCATCAT GCCCAGCACC

TGAGTTCCTG GGGGGACCAT CAGTCTTCCT GTTCCCCCCA AAACCCAAGG

ACACTCTCAT GATCTCCCGG ACCCCTGAGG TCACGTGCGT GGTGGTGGAC

GTGAGCCAGG AAGACCCCGA GGTCCAGTTC AACTGGTACG TGGATGGCGT

GGAGGTGCAT AATGCCAAGA CAAAGCCGCG GGAGGAGCAG TTCAACAGCA

CGTACCGTGT GGTCAGCGTC CTCACCGTCC TGCACCAGGA CTGGCTGAAC

GGCAAGGAGT ACAAGTGCAA GGTCTCCAAC AAAGGCCTCC CGTCCTCCAT

CGAGAAAACC ATCTCCAAAG CCAAAGGGCA GCCCCGAGAG CCACAGGTGT

ACACCCTGCC CCCATCCCAG GAGGAGATGA CCAAGAACCA GGTCAGCCTG

-continued

List of Sequences with short description

ACCTGCCTGG TCAAAGGCTT CTACCCCAGC GACATCGCCG TGGAGTGGGA

GAGCAATGGG CAGCCGGAGA ACAACTACAA GACCACGCCT CCCGTGCTGG

ACTCCGACGG CTCCTTCTTC CTCTACAGCA GGCTAACCGT GGACAAGAGC

AGGTGGCAGG AGGGGAATGT CTTCTCATGC TCCGTGATGC ATGAGGCTCT

GCACAACCAC TACACACAGA AGAGCCTCTC CCTGTCTCTG GGTAAATGAG

GGCCCGTTTA AACCCGCTGA TCAGCCTCGA CTGTGCCTTC TAGTTGCCAG

CCATCTGTTG TTTGCCCCTC CCCCGTGCCT TCCTTGACCC TGGAAGGTGC

CACTCCCACT GTCCTTTCCT AATAAAATGA GGAAATTGCA TCGCATTGTC

TGAGTAGGTG TCATTCTATT CTGGGGGGTG GGGTGGGGCA GGACAGCAAG

GGGGAGGATT GGGAAGACAA TAGCAGGCAT GCTGGGGATG CGGTGGGCTC

TATGGCTTCT GAGGCGGAAA GAACCAGCTG GGGCTCTAGG GGGTATCCCC

ACGCGCCCTG TAGCGGCGCA TTAAGCGCGG CGGGTGTGGT GGTTACGCGC

AGCGTGACCG CTACACTTGC CAGCGCCCTA GCGCCCGCTC CTTTCGCTTT

CTTCCCTTCC TTTCTCGCCA CGTTCGCCGG CTTTCCCCGT CAAGCTCTAA

ATCGGGGCAT CCCTTTAGGG TTCCGATTTA GTGCTTTACG GCACCTCGAC

CCCAAAAAAC TTGATTAGGG TGATGGTTCA CGTAGTGGGC CATCGCCCTG

ATAGACGGTT TTTCGCCCTT TGACGTTGGA GTCCACGTTC TTTAATAGTG

GACTCTTGTT CCAAACTGGA ACAACACTCA ACCCTATCTC GGTCTATTCT

TTTGATTTAT AAGGGATTTT GGGGATTTCG GCCTATTGGT TAAAAAATGA

GCTGATTTAA CAAAAATTTA ACGCGAATTA ATTCTGTGGA ATGTGTGTCA

GTTAGGGTGT GGAAAGTCCC CAGGCTCCCC AGGCAGGCAG AAGTATGCAA

AGCATGCATC TCAATTAGTC AGCAACCAGG TGTGGAAAGT CCCCAGGCTC

CCCAGCAGGC AGAAGTATGC AAAGCATGCA TCTCAATTAG TCAGCAACCA

TAGTCCCGCC CCTAACTCCG CCCATCCCGC CCCTAACTCC GCCCAGTTCC

GCCCATTCTC CGCCCCATGG CTGACTAATT TTTTTTATTT ATGCAGAGGC

CGAGGCCGCC TCTGCCTCTG AGCTATTCCA GAAGTAGTGA GGAGGCTTTT

TTGGAGGCCT AGGCTTTTGC AAAAAGCTCC CGGGAGCTTG TATATCCATT

TTCGGATCTG ATCAAGAGAC AGGATGAGGA TCGTTTCGCA TGATTGAACA

AGATGGATTG CACGCAGGTT CTCCGGCCGC TTGGGTGGAG AGGCTATTCG

GCTATGACTG GGCACAACAG ACAATCGGCT GCTCTGATGC CGCCGTGTTC

CGGCTGTCAG CGCAGGGGCG CCCGGTTCTT TTTGTCAAGA CCGACCTGTC

CGGTGCCCTG AATGAACTGC AGGACGAGGC AGCGCGGCTA TCGTGGCTGG

CCACGACGGG CGTTCCTTGC GCAGCTGTGC TCGACGTTGT CACTGAAGCG

GGAAGGGACT GGCTGCTATT GGGCGAAGTG CCGGGGCAGG ATCTCCTGTC

ATCTCACCTT GCTCCTGCCG AGAAAGTATC CATCATGGCT GATGCAATGC

GGCGGCTGCA TACGCTTGAT CCGGCTACCT GCCCATTCGA CCACCAAGCG

AAACATCGCA TCGAGCGAGC ACGTACTCGG ATGGAAGCCG GTCTTGTCGA

TCAGGATGAT CTGGACGAAG AGCATCAGGG GCTCGCGCCA GCCGAACTGT

TCGCCAGGCT CAAGGCGCGC ATGCCCGACG GCGAGGATCT CGTCGTGACC

-continued

List of Sequences with short description

CATGGCGATG CCTGCTTGCC GAATATCATG GTGGAAAATG GCCGCTTTTC
TGGATTCATC GACTGTGGCC GGCTGGGTGT GGCGGACCGC TATCAGGACA
TAGCGTTGGC TACCCGTGAT ATTGCTGAAG AGCTTGGCGG CGAATGGGCT
GACCGCTTCC TCGTGCTTTA CGGTATCGCC GCTCCCGATT CGCAGCGCAT
CGCCTTCTAT CGCCTTCTTG ACGAGTTCTT CTGAGCGGGA CTCTGGGGTT
CGAAATGACC GACCAAGCGA CGCCCAACCT GCCATCACGA GATTTCGATT
CCACCGCCGC CTTCTATGAA AGGTTGGGCT TCGGAATCGT TTTCCGGGAC
GCCGGCTGGA TGATCCTCCA GCGCGGGGAT CTCATGCTGG AGTTCTTCGC
CCACCCCAAC TTGTTTATTG CAGCTTATAA TGGTTACAAA TAAAGCAATA
GCATCACAAA TTTCACAAAT AAAGCATTTT TTTCACTGCA TTCTAGTTGT
GGTTTGTCCA AACTCATCAA TGTATCTTAT CATGTCTGTA TACCGTCGAC
CTCTAGCTAG AGCTTGGCGT AATCATGGTC ATAGCTGTTT CCTGTGTGAA
ATTGTTATCC GCTCACAATT CCACACAACA TACGAGCCGG AAGCATAAAG
TGTAAAGCCT GGGGTGCCTA ATGAGTGAGC TAACTCACAT TAATTGCGTT
GCGCTCACTG CCCGCTTTCC AGTCGGGAAA CCTGTCGTGC CAGCTGCATT
AATGAATCGG CCAACGCGCG GGGAGAGGCG GTTTGCGTAT TGGGCGCTCT
TCCGCTTCCT CGCTCACTGA CTCGCTGCGC TCGGTCGTTC GGCTGCGGCG
AGCGGTATCA GCTCACTCAA AGGCGGTAAT ACGGTTATCC ACAGAATCAG
GGGATAACGC AGGAAAGAAC ATGTGAGCAA AAGGCCAGCA AAAGGCCAGG
AACCGTAAAA AGGCCGCGTT GCTGGCGTTT TTCCATAGGC TCCGCCCCCC
TGACGAGCAT CACAAAAATC GACGCTCAAG TCAGAGGTGG CGAAACCCGA
CAGGACTATA AAGATACCAG GCGTTTCCCC CTGGAAGCTC CCTCGTGCGC
TCTCCTGTTC CGACCCTGCC GCTTACCGGA TACCTGTCCG CCTTTCTCCC
TTCGGGAAGC GTGGCGCTTT CTCAATGCTC ACGCTGTAGG TATCTCAGTT
CGGTGTAGGT CGTTCGCTCC AAGCTGGGCT GTGTGCACGA ACCCCCCGTT
CAGCCCGACC GCTGCGCCTT ATCCGGTAAC TATCGTCTTG AGTCCAACCC
GGTAAGACAC GACTTATCGC CACTGGCAGC AGCCACTGGT AACAGGATTA
GCAGAGCGAG GTATGTAGGC GGTGCTACAG AGTTCTTGAA GTGGTGGCCT
AACTACGGCT ACACTAGAAG GACAGTATTT GGTATCTGCG CTCTGCTGAA
GCCAGTTACC TTCGGAAAAA GAGTTGGTAG CTCTTGATCC GGCAAACAAA
CCACCGCTGG TAGCGGTGGT TTTTTTGTTT GCAAGCAGCA GATTACGCGC
AGAAAAAAAG GATCTCAAGA AGATCCTTTG ATCTTTTCTA CGGGGTCTGA
CGCTCAGTGG AACGAAAACT CACGTTAAGG GATTTTGGTC ATGAGATTAT
CAAAAAGGAT CTTCACCTAG ATCCTTTTAA ATTAAAAATG AAGTTTTAAA
TCAATCTAAA GTATATATGA GTAAACTTGG TCTGACAGTT ACCAATGCTT
AATCAGTGAG GCACCTATCT CAGCGATCTG TCTATTTCGT TCATCCATAG
TTGCCTGACT CCCCGTCGTG TAGATAACTA CGATACGGGA GGGCTTACCA
TCTGGCCCCA GTGCTGCAAT GATACCGCGA GACCCACGCT CACCGGCTCC
AGATTTATCA GCAATAAACC AGCCAGCCGG AAGGGCCGAG CGCAGAAGTG

-continued

| List of Sequences with short description |
|---|

GTCCTGCAAC TTTATCCGCC TCCATCCAGT CTATTAATTG TTGCCGGGAA

GCTAGAGTAA GTAGTTCGCC AGTTAATAGT TTGCGCAACG TTGTTGCCAT

TGCTACAGGC ATCGTGGTGT CACGCTCGTC GTTTGGTATG GCTTCATTCA

GCTCCGGTTC CCAACGATCA AGGCGAGTTA CATGATCCCC CATGTTGTGC

AAAAAAGCGG TTAGCTCCTT CGGTCCTCCG ATCGTTGTCA GAAGTAAGTT

GGCCGCAGTG TTATCACTCA TGGTTATGGC AGCACTGCAT AATTCTCTTA

CTGTCATGCC ATCCGTAAGA TGCTTTTCTG TGACTGGTGA GTACTCAACC

AAGTCATTCT GAGAATAGTG TATGCGGCGA CCGAGTTGCT CTTGCCCGGC

GTCAATACGG GATAATACCG CGCCACATAG CAGAACTTTA AAAGTGCTCA

TCATTGGAAA ACGTTCTTCG GGGCGAAAAC TCTCAAGGAT CTTACCGCTG

TTGAGATCCA GTTCGATGTA ACCCACTCGT GCACCCAACT GATCTTCAGC

ATCTTTTACT TTCACCAGCG TTTCTGGGTG AGCAAAAACA GGAAGGCAAA

ATGCCGCAAA AAAGGGAATA AGGGCGACAC GGAAATGTTG AATACTCATA

CTCTTCCTTT TTCAATATTA TTGAAGCATT TATCAGGGTT ATTGTCTCAT

GAGCGGATAC ATATTTGAAT GTATTTAGAA AAATAAACAA ATAGGGGTTC

CGCGCACATT TCCCCGAAAA GTGCCACCTG ACGTCGACGG ATCGGGAGAT

CTCCCGATCC CCTATGGTCG ACTCTCAGTA CAATCTGCTC TGATGCCGCA

TAGTTAAGCC AGTATCTGCT CCCTGCTTGT GTGTTGGAGG TCGCTGAGTA

GTGCGCGAGC AAAATTTAAG CTACAACAAG GCAAGGCTTG ACCGAC

IgG Lambda Chain Expression Vector pMORPH ®_h_Ig_lambda

SEQ ID NO: 41

AATTGCATGA AGAATCTGCT TAGGGTTAGG CGTTTTGCGC TGCTTCGCGA

TGTACGGGCC AGATATACGC GTTGACATTG ATTATTGACT AGTTATTAAT

AGTAATCAAT TACGGGGTCA TTAGTTCATA GCCCATATAT GGAGTTCCGC

GTTACATAAC TTACGGTAAA TGGCCCGCCT GGCTGACCGC CCAACGACCC

CCGCCCATTG ACGTCAATAA TGACGTATGT TCCCATAGTA ACGCCAATAG

GGACTTTCCA TTGACGTCAA TGGGTGGACT ATTTACGGTA AACTGCCCAC

TTGGCAGTAC ATCAAGTGTA TCATATGCCA AGTACGCCCC CTATTGACGT

CAATGACGGT AAATGGCCCG CCTGGCATTA TGCCCAGTAC ATGACCTTAT

GGGACTTTCC TACTTGGCAG TACATCTACG TATTAGTCAT CGCTATTACC

ATGGTGATGC GGTTTTGGCA GTACATCAAT GGGCGTGGAT AGCGGTTTGA

CTCACGGGGA TTTCCAAGTC TCCACCCCAT TGACGTCAAT GGGAGTTTGT

TTTGGCACCA AAATCAACGG GACTTTCCAA AATGTCGTAA CAACTCCGCC

CCATTGACGC AAATGGGCGG TAGGCGTGTA CGGTGGGAGG TCTATATAAG

CAGAGCTCTC TGGCTAACTA GAGAACCCAC TGCTTACTGG CTTATCGAAA

TTAATACGAC TCACTATAGG GAGACCCAAG CTGGCTAGCG CCACCATGGC

CTGGGCTCTG CTGCTCCTCA CCCTCCTCAC TCAGGGCACA GGATCCTGGG

CTGATATCGT GCTGACCCAG CCGCCTTCAG TGAGTGGCGC ACCAGGTCAG

CGTGTGACCA TCTCGTGTAG CGGCAGCAGC AGCAACATTG GTAATAATTA

TGTGTCTTGG TACCAGCAGT TGCCCGGGAC GGCGCCGAAA CTTCTGATTT

-continued

| List of Sequences with short description |
|---|
| CTCGTAATTC TAAGCGTCCC TCAGGCGTGC CGGATCGTTT TAGCGGATCC |
| AAAAGCGGCA CCAGCGCGAG CCTTGCGATT ACGGGCCTGC AAAGCGAAGA |
| CGAAGCGGAT TATTATTGCT CTACTTATGA TACTTTTTCT ATTGTGTTTG |
| GCGGCGGCAC GAAGTTAACC GTCCTAGGTC AGCCCAAGGC TGCCCCCTCG |
| GTCACTCTGT TCCCGCCCTC CTCTGAGGAG CTTCAAGCCA ACAAGGCCAC |
| ACTGGTGTGT CTCATAAGTG ACTTCTACCC GGGAGCCGTG ACAGTGGCCT |
| GGAAGGGAGA TAGCAGCCCC GTCAAGGCGG GAGTGGAGAC CACCACACCC |
| TCCAAACAAA GCAACAACAA GTACGCGGCC AGCAGCTATC TGAGCCTGAC |
| GCCTGAGCAG TGGAAGTCCC ACAGAAGCTA CAGCTGCCAG GTCACGCATG |
| AAGGGAGCAC CGTGGAGAAG ACAGTGGCCC CTACAGAATG TTCATAGGGG |
| CCCGTTTAAA CCCGCTGATC AGCCTCGACT GTGCCTTCTA GTTGCCAGCC |
| ATCTGTTGTT TGCCCCTCCC CCGTGCCTTC CTTGACCCTG GAAGGTGCCA |
| CTCCCACTGT CCTTTCCTAA TAAAATGAGG AAATTGCATC GCATTGTCTG |
| AGTAGGTGTC ATTCTATTCT GGGGGGTGGG GTGGGGCAGG ACAGCAAGGG |
| GGAGGATTGG GAAGACAATA GCAGGCATGC TGGGGATGCG GTGGGCTCTA |
| TGGCTTCTGA GGCGGAAAGA ACCAGCTGGG GCTCTAGGGG GTATCCCCAC |
| GCGCCCTGTA GCGGCGCATT AAGCGCGGCG GGTGTGGTGG TTACGCGCAG |
| CGTGACCGCT ACACTTGCCA GCGCCCTAGC GCCCGCTCCT TTCGCTTTCT |
| TCCCTTCCTT TCTCGCCACG TTCGCCGGCT TTCCCCGTCA AGCTCTAAAT |
| CGGGGCATCC CTTTAGGGTT CCGATTTAGT GCTTTACGGC ACCTCGACCC |
| CAAAAAACTT GATTAGGGTG ATGGTTCACG TAGTGGGCCA TCGCCCTGAT |
| AGACGGTTTT TCGCCCTTTG ACGTTGGAGT CCACGTTCTT TAATAGTGGA |
| CTCTTGTTCC AAACTGGAAC AACACTCAAC CCTATCTCGG TCTATTCTTT |
| TGATTTATAA GGGATTTTGG GGATTTCGGC CTATTGGTTA AAAAATGAGC |
| TGATTTAACA AAAATTTAAC GCGAATTAAT TCTGTGGAAT GTGTGTCAGT |
| TAGGGTGTGG AAAGTCCCCA GGCTCCCCAG GCAGGCAGAA GTATGCAAAG |
| CATGCATCTC AATTAGTCAG CAACCAGGTG TGGAAAGTCC CCAGGCTCCC |
| CAGCAGGCAG AAGTATGCAA AGCATGCATC TCAATTAGTC AGCAACCATA |
| GTCCCGCCCC TAACTCCGCC CATCCCGCCC CTAACTCCGC CCAGTTCCGC |
| CCATTCTCCG CCCCATGGCT GACTAATTTT TTTTATTTAT GCAGAGGCCG |
| AGGCCGCCTC TGCCTCTGAG CTATTCCAGA AGTAGTGAGG AGGCTTTTTT |
| GGAGGCCTAG GCTTTTGCAA AAAGCTCCCG GGAGCTTGTA TATCCATTTT |
| CGGATCTGAT CAGCACGTGT TGACAATTAA TCATCGGCAT AGTATATCGG |
| CATAGTATAA TACGACAAGG TGAGGAACTA AACCATGGCC AAGTTGACCA |
| GTGCCGTTCC GGTGCTCACC GCGCGCGACG TCGCCGGAGC GGTCGAGTTC |
| TGGACCGACC GGCTCGGGTT CTCCCGGGAC TTCGTGGAGG ACGACTTCGC |
| CGGTGTGGTC CGGGACGACG TGACCCTGTT CATCAGCGCG GTCCAGGACC |
| AGGTGGTGCC GGACAACACC CTGGCCTGGG TGTGGGTGCG CGGCCTGGAC |
| GAGCTGTACG CCGAGTGGTC GGAGGTCGTG TCCACGAACT TCCGGGACGC |

-continued

| List of Sequences with short description |
|---|
| CTCCGGGCCG GCCATGACCG AGATCGGCGA GCAGCCGTGG GGGCGGGAGT |
| TCGCCCTGCG CGACCCGGCC GGCAACTGCG TGCACTTCGT GGCCGAGGAG |
| CAGGACTGAC ACGTGCTACG AGATTTCGAT TCCACCGCCG CCTTCTATGA |
| AAGGTTGGGC TTCGGAATCG TTTTCCGGGA CGCCGGCTGG ATGATCCTCC |
| AGCGCGGGGA TCTCATGCTG GAGTTCTTCG CCCACCCCAA CTTGTTTATT |
| GCAGCTTATA ATGGTTACAA ATAAAGCAAT AGCATCACAA ATTTCACAAA |
| TAAAGCATTT TTTTCACTGC ATTCTAGTTG TGGTTTGTCC AAACTCATCA |
| ATGTATCTTA TCATGTCTGT ATACCGTCGA CCTCTAGCTA GAGCTTGGCG |
| TAATCATGGT CATAGCTGTT TCCTGTGTGA AATTGTTATC CGCTCACAAT |
| TCCACACAAC ATACGAGCCG GAAGCATAAA GTGTAAAGCC TGGGGTGCCT |
| AATGAGTGAG CTAACTCACA TTAATTGCGT TGCGCTCACT GCCCGCTTTC |
| CAGTCGGGAA ACCTGTCGTG CCAGCTGCAT TAATGAATCG GCCAACGCGC |
| GGGGAGAGGC GGTTTGCGTA TTGGGCGCTC TTCCGCTTCC TCGCTCACTG |
| ACTCGCTGCG CTCGGTCGTT CGGCTGCGGC GAGCGGTATC AGCTCACTCA |
| AAGGCGGTAA TACGGTTATC CACAGAATCA GGGGATAACG CAGGAAAGAA |
| CATGTGAGCA AAAGGCCAGC AAAAGGCCAG GAACCGTAAA AAGGCCGCGT |
| TGCTGGCGTT TTTCCATAGG CTCCGCCCCC CTGACGAGCA TCACAAAAAT |
| CGACGCTCAA GTCAGAGGTG GCGAAACCCG ACAGGACTAT AAAGATACCA |
| GGCGTTTCCC CCTGGAAGCT CCCTCGTGCG CTCTCCTGTT CCGACCCTGC |
| CGCTTACCGG ATACCTGTCC GCCTTTCTCC CTTCGGGAAG CGTGGCGCTT |
| TCTCAATGCT CACGCTGTAG GTATCTCAGT TCGGTGTAGG TCGTTCGCTC |
| CAAGCTGGGC TGTGTGCACG AACCCCCCGT TCAGCCCGAC CGCTGCGCCT |
| TATCCGGTAA CTATCGTCTT GAGTCCAACC CGGTAAGACA CGACTTATCG |
| CCACTGGCAG CAGCCACTGG TAACAGGATT AGCAGAGCGA GGTATGTAGG |
| CGGTGCTACA GAGTTCTTGA AGTGGTGGCC TAACTACGGC TACACTAGAA |
| GGACAGTATT TGGTATCTGC GCTCTGCTGA AGCCAGTTAC CTTCGGAAAA |
| AGAGTTGGTA GCTCTTGATC CGGCAAACAA ACCACCGCTG GTAGCGGTGG |
| TTTTTTTGTT TGCAAGCAGC AGATTACGCG CAGAAAAAAA GGATCTCAAG |
| AAGATCCTTT GATCTTTTCT ACGGGGTCTG ACGCTCAGTG GAACGAAAAC |
| TCACGTTAAG GGATTTTGGT CATGAGATTA TCAAAAAGGA TCTTCACCTA |
| GATCCTTTTA AATTAAAAAT GAAGTTTTAA ATCAATCTAA AGTATATATG |
| AGTAAACTTG GTCTGACAGT TACCAATGCT TAATCAGTGA GGCACCTATC |
| TCAGCGATCT GTCTATTTCG TTCATCCATA GTTGCCTGAC TCCCCGTCGT |
| GTAGATAACT ACGATACGGG AGGGCTTACC ATCTGGCCCC AGTGCTGCAA |
| TGATACCGCG AGACCCACGC TCACCGGCTC CAGATTTATC AGCAATAAAC |
| CAGCCAGCCG GAAGGGCCGA GCGCAGAAGT GGTCCTGCAA CTTTATCCGC |
| CTCCATCCAG TCTATTAATT GTTGCCGGGA AGCTAGAGTA AGTAGTTCGC |
| CAGTTAATAG TTTGCGCAAC GTTGTTGCCA TTGCTACAGG CATCGTGGTG |
| TCACGCTCGT CGTTTGGTAT GGCTTCATTC AGCTCCGGTT CCCAACGATC |

-continued

List of Sequences with short description

AAGGCGAGTT ACATGATCCC CCATGTTGTG CAAAAAAGCG GTTAGCTCCT
TCGGTCCTCC GATCGTTGTC AGAAGTAAGT TGGCCGCAGT GTTATCACTC
ATGGTTATGG CAGCACTGCA TAATTCTCTT ACTGTCATGC CATCCGTAAG
ATGCTTTTCT GTGACTGGTG AGTACTCAAC CAAGTCATTC TGAGAATAGT
GTATGCGGCG ACCGAGTTGC TCTTGCCCGG CGTCAATACG GGATAATACC
GCGCCACATA GCAGAACTTT AAAAGTGCTC ATCATTGGAA AACGTTCTTC
GGGGCGAAAA CTCTCAAGGA TCTTACCGCT GTTGAGATCC AGTTCGATGT
AACCCACTCG TGCACCCAAC TGATCTTCAG CATCTTTTAC TTTCACCAGC
GTTTCTGGGT GAGCAAAAAC AGGAAGGCAA AATGCCGCAA AAAAGGGAAT
AAGGGCGACA CGGAAATGTT GAATACTCAT ACTCTTCCTT TTTCAATATT
ATTGAAGCAT TTATCAGGGT TATTGTCTCA TGAGCGGATA CATATTTGAA
TGTATTTAGA AAAATAAACA AATAGGGGTT CCGCGCACAT TTCCCCGAAA
AGTGCCACCT GACGTCGACG GATCGGGAGA TCTCCCGATC CCCTATGGTC
GACTCTCAGT ACAATCTGCT CTGATGCCGC ATAGTTAAGC CAGTATCTGC
TCCCTGCTTG TGTGTTGGAG GTCGCTGAGT AGTGCGCGAG CAAAATTTAA
GCTACAACAA GGCAAGGCTT GACCGAC

IgG Kappa Chain Expression Vector pMORPH ®_h_Ig_kappa SEQ ID NO: 42

AATTGCATGA AGAATCTGCT TAGGGTTAGG CGTTTTGCGC TGCTTCGCGA
TGTACGGGCC AGATATACGC GTTGACATTG ATTATTGACT AGTTATTAAT
AGTAATCAAT TACGGGGTCA TTAGTTCATA GCCCATATAT GGAGTTCCGC
GTTACATAAC TTACGGTAAA TGGCCCGCCT GGCTGACCGC CCAACGACCC
CCGCCCATTG ACGTCAATAA TGACGTATGT TCCCATAGTA ACGCCAATAG
GGACTTTCCA TTGACGTCAA TGGGTGGAGT ATTTACGGTA AACTGCCCAC
TTGGCAGTAC ATCAAGTGTA TCATATGCCA AGTACGCCCC CTATTGACGT
CAATGACGGT AAATGGCCCG CCTGGCATTA TGCCCAGTAC ATGACCTTAT
GGGACTTTCC TACTTGGCAG TACATCTACG TATTAGTCAT CGCTATTACC
ATGGTGATGC GGTTTTGGCA GTACATCAAT GGGCGTGGAT AGCGGTTTGA
CTCACGGGGA TTTCCAAGTC TCCACCCCAT TGACGTCAAT GGGAGTTTGT
TTTGGCACCA AAATCAACGG GACTTTCCAA AATGTCGTAA CAACTCCGCC
CCATTGACGC AAATGGGCGG TAGGCGTGTA CGGTGGGAGG TCTATATAAG
CAGAGCTCTC TGGCTAACTA GAGAACCCAC TGCTTACTGG CTTATCGAAA
TTAATACGAC TCACTATAGG GAGACCCAAG CTGGCTAGCG CCACCATGGT
GTTGCAGACC CAGGTCTTCA TTTCTCTGTT GCTCTGGATC TCTGGTGCCT
ACGGGGATAT CCAGATGACC CAGAGCCCGT CTAGCCTGAG CGCGAGCGTG
GGTGATCGTG TGACCATTAC CTGCAGAGCG AGCCAGTCTA TTTCTAATTG
GCTGAATTGG TACCAGCAGA AACCAGGTAA AGCACCGAAA CTATTAATTT
ATAAGGCTTC TACTTTGCAA AGCGGGGTCC CGTCCCGTTT TAGCGGCTCT
GGATCCGGCA CTGATTTTAC CCTGACCATT AGCAGCCTGC AACCTGAAGA
CTTTGCGACT TATTATTGCC AGCAGTATGG TAATATTCCT ATTACCTTTG

-continued

| List of Sequences with short description |
|---|

GCCAGGGTAC GAAAGTTGAA ATTAAACGTA CGGTGGCTGC ACCATCTGTC

TTCATCTTCC CGCCATCTGA TGAGCAGTTG AAATCTGGAA CTGCCTCTGT

TGTGTGCCTG CTGAATAACT TCTATCCCAG AGAGGCCAAA GTACAGTGGA

AGGTGGATAA CGCCCTCCAA TCGGGTAACT CCCAGGAGAG TGTCACAGAG

CAGGACAGCA AGGACAGCAC CTACAGCCTC AGCAGCACCC TGACGCTGAG

CAAAGCAGAC TACGAGAAAC ACAAAGTCTA CGCCTGCGAA GTCACCCATC

AGGGCCTGAG CTCGCCCGTC ACAAAGAGCT TCAACAGGGG AGAGTGTTAG

GGGCCCGTTT AAACCCGCTG ATCAGCCTCG ACTGTGCCTT CTAGTTGCCA

GCCATCTGTT GTTTGCCCCT CCCCCGTGCC TTCCTTGACC CTGGAAGGTG

CCACTCCCAC TGTCCTTTCC TAATAAAATG AGGAAATTGC ATCGCATTGT

CTGAGTAGGT GTCATTCTAT TCTGGGGGGT GGGGTGGGGC AGGACAGCAA

GGGGGAGGAT TGGGAAGACA ATAGCAGGCA TGCTGGGGAT GCGGTGGGCT

CTATGGCTTC TGAGGCGGAA AGAACCAGCT GGGGCTCTAG GGGGTATCCC

CACGCGCCCT GTAGCGGCGC ATTAAGCGCG GCGGGTGTGG TGGTTACGCG

CAGCGTGACC GCTACACTTG CCAGCGCCCT AGCGCCCGCT CCTTTCGCTT

TCTTCCCTTC CTTTCTCGCC ACGTTCGCCG GCTTTCCCCG TCAAGCTCTA

AATCGGGGGC TCCCTTTAGG GTTCCGATTT AGTGCTTTAC GGCACCTCGA

CCCCAAAAAA CTTGATTAGG GTGATGGTTC ACGTAGTGGG CCATCGCCCT

GATAGACGGT TTTTCGCCCT TTGACGTTGG AGTCCACGTT CTTTAATAGT

GGACTCTTGT TCCAAACTGG AACAACACTC AACCCTATCT CGGTCTATTC

TTTTGATTTA TAAGGGATTT TGCCGATTTC GGCCTATTGG TTAAAAAATG

AGCTGATTTA ACAAAAATTT AACGCGAATT AATTCTGTGG AATGTGTGTC

AGTTAGGGTG TGGAAAGTCC CCAGGCTCCC CAGCAGGCAG AAGTATGCAA

AGCATGCATC TCAATTAGTC AGCAACCAGG TGTGGAAAGT CCCCAGGCTC

CCCAGCAGGC AGAAGTATGC AAAGCATGCA TCTCAATTAG TCAGCAACCA

TAGTCCCGCC CCTAACTCCG CCCATCCCGC CCCTAACTCC GCCCAGTTCC

GCCCATTCTC CGCCCCATGG CTGACTAATT TTTTTTATTT ATGCAGAGGC

CGAGGCCGCC TCTGCCTCTG AGCTATTCCA GAAGTAGTGA GGAGGCTTTT

TTGGAGGCCT AGGCTTTTGC AAAAAGCTCC CGGGAGCTTG TATATCCATT

TTCGGATCTG ATCAGCACGT GTTGACAATT AATCATCGGC ATAGTATATC

GGCATAGTAT AATACGACAA GGTGAGGAAC TAAACCATGG CCAAGTTGAC

CAGTGCCGTT CCGGTGCTCA CCGCGCGCGA CGTCGCCGGA GCGGTCGAGT

TCTGGACCGA CCGGCTCGGG TTCTCCCGGG ACTTCGTGGA GGACGACTTC

GCCGGTGTGG TCCGGGACGA CGTGACCCTG TTCATCAGCG CGGTCCAGGA

CCAGGTGGTG CCGGACAACA CCCTGGCCTG GGTGTGGGTG CGCGGCCTGG

ACGAGCTGTA CGCCGAGTGG TCGGAGGTCG TGTCCACGAA CTTCCGGGAC

GCCTCCGGGC CGGCCATGAC CGAGATCGGC GAGCAGCCGT GGGGGCGGGA

GTTCGCCCTG CGCGACCCGG CCGGCAACTG CGTGCACTTC GTGGCCGAGG

AGCAGGACTG ACACGTGCTA CGAGATTTCG ATTCCACCGC CGCCTTCTAT

-continued

List of Sequences with short description

GAAAGGTTGG GCTTCGGAAT CGTTTTCCGG GACGCCGGCT GGATGATCCT

CCAGCGCGGG GATCTCATGC TGGAGTTCTT CGCCCACCCC AACTTGTTTA

TTGCAGCTTA TAATGGTTAC AAATAAAGCA ATAGCATCAC AAATTTCACA

AATAAAGCAT TTTTTTCACT GCATTCTAGT TGTGGTTTGT CCAAACTCAT

CAATGTATCT TATCATGTCT GTATACCGTC GACCTCTAGC TAGAGCTTGG

CGTAATCATG GTCATAGCTG TTTCCTGTGT GAAATTGTTA TCCGCTCACA

ATTCCACACA ACATACGAGC CGGAAGCATA AAGTGTAAAG CCTGGGGTGC

CTAATGAGTG AGCTAACTCA CATTAATTGC GTTGCGCTCA CTGCCCGCTT

TCCAGTCGGG AAACCTGTCG TGCCAGCTGC ATTAATGAAT CGGCCAACGC

GCGGGGAGAG GCGGTTTGCG TATTGGGCGC TCTTCCGCTT CCTCGCTCAC

TGACTCGCTG CGCTCGGTCG TTCGGCTGCG GCGAGCGGTA TCAGCTCACT

CAAAGGCGGT AATACGGTTA TCCACAGAAT CAGGGGATAA CGCAGGAAAG

AACATGTGAG CAAAAGGCCA GCAAAAGGCC AGGAACCGTA AAAAGGCCGC

GTTGCTGGCG TTTTTCCATA GGCTCCGCCC CCCTGACGAG CATCACAAAA

ATCGACGCTC AAGTCAGAGG TGGCGAAACC CGACAGGACT ATAAAGATAC

CAGGCGTTTC CCCCTGGAAG CTCCCTCGTG CGCTCTCCTG TTCCGACCCT

GCCGCTTACC GGATACCTGT CCGCCTTTCT CCCTTCGGGA AGCGTGGCGC

TTTCTCATAG CTCACGCTGT AGGTATCTCA GTTCGGTGTA GGTCGTTCGC

TCCAAGCTGG GCTGTGTGCA CGAACCCCCC GTTCAGCCCG ACCGCTGCGC

CTTATCCGGT AACTATCGTC TTGAGTCCAA CCCGGTAAGA CACGACTTAT

CGCCACTGGC AGCAGCCACT GGTAACAGGA TTAGCAGAGC GAGGTATGTA

GGCGGTGCTA CAGAGTTCTT GAAGTGGTGG CCTAACTACG GCTACACTAG

AAGAACAGTA TTTGGTATCT GCGCTCTGCT GAAGCCAGTT ACCTTCGGAA

AAAGAGTTGG TAGCTCTTGA TCCGGCAAAC AAACCACCGC TGGTAGCGGT

GGTTTTTTTG TTTGCAAGCA GCAGATTACG CGCAGAAAAA AAGGATCTCA

AGAAGATCCT TTGATCTTTT CTACGGGGTC TGACGCTCAG TGGAACGAAA

ACTCACGTTA AGGGATTTTG GTCATGAGAT TATCAAAAAG GATCTTCACC

TAGATCCTTT TAAATTAAAA ATGAAGTTTT AAATCAATCT AAAGTATATA

TGAGTAAACT TGGTCTGACA GTTACCAATG CTTAATCAGT GAGGCACCTA

TCTCAGCGAT CTGTCTATTT CGTTCATCCA TAGTTGCCTG ACTCCCCGTC

GTGTAGATAA CTACGATACG GGAGGGCTTA CCATCTGGCC CCAGTGCTGC

AATGATACCG CGAGACCCAC GCTCACCGGC TCCAGATTTA TCAGCAATAA

ACCAGCCAGC CGGAAGGGCC GAGCGCAGAA GTGGTCCTGC AACTTTATCC

GCCTCCATCC AGTCTATTAA TTGTTGCCGG GAAGCTAGAG TAAGTAGTTC

GCCAGTTAAT AGTTTGCGCA ACGTTGTTGC CATTGCTACA GGCATCGTGG

TGTCACGCTC GTCGTTTGGT ATGGCTTCAT TCAGCTCCGG TTCCCAACGA

TCAAGGCGAG TTACATGATC CCCCATGTTG TGCAAAAAAG CGGTTAGCTC

CTTCGGTCCT CCGATCGTTG TCAGAAGTAA GTTGGCCGCA GTGTTATCAC

TCATGGTTAT GGCAGCACTG CATAATTCTC TTACTGTCAT GCCATCCGTA

-continued

List of Sequences with short description

AGATGCTTTT CTGTGACTGG TGAGTACTCA ACCAAGTCAT TCTGAGAATA

GTGTATGCGG CGACCGAGTT GCTCTTGCCC GGCGTCAATA CGGGATAATA

CCGCGCCACA TAGCAGAACT TTAAAAGTGC TCATCATTGG AAAACGTTCT

TCGGGGCGAA AACTCTCAAG GATCTTACCG CTGTTGAGAT CCAGTTCGAT

GTAACCCACT CGTGCACCCA ACTGATCTTC AGCATCTTTT ACTTTCACCA

GCGTTTCTGG GTGAGCAAAA ACAGGAAGGC AAAATGCCGC AAAAAAGGGA

ATAAGGGCGA CACGGAAATG TTGAATACTC ATACTCTTCC TTTTTCAATA

TTATTGAAGC ATTTATCAGG GTTATTGTCT CATGAGCGGA TACATATTTG

AATGTATTTA GAAAAATAAA CAAATAGGGG TTCCGCGCAC ATTTCCCCGA

AAAGTGCCAC CTGACGTCGA CGGATCGGGA GATCTCCCGA TCCCCTATGG

TGCACTCTCA GTACAATCTG CTCTGATGCC GCATAGTTAA GCCAGTATCT

GCTCCCTGCT TGTGTGTTGG AGGTCGCTGA GTAGTGCGCG AGCAAAATTT

AAGCTACAAC AAGGCAAGGC TTGACCGAC

IgG4 Expression Vector pMORPH2 ®_h_Igγ4

SEQ ID NO: 43

TAATACGACT CACTATAGGG AGACCCAAGC TGGCTAGCGC CACCATGAAA

CACCTGTGGT TCTTCCTCCT GCTGGTGGCA GCTCCCAGAT GGGTCCTGTC

CCAGGTGCAA TTGCAACAGT CTGGTCCGGG CCTGGTGAAA CCGAGCCAAA

CCCTGAGCCT GACCTGTGCG ATTTCCGGAG ATAGCGTGAG CGATAATTCT

GCTGCTTGGT CTTGGATTCG CCAGTCTCCT GGGCGTGGCC TCGAGTGGCT

GGGCCTTATC TATCTTCGTA GCAAGTGGGA TAACGATTAT GCGGTGAGCG

TGAAAAGCCG GATTACCATC AACCCGGATA CTTCGAAAAA CCAGTTTAGC

CTGCAACTGA ACAGCGTGAC CCCGGAAGAT ACGGCCGTGT ATTATTGCGC

GCGTACTGGT CGTGCTGATG AGTTTGATGT TTGGGGCCAA GGCACCCTGG

TGACGGTTAG CTCAGCTTCC ACCAAGGGAC CATCCGTCTT CCCCCTGGCG

CCCTGCTCCA GGAGCACCTC CGAGAGCACA GCCGCCCTGG GCTGCCTGGT

CAAGGACTAC TTCCCCGAAC CGGTGACGGT GTCGTGGAAC TCAGGCGCCC

TGACCAGCGG CGTGCACACC TTCCCGGCTG TCCTACAGTC CTCAGGACTC

TACTCCCTCA GCAGCGTGGT GACCGTGCCC TCCAGCAGCT TGGGCACGAA

GACCTACACC TGCAACGTAG ATCACAAGCC CAGCAACACC AAGGTGGACA

AGAGAGTTGA GTCCAAATAT GGTCCCCCAT GCCCATCATG CCCAGCACCT

GAGTTCCTGG GGGGACCATC AGTCTTCCTG TTCCCCCCAA AACCCAAGGA

CACTCTCATG ATCTCCCGGA CCCCTGAGGT CACGTGCGTG GTGGTGGACG

TGAGCCAGGA AGACCCCGAG GTCCAGTTCA ACTGGTACGT GGATGGCGTG

GAGGTGCATA ATGCCAAGAC AAAGCCGCGG GAGGAGCAGT TCAACAGCAC

GTACCGTGTG GTCAGCGTCC TCACCGTCCT GCACCAGGAC TGGCTGAACG

GCAAGGAGTA CAAGTGCAAG GTCTCCAACA AAGGCCTCCC GTCCTCCATC

GAGAAAACCA TCTCCAAAGC CAAAGGGCAG CCCCGAGAGC CACAGGTGTA

CACCCTGCCC CCATCCCAGG AGGAGATGAC CAAGAACCAG GTCAGCCTGA

CCTGCCTGGT CAAAGGCTTC TACCCCAGCG ACATCGCCGT GGAGTGGGAG

-continued

List of Sequences with short description

AGCAATGGGC AGCCGGAGAA CAACTACAAG ACCACGCCTC CCGTGCTGGA

CTCCGACGGC TCCTTCTTCC TCTACAGCAG GCTAACCGTG GACAAGAGCA

GGTGGCAGGA GGGGAATGTC TTCTCATGCT CCGTGATGCA TGAGGCTCTG

CACAACCACT ACACACAGAA GAGCCTCTCC CTGTCTCTGG GTAAATGAGG

GCCCGTTTAA ACGGGTGGCA TCCCTGTGAC CCCTCCCCAG TGCCTCTCCT

GGCCCTGGAA GTTGCCACTC CAGTGCCCAC CAGCCTTGTC CTAATAAAAT

TAAGTTGCAT CATTTTGTCT GACTAGGTGT CCTTCTATAA TATTATGGGG

TGGAGGGGGG TGGTATGGAG CAAGGGGCAA GTTGGGAAGA CAACCTGTAG

GGCCTGCGGG GTCTATTGGG AACCAAGCTG GAGTGCAGTG GCACAATCTT

GGCTCACTGC AATCTCCGCC TCCTGGGTTC AAGCGATTCT CCTGCCTCAG

CCTCCCGAGT TGTTGGGATT CCAGGCATGC ATGACCAGGC TCACCTAATT

TTTGTTTTTT TGGTAGAGAC GGGGTTTCAC CATATTGGCC AGGCTGGTCT

CCAACTCCTA ATCTCAGGTG ATCTACCCAC CTTGGCCTCC CAAATTGCTG

GGATTACAGG CGTGAACCAC TGCTCCCTTC CCTGTCCTTC TGATTTTAAA

ATAACTATAC CAGCAGGAGG ACGTCCAGAC ACAGCATAGG CTACCTGGCC

ATGCCCAACC GGTGGGACAT TTGAGTTGCT TGCTTGGCAC TGTCCTCTCA

TGCGTTGGGT CCACTCAGTA GATGCCTGTT GAATTGGGTA CGCGGCATCG

ATTCCACGCG CCCTGTAGCG GCGCATTAAG CGCGGCGGGT GTGGTGGTTA

CGCGCAGCGT GACCGCTACA CTTGCCAGCG CCCTAGCGCC CGCTCCTTTC

GCTTTCTTCC CTTCCTTTCT CGCCACGTTC GCCGGCTTTC CCCGTCAAGC

TCTAAATCGG GGGCTCCCTT TAGGGTTCCG ATTTAGTGCT TTACGGCACC

TCGACCCCAA AAAACTTGAT TAGGGTGATG GTTCACGTAG TGGGCCATCG

CCCTGATAGA CGGTTTTTCG CCCTTTGACG TTGGAGTCCA CGTTCTTTAA

TAGTGGACTC TTGTTCCAAA CTGGAACAAC ACTCAACCCT ATCTCGGTCT

ATTCTTTTGA TTTATAAGGG ATTTTGCCGA TTTCGGCCTA TTGGTTAAAA

AATGAGCTGA TTTAACAAAA ATTTAACGCG AATTAATTCT GTGGAATGTG

TGTCAGTTAG GGTGTGGAAA GTCCCCAGGC TCCCCAGCAG GCAGAAGTAT

GCAAAGCATG CATCTCAATT AGTCAGCAAC CAGGTGTGGA AAGTCCCCAG

GCTCCCCAGC AGGCAGAAGT ATGCAAAGCA TGCATCTCAA TTAGTCAGCA

ACCATAGTCC CGCCCCTAAC TCCGCCCATC CCGCCCCTAA CTCCGCCCAG

TTCCGCCCAT TCTCCGCCCC ATGGCTGACT AATTTTTTTT ATTTATGCAG

AGGCCGAGGC CGCCTCTGCC TCTGAGCTAT TCCAGAAGTA GTGAGGAGGC

TTTTTTGGAG GCCTAGGCTT TTGCAAAAAG CTCCCGGGAG CTTGTATATC

CATTTTCGGA TCTGATCAAG AGACAGGATG AGGATCGTTT CGCATGATTG

AACAAGATGG ATTGCACGCA GGTTCTCCGG CCGCTTGGGT GGAGAGGCTA

TTCGGCTATG ACTGGGCACA ACAGACAATC GGCTGCTCTG ATGCCGCCGT

GTTCCGGCTG TCAGCGCAGG GGCGCCCGGT TCTTTTTGTC AAGACCGACC

TGTCCGGTGC CCTGAATGAA CTGCAGGACG AGGCAGCGCG GCTATCGTGG

CTGGCCACGA CGGGCGTTCC TTGCGCAGCT GTGCTCGACG TTGTCACTGA

-continued

| List of Sequences with short description |
|---|
| AGCGGGAAGG GACTGGCTGC TATTGGGCGA AGTGCCGGGG CAGGATCTCC |
| TGTCATCTCA CCTTGCTCCT GCCGAGAAAG TATCCATCAT GGCTGATGCA |
| ATGCGGCGGC TGCATACGCT TGATCCGGCT ACCTGCCCAT TCGACCACCA |
| AGCGAAACAT CGCATCGAGC GAGCACGTAC TCGGATGGAA GCCGGTCTTG |
| TCGATCAGGA TGATCTGGAC GAAGAGCATC AGGGGCTCGC GCCAGCCGAA |
| CTGTTCGCCA GGCTCAAGGC GCGCATGCCC GACGGCGAGG ATCTCGTCGT |
| GACCCATGGC GATGCCTGCT TGCCGAATAT CATGGTGGAA AATGGCCGCT |
| TTTCTGGATT CATCGACTGT GGCCGGCTGG GTGTGGCGGA CCGCTATCAG |
| GACATAGCGT TGGCTACCCG TGATATTGCT GAAGAGCTTG GCGGCGAATG |
| GGCTGACCGC TTCCTCGTGC TTTACGGTAT CGCCGCTCCC GATTCGCAGC |
| GCATCGCCTT CTATCGCCTT CTTGACGAGT TCTTCTGAGC GGGACTCTGG |
| GGTTCGAAAT GACCGACCAA GCGACGCCCA ACCTGCCATC ACGAGATTTC |
| GATTCCACCG CCGCCTTCTA TGAAAGGTTG GGCTTCGGAA TCGTTTTCCG |
| GGACGCCGGC TGGATGATCC TCCAGCGCGG GGATCTCATG CTGGAGTTCT |
| TCGCCCACCC CAACTTGTTT ATTGCAGCTT ATAATGGTTA CAAATAAAGC |
| AATAGCATCA CAAATTTCAC AAATAAAGCA TTTTTTTCAC TGCATTCTAG |
| TTGTGGTTTG TCCAAACTCA TCAATGTATC TTATCATGTC TGTATACCGT |
| CGACCTCTAG CTAGAGCTTG GCGTAATCAT GGTCATAGCT GTTTCCTGTG |
| TGAAATTGTT ATCCGCTCAC AATTCCACAC AACATACGAG CCGGAAGCAT |
| AAAGTGTAAA GCCTGGGGTG CCTAATGAGT GAGCTAACTC ACATTAATTG |
| CGTTGCGCTC ACTGCCCGCT TTCCAGTCGG GAAACCTGTC GTGCCAGCTG |
| CATTAATGAA TCGGCCAACG CGCGGGGAGA GGCGGTTTGC GTATTGGGCG |
| CTCTTCCGCT TCCTCGCTCA CTGACTCGCT GCGCTCGGTC GTTCGGCTGC |
| GGCGAGCGGT ATCAGCTCAC TCAAAGGCGG TAATACGGTT ATCCACAGAA |
| TCAGGGGATA ACGCAGGAAA GAACATGTGA GCAAAAGGCC AGCAAAAGGC |
| CAGGAACCGT AAAAAGGCCG CGTTGCTGGC GTTTTTCCAT AGGCTCCGCC |
| CCCCTGACGA GCATCACAAA AATCGACGCT CAAGTCAGAG GTGGCGAAAC |
| CCGACAGGAC TATAAAGATA CCAGGCGTTT CCCCCTGGAA GCTCCCTCGT |
| GCGCTCTCCT GTTCCGACCC TGCCGCTTAC CGGATACCTG TCCGCCTTTC |
| TCCCTTCGGG AAGCGTGGCG CTTTCTCATA GCTCACGCTG TAGGTATCTC |
| AGTTCGGTGT AGGTCGTTCG CTCCAAGCTG GGCTGTGTGC ACGAACCCCC |
| CGTTCAGCCC GACCGCTGCG CCTTATCCGG TAACTATCGT CTTGAGTCCA |
| ACCCGGTAAG ACACGACTTA TCGCCACTGG CAGCAGCCAC TGGTAACAGG |
| ATTAGCAGAG CGAGGTATGT AGGCGGTGCT ACAGAGTTCT TGAAGTGGTG |
| GCCTAACTAC GGCTACACTA GAAGAACAGT ATTTGGTATC TGCGCTCTGC |
| TGAAGCCAGT TACCTTCGGA AAAAGAGTTG GTAGCTCTTG ATCCGGCAAA |
| CAAACCACCG CTGGTAGCGG TGGTTTTTTT GTTTGCAAGC AGCAGATTAC |
| GCGCAGAAAA AAAGGATCTC AAGAAGATCC TTTGATCTTT TCTACGGGGT |
| CTGACGCTCA GTGGAACGAA AACTCACGTT AAGGGATTTT GGTCATGAGA |

-continued

List of Sequences with short description

TTATCAAAAA GGATCTTCAC CTAGATCCTT TTAAATTAAA AATGAAGTTT

TAAATCAATC TAAAGTATAT ATGAGTAAAC TTGGTCTGAC AGTTACCAAT

GCTTAATCAG TGAGGCACCT ATCTCAGCGA TCTGTCTATT TCGTTCATCC

ATAGTTGCCT GACTCCCCGT CGTGTAGATA ACTACGATAC GGGAGGGCTT

ACCATCTGGC CCCAGTGCTG CAATGATACC GCGAGACCCA CGCTCACCGG

CTCCAGATTT ATCAGCAATA AACCAGCCAG CCGGAAGGGC CGAGCGCAGA

AGTGGTCCTG CAACTTTATC CGCCTCCATC CAGTCTATTA ATTGTTGCCG

GGAAGCTAGA GTAAGTAGTT CGCCAGTTAA TAGTTTGCGC AACGTTGTTG

CCATTGCTAC AGGCATCGTG GTGTCACGCT CGTCGTTTGG TATGGCTTCA

TTCAGCTCCG GTTCCCAACG ATCAAGGCGA GTTACATGAT CCCCCATGTT

GTGCAAAAAA GCGGTTAGCT CCTTCGGTCC TCCGATCGTT GTCAGAAGTA

AGTTGGCCGC AGTGTTATCA CTCATGGTTA TGGCAGCACT GCATAATTCT

CTTACTGTCA TGCCATCCGT AAGATGCTTT TCTGTGACTG GTGAGTACTC

AACCAAGTCA TTCTGAGAAT AGTGTATGCG GCGACCGAGT TGCTCTTGCC

CGGCGTCAAT ACGGGATAAT ACCGCGCCAC ATAGCAGAAC TTTAAAAGTG

CTCATCATTG GAAAACGTTC TTCGGGGCGA AAACTCTCAA GGATCTTACC

GCTGTTGAGA TCCAGTTCGA TGTAACCCAC TCGTGCACCC AACTGATCTT

CAGCATCTTT TACTTTCACC AGCGTTTCTG GGTGAGCAAA AACAGGAAGG

CAAAATGCCG CAAAAAAGGG AATAAGGGCG ACACGGAAAT GTTGAATACT

CATACTCTTC CTTTTTCAAT ATTATTGAAG CATTTATCAG GGTTATTGTC

TCATGAGCGG ATACATATTT GAATGTATTT AGAAAAATAA ACAAATAGGG

GTTCCGCGCA CATTTCCCCG AAAAGTGCCA CCTGACGTCG ACGGATCGGG

AGATCTCCCG ATCCCCTATG GTGCACTCTC AGTACAATCT GCTCTGATGC

CGCATAGTTA AGCCAGTATC TGCTCCCTGC TTGTGTGTTG GAGGTCGCTG

AGTAGTGCGC GAGCAAAATT TAAGCTACAA CAAGGCAAGG CTTGACCGAC

ATTTGCATGA AGAATCTGCT TAGGGTTAGG CGTTTTGCGC TGCTTCGCGA

TGTACGGGCC AGATATACGC GTTGACATTG ATTATTGACT AGTTATTAAT

AGTAATCAAT TACGGGGTCA TTAGTTCATA GCCCATATAT GGAGTTCCGC

GTTACATAAC TTACGGTAAA TGGCCCGCCT GGCTGACCGC CCAACGACCC

CCGCCCATTG ACGTCAATAA TGACGTATGT TCCCATAGTA ACGCCAATAG

GGACTTTCCA TTGACGTCAA TGGGTGGAGT ATTTACGGTA AACTGCCCAC

TTGGCAGTAC ATCAAGTGTA TCATATGCCA AGTACGCCCC CTATTGACGT

CAATGACGGT AAATGGCCCG CCTGGCATTA TGCCCAGTAC ATGACCTTAT

GGGACTTTCC TACTTGGCAG TACATCTACG TATTAGTCAT CGCTATTACC

ATGGTGATGC GGTTTTGGCA GTACATCAAT GGGCGTGGAT AGCGGTTTGA

CTCACGGGGA TTTCCAAGTC TCCACCCCAT TGACGTCAAT GGGAGTTTGT

TTTGGCACCA AAATCAACGG GACTTTCCAA AATGTCGTAA CAACTCCGCC

CCATTGACGC AAATGGGCGG TAGGCGTGTA CGGTGGGAGG TCTATATAAG

CAGAGCTCTC TGGCTAACTA GAGAACCCAC TGCTTACTGG CTTATCGAAA

-continued

List of Sequences with short description

T

IgG Lambda Chain Expression Vector pMORPH ® 2_h_Ig_lambda2
SEQ ID NO: 44

TAATACGACT CACTATAGGG AGACCCAAGC TGGCTAGCGC CACCATGGCC

TGGGCTCTGC TGCTCCTCAC CCTCCTCACT CAGGGCACAG GATCCTGGGC

TGATATCGTG CTGACCCAGC CGCCTTCAGT GAGTGGCGCA CCAGGTCAGC

GTGTGACCAT CTCGTGTAGC GGCAGCAGCA GCAACATTGG TAATAATTAT

GTGTCTTGGT ACCAGCAGTT GCCCGGGACG GCGCCGAAAC TTCTGATTTC

TCGTAATTCT AAGCGTCCCT CAGGCGTGCC GGATCGTTTT AGCGGATCCA

AAAGCGGCAC CAGCGCGAGC CTTGCGATTA CGGGCCTGCA AAGCGAAGAC

GAAGCGGATT ATTATTGCTC TACTTATGAT ACTTTTTCTA TTGTGTTTGG

CGGCGGCACG AAGTTAACCG TCCTAGGTCA GCCCAAGGCT GCCCCCTCGG

TCACTCTGTT CCCGCCCTCC TCTGAGGAGC TTCAAGCCAA CAAGGCCACA

CTGGTGTGTC TCATAAGTGA CTTCTACCCG GGAGCCGTGA CAGTGGCCTG

GAAGGCAGAT AGCAGCCCCG TCAACGCGGG AGTGGAGACC ACCACACCCT

CCAAACAAAG CAACAACAAG TACGCGGCCA GCAGCTATCT GAGCCTGACG

CCTGAGCAGT GGAAGTCCCA CAGAAGCTAC AGCTGCCAGG TCACGCATGA

AGGGAGCACC GTGGAGAAGA CAGTGGCCCC TACAGAATGT TCATAGGGGC

CCGTTTAAAC GGGTGGCATC CCTGTGACCC CTCCCCAGTG CCTCTCCTGG

CCCTGGAAGT TGCCACTCCA GTGCCCACCA GCCTTGTCCT AATAAAATTA

AGTTGCATCA TTTTGTCTGA CTAGGTGTCC TTCTATAATA TTATGGGGTG

GAGGGGGGTG GTATGGAGCA AGGGGCAAGT TGGGAAGACA ACCTGTAGGG

CCTGCGGGGT CTATTGGGAA CCAAGCTGGA GTGCAGTGGC ACAATCTTGG

CTCACTGCAA TCTCCGCCTC CTGGGTTCAA GCGATTCTCC TGCCTCAGCC

TCCCGAGTTG TTGGGATTCC AGGCATGCAT GACCAGGCTC ACCTAATTTT

TGTTTTTTTG GTAGAGACGG GGTTTCACCA TATTGGCCAG GCTGGTCTCC

AACTCCTAAT CTCAGGTGAT CTACCCACCT TGGCCTCCCA AATTGCTGGG

ATTACAGGCG TGAACCACTG CTCCCTTCCC TGTCCTTCTG ATTTTAAAAT

AACTATACCA GCAGGAGGAC GTCCAGACAC AGCATAGGCT ACCTGGCCAT

GCCCAACCGG TGGGACATTT GAGTTGCTTG CTTGGCACTG TCCTCTCATG

CGTTGGGTCC ACTCAGTAGA TGCCTGTTGA ATTGGGTACG CGGCATCGAT

TCCACGCGCC CTGTAGCGGC GCATTAAGCG CGGCGGGTGT GGTGGTTACG

CGCAGCGTGA CCGCTACACT TGCCAGCGCC CTAGCGCCCG CTCCTTTCGC

TTTCTTCCCT TCCTTTCTCG CCACGTTCGC CGGCTTTCCC CGTCAAGCTC

TAAATCGGGG GCTCCCTTTA GGGTTCCGAT TTAGTGCTTT ACGGCACCTC

GACCCCAAAA AACTTGATTA GGGTGATGGT TCACGTAGTG GGCCATCGCC

CTGATAGACG GTTTTTCGCC CTTTGACGTT GGAGTCCACG TTCTTTAATA

GTGGACTCTT GTTCCAAACT GGAACAACAC TCAACCCTAT CTCGGTCTAT

TCTTTTGATT TATAAGGGAT TTTGGGGATT TCGGCCTATT GGTTAAAAAA

TGAGCTGATT TAACAAAAAT TTAACGCGAA TTAATTCTGT GGAATGTGTG

-continued

List of Sequences with short description

TCAGTTAGGG TGTGGAAAGT CCCCAGGCTC CCCAGGCAGG CAGAAGTATG

CAAAGCATGC ATCTCAATTA GTCAGCAACC AGGTGTGGAA AGTCCCCAGG

CTCCCCAGCA GGCAGAAGTA TGCAAAGCAT GCATCTCAAT TAGTCAGCAA

CCATAGTCCC GCCCCTAACT CCGCCCATCC CGCCCCTAAC TCCGCCCAGT

TCCGCCCATT CTCCGCCCCA TGGCTGACTA ATTTTTTTTA TTTATGCAGA

GGCCGAGGCC GCCTCTGCCT CTGAGCTATT CCAGAAGTAG TGAGGAGGCT

TTTTTGGAGG CCTAGGCTTT TGCAAAAAGC TCCCGGGAGC TTGTATATCC

ATTTTCGGAT CTGATCAGCA CGTGTTGACA ATTAATCATC GGCATAGTAT

ATCGGCATAG TATAATACGA CAAGGTGAGG AACTAAACCA TGGCCAAGTT

GACCAGTGCC GTTCCGGTGC TCACCGCGCG CGACGTCGCC GGAGCGGTCG

AGTTCTGGAC CGACCGGCTC GGGTTCTCCC GGGACTTCGT GGAGGACGAC

TTCGCCGGTG TGGTCCGGGA CGACGTGACC CTGTTCATCA GCGCGGTCCA

GGACCAGGTG GTGCCGGACA ACACCCTGGC CTGGGTGTGG GTGCGCGGCC

TGGACGAGCT GTACGCCGAG TGGTCGGAGG TCGTGTCCAC GAACTTCCGG

GACGCCTCCG GGCCGGCCAT GACCGAGATC GGCGAGCAGC CGTGGGGGCG

GGAGTTCGCC CTGCGCGACC CGGCCGGCAA CTGCGTGCAC TTCGTGGCCG

AGGAGCAGGA CTGACACGTG CTACGAGATT TCGATTCCAC CGCCGCCTTC

TATGAAAGGT TGGGCTTCGG AATCGTTTTC CGGGACGCCG GCTGGATGAT

CCTCCAGCGC GGGGATCTCA TGCTGGAGTT CTTCGCCCAC CCCAACTTGT

TTATTGCAGC TTATAATGGT TACAAATAAA GCAATAGCAT CACAAATTTC

ACAAATAAAG CATTTTTTTC ACTGCATTCT AGTTGTGGTT TGTCCAAACT

CATCAATGTA TCTTATCATG TCTGTATACC GTCGACCTCT AGCTAGAGCT

TGGCGTAATC ATGGTCATAG CTGTTTCCTG TGTGAAATTG TTATCCGCTC

ACAATTCCAC ACAACATACG AGCCGGAAGC ATAAAGTGTA AAGCCTGGGG

TGCCTAATGA GTGAGCTAAC TCACATTAAT TGCGTTGCGC TCACTGCCCG

CTTTCCAGTC GGGAAACCTG TCGTGCCAGC TGCATTAATG AATCGGCCAA

CGCGCGGGGA GAGGCGGTTT GCGTATTGGG CGCTCTTCCG CTTCCTCGCT

CACTGACTCG CTGCGCTCGG TCGTTCGGCT GCGGCGAGCG GTATCAGCTC

ACTCAAAGGC GGTAATACGG TTATCCACAG AATCAGGGGA TAACGCAGGA

AAGAACATGT GAGCAAAAGG CCAGCAAAAG GCCAGGAACC GTAAAAAGGC

CGCGTTGCTG GCGTTTTTCC ATAGGCTCCG CCCCCCTGAC GAGCATCACA

AAAATCGACG CTCAAGTCAG AGGTGGCGAA ACCCGACAGG ACTATAAAGA

TACCAGGCGT TTCCCCCTGG AAGCTCCCTC GTGCGCTCTC CTGTTCCGAC

CCTGCCGCTT ACCGGATACC TGTCCGCCTT TCTCCCTTCG GGAAGCGTGG

CGCTTTCTCA ATGCTCACGC TGTAGGTATC TCAGTTCGGT GTAGGTCGTT

CGCTCCAAGC TGGGCTGTGT GCACGAACCC CCCGTTCAGC CCGACCGCTG

CGCCTTATCC GGTAACTATC GTCTTGAGTC CAACCCGGTA AGACACGACT

TATCGCCACT GGCAGCAGCC ACTGGTAACA GGATTAGCAG AGCGAGGTAT

GTAGGCGGTG CTACAGAGTT CTTGAAGTGG TGGCCTAACT ACGGCTACAC

-continued

| List of Sequences with short description |
| --- |

TAGAAGGACA GTATTTGGTA TCTGCGCTCT GCTGAAGCCA GTTACCTTCG

GAAAAAGAGT TGGTAGCTCT TGATCCGGCA AACAAACCAC CGCTGGTAGC

GGTGGTTTTT TTGTTTGCAA GCAGCAGATT ACGCGCAGAA AAAAAGGATC

TCAAGAAGAT CCTTTGATCT TTTCTACGGG GTCTGACGCT CAGTGGAACG

AAAACTCACG TTAAGGGATT TTGGTCATGA GATTATCAAA AAGGATCTTC

ACCTAGATCC TTTTAAATTA AAAATGAAGT TTTAAATCAA TCTAAAGTAT

ATATGAGTAA ACTTGGTCTG ACAGTTACCA ATGCTTAATC AGTGAGGCAC

CTATCTCAGC GATCTGTCTA TTTCGTTCAT CCATAGTTGC CTGACTCCCC

GTCGTGTAGA TAACTACGAT ACGGGAGGGC TTACCATCTG GCCCCAGTGC

TGCAATGATA CCGCGAGACC CACGCTCACC GGCTCCAGAT TTATCAGCAA

TAAACCAGCC AGCCGGAAGG GCCGAGCGCA GAAGTGGTCC TGCAACTTTA

TCCGCCTCCA TCCAGTCTAT TAATTGTTGC CGGGAAGCTA GAGTAAGTAG

TTCGCCAGTT AATAGTTTGC GCAACGTTGT TGCCATTGCT ACAGGCATCG

TGGTGTCACG CTCGTCGTTT GGTATGGCTT CATTCAGCTC CGGTTCCCAA

CGATCAAGGC GAGTTACATG ATCCCCCATG TTGTGCAAAA AAGCGGTTAG

CTCCTTCGGT CCTCCGATCG TTGTCAGAAG TAAGTTGGCC GCAGTGTTAT

CACTCATGGT TATGGCAGCA CTGCATAATT CTCTTACTGT CATGCCATCC

GTAAGATGCT TTTCTGTGAC TGGTGAGTAC TCAACCAAGT CATTCTGAGA

ATAGTGTATG CGGCGACCGA GTTGCTCTTG CCCGGCGTCA ATACGGGATA

ATACCGCGCC ACATAGCAGA ACTTTAAAAG TGCTCATCAT TGGAAAACGT

TCTTCGGGGC GAAAACTCTC AAGGATCTTA CCGCTGTTGA GATCCAGTTC

GATGTAACCC ACTCGTGCAC CCAACTGATC TTCAGCATCT TTTACTTTCA

CCAGCGTTTC TGGGTGAGCA AAAACAGGAA GGCAAAATGC CGCAAAAAAG

GGAATAAGGG CGACACGGAA ATGTTGAATA CTCATACTCT TCCTTTTTCA

ATATTATTGA AGCATTTATC AGGGTTATTG TCTCATGAGC GGATACATAT

TTGAATGTAT TTAGAAAAAT AAACAAATAG GGGTTCCGCG CACATTTCCC

CGAAAAGTGC CACCTGACGT CGACGGATCG GGAGATCTCC CGATCCCCTA

TGGTCGACTC TCAGTACAAT CTGCTCTGAT GCCGCATAGT TAAGCCAGTA

TCTGCTCCCT GCTTGTGTGT TGGAGGTCGC TGAGTAGTGC GCGAGCAAAA

TTTAAGCTAC AACAAGGCAA GGCTTGACCG ACAATTGCAT GAAGAATCTG

CTTAGGGTTA GGCGTTTTGC GCTGCTTCGC GATGTACGGG CCAGATATAC

GCGTTGACAT TGATTATTGA CTAGTTATTA ATAGTAATCA ATTACGGGGT

CATTAGTTCA TAGCCCATAT ATGGAGTTCC GCGTTACATA ACTTACGGTA

AATGGCCCGC CTGGCTGACC GCCCAACGAC CCCCGCCCAT TGACGTCAAT

AATGACGTAT GTTCCCATAG TAACGCCAAT AGGGACTTTC CATTGACGTC

AATGGGTGGA CTATTTACGG TAAACTGCCC ACTTGGCAGT ACATCAAGTG

TATCATATGC CAAGTACGCC CCCTATTGAC GTCAATGACG GTAAATGGCC

CGCCTGGCAT TATGCCCAGT ACATGACCTT ATGGGACTTT CCTACTTGGC

AGTACATCTA CGTATTAGTC ATCGCTATTA CCATGGTCAT GCGGTTTTGG

-continued

List of Sequences with short description

CAGTACATCA ATGGGCGTGG ATAGCGGTTT GACTCACGGG GATTTCCAAG

TCTCCACCCC ATTGACGTCA ATGGGAGTTT GTTTTGGCAC CAAAATCAAC

GGGACTTTCC AAAATGTCGT AACAACTCCG CCCCATTGAC GCAAATGGGC

GGTAGGCGTG TACGGTGGGA GGTCTATATA AGCAGAGCTC TCTGGCTAAC

TAGAGAACCC ACTGCTTACT GGCTTATCGA AAT

IqG kappa Chain Expression Vector pMORPH ® 2_h_Ig_kappa

SEQ ID NO: 45

TAATACGACT CACTATAGGG AGACCCAAGC TGGCTAGCGC CACCATGGTG

TTGCAGACCC AGGTCTTCAT TTCTCTGTTG CTCTGGATCT CTGGTGCCTA

CGGGGATATC CAGATGACCC AGAGCCCGTC TAGCCTGAGC GCGAGCGTGG

GTGATCGTGT GACCATTACC TGCAGAGCGA GCCAGTCTAT TTCTAATTGG

CTGAATTGGT ACCAGCAGAA ACCAGGTAAA GCACCGAAAC TATTAATTTA

TAAGGCTTCT ACTTTGCAAA GCGGGGTCCC GTCCCGTTTT AGCGGCTCTG

GATCCGGCAC TGATTTTACC CTGACCATTA GCAGCCTGCA ACCTGAAGAC

TTTGCGACTT ATTATTGCCA GCAGTATGGT AATATTCCTA TTACCTTTGG

CCAGGGTACG AAAGTTGAAA TTAAACGTAC GGTGGCTGCA CCATCTGTCT

TCATCTTCCC GCCATCTGAT GAGCAGTTGA AATCTGGAAC TGCCTCTGTT

GTGTGCCTGC TGAATAACTT CTATCCCAGA GAGGCCAAAG TACAGTGGAA

GGTGGATAAC GCCCTCCAAT CGGGTAACTC CCAGGAGAGT GTCACAGAGC

AGGACAGCAA GGACAGCACC TACAGCCTCA GCAGCACCCT GACGCTGAGC

AAAGCAGACT ACGAGAAACA CAAAGTCTAC GCCTGCGAAG TCACCCATCA

GGGCCTGAGC TCGCCCGTCA CAAAGAGCTT CAACAGGGGA GAGTGTTAGG

GGCCCGTTTA AACGGGTGGC ATCCCTGTGA CCCCTCCCCA GTGCCTCTCC

TGGCCCTGGA AGTTGCCACT CCAGTGCCCA CCAGCCTTGT CCTAATAAAA

TTAAGTTGCA TCATTTTGTC TGACTAGGTG TCCTTCTATA ATATTATGGG

GTGGAGGGGG GTGGTATGGA GCAAGGGGCA AGTTGGGAAG ACAACCTGTA

GGGCCTGCGG GGTCTATTGG GAACCAAGCT GGAGTGCAGT GGCACAATCT

TGGCTCACTG CAATCTCCGC CTCCTGGGTT CAAGCGATTC TCCTGCCTCA

GCCTCCCGAG TTGTTGGGAT TCCAGGCATG CATGACCAGG CTCACCTAAT

TTTTGTTTTT TTGGTAGAGA CGGGGTTTCA CCATATTGGC CAGGCTGGTC

TCCAACTCCT AATCTCAGGT GATCTACCCA CCTTGGCCTC CCAAATTGCT

GGGATTACAG GCGTGAACCA CTGCTCCCTT CCCTGTCCTT CTGATTTTAA

AATAACTATA CCAGCAGGAG GACGTCCAGA CACAGCATAG GCTACCTGGC

CATGCCCAAC CGGTGGGACA TTTGAGTTGC TTGCTTGGCA CTGTCCTCTC

ATGCGTTGGG TCCACTCAGT AGATGCCTGT TGAATTGGGT ACGCGGCATC

GATTCCACGC GCCCTGTAGC GGCGCATTAA GCGCGGCGGG TGTGGTGGTT

ACGCGCAGCG TGACCGCTAC ACTTGCCAGC GCCCTAGCGC CCGCTCCTTT

CGCTTTCTTC CCTTCCTTTC TCGCCACGTT CGCCGGCTTT CCCCGTCAAG

CTCTAAATCG GGGGCTCCCT TTAGGGTTCC GATTTAGTGC TTTACGGCAC

CTCGACCCCA AAAAACTTGA TTAGGGTGAT GGTTCACGTA GTGGGCCATC

-continued

List of Sequences with short description

GCCCTGATAG ACGGTTTTTC GCCCTTTGAC GTTGGAGTCC ACGTTCTTTA

ATAGTGGACT CTTGTTCCAA ACTGGAACAA CACTCAACCC TATCTCGGTC

TATTCTTTTG ATTTATAAGG GATTTTGGGG ATTTCGGCCT ATTGGTTAAA

AAATGAGCTG ATTTAACAAA AATTTAACGC GAATTAATTC TGTGGAATGT

GTGTCAGTTA GGGTGTGGAA AGTCCCCAGG CTCCCCAGGC AGGCAGAAGT

ATGCAAAGCA TGCATCTCAA TTAGTCAGCA ACCAGGTGTG GAAAGTCCCC

AGGCTCCCCA GCAGGCAGAA GTATGCAAAG CATGCATCTC AATTAGTCAG

CAACCATAGT CCCGCCCCTA ACTCCGCCCA TCCCGCCCCT AACTCCGCCC

AGTTCCGCCC ATTCTCCGCC CCATGGCTGA CTAATTTTTT TTATTTATGC

AGAGGCCGAG GCCGCCTCTG CCTCTGAGCT ATTCCAGAAG TAGTGAGGAG

GCTTTTTTGG AGGCCTAGGC TTTTGCAAAA AGCTCCCGGG AGCTTGTATA

TCCATTTTCG GATCTGATCA GCACGTGTTG ACAATTAATC ATCGGCATAG

TATATCGGCA TAGTATAATA CGACAAGGTG AGGAACTAAA CCATGGCCAA

GTTGACCAGT GCCGTTCCGG TGCTCACCGC GCGCGACGTC GCCGGAGCGG

TCGAGTTCTG GACCGACCGG CTCGGGTTCT CCCGGGACTT CGTGGAGGAC

GACTTCGCCG GTGTGGTCCG GGACGACGTG ACCCTGTTCA TCAGCGCGGT

CCAGGACCAG GTGGTGCCGG ACAACACCCT GGCCTGGGTG TGGGTGCGCG

GCCTGGACGA GCTGTACGCC GAGTGGTCGG AGGTCGTGTC CACGAACTTC

CGGGACGCCT CCGGGCCGGC CATGACCGAG ATCGGCGAGC AGCCGTGGGG

GCGGGAGTTC GCCCTGCGCG ACCCGGCCGG CAACTGCGTG CACTTCGTGG

CCGAGGAGCA GGACTGACAC GTGCTACGAG ATTTCGATTC CACCGCCGCC

TTCTATGAAA GGTTGGGCTT CGGAATCGTT TTCCGGGACG CCGGCTGGAT

GATCCTCCAG CGCGGGGATC TCATGCTGGA GTTCTTCGCC CACCCCAACT

TGTTTATTGC AGCTTATAAT GGTTACAAAT AAAGCAATAG CATCACAAAT

TTCACAAATA AAGCATTTTT TTCACTGCAT TCTAGTTGTG GTTTGTCCAA

ACTCATCAAT GTATCTTATC ATGTCTGTAT ACCGTCGACC TCTAGCTAGA

GCTTGGCGTA ATCATGGTCA TAGCTGTTTC CTGTGTGAAA TTGTTATCCG

CTCACAATTC CACACAACAT ACGAGCCGGA AGCATAAAGT GTAAAGCCTG

GGGTGCCTAA TGAGTGAGCT AACTCACATT AATTGCGTTG CGCTCACTGC

CCGCTTTCCA GTCGGGAAAC CTGTCGTGCC AGCTGCATTA ATGAATCGGC

CAACGCGCGG GGAGAGGCGG TTTGCGTATT GGGCGCTCTT CCGCTTCCTC

GCTCACTGAC TCGCTGCGCT CGGTCGTTCG GCTGCGGCGA GCGGTATCAG

CTCACTCAAA GGCGGTAATA CGGTTATCCA CAGAATCAGG GGATAACGCA

GGAAAGAACA TGTGAGCAAA AGGCCAGCAA AAGGCCAGGA ACCGTAAAAA

GGCCGCGTTG CTGGCGTTTT TCCATAGGCT CCGCCCCCCT GACGAGCATC

ACAAAAATCG ACGCTCAAGT CAGAGGTGGC GAAACCCGAC AGGACTATAA

AGATACCAGG CGTTTCCCCC TGGAAGCTCC CTCGTGCGCT CTCCTGTTCC

GACCCTGCCG CTTACCGGAT ACCTGTCCGC CTTTCTCCCT TCGGGAAGCG

TGGCGCTTTC TCAATGCTCA CGCTGTAGGT ATCTCAGTTC GGTGTAGGTC

-continued

| List of Sequences with short description |
| --- |

GTTCGCTCCA AGCTGGGCTG TGTGCACGAA CCCCCCGTTC AGCCCGACCG

CTGCGCCTTA TCCGGTAACT ATCGTCTTGA GTCCAACCCG GTAAGACACG

ACTTATCGCC ACTGGCAGCA GCCACTGGTA ACAGGATTAG CAGAGCGAGG

TATGTAGGCG GTGCTACAGA GTTCTTGAAG TGGTGGCCTA ACTACGGCTA

CACTAGAAGG ACAGTATTTG GTATCTGCGC TCTGCTGAAG CCAGTTACCT

TCGGAAAAAG AGTTGGTAGC TCTTGATCCG GCAAACAAAC CACCGCTGGT

AGCGGTGGTT TTTTTGTTTG CAAGCAGCAG ATTACGCGCA GAAAAAAAGG

ATCTCAAGAA GATCCTTTGA TCTTTTCTAC GGGGTCTGAC GCTCAGTGGA

ACGAAAACTC ACGTTAAGGG ATTTTGGTCA TGAGATTATC AAAAAGGATC

TTCACCTAGA TCCTTTTAAA TTAAAAATGA AGTTTTAAAT CAATCTAAAG

TATATATGAG TAAACTTGGT CTGACAGTTA CCAATGCTTA ATCAGTGAGG

CACCTATCTC AGCGATCTGT CTATTTCGTT CATCCATAGT TGCCTGACTC

CCCGTCGTGT AGATAACTAC GATACGGGAG GGCTTACCAT CTGGCCCCAG

TGCTGCAATG ATACCGCGAG ACCCACGCTC ACCGGCTCCA GATTTATCAG

CAATAAACCA GCCAGCCGGA AGGGCCGAGC GCAGAAGTGG TCCTGCAACT

TTATCCGCCT CCATCCAGTC TATTAATTGT TGCCGGGAAG CTAGAGTAAG

TAGTTCGCCA GTTAATAGTT TGCGCAACGT TGTTGCCATT GCTACAGGCA

TCGTGGTGTC ACGCTCGTCG TTTGGTATGG CTTCATTCAG CTCCGGTTCC

CAACGATCAA GGCGAGTTAC ATGATCCCCC ATGTTGTGCA AAAAAGCGGT

TAGCTCCTTC GGTCCTCCGA TCGTTGTCAG AAGTAAGTTG GCCGCAGTGT

TATCACTCAT GGTTATGGCA GCACTGCATA ATTCTCTTAC TGTCATGCCA

TCCGTAAGAT GCTTTTCTGT GACTGGTGAG TACTCAACCA AGTCATTCTG

AGAATAGTGT ATGCGGCGAC CGAGTTGCTC TTGCCCGGCG TCAATACGGG

ATAATACCGC GCCACATAGC AGAACTTTAA AAGTGCTCAT CATTGGAAAA

CGTTCTTCGG GGCGAAAACT CTCAAGGATC TTACCGCTGT TGAGATCCAG

TTCGATGTAA CCCACTCGTG CACCCAACTG ATCTTCAGCA TCTTTTACTT

TCACCAGCGT TTCTGGGTGA GCAAAAACAG GAAGGCAAAA TGCCGCAAAA

AAGGGAATAA GGGCGACACG GAAATGTTGA ATACTCATAC TCTTCCTTTT

TCAATATTAT TGAAGCATTT ATCAGGGTTA TTGTCTCATG AGCGGATACA

TATTTGAATG TATTTAGAAA AATAAACAAA TAGGGGTTCC GCGCACATTT

CCCCGAAAAG TGCCACCTGA CGTCGACGGA TCGGGAGATC TCCCGATCCC

CTATGGTCGA CTCTCAGTAC AATCTGCTCT GATGCCGCAT AGTTAAGCCA

GTATCTGCTC CCTGCTTGTG TGTTGGAGGT CGCTGAGTAG TGCGCGAGCA

AAATTTAAGC TACAACAAGG CAAGGCTTGA CCGACAATTG CATGAAGAAT

CTGCTTAGGG TTAGGCGTTT TGCGCTGCTT CGCGATGTAC GGGCCAGATA

TACGCGTTGA CATTGATTAT TGACTAGTTA TTAATAGTAA TCAATTACGG

GGTCATTAGT TCATAGCCCA TATATGGAGT TCCGCGTTAC ATAACTTACG

GTAAATGGCC CGCCTGGCTG ACCGCCCAAC GACCCCCGCC CATTGACGTC

AATAATGACG TATGTTCCCA TAGTAACGCC AATAGGGACT TTCCATTGAC

-continued

List of Sequences with short description

GTCAATGGGT GGACTATTTA CGGTAAACTG CCCACTTGGC AGTACATCAA

GTGTATCATA TGCCAAGTAC GCCCCCTATT GACGTCAATG ACGGTAAATG

GCCCGCCTGG CATTATGCCC AGTACATGAC CTTATGGGAC TTTCCTACTT

GGCAGTACAT CTACGTATTA GTCATCGCTA TTACCATGGT GATGCGGTTT

TGGCAGTACA TCAATGGGCG TGGATAGCGG TTTGACTCAC GGGGATTTCC

AAGTCTCCAC CCCATTGACG TCAATGGGAG TTTGTTTTGG CACCAAAATC

AACGGGACTT TCCAAAATGT CGTAACAACT CCGCCCCATT GACGCAAATG

GGCGGTAGGC GTGTACGGTG GGAGGTCTAT ATAAGCAGAG CTCTCTGGCT

AACTAGAGAA CCCACTGCTT ACTGGCTTAT CGAAAT

The invention claimed is:

1. A monoclonal antibody, or antigen binding fragment thereof, which is capable of binding to a LINGO-1 protein having an amino acid sequence of SEQ ID NO: 1, SEQ ID NO: 2 or SEQ ID NO: 3, with a dissociation constant <1000 nM, said antibody comprising a heavy chain variable domain CDR-H1, CDR-H2 and CDR-H3 comprising the sequence of SEQ ID NO.: 18, 19, and 20, respectively, and a light chain variable domain CDR-L1, CDR-L2 and CDR-L3 comprising the sequence of SEQ ID NO.: 21, 22 and 23, respectively.

2. The antibody, or antigen binding fragment, according to claim 1, comprising a heavy chain variable domain and a light chain variable domain, wherein the heavy chain variable domain sequence comprises SEQ ID NO: 7 and the light chain variable domain comprises SEQ ID NO: 6.

3. The antibody, or antigen binding fragment, according to claim 1, which is a human, a chimeric or a humanized monoclonal antibody.

4. A composition comprising the antibody, or antigen binding fragment thereof, according to claims 1 or 2 together with at least one pharmaceutically acceptable carrier or diluent.

5. The antibody, or antigen binding fragment, according to claim 1, wherein said antibody has a dissociation constant of <100 nM.

6. The antibody, or antigen binding fragment, according to claim 1, wherein said antibody has a dissociation constant of <10 nM.

* * * * *

SEQUENCE LISTING

```
<160> NUMBER OF SEQ ID NOS: 51

<210> SEQ ID NO 1
<211> LENGTH: 517
<212> TYPE: PRT
<213> ORGANISM: Rattus sp.

<400> SEQUENCE: 1

Thr Gly Cys Pro Pro Arg Cys Glu Cys Ser Ala Gln Asp Arg Ala Val
1               5                   10                  15

Leu Cys His Arg Lys Arg Phe Val Ala Val Pro Glu Gly Ile Pro Thr
            20                  25                  30

Glu Thr Arg Leu Leu Asp Leu Gly Lys Asn Arg Ile Lys Thr Leu Asn
        35                  40                  45

Gln Asp Glu Phe Ala Ser Phe Pro His Leu Glu Glu Leu Glu Leu Asn
    50                  55                  60

Glu Asn Ile Val Ser Ala Val Glu Pro Gly Ala Phe Asn Asn Leu Phe
65                  70                  75                  80

Asn Leu Arg Thr Leu Gly Leu Arg Ser Asn Arg Leu Lys Leu Ile Pro
                85                  90                  95

Leu Gly Val Phe Thr Gly Leu Ser Asn Leu Thr Lys Leu Asp Ile Ser
            100                 105                 110

Glu Asn Lys Ile Val Ile Leu Leu Asp Tyr Met Phe Gln Asp Leu Tyr
        115                 120                 125

Asn Leu Lys Ser Leu Glu Val Gly Asp Asn Asp Leu Val Tyr Ile Ser
    130                 135                 140

His Arg Ala Phe Ser Gly Leu Asn Ser Leu Glu Gln Leu Thr Leu Glu
145                 150                 155                 160

Lys Cys Asn Leu Thr Ser Ile Pro Thr Glu Ala Leu Ser His Leu His
                165                 170                 175

Gly Leu Ile Val Leu Arg Leu Arg His Leu Asn Ile Asn Ala Ile Arg
            180                 185                 190

Asp Tyr Ser Phe Lys Arg Leu Tyr Arg Leu Lys Val Leu Glu Ile Ser
        195                 200                 205

His Trp Pro Tyr Leu Asp Thr Met Thr Pro Asn Cys Leu Tyr Gly Leu
    210                 215                 220
```

Asn Leu Thr Ser Leu Ser Ile Thr His Cys Asn Leu Thr Ala Val Pro
225 230 235 240

Tyr Leu Ala Val Arg His Leu Val Tyr Leu Arg Phe Leu Asn Leu Ser
245 250 255

Tyr Asn Pro Ile Gly Thr Ile Glu Gly Ser Met Leu His Glu Leu Leu
260 265 270

Arg Leu Gln Glu Ile Gln Leu Val Gly Gly Gln Leu Ala Val Val Glu
275 280 285

Pro Tyr Ala Phe Arg Gly Leu Asn Tyr Leu Arg Val Leu Asn Val Ser
290 295 300

Gly Asn Gln Leu Thr Thr Leu Glu Glu Ser Ala Phe His Ser Val Gly
305 310 315 320

Asn Leu Glu Thr Leu Ile Leu Asp Ser Asn Pro Leu Ala Cys Asp Cys
325 330 335

Arg Leu Leu Trp Val Phe Arg Arg Arg Trp Arg Leu Asn Phe Asn Arg
340 345 350

Gln Gln Pro Thr Cys Ala Thr Pro Glu Phe Val Gln Gly Lys Glu Phe
355 360 365

Lys Asp Phe Pro Asp Val Leu Leu Pro Asn Tyr Phe Thr Cys Arg Arg
370 375 380

Ala His Ile Arg Asp Arg Lys Ala Gln Gln Val Phe Val Asp Glu Gly
385 390 395 400

His Thr Val Gln Phe Val Cys Arg Ala Asp Gly Asp Pro Pro Pro Ala
405 410 415

Ile Leu Trp Leu Ser Pro Arg Lys His Leu Val Ser Ala Lys Ser Asn
420 425 430

Gly Arg Leu Thr Val Phe Pro Asp Gly Thr Leu Glu Val Arg Tyr Ala
435 440 445

Gln Val Gln Asp Asn Gly Thr Tyr Leu Cys Ile Ala Ala Asn Ala Gly
450 455 460

Gly Asn Asp Ser Met Pro Ala His Leu His Val Arg Ser Tyr Ser Pro
465 470 475 480

Asp Trp Pro His Gln Pro Asn Lys Thr Phe Ala Phe Ile Ser Asn Gln
485 490 495

Pro Gly Glu Gly Glu Ala Asn Ser Thr Arg Ala Thr Val Pro Phe Pro
500 505 510

Phe Asp Ile Lys Thr
515

<210> SEQ ID NO 2
<211> LENGTH: 517
<212> TYPE: PRT
<213> ORGANISM: Macaca fascicularis

<400> SEQUENCE: 2

Thr Gly Cys Pro Pro Arg Cys Glu Cys Ser Ala Gln Asp Arg Ala Val
1 5 10 15

Leu Cys His Arg Lys Arg Phe Val Ala Val Pro Glu Gly Ile Pro Thr
20 25 30

Glu Thr Arg Leu Leu Asp Leu Gly Lys Asn Arg Ile Lys Thr Leu Asn
35 40 45

Gln Asp Glu Phe Ala Ser Phe Pro His Leu Glu Glu Leu Glu Leu Asn
50 55 60

Glu Asn Ile Val Ser Ala Val Glu Pro Gly Ala Phe Asn Asn Leu Phe
65 70 75 80

```
Asn Leu Arg Thr Leu Gly Leu Arg Ser Asn Arg Leu Lys Leu Ile Pro
                85                  90                  95

Leu Gly Val Phe Thr Gly Leu Ser Asn Leu Thr Lys Leu Asp Ile Ser
            100                 105                 110

Glu Asn Lys Ile Val Ile Leu Leu Asp Tyr Met Phe Gln Asp Leu Tyr
        115                 120                 125

Asn Leu Lys Ser Leu Glu Val Gly Asp Asn Asp Leu Val Tyr Ile Ser
    130                 135                 140

His Arg Ala Phe Ser Gly Leu Asn Ser Leu Glu Gln Leu Thr Leu Glu
145                 150                 155                 160

Lys Cys Asn Leu Thr Ser Ile Pro Thr Glu Ala Leu Ser His Leu His
                165                 170                 175

Gly Leu Ile Val Leu Arg Leu Arg His Leu Asn Ile Asn Ala Ile Arg
            180                 185                 190

Asp Tyr Ser Phe Lys Arg Leu Tyr Arg Leu Lys Val Leu Glu Ile Ser
        195                 200                 205

His Trp Pro Tyr Leu Asp Thr Met Thr Pro Asn Cys Leu Tyr Gly Leu
    210                 215                 220

Asn Leu Thr Ser Leu Ser Ile Thr His Cys Asn Leu Thr Ala Val Pro
225                 230                 235                 240

Tyr Leu Ala Val Arg His Leu Val Tyr Leu Arg Phe Leu Asn Leu Ser
                245                 250                 255

Tyr Asn Pro Ile Ser Thr Ile Glu Gly Ser Met Leu His Glu Leu Leu
            260                 265                 270

Arg Leu Gln Glu Ile Gln Leu Val Gly Gly Gln Leu Ala Met Val Glu
        275                 280                 285

Pro Tyr Ala Phe Arg Gly Leu Asn Tyr Leu Arg Val Leu Asn Val Ser
    290                 295                 300

Gly Asn Gln Leu Thr Thr Leu Glu Glu Ser Val Phe His Ser Val Gly
305                 310                 315                 320

Asn Leu Glu Thr Leu Ile Leu Asp Ser Asn Pro Leu Ala Cys Asp Cys
                325                 330                 335

Arg Leu Leu Trp Val Phe Arg Arg Arg Trp Arg Leu Asn Phe Asn Arg
            340                 345                 350

Gln Gln Pro Thr Cys Ala Thr Pro Glu Phe Val Gln Gly Lys Glu Phe
        355                 360                 365

Lys Asp Phe Pro Asp Val Leu Leu Pro Asn Tyr Phe Thr Cys Arg Arg
    370                 375                 380

Ala Arg Ile Arg Asp Arg Lys Ala Gln Gln Val Phe Val Asp Glu Gly
385                 390                 395                 400

His Thr Val Gln Phe Val Cys Arg Ala Asp Gly Asp Pro Pro Pro Ala
                405                 410                 415

Ile Leu Trp Leu Ser Pro Arg Lys His Leu Val Ser Ala Lys Ser Asn
            420                 425                 430

Gly Arg Leu Thr Val Phe Pro Asp Gly Thr Leu Glu Val Arg Tyr Ala
        435                 440                 445

Gln Val Gln Asp Asn Gly Thr Tyr Leu Cys Ile Ala Ala Asn Ala Gly
    450                 455                 460

Gly Asn Asp Ser Met Pro Ala His Leu His Val Arg Ser Tyr Ser Pro
465                 470                 475                 480

Asp Trp Pro His Gln Pro Asn Lys Thr Phe Ala Phe Ile Pro Asn Gln
                485                 490                 495

Pro Gly Glu Gly Glu Ala Asn Ser Thr Arg Ala Thr Val Pro Phe Pro
            500                 505                 510
```

```
Phe Asp Ile Lys Thr
        515


<210> SEQ ID NO 3
<211> LENGTH: 517
<212> TYPE: PRT
<213> ORGANISM: Homo sapiens

<400> SEQUENCE: 3

Thr Gly Cys Pro Pro Arg Cys Glu Cys Ser Ala Gln Asp Arg Ala Val
1               5                   10                  15

Leu Cys His Arg Lys Arg Phe Val Ala Val Pro Glu Gly Ile Pro Thr
            20                  25                  30

Glu Thr Arg Leu Leu Asp Leu Gly Lys Asn Arg Ile Lys Thr Leu Asn
        35                  40                  45

Gln Asp Glu Phe Ala Ser Phe Pro His Leu Glu Glu Leu Glu Leu Asn
    50                  55                  60

Glu Asn Ile Val Ser Ala Val Glu Pro Gly Ala Phe Asn Asn Leu Phe
65                  70                  75                  80

Asn Leu Arg Thr Leu Gly Leu Arg Ser Asn Arg Leu Lys Leu Ile Pro
                85                  90                  95

Leu Gly Val Phe Thr Gly Leu Ser Asn Leu Thr Lys Leu Asp Ile Ser
            100                 105                 110

Glu Asn Lys Ile Val Ile Leu Leu Asp Tyr Met Phe Gln Asp Leu Tyr
        115                 120                 125

Asn Leu Lys Ser Leu Glu Val Gly Asp Asn Asp Leu Val Tyr Ile Ser
    130                 135                 140

His Arg Ala Phe Ser Gly Leu Asn Ser Leu Glu Gln Leu Thr Leu Glu
145                 150                 155                 160

Lys Cys Asn Leu Thr Ser Ile Pro Thr Glu Ala Leu Ser His Leu His
                165                 170                 175

Gly Leu Ile Val Leu Arg Leu Arg His Leu Asn Ile Asn Ala Ile Arg
            180                 185                 190

Asp Tyr Ser Phe Lys Arg Leu Tyr Arg Leu Lys Val Leu Glu Ile Ser
        195                 200                 205

His Trp Pro Tyr Leu Asp Thr Met Thr Pro Asn Cys Leu Tyr Gly Leu
    210                 215                 220

Asn Leu Thr Ser Leu Ser Ile Thr His Cys Asn Leu Thr Ala Val Pro
225                 230                 235                 240

Tyr Leu Ala Val Arg His Leu Val Tyr Leu Arg Phe Leu Asn Leu Ser
                245                 250                 255

Tyr Asn Pro Ile Ser Thr Ile Glu Gly Ser Met Leu His Glu Leu Leu
            260                 265                 270

Arg Leu Gln Glu Ile Gln Leu Val Gly Gly Gln Leu Ala Val Val Glu
        275                 280                 285

Pro Tyr Ala Phe Arg Gly Leu Asn Tyr Leu Arg Val Leu Asn Val Ser
    290                 295                 300

Gly Asn Gln Leu Thr Thr Leu Glu Glu Ser Val Phe His Ser Val Gly
305                 310                 315                 320

Asn Leu Glu Thr Leu Ile Leu Asp Ser Asn Pro Leu Ala Cys Asp Cys
                325                 330                 335

Arg Leu Leu Trp Val Phe Arg Arg Arg Trp Arg Leu Asn Phe Asn Arg
            340                 345                 350

Gln Gln Pro Thr Cys Ala Thr Pro Glu Phe Val Gln Gly Lys Glu Phe
        355                 360                 365
```

```
Lys Asp Phe Pro Asp Val Leu Leu Pro Asn Tyr Phe Thr Cys Arg Arg
    370                 375                 380

Ala Arg Ile Arg Asp Arg Lys Ala Gln Gln Val Phe Val Asp Glu Gly
385                 390                 395                 400

His Thr Val Gln Phe Val Cys Arg Ala Asp Gly Asp Pro Pro Pro Ala
                405                 410                 415

Ile Leu Trp Leu Ser Pro Arg Lys His Leu Val Ser Ala Lys Ser Asn
            420                 425                 430

Gly Arg Leu Thr Val Phe Pro Asp Gly Thr Leu Glu Val Arg Tyr Ala
        435                 440                 445

Gln Val Gln Asp Asn Gly Thr Tyr Leu Cys Ile Ala Ala Asn Ala Gly
    450                 455                 460

Gly Asn Asp Ser Met Pro Ala His Leu His Val Arg Ser Tyr Ser Pro
465                 470                 475                 480

Asp Trp Pro His Gln Pro Asn Lys Thr Phe Ala Phe Ile Ser Asn Gln
                485                 490                 495

Pro Gly Glu Gly Glu Ala Asn Ser Thr Arg Ala Thr Val Pro Phe Pro
            500                 505                 510

Phe Asp Ile Lys Thr
        515


<210> SEQ ID NO 4
<211> LENGTH: 108
<212> TYPE: PRT
<213> ORGANISM: artificial
<220> FEATURE:
<223> OTHER INFORMATION: 4784 VL

<400> SEQUENCE: 4

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Asn Tyr Tyr Val
            20                  25                  30

Tyr Trp Tyr Gln Gln Lys Pro Gly Gln Ala Pro Val Leu Val Ile Tyr
        35                  40                  45

Glu Asp Thr Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Asn Leu His Glu Gln
                85                  90                  95

Val Phe Gly Gly Gly Thr Lys Leu Thr Val Leu Gly
            100                 105


<210> SEQ ID NO 5
<211> LENGTH: 124
<212> TYPE: PRT
<213> ORGANISM: Artificial
<220> FEATURE:
<223> OTHER INFORMATION: 4784 VH

<400> SEQUENCE: 5

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Ser Ser
            20                  25                  30

Gly Val Gly Val Gly Trp Ile Arg Gln Pro Pro Gly Lys Ala Leu Glu
        35                  40                  45
```

```
Trp Leu Ala His Ile Gly Ser Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Asn Gln Gln Tyr Gly Asp Gly Tyr Pro Gly Tyr Phe Asp
            100                 105                 110

Tyr Trp Gly Gln Gly Thr Leu Val Thr Val Ser Ser
        115                 120
```

```
<210> SEQ ID NO 6
<211> LENGTH: 109
<212> TYPE: PRT
<213> ORGANISM: Artificial
<220> FEATURE:
<223> OTHER INFORMATION: 4785 VL

<400> SEQUENCE: 6

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Ser Arg Asn Ser Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ser Thr Tyr Asp Thr Phe Ser
                85                  90                  95

Ile Val Phe Gly Gly Gly Thr Lys Leu Thr Val Leu Gly
            100                 105
```

```
<210> SEQ ID NO 7
<211> LENGTH: 121
<212> TYPE: PRT
<213> ORGANISM: artificial
<220> FEATURE:
<223> OTHER INFORMATION: 4785 VH

<400> SEQUENCE: 7

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Asp Asn
            20                  25                  30

Ser Ala Ala Trp Ser Trp Ile Arg Gln Ser Pro Gly Arg Gly Leu Glu
        35                  40                  45

Trp Leu Gly Leu Ile Tyr Leu Arg Ser Lys Trp Asp Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Thr Gly Arg Ala Asp Glu Phe Asp Val Trp Gly
            100                 105                 110

Gln Gly Thr Leu Val Thr Val Ser Ser
        115                 120
```

<210> SEQ ID NO 8
<211> LENGTH: 372
<212> TYPE: DNA
<213> ORGANISM: artificial
<220> FEATURE:
<223> OTHER INFORMATION: DNA 4784 VH

<400> SEQUENCE: 8
caggtgcaat tgaaagaaag cggcccggcc ctggtgaaac cgacccaaac cctgaccctg 60
acctgtacct tttccggatt tagcctgtct tcttctggtg ttggtgtggg ttggattcgc 120
cagccgcctg ggaaagccct cgagtggctg gctcatatcg gttctgatga tgataagtat 180
tatagcacca gcctgaaaac gcgtctgacc attagcaaag atacttcgaa aaatcaggtg 240
gtgctgacta tgaccaacat ggacccggtg gatacggcca cctattattg cgcgcgtaat 300
cagcagtatg gtgatggtta tcctggttat tttgattatt ggggccaagg caccctggtg 360
acggttagct ca 372

<210> SEQ ID NO 9
<211> LENGTH: 363
<212> TYPE: DNA
<213> ORGANISM: artificial
<220> FEATURE:
<223> OTHER INFORMATION: DNA 4785 VH

<400> SEQUENCE: 9
caggtgcaat tgcaacagtc tggtccgggc ctggtgaaac cgagccaaac cctgagcctg 60
acctgtgcga tttccggaga tagcgtgagc gataattctg ctgcttggtc ttggattcgc 120
cagtctcctg ggcgtggcct cgagtggctg ggccttatct atcttcgtag caagtgggat 180
aacgattatg cggtgagcgt gaaaagccgg attaccatca acccggatac ttcgaaaaac 240
cagtttagcc tgcaactgaa cagcgtgacc ccggaagata cggccgtgta ttattgcgcg 300
cgtactggtc gtgctgatga gtttgatgtt tggggccaag gcaccctggt gacggttagc 360
tca 363

<210> SEQ ID NO 10
<211> LENGTH: 327
<212> TYPE: DNA
<213> ORGANISM: artificial
<220> FEATURE:
<223> OTHER INFORMATION: DNA 4784 VL

<400> SEQUENCE: 10
gatatcgaac tgacccagcc gccttcagtg agcgttgcac caggtcagac cgcgcgtatc 60
tcgtgtagcg gcgataatat tggtaattat tatgtttatt ggtaccagca gaaacccggg 120
caggcgccag ttcttgtgat ttatgaggat actaatcgtc cctcaggcat cccggaacgc 180
tttagcggat ccaacagcgg caacaccgcg accctgacca ttagcggcac tcaggcggaa 240
gacgaagcgg attattattg ccagtcttat gataatcttc atgagcaggt gtttggcggc 300
ggcacgaagt taaccgttct tggccag 327

<210> SEQ ID NO 11
<211> LENGTH: 330
<212> TYPE: DNA
<213> ORGANISM: artificial
<220> FEATURE:
<223> OTHER INFORMATION: DNA 4785 VL

<400> SEQUENCE: 11

```
gatatcgtgc tgacccagcc gccttcagtg agtggcgcac caggtcagcg tgtgaccatc      60

tcgtgtagcg gcagcagcag caacattggt aataattatg tgtcttggta ccagcagttg     120

cccgggacgg cgccgaaact tctgatttct cgtaattcta agcgtccctc aggcgtgccg     180

gatcgtttta gcggatccaa aagcggcacc agcgcgagcc ttgcgattac gggcctgcaa     240

agcgaagacg aagcggatta ttattgctct acttatgata ctttttctat tgtgtttggc     300

ggcggcacga agttaaccgt tcttggccag                                      330


<210> SEQ ID NO 12
<211> LENGTH: 7
<212> TYPE: PRT
<213> ORGANISM: artificial
<220> FEATURE:
<223> OTHER INFORMATION: Antibody 4784 CDR-H1

<400> SEQUENCE: 12

Ser Ser Gly Val Gly Val Gly
1               5


<210> SEQ ID NO 13
<211> LENGTH: 16
<212> TYPE: PRT
<213> ORGANISM: artificial
<220> FEATURE:
<223> OTHER INFORMATION: Antibody 4784 CDR-H2

<400> SEQUENCE: 13

His Ile Gly Ser Asp Asp Asp Lys Tyr Tyr Ser Thr Ser Leu Lys Thr
1               5                   10                  15


<210> SEQ ID NO 14
<211> LENGTH: 14
<212> TYPE: PRT
<213> ORGANISM: artificial
<220> FEATURE:
<223> OTHER INFORMATION: Antibody 4784 CDR-H3

<400> SEQUENCE: 14

Asn Gln Gln Tyr Gly Asp Gly Tyr Pro Gly Tyr Phe Asp Tyr
1               5                   10


<210> SEQ ID NO 15
<211> LENGTH: 11
<212> TYPE: PRT
<213> ORGANISM: artificial
<220> FEATURE:
<223> OTHER INFORMATION: Antibody 4784 CDR-L1

<400> SEQUENCE: 15

Ser Gly Asp Asn Ile Gly Asn Tyr Tyr Val Tyr
1               5                   10


<210> SEQ ID NO 16
<211> LENGTH: 7
<212> TYPE: PRT
<213> ORGANISM: artificial
<220> FEATURE:
<223> OTHER INFORMATION: Antibody 4784 CDR-L2

<400> SEQUENCE: 16

Glu Asp Thr Asn Arg Pro Ser
1               5


<210> SEQ ID NO 17
```

<211> LENGTH: 10
<212> TYPE: PRT
<213> ORGANISM: artificial
<220> FEATURE:
<223> OTHER INFORMATION: Antibody 4784 CDR-L3

<400> SEQUENCE: 17

Gln Ser Tyr Asp Asn Leu His Glu Gln Val
1 5 10

<210> SEQ ID NO 18
<211> LENGTH: 7
<212> TYPE: PRT
<213> ORGANISM: artificial
<220> FEATURE:
<223> OTHER INFORMATION: Antibody 4785 CDR'-H1

<400> SEQUENCE: 18

Asp Asn Ser Ala Ala Trp Ser
1 5

<210> SEQ ID NO 19
<211> LENGTH: 18
<212> TYPE: PRT
<213> ORGANISM: artificial
<220> FEATURE:
<223> OTHER INFORMATION: Antibody 4785 CDR'-H2

<400> SEQUENCE: 19

Leu Ile Tyr Leu Arg Ser Lys Trp Asp Asn Asp Tyr Ala Val Ser Val
1 5 10 15

Lys Ser

<210> SEQ ID NO 20
<211> LENGTH: 9
<212> TYPE: PRT
<213> ORGANISM: artificial
<220> FEATURE:
<223> OTHER INFORMATION: Antibody 4785 CDR'-H3

<400> SEQUENCE: 20

Thr Gly Arg Ala Asp Glu Phe Asp Val
1 5

<210> SEQ ID NO 21
<211> LENGTH: 13
<212> TYPE: PRT
<213> ORGANISM: artificial
<220> FEATURE:
<223> OTHER INFORMATION: Antibody 4785 CDR'-L1

<400> SEQUENCE: 21

Ser Gly Ser Ser Ser Asn Ile Gly Asn Asn Tyr Val Ser
1 5 10

<210> SEQ ID NO 22
<211> LENGTH: 7
<212> TYPE: PRT
<213> ORGANISM: artificial
<220> FEATURE:
<223> OTHER INFORMATION: Antibody 4785 CDR'-L2

<400> SEQUENCE: 22

Arg Asn Ser Lys Arg Pro Ser
1 5

<210> SEQ ID NO 23

<211> LENGTH: 9
<212> TYPE: PRT
<213> ORGANISM: artificial
<220> FEATURE:
<223> OTHER INFORMATION: Antibody 4785 CDR'-L3

<400> SEQUENCE: 23

Ser Thr Tyr Asp Thr Phe Ser Ile Val
1 5

<210> SEQ ID NO 24
<211> LENGTH: 28
<212> TYPE: DNA
<213> ORGANISM: artificial
<220> FEATURE:
<223> OTHER INFORMATION: DM22

<400> SEQUENCE: 24
ggttatctcg agaccggctg cccgcccc 28

<210> SEQ ID NO 25
<211> LENGTH: 37
<212> TYPE: DNA
<213> ORGANISM: artificial
<220> FEATURE:
<223> OTHER INFORMATION: DM23

<400> SEQUENCE: 25
ggcccttcta gatcactcgc ctggctggtt ggagatg 37

<210> SEQ ID NO 26
<211> LENGTH: 6602
<212> TYPE: DNA
<213> ORGANISM: artificial
<220> FEATURE:
<223> OTHER INFORMATION: APtag-5-NHIS vector

<400> SEQUENCE: 26
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
caccatggag acagacacac tcctgctatg ggtactgctg ctctgggttc caggttccac 960
tggtgacgcg gcccagccgg cccatcatca tcatcatcat gaagcttacg taagatcttc 1020
cggaatcatc ccagttgagg aggagaaccc ggacttctgg aaccgcgagg cagccgaggc 1080

-continued

```
cctgggtgcc gccaagaagc tgcagcctgc acagacagcc gccaagaacc tcatcatctt   1140

cctgggcgat gggatggggg tgtctacggt gacagctgcc aggatcctaa aagggcagaa   1200

gaaggacaaa ctggggcctg agataccccct ggccatggac cgcttcccat atgtggctct   1260

gtccaagaca tacaatgtag acaaacatgt gccagacagt ggagccacag ccacggccta   1320

cctgtgcggg gtcaagggca acttccagac cattggcttg agtgcagccg cccgctttaa   1380

ccagtgcaac acgacacgcg gcaacgaggt catctccgtg atgaatcggg ccaagaaagc   1440

agggaagtca gtgggagtgg taaccaccac acgagtgcag cacgcctcgc cagccggcac   1500

ctacgcccac acggtgaacc gcaactggta ctcggacgcc gacgtgcctg cctcggcccg   1560

ccaggagggg tgccaggaca tcgctacgca gctcatctcc aacatggaca ttgacgtgat   1620

cctaggtgga ggccgaaagt acatgtttcg catgggaacc ccagaccctg agtacccaga   1680

tgactacagc caaggtggga ccaggctgga cgggaagaat ctggtgcagg aatggctggc   1740

gaagcgccag ggtgcccggt atgtgtggaa ccgcactgag ctcatgcagg cttccctgga   1800

cccgtctgtg acccatctca tgggtctctt tgagcctgga gacatgaaat acgagatcca   1860

ccgagactcc acactggacc cctccctgat ggagatgaca gaggctgccc tgcgcctgct   1920

gagcaggaac ccccgcggct tcttcctctt cgtggagggt ggtcgcatcg accatggtca   1980

tcatgaaagc agggcttacc gggcactgac tgagacgatc atgttcgacg acgccattga   2040

gagggcgggc cagctcacca gcgaggagga cacgctgagc ctcgtcactg ccgaccactc   2100

ccacgtcttc tccttcggag gctacccccct gcgagggagc tccatcttcg ggctggcccc   2160

tggcaaggcc cgggacagga aggcctacac ggtcctccta tacggaaacg gtccaggcta   2220

tgtgctcaag gacggcgccc ggccggatgt taccgagagc gagagcggga gccccgagta   2280

tcggcagcag tcagcagtgc cctggacga agagacccac gcaggcgagg acgtggcggt   2340

gttcgcgcgc ggcccgcagg cgcacctggt tcacggcgtg caggagcaga ccttcatagc   2400

gcacgtcatg gccttcgccg cctgcctgga gccctacacc gcctgcgacc tggcgccccc   2460

cgccggcacc accgacgccg cgcacccggg ttatctcgag gaagcgctct ctctagaagg   2520

gcccgaacaa aaactcatct cagaagagga tctgaatagc gccgtcgacc atcatcatca   2580

tcatcattga gtttaaaccc gctgatcagc ctcgactgtg ccttctagtt gccagccatc   2640

tgttgtttgc ccctcccccg tgccttcctt gaccctggaa ggtgccactc ccactgtcct   2700

ttcctaataa aatgaggaaa ttgcatcgca ttgtctgagt aggtgtcatt ctattctggg   2760

gggtggggtg gggcaggaca gcaaggggga ggattgggaa gacaatagca ggcatgctgg   2820

ggatgcggtg ggctctatgg cttctgaggc ggaaagaacc agctggggct ctagggggta   2880

tccccacgcg ccctgtagcg gcgcattaag cgcggcgggt gtggtggtta cgcgcagcgt   2940

gaccgctaca cttgccagcg ccctagcgcc cgctcctttc gctttcttcc cttcctttct   3000

cgccacgttc gccggctttc cccgtcaagc tctaaatcgg ggcatccctt tagggttccg   3060

atttagtgct ttacggcacc tcgaccccaa aaaacttgat tagggtgatg gttcacgtag   3120

tgggccatcg ccctgataga cggtttttcg ccctttgacg ttggagtcca cgttctttaa   3180

tagtggactc ttgttccaaa ctggaacaac actcaaccct atctcggtct attcttttga   3240

tttataaggg attttgggga tttcggccta ttggttaaaa aatgagctga tttaacaaaa   3300

atttaacgcg aattaattct gtggaatgtg tgtcagttag ggtgtggaaa gtccccaggc   3360

tccccagcag gcagaagtat gcaaagcatg catctcaatt agtcagcaac caggtgtgga   3420

aagtccccag gctccccagc aggcagaagt atgcaaagca tgcatctcaa ttagtcagca   3480
```

-continued

```
accatagtcc cgcccctaac tccgcccatc ccgcccctaa ctccgcccag ttccgcccat   3540
tctccgcccc atggctgact aattttttt atttatgcag aggccgaggc cgcctctgcc   3600
tctgagctat tccagaagta gtgaggaggc ttttttggag gcctaggctt ttgcaaaaag   3660
ctcccgggag cttgtatatc cattttcgga tctgatcagc acgtgttgac aattaatcat   3720
cggcatagta tatcggcata gtataatacg acaaggtgag gaactaaacc atggccaagt   3780
tgaccagtgc cgttccggtg ctcaccgcgc gcgacgtcgc cggagcggtc gagttctgga   3840
ccgaccggct cgggttctcc cgggacttcg tggaggacga cttcgccggt gtggtccggg   3900
acgacgtgac cctgttcatc agcgcggtcc aggaccaggt ggtgccggac aacaccctgg   3960
cctgggtgtg ggtgcgcggc ctggacgagc tgtacgccga gtggtcggag gtcgtgtcca   4020
cgaacttccg ggacgcctcc gggccggcca tgaccgagat cggcgagcag ccgtgggggc   4080
gggagttcgc cctgcgcgac ccggccggca actgcgtgca cttcgtggcc gaggagcagg   4140
actgacacgt gctacgagat ttcgattcca ccgccgcctt ctatgaaagg ttgggcttcg   4200
gaatcgtttt ccgggacgcc ggctggatga tcctccagcg cggggatctc atgctggagt   4260
tcttcgccca ccccaacttg tttattgcag cttataatgg ttacaaataa agcaatagca   4320
tcacaaattt cacaaataaa gcattttttt cactgcattc tagttgtggt ttgtccaaac   4380
tcatcaatgt atcttatcat gtctgtatac cgtcgacctc tagctagagc ttggcgtaat   4440
catggtcata gctgtttcct gtgtgaaatt gttatccgct cacaattcca cacaacatac   4500
gagccggaag cataaagtgt aaagcctggg gtgcctaatg agtgagctaa ctcacattaa   4560
ttgcgttgcg ctcactgccc gctttccagt cgggaaacct gtcgtgccag ctgcattaat   4620
gaatcggcca acgcgcgggg agaggcggtt tgcgtattgg gcgctcttcc gcttcctcgc   4680
tcactgactc gctgcgctcg gtcgttcggc tgcggcgagc ggtatcagct cactcaaagg   4740
cggtaatacg gttatccaca gaatcagggg ataacgcagg aaagaacatg tgagcaaaag   4800
gccagcaaaa ggccaggaac cgtaaaaagg ccgcgttgct ggcgtttttc cataggctcc   4860
gcccccctga cgagcatcac aaaaatcgac gctcaagtca gaggtggcga aacccgacag   4920
gactataaag ataccaggcg tttccccctg gaagctccct cgtgcgctct cctgttccga   4980
ccctgccgct taccggatac ctgtccgcct ttctcccttc gggaagcgtg gcgctttctc   5040
aatgctcacg ctgtaggtat ctcagttcgg tgtaggtcgt tcgctccaag ctgggctgtg   5100
tgcacgaacc ccccgttcag cccgaccgct gcgccttatc cggtaactat cgtcttgagt   5160
ccaacccggt aagacacgac ttatcgccac tggcagcagc cactggtaac aggattagca   5220
gagcgaggta tgtaggcggt gctacagagt tcttgaagtg gtggcctaac tacggctaca   5280
ctagaaggac agtatttggt atctgcgctc tgctgaagcc agttaccttc ggaaaaagag   5340
ttggtagctc ttgatccggc aaacaaacca ccgctggtag cggtggtttt tttgtttgca   5400
agcagcagat tacgcgcaga aaaaaaggat ctcaagaaga tcctttgatc ttttctacgg   5460
ggtctgacgc tcagtggaac gaaaactcac gttaagggat tttggtcatg agattatcaa   5520
aaaggatctt cacctagatc cttttaaatt aaaaatgaag ttttaaatca atctaaagta   5580
tatatgagta aacttggtct gacagttacc aatgcttaat cagtgaggca cctatctcag   5640
cgatctgtct atttcgttca tccatagttg cctgactccc cgtcgtgtag ataactacga   5700
tacgggaggg cttaccatct ggccccagtg ctgcaatgat accgcgagac ccacgctcac   5760
cggctccaga tttatcagca ataaaccagc cagccggaag ggccgagcgc agaagtggtc   5820
ctgcaacttt atccgcctcc atccagtcta ttaattgttg ccgggaagct agagtaagta   5880
```

gttcgccagt taatagtttg cgcaacgttg ttgccattgc tacaggcatc gtggtgtcac 5940
gctcgtcgtt tggtatggct tcattcagct ccggttccca acgatcaagg cgagttacat 6000
gatcccccat gttgtgcaaa aaagcggtta gctccttcgg tcctccgatc gttgtcagaa 6060
gtaagttggc cgcagtgtta tcactcatgg ttatggcagc actgcataat tctcttactg 6120
tcatgccatc cgtaagatgc ttttctgtga ctggtgagta ctcaaccaag tcattctgag 6180
aatagtgtat gcggcgaccg agttgctctt gcccggcgtc aatacgggat aataccgcgc 6240
cacatagcag aactttaaaa gtgctcatca ttggaaaacg ttcttcgggg cgaaaactct 6300
caaggatctt accgctgttg agatccagtt cgatgtaacc cactcgtgca cccaactgat 6360
cttcagcatc ttttactttc accagcgttt ctgggtgagc aaaaacagga aggcaaaatg 6420
ccgcaaaaaa gggaataagg gcgacacgga aatgttgaat actcatactc ttcctttttc 6480
aatattattg aagcatttat cagggttatt gtctcatgag cggatacata tttgaatgta 6540
tttagaaaaa taaacaaata ggggttccgc gcacatttcc ccgaaaagtg ccacctgacg 6600
tc 6602

<210> SEQ ID NO 27
<211> LENGTH: 1743
<212> TYPE: DNA
<213> ORGANISM: Homo sapiens

<400> SEQUENCE: 27
acgggctgcc cgccccgctg cgagtgctcc gcccaggacc gcgctgtgct gtgccaccgc 60
aagcgctttg tggcagtccc cgagggcatc cccaccgaga cgcgcctgct ggacctaggc 120
aagaaccgca tcaaaacgct caaccaggac gagttcgcca gcttcccgca cctggaggag 180
ctggagctca acgagaacat cgtgagcgcc gtggagcccg gcgccttcaa caacctcttc 240
aacctccgga cgctgggtct ccgcagcaac cgcctgaagc tcatcccgct aggcgtcttc 300
actggcctca gcaacctgac caagctggac atcagcgaga acaagattgt tatcctgctg 360
gactacatgt ttcaggacct gtacaacctc aagtcactgg aggttggcga caatgacctc 420
gtctacatct ctcaccgcgc cttcagcggc ctcaacagcc tggagcagct gacgctggag 480
aaatgcaacc tgacctccat ccccaccgag gcgctgtccc acctgcacgg cctcatcgtc 540
ctgaggctcc ggcacctcaa catcaatgcc atccgggact actccttcaa gaggctctac 600
cgactcaagg tcttggagat ctcccactgg ccctacttgg acaccatgac acccaactgc 660
ctctacggcc tcaacctgac gtccctgtcc atcacacact gcaatctgac cgctgtgccc 720
tacctggccg tccgccacct agtctatctc cgcttcctca acctctccta caaccccatc 780
agcaccattg agggctccat gttgcatgag ctgctccggc tgcaggagat ccagctggtg 840
ggcgggcagc tggccgtggt ggagccctat gccttccgcg gcctcaacta cctgcgcgtg 900
ctcaatgtct ctggcaacca gctgaccaca ctggaggaat cagtcttcca ctcggtgggc 960
aacctggaga cactcatcct ggactccaac ccgctggcct gcgactgtcg gctcctgtgg 1020
gtgttccggc gccgctggcg gctcaacttc aaccggcagc agcccacgtg cgccacgccc 1080
gagtttgtcc agggcaagga gttcaaggac ttccctgatg tgctactgcc caactacttc 1140
acctgccgcc gcgcccgcat ccgggaccgc aaggcccagc aggtgtttgt ggacgagggc 1200
cacacggtgc agtttgtgtg ccgggccgat ggcgacccgc cgcccgccat cctctggctc 1260
tcaccccgaa agcacctggt ctcagccaag agcaatgggc ggctcacagt cttccctgat 1320
ggcacgctgg aggtgcgcta cgcccaggta caggacaacg gcacgtacct gtgcatcgcg 1380
gccaacgcgg gcggcaacga ctccatgccc gcccacctgc atgtgcgcag ctactcgccc 1440
gactggcccc atcagcccaa caagaccttc gctttcatct ccaaccagcc gggcgaggga 1500
gaggccaaca gcacccgcgc cactgtgcct ttccccttcg acatcaagac cctcatcatc 1560
gccaccacca tgggcttcat ctctttcctg ggcgtcgtcc tcttctgcct ggtgctgctg 1620
tttctctgga gccggggcaa gggcaacaca aagcacaaca tcgagatcga gtatgtgccc 1680
cgaaagtcgg acgcaggcat cagctccgcc gacgcgcccc gcaagttcaa catgaagatg 1740
ata 1743

<210> SEQ ID NO 28
<211> LENGTH: 1743
<212> TYPE: DNA
<213> ORGANISM: Macaca fascicularis

<400> SEQUENCE: 28
acgggctgcc cgccccgctg cgagtgctcc gcccaggacc gggctgtgct ctgccaccgc 60
aagcgctttg tggcagtgcc tgagggcatc cccacggaga cgcgcctgct ggacctgggg 120
aagaaccgca tcaaaacgct caaccaggac gagttcgcca gcttcccgca cctggaggag 180
ctggagctca acgagaacat cgtgagcgcc gtggagcctg gcgccttcaa caaccttttc 240
aacctccgga cgctgggtct ccgcagcaac cgcctgaagc tcatcccgct gggcgtcttc 300
actggcctca gcaacttgac caagctggac atcagcgaga acaagatcgt tatcctgctg 360
gactacatgt tccaggacct gtacaacctc aagtcactgg aggttggcga caatgacctc 420
gtctacatct cccaccgcgc cttcagcggc ctcaacagcc tggagcagct gacgctggag 480
aaatgcaacc tgacctccat ccccaccgag gcgctgtccc acctgcacgg cctcatcgtc 540
ctgaggctcc ggcacctcaa catcaatgcc atccgggact actccttcaa gaggttgtac 600
cgactcaagg tcttggagat ctcccactgg ccctacttgg acaccatgac acccaactgc 660
ctctacggcc tcaacctgac gtccctgtcc atcacgcact gcaatctgac cgctgtgccc 720
tacctggccg tccgccacct ggtctatctc cgcttcctca acctctccta caaccccatc 780
agcaccattg agggctccat gttgcatgag ctgctccggc tgcaggagat ccagctggtg 840
ggcgggcagc tggccatggt ggagccctat gccttccgcg gcctcaacta cctgcgcgtg 900
ctcaatgtct ctggcaacca gctgaccacg ctggaagaat cagtcttcca ctcggtgggc 960
aacctggaga cgctcatcct ggactccaac ccactggcct gcgactgtcg gctcctgtgg 1020
gtgttccggc gccgctggcg gctcaacttc aaccggcagc agcccacgtg cgccacgccc 1080
gagttcgtcc agggcaagga gttcaaggac ttccctgatg tgctactgcc caactacttc 1140
acctgccgcc gcgcccgcat ccgggatcgc aaggcccagc aggtgtttgt ggatgagggc 1200
cacacggtgc agtttgtgtg ccgggccgat ggcgacccgc cgcccgccat cctctggctc 1260
tcaccccgaa agcacctggt ctcagccaag agcaatgggc ggctcacagt cttccctgat 1320
ggcacgctgg aggtgcgcta cgcccaggta caggacaatg gcacgtacct gtgcatcgcg 1380
gccaatgcag gcggcaacga ctccatgcct gcccacctgc atgtgcgcag ctactcaccc 1440
gactggcccc atcagcccaa caagaccttc gccttcatcc ccaaccagcc gggcgaggga 1500
gaggccaaca gcacccgagc cactgtgcct ttccccttcg acatcaagac cctcatcatc 1560
gccaccacca tgggcttcat ctctttcctg ggcgtcgtcc tcttctgcct ggtgctgctg 1620
tttctctgga gccggggcaa gggcaacacg aagcacaaca tcgagatcga gtatgtcccc 1680
cgaaagtcgg acgcaggcat cagctccgcc gacgcgcccc gcaagttcaa catgaagatg 1740

```
ata                                                              1743


<210> SEQ ID NO 29
<211> LENGTH: 1743
<212> TYPE: DNA
<213> ORGANISM: Rattus sp.

<400> SEQUENCE: 29

accggctgcc cgccccgctg cgagtgctca gcgcaggacc gagcagtgct ctgtcaccgc     60

aagcgctttg tggcggtgcc cgagggcatc cccaccgaga ctcgcctgct ggacctgggc    120

aaaaaccgca tcaagacact caaccaggac gagtttgcca gtttcccaca cctggaggag    180

ctagaactca atgagaacat tgtgagcgct gtggagccgg gcgccttcaa caacctcttc    240

aacctgagga cgctggggct tcgcagcaac cgcctgaagc tcatcccgct gggcgtcttc    300

accggcctca gcaacttgac caagctggac atcagcgaga acaagatcgt catcctgcta    360

gactacatgt tccaagacct atacaacctc aagtcgctgg aggtcggcga caatgacctc    420

gtctacatct cccatcgagc cttcagcggc ctcaacagcc tggaacagct gacgctggag    480

aaatgcaatc tgacctccat ccccactgag gcactctccc acctgcatgg cctcatcgtc    540

ctgcggctac gacacctcaa catcaatgcc atacgggact actccttcaa gaggctgtac    600

cgactcaagg tcttagagat ctcccactgg ccctacctgg acaccatgac ccccaactgc    660

ctctacggcc tcaacctgac atccctatct atcacgcact gcaacctgac agccgtgccc    720

tatctggcag tgcgccacct ggtctatctc cgtttcctca atctttccta caaccccatc    780

ggtacaatcg agggctccat gctgcatgag ctgctgcggt tgcaagagat ccaactggtg    840

ggcgggcagc tggccgtggt ggagccctac gcctttcgtg ggctcaatta cctgcgtgtg    900

ctcaatgttt ctggcaacca gctgaccacc ctggaggagt cagccttcca ctcggtgggc    960

aacctggaga cgctcattct ggactccaac ccactggcct gtgactgccg gctgctgtgg   1020

gtgttccggc gccgctggcg gctcaacttc aacaggcagc agcctacctg cgccacacct   1080

gagttcgtcc agggcaagga gttcaaggac ttccccgatg tgctcctacc caactacttc   1140

acctgccgcc gggcccacat ccgggaccgc aaggcacagc aggtgtttgt agatgagggc   1200

cacacggtgc agttcgtatg ccgggcagat ggcgaccctc caccagctat cctttggctc   1260

tcaccccgca agcacttggt ctcagccaag agcaatgggc ggctcacagt cttccctgat   1320

ggcacgctgg aggtgcgcta cgcccaggta caggacaacg gcacgtacct gtgcatcgca   1380

gccaatgcag gcggcaacga ctccatgccc gcccacttgc atgtgcgcag ctactcgcct   1440

gactggcccc atcaacccaa caagaccttc gccttcatct ccaaccagcc aggcgaggga   1500

gaggccaaca gcacccgcgc cactgtgcct ttccccttcg acatcaagac gctcatcatc   1560

gccaccacca tgggcttcat ctccttcctg ggcgtggtcc tattctgcct ggtgctgctg   1620

tttctatgga gccggggcaa aggcaacaca aagcacaaca tcgaaattga atatgtgccc   1680

cggaaatcgg acgcaggcat cagctcagct gatgcacccc gcaagttcaa catgaagatg   1740

ata                                                              1743


<210> SEQ ID NO 30
<211> LENGTH: 30
<212> TYPE: DNA
<213> ORGANISM: artificial
<220> FEATURE:
<223> OTHER INFORMATION: DM14

<400> SEQUENCE: 30
```

ctacgtctag aacgggctgc ccgccccgct 30

<210> SEQ ID NO 31
<211> LENGTH: 30
<212> TYPE: DNA
<213> ORGANISM: artificial
<220> FEATURE:
<223> OTHER INFORMATION: DM15

<400> SEQUENCE: 31
ctacgtctag aacgggctgc ccgccccgct 30

<210> SEQ ID NO 32
<211> LENGTH: 5045
<212> TYPE: DNA
<213> ORGANISM: artificial
<220> FEATURE:
<223> OTHER INFORMATION: pSecTag2-V5 vector

<400> SEQUENCE: 32
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggac tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
caccatggag acagacacac tcctgctatg ggtactgctg ctctgggttc caggttccac 960
tggtgacgcg gcccagcccg gtaagcctat ccctaaccct ctcctcggtc tcgattctac 1020
gtctagatat cctcgagaaa cccgctgatc agcctcgact gtgccttcta gttgccagcc 1080
atctgttgtt tgcccctccc ccgtgccttc cttgaccctg gaaggtgcca ctcccactgt 1140
cctttcctaa taaaatgagg aaattgcatc gcattgtctg agtaggtgtc attctattct 1200
ggggggtggg gtggggcagg acagcaaggg ggaggattgg gaagacaata gcaggcatgc 1260
tggggatgcg gtgggctcta tggcttctga ggcggaaaga accagctggg gctctagggg 1320
gtatccccac gcgccctgta gcggcgcatt aagcgcggcg ggtgtggtgg ttacgcgcag 1380
cgtgaccgct acacttgcca gcgccctagc gcccgctcct ttcgctttct tcccttcctt 1440
tctcgccacg ttcgccggct ttccccgtca agctctaaat cggggcatcc ctttagggtt 1500
ccgatttagt gctttacggc acctcgaccc caaaaaactt gattagggtg atggttcacg 1560
tagtgggcca tcgccctgat agacggtttt tcgccctttg acgttggagt ccacgttctt 1620
taatagtgga ctcttgttcc aaactggaac aacactcaac cctatctcgg tctattcttt 1680
tgatttataa gggattttgg ggatttcggc ctattggtta aaaaatgagc tgatttaaca 1740
aaaatttaac gcgaattaat tctgtggaat gtgtgtcagt tagggtgtgg aaagtcccca 1800
ggctccccag caggcagaag tatgcaaagc atgcatctca attagtcagc aaccaggtgt 1860
ggaaagtccc caggctcccc agcaggcaga agtatgcaaa gcatgcatct caattagtca 1920
gcaaccatag tcccgcccct aactccgccc atcccgcccc taactccgcc cagttccgcc 1980
cattctccgc cccatggctg actaattttt tttatttatg cagaggccga ggccgcctct 2040
gcctctgagc tattccagaa gtagtgagga ggcttttttg gaggcctagg cttttgcaaa 2100
aagctcccgg gagcttgtat atccattttc ggatctgatc agcacgtgtt gacaattaat 2160
catcggcata gtatatcggc atagtataat acgacaaggt gaggaactaa accatggcca 2220
agttgaccag tgccgttccg gtgctcaccg cgcgcgacgt cgccggagcg gtcgagttct 2280
ggaccgaccg gctcgggttc tcccgggact tcgtggagga cgacttcgcc ggtgtggtcc 2340
gggacgacgt gaccctgttc atcagcgcgg tccaggacca ggtggtgccg gacaacaccc 2400
tggcctgggt gtgggtgcgc ggcctggacg agctgtacgc cgagtggtcg gaggtcgtgt 2460
ccacgaactt ccgggacgcc tccgggccgg ccatgaccga gatcggcgag cagccgtggg 2520
ggcgggagtt cgccctgcgc gacccggccg gcaactgcgt gcacttcgtg gccgaggagc 2580
aggactgaca cgtgctacga gatttcgatt ccaccgccgc cttctatgaa aggttgggct 2640
tcggaatcgt tttccgggac gccggctgga tgatcctcca gcgcggggat ctcatgctgg 2700
agttcttcgc ccaccccaac ttgtttattg cagcttataa tggttacaaa taaagcaata 2760
gcatcacaaa tttcacaaat aaagcatttt tttcactgca ttctagttgt ggtttgtcca 2820
aactcatcaa tgtatcttat catgtctgta taccgtcgac ctctagctag agcttggcgt 2880
aatcatggtc atagctgttt cctgtgtgaa attgttatcc gctcacaatt ccacacaaca 2940
tacgagccgg aagcataaag tgtaaagcct ggggtgccta atgagtgagc taactcacat 3000
taattgcgtt gcgctcactg cccgctttcc agtcgggaaa cctgtcgtgc cagctgcatt 3060
aatgaatcgg ccaacgcgcg gggagaggcg gtttgcgtat tgggcgctct tccgcttcct 3120
cgctcactga ctcgctgcgc tcggtcgttc ggctgcggcg agcggtatca gctcactcaa 3180
aggcggtaat acggttatcc acagaatcag gggataacgc aggaaagaac atgtgagcaa 3240
aaggccagca aaaggccagg aaccgtaaaa aggccgcgtt gctggcgttt ttccataggc 3300
tccgcccccc tgacgagcat cacaaaaatc gacgctcaag tcagaggtgg cgaaacccga 3360
caggactata aagataccag gcgtttcccc ctggaagctc cctcgtgcgc tctcctgttc 3420
cgaccctgcc gcttaccgga tacctgtccg cctttctccc ttcgggaagc gtggcgcttt 3480
ctcaatgctc acgctgtagg tatctcagtt cggtgtaggt cgttcgctcc aagctgggct 3540
gtgtgcacga accccccgtt cagcccgacc gctgcgcctt atccggtaac tatcgtcttg 3600
agtccaaccc ggtaagacac gacttatcgc cactggcagc agccactggt aacaggatta 3660
gcagagcgag gtatgtaggc ggtgctacag agttcttgaa gtggtggcct aactacggct 3720
acactagaag gacagtattt ggtatctgcg ctctgctgaa gccagttacc ttcggaaaaa 3780
gagttggtag ctcttgatcc ggcaaacaaa ccaccgctgg tagcggtggt ttttttgttt 3840
gcaagcagca gattacgcgc agaaaaaaag gatctcaaga agatcctttg atcttttcta 3900
cggggtctga cgctcagtgg aacgaaaact cacgttaagg gattttggtc atgagattat 3960
caaaaaggat cttcacctag atccttttaa attaaaaatg aagttttaaa tcaatctaaa 4020
gtatatatga gtaaacttgg tctgacagtt accaatgctt aatcagtgag gcacctatct 4080

-continued cagcgatctg tctatttcgt tcatccatag ttgcctgact ccccgtcgtg tagataacta 4140
cgatacggga gggcttacca tctggcccca gtgctgcaat gataccgcga gacccacgct 4200
caccggctcc agatttatca gcaataaacc agccagccgg aagggccgag cgcagaagtg 4260
gtcctgcaac tttatccgcc tccatccagt ctattaattg ttgccgggaa gctagagtaa 4320
gtagttcgcc agttaatagt ttgcgcaacg ttgttgccat tgctacaggc atcgtggtgt 4380
cacgctcgtc gtttggtatg gcttcattca gctccggttc ccaacgatca aggcgagtta 4440
catgatcccc catgttgtgc aaaaaagcgg ttagctcctt cggtcctccg atcgttgtca 4500
gaagtaagtt ggccgcagtg ttatcactca tggttatggc agcactgcat aattctctta 4560
ctgtcatgcc atccgtaaga tgcttttctg tgactggtga gtactcaacc aagtcattct 4620
gagaatagtg tatgcggcga ccgagttgct cttgcccggc gtcaatacgg gataataccg 4680
cgccacatag cagaacttta aaagtgctca tcattggaaa acgttcttcg gggcgaaaac 4740
tctcaaggat cttaccgctg ttgagatcca gttcgatgta acccactcgt gcacccaact 4800
gatcttcagc atcttttact ttcaccagcg tttctgggtg agcaaaaaca ggaaggcaaa 4860
atgccgcaaa aaagggaata agggcgacac ggaaatgttg aatactcata ctcttccttt 4920
ttcaatatta ttgaagcatt tatcagggtt attgtctcat gagcggatac atatttgaat 4980
gtatttagaa aaataaacaa ataggggttc cgcgcacatt tccccgaaaa gtgccacctg 5040
acgtc 5045

<210> SEQ ID NO 33
<211> LENGTH: 1743
<212> TYPE: DNA
<213> ORGANISM: Homo sapiens

<400> SEQUENCE: 33
attggctgcc ccgctcgctg tgagtgctct gcccagaaca aatctgttag ctgtcacaga 60
aggcgattga tcgccatccc agagggcatt cccatcgaaa ccaaaatctt ggacctcagt 120
aaaaacaggc taaaaagcgt caaccctgaa gaattcatat catatcctct gctggaagag 180
atagacttga gtgacaacat cattgccaat gtggaaccag gagcattcaa caatctcttt 240
aacctgcgtt ccctccgcct aaaaggcaat cgtctaaagc tggtcccttt gggagtattc 300
acggggctgt ccaatctcac taagcttgac attagtgaga ataagattgt cattttacta 360
gactacatgt tccaagatct acataacctg aagtctctag aagtggggga caatgatttg 420
gtttatatat cacacagggc attcagtggg cttcttagct tggagcagct caccctggag 480
aaatgcaact taacagcagt accaacagaa gccctctccc acctccgcag cctcatcagc 540
ctgcatctga agcatctcaa tatcaacaat atgcctgtgt atgcctttaa aagattgttc 600
cacctgaaac acctagagat tgactattgg cctttactgg atatgatgcc tgccaatagc 660
ctctacggtc tcaacctcac atccctttca gtcaccaaca ccaatctgtc tactgtaccc 720
ttccttgcct ttaaacacct ggtatacctg actcacctta acctctccta caatcccatc 780
agcactattg aagcaggcat gttctctgac ctgatccgcc ttcaggagct tcatatagtg 840
ggggcccagc ttcgcaccat tgagcctcac tccttccaag ggctccgctt cctacgcgtg 900
ctcaatgtgt ctcagaacct gctggaaact ttggaagaga atgtcttctc ctcccctagg 960
gctctggagg tcttgagcat taacaacaac cctctggcct gtgactgccg ccttctctgg 1020
atcttgcagc gacagcccac cctgcagttt ggtggccagc aacctatgtg tgctggccca 1080
gacaccatcc gtgagaggtc tttcaaggat ttccatagca ctgccctttc tttttacttt 1140
acctgcaaaa aacccaaaat ccgtgaaaag aagttgcagc atctgctagt agatgaaggg 1200
cagacagtcc agctagaatg cagtgcagat ggagacccgc agcctgtgat ttcctgggtg 1260
acaccccgaa ggcgtttcat caccaccaag tccaatggaa gagccaccgt gttgggtgat 1320
ggcaccttgg aaatccgctt tgcccaggat caagacagcg ggatgtatgt ttgcatcgct 1380
agcaatgctg ctgggaatga taccttcaca gcctccttaa ctgtgaaagg attcgcttca 1440
gatcgttttc tttatgcgaa caggacccct atgtacatga ccgactccaa tgacaccatt 1500
tccaatggca ccaatgccaa tactttttcc ctggacctta aaacaatact ggtgtctaca 1560
gctatgggct gcttcacatt cctgggagtg gttttatttt gttttcttct cctttttgtg 1620
tggagccgag ggaaaggcaa gcacaaaaac agcattgacc ttgagtatgt gcccagaaaa 1680
aacaatggtg ctgttgtgga aggggaggta gctggaccca ggaggttcaa catgaaaatg 1740
att 1743

<210> SEQ ID NO 34
<211> LENGTH: 30
<212> TYPE: DNA
<213> ORGANISM: artificial
<220> FEATURE:
<223> OTHER INFORMATION: DM16

<400> SEQUENCE: 34
ctacgtctag aattggctgc cccgctcgct 30

<210> SEQ ID NO 35
<211> LENGTH: 39
<212> TYPE: DNA
<213> ORGANISM: artificial
<220> FEATURE:
<223> OTHER INFORMATION: DM17

<400> SEQUENCE: 35
ggtttctcga gtcaaatcat tttcatgttg aacctcctg 39

<210> SEQ ID NO 36
<211> LENGTH: 7086
<212> TYPE: DNA
<213> ORGANISM: artificial
<220> FEATURE:
<223> OTHER INFORMATION: pRS5a-IgG

<400> SEQUENCE: 36
tcgacggatc gggagatccg ggacatgtac ctcccagggg cccaggaaga ctacgggagg 60
ctacaccaac gtcaatcaga ggggcctgtg tagctaccga taagcggacc ctcaagaggg 120
cattagcaat agtgtttata aggccccctt gttaacccta aacgggtagc atatgcttcc 180
cgggtagtag tatatactat ccagactaac cctaattcaa tagcatatgt tacccaacgg 240
gaagcatatg ctatcgaatt agggttagta aaagggtcct aaggaacagc gatatctccc 300
accccatgag ctgtcacggt tttatttaca tggggtcagg attccacgag ggtagtgaac 360
cattttagtc acaagggcag tggctgaaga tcaaggagcg ggcagtgaac tctcctgaat 420
cttcgcctgc ttcttcattc tccttcgttt agctaataga ataactgctg agttgtgaac 480
agtaaggtgt atgtgaggtg ctcgaaaaca aggtttcagg tgacgccccc agaataaaat 540
ttggacgggg ggttcagtgg tggcattgtg ctatgacacc aatataaccc tcacaaaccc 600
cttgggcaat aaatactagt gtaggaatga aacattctga atatctttaa caatagaaat 660
ccatggggtg gggacaagcc gtaaagactg gatgtccatc tcacacgaat ttatggctat 720

-continued

```
gggcaacaca taatcctagt gcaatatgat actggggtta ttaagatgtg tcccaggcag    780
ggaccaagac aggtgaacca tgttgttaca ctctatttgt aacaagggga aagagagtgg    840
acgccgacag cagcggactc cactggttgt ctctaacacc cccgaaaatt aaacggggct    900
ccacgccaat ggggcccata aacaaagaca agtggccact cttttttttg aaattgtgga    960
gtgggggcac gcgtcagccc ccacacgccg ccctgcggtt ttggactgta aaataagggt   1020
gtaataactt ggctgattgt aaccccgcta accactgcgg tcaaaccact tgcccacaaa   1080
accactaatg gcaccccggg gaatacctgc ataagtaggt gggcgggcca agataggggc   1140
gcgattgctg cgatctggag gacaaattac acacacttgc gcctgagcgc caagcacagg   1200
gttgttggtc ctcatattca cgaggtcgct gagagcacgg tgggctaatg ttgccatggg   1260
tagcatatac tacccaaata tctggatagc atatgctatc ctaatctata tctgggtagc   1320
ataggctatc ctaatctata tctgggtagc atatgctatc ctaatctata tctgggtagt   1380
atatgctatc ctaatttata tctgggtagc ataggctatc ctaatctata tctgggtagc   1440
atatgctatc ctaatctata tctgggtagt atatgctatc ctaatctgta tccgggtagc   1500
atatgctatc ctaatagaga ttagggtagt atatgctatc ctaatttata tctgggtagc   1560
atatactacc caaatatctg gatagcatat gctatcctaa tctatatctg ggtagcatat   1620
gctatcctaa tctatatctg ggtagcatag gctatcctaa tctatatctg ggtagcatat   1680
gctatcctaa tctatatctg ggtagtatat gctatcctaa tttatatctg ggtagcatag   1740
gctatcctaa tctatatctg ggtagcatat gctatcctaa tctatatctg ggtagtatat   1800
gctatcctaa tctgtatccg ggtagcatat gctatcctca tgcatataca gtcagcatat   1860
gatacccagt agtagagtgg gagtgctatc ctttgcatat gccgccacct cccaaggggg   1920
cgtgaatttt cgctgcttgt ccttttcctg catgcggatc ttcaatattg gccattagcc   1980
atattattca ttggttatat agcataaatc aatattggct attggccatt gcatacgttg   2040
tatctatatc ataatatgta catttatatt ggctcatgtc caatatgacc gccatgttgg   2100
cattgattat tgactagtta ttaatagtaa tcaattacgg ggtcattagt tcatagccca   2160
tatatggagt tccgcgttac ataacttacg gtaaatggcc cgcctggctg accgcccaac   2220
gacccccgcc cattgacgtc aataatgacg tatgttccca tagtaacgcc aatagggact   2280
ttccattgac gtcaatgggt ggagtattta cggtaaactg cccacttggc agtacatcaa   2340
gtgtatcata tgccaagtcc gccccctatt gacgtcaatg acggtaaatg gcccgcctgg   2400
cattatgccc agtacatgac cttacgggac tttcctactt ggcagtacat ctacgtatta   2460
gtcatcgcta ttaccatggt gatgcggttt tggcagtaca ccaatgggcg tggatagcgg   2520
tttgactcac ggggatttcc aagtctccac cccattgacg tcaatgggag tttgttttgg   2580
caccaaaatc aacgggactt tccaaaatgt cgtaataacc ccgccccgtt gacgcaaatg   2640
ggcggtaggc gtgtacggtg ggaggtctat ataagcagag ctcgtttagt gaaccgtcag   2700
atcgcctgga gacgccatcc acgctgtttt gacctccata gaagacaccg ggaccgatcc   2760
agcctccgcg gccgggaacg gtgcattgga acgcggattc cccgtgccaa gagtgacgta   2820
agtaccgcct atagagtcta taggcccacc cccttggctt cgttagaacg cggctacaat   2880
taatacataa ccttatgtat catacacata cgatttaggt gacactatag aataacatcc   2940
actttgcctt tctctccaca ggtgtccact cccaggtcca actgcacgga agcttcaatt   3000
gggatccctc gaggttctgt tccagggtcc gaaatcttgt gacaaaactc acacatgccc   3060
accgtgccca gcacctgaac tcctgggggg accgtcagtc ttcctcttcc ccccaaaacc   3120
```

-continued caaggacacc ctcatgatct cccggacccc tgaggtcaca tgcgtggtgg tggacgtgag 3180
ccacgaagac cctgaggtca agttcaactg gtacgtggac ggcgtggagg tgcataatgc 3240
caagacaaag ccgcgggagg agcagtacaa cagcacgtac cgtgtggtca gcgtcctcac 3300
cgtcctgcac caggactggc tgaatggcaa ggagtacaag tgcaaggtct ccaacaaagc 3360
cctcccagcc cccatcgaga aaaccatctc caaagccaaa gggcagcccc gagaaccaca 3420
ggtgtacacc ctgcccccat cccgggatga gctgaccaag aaccaggtca gcctgacctg 3480
cctggtcaaa ggcttctatc ccagcgacat cgccgtggag tgggagagca atgggcagcc 3540
ggagaacaac tacaagacca cgcctcccgt gctggactcc gacggctcct tcttcctcta 3600
cagcaagctc accgtggaca agagcaggtg gcagcagggg aacgtcttct catgctccgt 3660
gatgcatgag gctctgcaca accactacac gcagaagagc ctctccctgt ctccgggtaa 3720
atgagatctg gtacctcgcg atggcggccg ctctagaggg cccgtttaaa cccgctgatc 3780
agcctcgact gtgccttcta gttgccagcc atctgttgtt tgcccctccc ccgtgccttc 3840
cttgaccctg gaaggtgcca ctcccactgt cctttcctaa taaaatgagg aaattgcatc 3900
gcattgtctg agtaggtgtc attctattct ggggggtggg gtggggcagg acagcaaggg 3960
ggaggattgg gaagacaata gcaggcatgc tggggatgcg gtgggctcta tggcttctga 4020
ggcggaaaga accagctagc tcgatcgagg caggcagaag tatgcaaagc atgcatctca 4080
attagtcagc aaccaggtgt ggaaagtccc caggctcccc agcaggcaga agtatgcaaa 4140
gcatgcatct caattagtca gcaaccatag tcccgcccct aactccgccc atcccgcccc 4200
taactccgcc cagttccgcc cattctccgc cccatggctg actaattttt tttatttatg 4260
cagaggccga ggccgcctct gcctctgagc tattccagaa gtagtgagga ggcttttttg 4320
gaggcctagg cttttgcaaa aagctcccgg gagcttgtat atccattttc ggatctgatc 4380
agcacgtgtt gacaattaat catcggcata gtatatcggc atagtataat acgacaaggt 4440
gaggaactaa accatggcca agttgaccag tgccgttccg gtgctcaccg cgcgcgacgt 4500
cgccggagcg gtcgagttct ggaccgaccg gctcgggttc tcccgggact tcgtggagga 4560
cgacttcgcc ggtgtggtcc gggacgacgt gaccctgttc atcagcgcgg tccaggacca 4620
ggtggtgccg gacaacaccc tggcctgggt gtgggtgcgc ggcctggacg agctgtacgc 4680
cgagtggtcg gaggtcgtgt ccacgaactt ccgggacgcc tccgggccgg ccatgaccga 4740
gatcggcgag cagccgtggg ggcgggagtt cgccctgcgc gacccggccg gcaactgcgt 4800
gcacttcgtg gccgaggagc aggactgaca cgtgctacga gatttcgatt ccaccgccgc 4860
cttctatgaa aggttgggct tcggaatcgt tttccgggac gccggctgga tgatcctcca 4920
gcgcggggat ctcatgctgg agttcttcgc ccaccccaac ttgtttattg cagcttataa 4980
tggttacaaa taaagcaata gcatcacaaa tttcacaaat aaagcatttt tttcactgca 5040
ttctagttgt ggtttgtcca aactcatcaa tgtatcttat catgtctgaa ttttgcatta 5100
atgaatcggc caacgcgcgg ggagaggcgg tttgcgtatt gggcgctctt ccgcttcctc 5160
gctcactgac tcgctgcgct cggtcgttcg gctgcggcga gcggtatcag ctcactcaaa 5220
ggcggtaata cggttatcca cagaatcagg ggataacgca ggaaagaaca tgtgagcaaa 5280
aggccagcaa aaggccagga accgtaaaaa ggccgcgttg ctggcgtttt tccataggct 5340
ccgcccccct gacgagcatc acaaaaatcg acgctcaagt cagaggtggc gaaacccgac 5400
aggactataa agataccagg cgtttccccc tggaagctcc ctcgtgcgct ctcctgttcc 5460
gaccctgccg cttaccggat acctgtccgc ctttctccct tcgggaagcg tggcgctttc 5520
tcaatgctca cgctgtaggt atctcagttc ggtgtaggtc gttcgctcca agctgggctg 5580
tgtgcacgaa ccccccgttc agcccgaccg ctgcgcctta tccggtaact atcgtcttga 5640
gtccaacccg gtaagacacg acttatcgcc actggcagca gccactggta acaggattag 5700
cagagcgagg tatgtaggcg gtgctacaga gttcttgaag tggtggccta actacggcta 5760
cactagaagg acagtatttg gtatctgcgc tctgctgaag ccagttacct tcggaaaaag 5820
agttggtagc tcttgatccg gcaaacaaac caccgctggt agcggtggtt tttttgtttg 5880
caagcagcag attacgcgca gaaaaaaagg atctcaagaa gatcctttga tcttttctac 5940
ggggtctgac gctcagtgga acgaaaactc acgttaaggg attttggtca tgagattatc 6000
aaaaaggatc ttcacctaga tccttttaaa ttaaaaatga agttttaaat caatctaaag 6060
tatatatgag taaacttggt ctgacagtta ccaatgctta atcagtgagg cacctatctc 6120
agcgatctgt ctatttcgtt catccatagt tgcctgactc cccgtcgtgt agataactac 6180
gatacgggag ggcttaccat ctggccccag tgctgcaatg ataccgcgag acccacgctc 6240
accggctcca gatttatcag caataaacca gccagccgga agggccgagc gcagaagtgg 6300
tcctgcaact ttatccgcct ccatccagtc tattaattgt tgccgggaag ctagagtaag 6360
tagttcgcca gttaatagtt tgcgcaacgt tgttgccatt gctacaggca tcgtggtgtc 6420
acgctcgtcg tttggtatgg cttcattcag ctccggttcc caacgatcaa ggcgagttac 6480
atgatccccc atgttgtgca aaaaagcggt tagctccttc ggtcctccga tcgttgtcag 6540
aagtaagttg gccgcagtgt tatcactcat ggttatggca gcactgcata attctcttac 6600
tgtcatgcca tccgtaagat gcttttctgt gactggtgag tactcaacca agtcattctg 6660
agaatagtgt atgcggcgac cgagttgctc ttgcccggcg tcaatacggg ataataccgc 6720
gccacatagc agaactttaa aagtgctcat cattggaaaa cgttcttcgg ggcgaaaact 6780
ctcaaggatc ttaccgctgt tgagatccag ttcgatgtaa cccactcgtg cacccaactg 6840
atcttcagca tcttttactt tcaccagcgt ttctgggtga gcaaaaacag gaaggcaaaa 6900
tgccgcaaaa aagggaataa gggcgacacg gaaatgttga atactcatac tcttcctttt 6960
tcaatattat tgaagcattt atcagggtta ttgtctcatg agcggataca tatttgaatg 7020
tatttagaaa aataaacaaa taggggttcc gcgcacattt ccccgaaaag tgccacctga 7080
cgtcga 7086

<210> SEQ ID NO 37
<211> LENGTH: 8751
<212> TYPE: DNA
<213> ORGANISM: artificial
<220> FEATURE:
<223> OTHER INFORMATION: natleader-hsLINGO-1-Fc/pRS5a

<400> SEQUENCE: 37
tcgacggatc gggagatccg ggacatgtac ctcccagggg cccaggaaga ctacgggagg 60
ctacaccaac gtcaatcaga ggggcctgtg tagctaccga taagcggacc ctcaagaggg 120
cattagcaat agtgtttata aggcccccctt gttaacccta aacgggtagc atatgcttcc 180
cgggtagtag tatatactat ccagactaac cctaattcaa tagcatatgt tacccaacgg 240
gaagcatatg ctatcgaatt agggttagta aaagggtcct aaggaacagc gatatctccc 300
accccatgag ctgtcacggt tttatttaca tggggtcagg attccacgag ggtagtgaac 360
cattttagtc acaagggcag tggctgaaga tcaaggagcg ggcagtgaac tctcctgaat 420
cttcgcctgc ttcttcattc tccttcgttt agctaataga ataactgctg agttgtgaac 480

-continued

```
agtaaggtgt atgtgaggtg ctcgaaaaca aggtttcagg tgacgccccc agaataaaat    540
ttggacgggg ggttcagtgg tggcattgtg ctatgacacc aatataaccc tcacaaaccc    600
cttgggcaat aaatactagt gtaggaatga aacattctga atatctttaa caatagaaat    660
ccatggggtg gggacaagcc gtaaagactg gatgtccatc tcacacgaat ttatggctat    720
gggcaacaca taatcctagt gcaatatgat actggggtta ttaagatgtg tcccaggcag    780
ggaccaagac aggtgaacca tgttgttaca ctctatttgt aacaagggga aagagagtgg    840
acgccgacag cagcggactc cactggttgt ctctaacacc cccgaaaatt aaacggggct    900
ccacgccaat ggggcccata aacaaagaca agtggccact ctttttttttg aaattgtgga    960
gtgggggcac gcgtcagccc ccacacgccg ccctgcggtt ttggactgta aaataagggt   1020
gtaataactt ggctgattgt aaccccgcta accactgcgg tcaaaccact tgcccacaaa   1080
accactaatg gcaccccggg gaatacctgc ataagtaggt gggcgggcca agataggggc   1140
gcgattgctg cgatctggag gacaaattac acacacttgc gcctgagcgc caagcacagg   1200
gttgttggtc ctcatattca cgaggtcgct gagagcacgg tgggctaatg ttgccatggg   1260
tagcatatac tacccaaata tctggatagc atatgctatc ctaatctata tctgggtagc   1320
ataggctatc ctaatctata tctgggtagc atatgctatc ctaatctata tctgggtagt   1380
atatgctatc ctaatttata tctgggtagc ataggctatc ctaatctata tctgggtagc   1440
atatgctatc ctaatctata tctgggtagt atatgctatc ctaatctgta tccgggtagc   1500
atatgctatc ctaatagaga ttagggtagt atatgctatc ctaatttata tctgggtagc   1560
atatactacc caaatatctg gatagcatat gctatcctaa tctatatctg ggtagcatat   1620
gctatcctaa tctatatctg ggtagcatag gctatcctaa tctatatctg ggtagcatat   1680
gctatcctaa tctatatctg ggtagtatat gctatcctaa tttatatctg ggtagcatag   1740
gctatcctaa tctatatctg ggtagcatat gctatcctaa tctatatctg ggtagtatat   1800
gctatcctaa tctgtatccg ggtagcatat gctatcctca tgcatataca gtcagcatat   1860
gatacccagt agtagagtgg gagtgctatc ctttgcatat gccgccacct cccaaggggg   1920
cgtgaatttt cgctgcttgt ccttttcctg catgcggatc ttcaatattg gccattagcc   1980
atattattca ttggttatat agcataaatc aatattggct attggccatt gcatacgttg   2040
tatctatatc ataatatgta catttatatt ggctcatgtc caatatgacc gccatgttgg   2100
cattgattat tgactagtta ttaatagtaa tcaattacgg ggtcattagt tcatagccca   2160
tatatggagt tccgcgttac ataacttacg gtaaatggcc cgcctggctg accgcccaac   2220
gacccccgcc cattgacgtc aataatgacg tatgttccca tagtaacgcc aatagggact   2280
ttccattgac gtcaatgggt ggagtattta cggtaaactg cccacttggc agtacatcaa   2340
gtgtatcata tgccaagtcc gccccctatt gacgtcaatg acggtaaatg gcccgcctgg   2400
cattatgccc agtacatgac cttacgggac tttcctactt ggcagtacat ctacgtatta   2460
gtcatcgcta ttaccatggt gatgcggttt tggcagtaca ccaatgggcg tggatagcgg   2520
tttgactcac ggggatttcc aagtctccac cccattgacg tcaatgggag tttgttttgg   2580
caccaaaatc aacgggactt tccaaaatgt cgtaataacc ccgccccgtt gacgcaaatg   2640
ggcggtaggc gtgtacggtg ggaggtctat ataagcagag ctcgtttagt gaaccgtcag   2700
atcgcctgga gacgccatcc acgctgtttt gacctccata gaagacaccg ggaccgatcc   2760
agcctccgcg gccgggaacg gtgcattgga acgcggattc cccgtgccaa gagtgacgta   2820
agtaccgcct atagagtcta taggcccacc cccttggctt cgttagaacg cggctacaat   2880
```

-continued

```
taatacataa ccttatgtat catacacata cgatttaggt gacactatag aataacatcc   2940
actttgcctt tctctccaca ggtgtccact cccaggtcca actgcacgga agcttgccgc   3000
caccatgcag gtgagcaaga ggatgctggc ggggggcgtg aggagcatgc ccagcccccct  3060
cctggcctgc tggcagccca tcctcctgct ggtgctgggc tcagtgctgt caggctcggc   3120
cacgggctgc ccgccccgct gcgagtgctc cgcccaggac cgcgctgtgc tgtgccaccg   3180
caagcgcttt gtggcagtcc ccgagggcat ccccaccgag acgcgcctgc tggacctagg   3240
caagaaccgc atcaaaacgc tcaaccagga cgagttcgcc agcttcccgc acctggagga   3300
gctggagctc aacgagaaca tcgtgagcgc cgtggagccc ggcgccttca acaacctctt   3360
caacctccgg acgctgggtc tccgcagcaa ccgcctgaag ctcatcccgc taggcgtctt   3420
cactggcctc agcaacctga ccaagctgga catcagcgag aacaagatcg ttatcctact   3480
ggactacatg tttcaggacc tgtacaacct caagtcactg gaggttggcg acaatgacct   3540
cgtctacatc tctcaccgcg ccttcagcgg cctcaacagc ctggagcagc tgacgctgga   3600
gaaatgcaac ctgacctcca tccccaccga ggcgctgtcc cacctgcacg gcctcatcgt   3660
cctgaggctc cggcacctca acatcaatgc catccgggac tactccttca agaggctgta   3720
ccgactcaag gtcttggaga tctcccactg gccctacttg gacaccatga cacccaactg   3780
cctctacggc ctcaacctga cgtccctgtc catcacacac tgcaatctga ccgctgtgcc   3840
ctacctggcc gtccgccacc tagtctatct ccgcttcctc aacctctcct acaaccccat   3900
cagcaccatt gagggctcca tgttgcatga gctgctccgg ctgcaggaga tccagctggt   3960
gggcgggcag ctggccgtgg tggagcccta tgccttccgc ggcctcaact acctgcgcgt   4020
gctcaatgtc tctggcaacc agctgaccac actggaggaa tcagtcttcc actcggtggg   4080
caacctggag acactcatcc tggactccaa cccgctggcc tgcgactgtc ggctcctgtg   4140
ggtgttccgg cgccgctggc ggctcaactt caaccggcag cagcccacgt gcgccacgcc   4200
cgagtttgtc cagggcaagg agttcaagga cttccctgat gtgctactgc ccaactactt   4260
cacctgccgc cgcgcccgca tccgggaccg caaggcccag caggtgtttg tggacgaggg   4320
ccacacggtg cagtttgtgt gccgggccga tggcgacccg ccgcccgcca tcctctggct   4380
ctcaccccga aagcacctgg tctcagccaa gagcaatggg cggctcacag tcttccctga   4440
tggcacgctg gaggtgcgct acgcccaggt acaggacaac ggcacgtacc tgtgcatcgc   4500
ggccaacgcg ggcggcaacg actccatgcc cgcccacctg catgtgcgca gctactcgcc   4560
cgactggccc catcagccca acaagacctt cgctttcatc tccaaccagc cgggcgaggg   4620
agaggccaac agcacccgcg ccactgtgcc tttccccttc gacatcaaga ccctcgaggt   4680
tctgttccag ggtccgaaat cttgtgacaa aactcacaca tgcccaccgt gcccagcacc   4740
tgaactcctg gggggaccgt cagtcttcct cttcccccca aaacccaagg acaccctcat   4800
gatctcccgg acccctgagg tcacatgcgt ggtggtggac gtgagccacg aagaccctga   4860
ggtcaagttc aactggtacg tggacggcgt ggaggtgcat aatgccaaga caaagccgcg   4920
ggaggagcag tacaacagca cgtaccgtgt ggtcagcgtc ctcaccgtcc tgcaccagga   4980
ctggctgaat ggcaaggagt acaagtgcaa ggtctccaac aaagccctcc cagcccccat   5040
cgagaaaacc atctccaaag ccaaagggca gccccgagaa ccacaggtgt acaccctgcc   5100
cccatcccgg gatgagctga ccaagaacca ggtcagcctg acctgcctgg tcaaaggctt   5160
ctatcccagc gacatcgccg tggagtggga gagcaatggg cagccggaga acaactacaa   5220
gaccacgcct cccgtgctgg actccgacgg ctccttcttc ctctacagca agctcaccgt   5280
```

-continued

```
ggacaagagc aggtggcagc aggggaacgt cttctcatgc tccgtgatgc atgaggctct   5340
gcacaaccac tacacgcaga agagcctctc cctgtctccg ggtaaatgag atctggtacc   5400
tcgcgatggc ggccgctcta gagggcccgt ttaaacccgc tgatcagcct cgactgtgcc   5460
ttctagttgc cagccatctg ttgtttgccc ctcccccgtg ccttccttga ccctggaagg   5520
tgccactccc actgtccttt cctaataaaa tgaggaaatt gcatcgcatt gtctgagtag   5580
gtgtcattct attctggggg gtggggtggg gcaggacagc aagggggagg attgggaaga   5640
caatagcagg catgctgggg atgcggtggg ctctatggct tctgaggcgg aaagaaccag   5700
ctagctcgat cgaggcaggc agaagtatgc aaagcatgca tctcaattag tcagcaacca   5760
ggtgtggaaa gtccccaggc tccccagcag gcagaagtat gcaaagcatg catctcaatt   5820
agtcagcaac catagtcccg cccctaactc cgcccatccc gcccctaact ccgcccagtt   5880
ccgcccattc tccgccccat ggctgactaa ttttttttat ttatgcagag gccgaggccg   5940
cctctgcctc tgagctattc cagaagtagt gaggaggctt ttttggaggc ctaggctttt   6000
gcaaaaagct cccgggagct tgtatatcca ttttcggatc tgatcagcac gtgttgacaa   6060
ttaatcatcg gcatagtata tcggcatagt ataatacgac aaggtgagga actaaaccat   6120
ggccaagttg accagtgccg ttccggtgct caccgcgcgc gacgtcgccg gagcggtcga   6180
gttctggacc gaccggctcg ggttctcccg ggacttcgtg gaggacgact tcgccggtgt   6240
ggtccgggac gacgtgaccc tgttcatcag cgcggtccag gaccaggtgg tgccggacaa   6300
caccctggcc tgggtgtggg tgcgcggcct ggacgagctg tacgccgagt ggtcggaggt   6360
cgtgtccacg aacttccggg acgcctccgg gccggccatg accgagatcg gcgagcagcc   6420
gtgggggcgg gagttcgccc tgcgcgaccc ggccggcaac tgcgtgcact tcgtggccga   6480
ggagcaggac tgacacgtgc tacgagattt cgattccacc gccgccttct atgaaaggtt   6540
gggcttcgga atcgttttcc gggacgccgg ctggatgatc ctccagcgcg gggatctcat   6600
gctggagttc ttcgcccacc ccaacttgtt tattgcagct tataatggtt acaaataaag   6660
caatagcatc acaaatttca caaataaagc atttttttca ctgcattcta gttgtggttt   6720
gtccaaactc atcaatgtat cttatcatgt ctgaattttg cattaatgaa tcggccaacg   6780
cgcggggaga ggcggtttgc gtattgggcg ctcttccgct tcctcgctca ctgactcgct   6840
gcgctcggtc gttcggctgc ggcgagcggt atcagctcac tcaaaggcgg taatacggtt   6900
atccacagaa tcaggggata acgcaggaaa gaacatgtga gcaaaaggcc agcaaaaggc   6960
caggaaccgt aaaaaggccg cgttgctggc gtttttccat aggctccgcc cccctgacga   7020
gcatcacaaa aatcgacgct caagtcagag gtggcgaaac ccgacaggac tataaagata   7080
ccaggcgttt ccccctggaa gctccctcgt gcgctctcct gttccgaccc tgccgcttac   7140
cggatacctg tccgcctttc tcccttcggg aagcgtggcg ctttctcaat gctcacgctg   7200
taggtatctc agttcggtgt aggtcgttcg ctccaagctg ggctgtgtgc acgaaccccc   7260
cgttcagccc gaccgctgcg ccttatccgg taactatcgt cttgagtcca acccggtaag   7320
acacgactta tcgccactgg cagcagccac tggtaacagg attagcagag cgaggtatgt   7380
aggcggtgct acagagttct tgaagtggtg gcctaactac ggctacacta gaaggacagt   7440
atttggtatc tgcgctctgc tgaagccagt taccttcgga aaaagagttg gtagctcttg   7500
atccggcaaa caaaccaccg ctggtagcgg tggttttttt gtttgcaagc agcagattac   7560
gcgcagaaaa aaaggatctc aagaagatcc tttgatcttt tctacggggt ctgacgctca   7620
gtggaacgaa aactcacgtt aagggatttt ggtcatgaga ttatcaaaaa ggatcttcac   7680
```

```
ctagatcctt ttaaattaaa aatgaagttt taaatcaatc taaagtatat atgagtaaac   7740
ttggtctgac agttaccaat gcttaatcag tgaggcacct atctcagcga tctgtctatt   7800
tcgttcatcc atagttgcct gactccccgt cgtgtagata actacgatac gggagggctt   7860
accatctggc cccagtgctg caatgatacc gcgagaccca cgctcaccgg ctccagattt   7920
atcagcaata aaccagccag ccggaagggc cgagcgcaga agtggtcctg caactttatc   7980
cgcctccatc cagtctatta attgttgccg ggaagctaga gtaagtagtt cgccagttaa   8040
tagtttgcgc aacgttgttg ccattgctac aggcatcgtg gtgtcacgct cgtcgtttgg   8100
tatggcttca ttcagctccg gttcccaacg atcaaggcga gttacatgat cccccatgtt   8160
gtgcaaaaaa gcggttagct ccttcggtcc tccgatcgtt gtcagaagta agttggccgc   8220
agtgttatca ctcatggtta tggcagcact gcataattct cttactgtca tgccatccgt   8280
aagatgcttt tctgtgactg gtgagtactc aaccaagtca ttctgagaat agtgtatgcg   8340
gcgaccgagt tgctcttgcc cggcgtcaat acgggataat accgcgccac atagcagaac   8400
tttaaaagtg ctcatcattg gaaaacgttc ttcggggcga aaactctcaa ggatcttacc   8460
gctgttgaga tccagttcga tgtaacccac tcgtgcaccc aactgatctt cagcatcttt   8520
tactttcacc agcgtttctg ggtgagcaaa aacaggaagg caaaatgccg caaaaaaggg   8580
aataagggcg acacggaaat gttgaatact catactcttc ctttttcaat attattgaag   8640
catttatcag ggttattgtc tcatgagcgg atacatattt gaatgtattt agaaaaataa   8700
acaaataggg gttccgcgca catttccccg aaaagtgcca cctgacgtcg a            8751
```

```
<210> SEQ ID NO 38
<211> LENGTH: 7830
<212> TYPE: DNA
<213> ORGANISM: artificial
<220> FEATURE:
<223> OTHER INFORMATION: Igleader-hsLINGO-1-?LRR-Fc/pRS5a

<400> SEQUENCE: 38
```

```
tcgacggatc gggagatccg ggacatgtac ctcccagggg cccaggaaga ctacgggagg     60
ctacaccaac gtcaatcaga ggggcctgtg tagctaccga taagcggacc ctcaagaggg    120
cattagcaat agtgtttata aggcccccctt gttaacccta aacgggtagc atatgcttcc   180
cgggtagtag tatatactat ccagactaac cctaattcaa tagcatatgt tacccaacgg    240
gaagcatatg ctatcgaatt agggttagta aaagggtcct aaggaacagc gatatctccc    300
accccatgag ctgtcacggt tttatttaca tggggtcagg attccacgag ggtagtgaac    360
cattttagtc acaagggcag tggctgaaga tcaaggagcg ggcagtgaac tctcctgaat    420
cttcgcctgc ttcttcattc tccttcgttt agctaataga ataactgctg agttgtgaac    480
agtaaggtgt atgtgaggtg ctcgaaaaca aggtttcagg tgacgccccc agaataaaat    540
ttggacgggg ggttcagtgg tggcattgtg ctatgacacc aatataaccc tcacaaaccc    600
cttgggcaat aaatactagt gtaggaatga aacattctga atatctttaa caatagaaat    660
ccatggggtg gggacaagcc gtaaagactg gatgtccatc tcacacgaat ttatggctat    720
gggcaacaca taatcctagt gcaatatgat actggggtta ttaagatgtg tcccaggcag    780
ggaccaagac aggtgaacca tgttgttaca ctctatttgt aacaagggga aagagagtgg    840
acgccgacag cagcggactc cactggttgt ctctaacacc cccgaaaatt aaacggggct    900
ccacgccaat ggggcccata aacaaagaca agtggccact cttttttttg aaattgtgga    960
gtgggggcac gcgtcagccc ccacacgccg ccctgcggtt ttggactgta aaataagggt   1020
```

-continued

```
gtaataactt ggctgattgt aaccccgcta accactgcgg tcaaaccact tgcccacaaa   1080
accactaatg gcaccccggg gaatacctgc ataagtaggt gggcgggcca agataggggc   1140
gcgattgctg cgatctggag gacaaattac acacacttgc gcctgagcgc caagcacagg   1200
gttgttggtc ctcatattca cgaggtcgct gagagcacgg tgggctaatg ttgccatggg   1260
tagcatatac tacccaaata tctggatagc atatgctatc ctaatctata tctgggtagc   1320
ataggctatc ctaatctata tctgggtagc atatgctatc ctaatctata tctgggtagt   1380
atatgctatc ctaatttata tctgggtagc ataggctatc ctaatctata tctgggtagc   1440
atatgctatc ctaatctata tctgggtagt atatgctatc ctaatctgta tccgggtagc   1500
atatgctatc ctaatagaga ttagggtagt atatgctatc ctaatttata tctgggtagc   1560
atatactacc caaatatctg gatagcatat gctatcctaa tctatatctg ggtagcatat   1620
gctatcctaa tctatatctg ggtagcatag gctatcctaa tctatatctg ggtagcatat   1680
gctatcctaa tctatatctg ggtagtatat gctatcctaa tttatatctg ggtagcatag   1740
gctatcctaa tctatatctg ggtagcatat gctatcctaa tctatatctg ggtagtatat   1800
gctatcctaa tctgtatccg ggtagcatat gctatcctca tgcatataca gtcagcatat   1860
gatacccagt agtagagtgg gagtgctatc ctttgcatat gccgccacct cccaaggggg   1920
cgtgaatttt cgctgcttgt ccttttcctg catgcggatc ttcaatattg gccattagcc   1980
atattattca ttggttatat agcataaatc aatattggct attggccatt gcatacgttg   2040
tatctatatc ataatatgta catttatatt ggctcatgtc caatatgacc gccatgttgg   2100
cattgattat tgactagtta ttaatagtaa tcaattacgg ggtcattagt tcatagccca   2160
tatatggagt tccgcgttac ataacttacg gtaaatggcc cgcctggctg accgcccaac   2220
gacccccgcc cattgacgtc aataatgacg tatgttccca tagtaacgcc aatagggact   2280
ttccattgac gtcaatgggt ggagtattta cggtaaactg cccacttggc agtacatcaa   2340
gtgtatcata tgccaagtcc gccccctatt gacgtcaatg acggtaaatg gcccgcctgg   2400
cattatgccc agtacatgac cttacgggac tttcctactt ggcagtacat ctacgtatta   2460
gtcatcgcta ttaccatggt gatgcggttt tggcagtaca ccaatgggcg tggatagcgg   2520
tttgactcac ggggatttcc aagtctccac cccattgacg tcaatgggag tttgttttgg   2580
caccaaaatc aacgggactt tccaaaatgt cgtaataacc ccgccccgtt gacgcaaatg   2640
ggcggtaggc gtgtacggtg ggaggtctat ataagcagag ctcgtttagt gaaccgtcag   2700
atcgcctgga gacgccatcc acgctgtttt gacctccata gaagacaccg ggaccgatcc   2760
agcctccgcg gccgggaacg gtgcattgga acgcggattc cccgtgccaa gagtgacgta   2820
agtaccgcct atagagtcta taggcccacc cccttggctt cgttagaacg cggctacaat   2880
taatacataa ccttatgtat catacacata cgatttaggt gacactatag aataacatcc   2940
actttgcctt tctctccaca ggtgtccact cccaggtcca actgcacgga agcttgccgc   3000
caccatgagt gtgctcactc aggtcctggc gttgctgctg ctgtggctta caggtacgcg   3060
ttgtacgggc tgcccgcccc gctgcgagtg ctccgcccag gaccgcgctg tgctgtgcca   3120
ccgcaagcgc tttgtggcag tccccgaggg catccccacc aacctggaga cactcatcct   3180
ggactccaac ccgctggcct gcgactgtcg gctcctgtgg gtgttccggc gccgctggcg   3240
gctcaacttc aaccggcagc agcccacgtg cgccacgccc gagtttgtcc agggcaagga   3300
gttcaaggac ttccctgatg tgctactgcc caactacttc acctgccgcc gcgcccgcat   3360
ccgggaccgc aaggcccagc aggtgtttgt ggacgagggc cacacggtgc agtttgtgtg   3420
```

```
ccgggccgat ggcgacccgc cgcccgccat cctctggctc tcaccccgaa agcacctggt   3480
ctcagccaag agcaatgggc ggctcacagt cttccctgat ggcacgctgg aggtgcgcta   3540
cgcccaggta caggacaacg gcacgtacct gtgcatcgcg gccaacgcgg gcggcaacga   3600
ctccatgccc gcccacctgc atgtgcgcag ctactcgccc gactggcccc atcagcccaa   3660
caagaccttc gctttcatct ccaaccagcc gggcgaggga gaggccaaca gcacccgcgc   3720
cactgtgcct ttccccttcg acatcaagac cctcgaggtt ctgttccagg gtccgaaatc   3780
ttgtgacaaa actcacacat gcccaccgtg cccagcacct gaactcctgg ggggaccgtc   3840
agtcttcctc ttccccccaa aacccaagga caccctcatg atctcccgga cccctgaggt   3900
cacatgcgtg gtggtggacg tgagccacga agaccctgag gtcaagttca actggtacgt   3960
ggacggcgtg gaggtgcata atgccaagac aaagccgcgg gaggagcagt acaacagcac   4020
gtaccgtgtg gtcagcgtcc tcaccgtcct gcaccaggac tggctgaatg gcaaggagta   4080
caagtgcaag gtctccaaca aagccctccc agcccccatc gagaaaacca tctccaaagc   4140
caaagggcag ccccgagaac cacaggtgta caccctgccc ccatcccggg atgagctgac   4200
caagaaccag gtcagcctga cctgcctggt caaaggcttc tatcccagcg acatcgccgt   4260
ggagtgggag agcaatgggc agccggagaa caactacaag accacgcctc ccgtgctgga   4320
ctccgacggc tccttcttcc tctacagcaa gctcaccgtg gacaagagca ggtggcagca   4380
ggggaacgtc ttctcatgct ccgtgatgca tgaggctctg cacaaccact acacgcagaa   4440
gagcctctcc ctgtctccgg gtaaatgaga tctggtacct cgcgatggcg gccgctctag   4500
agggcccgtt taaacccgct gatcagcctc gactgtgcct tctagttgcc agccatctgt   4560
tgtttgcccc tcccccgtgc cttccttgac cctggaaggt gccactccca ctgtcctttc   4620
ctaataaaat gaggaaattg catcgcattg tctgagtagg tgtcattcta ttctgggggg   4680
tggggtgggg caggacagca agggggagga ttgggaagac aatagcaggc atgctgggga   4740
tgcggtgggc tctatggctt ctgaggcgga aagaaccagc tagctcgatc gaggcaggca   4800
gaagtatgca aagcatgcat ctcaattagt cagcaaccag gtgtggaaag tccccaggct   4860
ccccagcagg cagaagtatg caaagcatgc atctcaatta gtcagcaacc atagtcccgc   4920
ccctaactcc gcccatcccg cccctaactc cgcccagttc cgcccattct ccgccccatg   4980
gctgactaat tttttttatt tatgcagagg ccgaggccgc ctctgcctct gagctattcc   5040
agaagtagtg aggaggcttt tttggaggcc taggcttttg caaaaagctc ccgggagctt   5100
gtatatccat tttcggatct gatcagcacg tgttgacaat taatcatcgg catagtatat   5160
cggcatagta taatacgaca aggtgaggaa ctaaaccatg gccaagttga ccagtgccgt   5220
tccggtgctc accgcgcgcg acgtcgccgg agcggtcgag ttctggaccg accggctcgg   5280
gttctcccgg gacttcgtgg aggacgactt cgccggtgtg gtccgggacg acgtgaccct   5340
gttcatcagc gcggtccagg accaggtggt gccggacaac accctggcct gggtgtgggt   5400
gcgcggcctg gacgagctgt acgccgagtg gtcggaggtc gtgtccacga acttccggga   5460
cgcctccggg ccggccatga ccgagatcgg cgagcagccg tgggggcggg agttcgccct   5520
gcgcgacccg gccggcaact gcgtgcactt cgtggccgag gagcaggact gacacgtgct   5580
acgagatttc gattccaccg ccgccttcta tgaaaggttg ggcttcggaa tcgttttccg   5640
ggacgccggc tggatgatcc tccagcgcgg ggatctcatg ctggagttct tcgcccaccc   5700
caacttgttt attgcagctt ataatggtta caaataaagc aatagcatca caaatttcac   5760
aaataaagca tttttttcac tgcattctag ttgtggtttg tccaaactca tcaatgtatc   5820
```

-continued ttatcatgtc tgaattttgc attaatgaat cggccaacgc gcggggagag gcggtttgcg 5880
tattgggcgc tcttccgctt cctcgctcac tgactcgctg cgctcggtcg ttcggctgcg 5940
gcgagcggta tcagctcact caaaggcggt aatacggtta tccacagaat caggggataa 6000
cgcaggaaag aacatgtgag caaaaggcca gcaaaaggcc aggaaccgta aaaaggccgc 6060
gttgctggcg tttttccata ggctccgccc ccctgacgag catcacaaaa atcgacgctc 6120
aagtcagagg tggcgaaacc cgacaggact ataaagatac caggcgtttc cccctggaag 6180
ctccctcgtg cgctctcctg ttccgaccct gccgcttacc ggatacctgt ccgcctttct 6240
cccttcggga agcgtggcgc tttctcaatg ctcacgctgt aggtatctca gttcggtgta 6300
ggtcgttcgc tccaagctgg gctgtgtgca cgaacccccc gttcagcccg accgctgcgc 6360
cttatccggt aactatcgtc ttgagtccaa cccggtaaga cacgacttat cgccactggc 6420
agcagccact ggtaacagga ttagcagagc gaggtatgta ggcggtgcta cagagttctt 6480
gaagtggtgg cctaactacg gctacactag aaggacagta tttggtatct gcgctctgct 6540
gaagccagtt accttcggaa aaagagttgg tagctcttga tccggcaaac aaaccaccgc 6600
tggtagcggt ggtttttttg tttgcaagca gcagattacg cgcagaaaaa aaggatctca 6660
agaagatcct ttgatctttt ctacggggtc tgacgctcag tggaacgaaa actcacgtta 6720
agggattttg gtcatgagat tatcaaaaag gatcttcacc tagatccttt taaattaaaa 6780
atgaagtttt aaatcaatct aaagtatata tgagtaaact tggtctgaca gttaccaatg 6840
cttaatcagt gaggcaccta tctcagcgat ctgtctattt cgttcatcca tagttgcctg 6900
actccccgtc gtgtagataa ctacgatacg ggagggctta ccatctggcc ccagtgctgc 6960
aatgataccg cgagacccac gctcaccggc tccagattta tcagcaataa accagccagc 7020
cggaagggcc gagcgcagaa gtggtcctgc aactttatcc gcctccatcc agtctattaa 7080
ttgttgccgg gaagctagag taagtagttc gccagttaat agtttgcgca acgttgttgc 7140
cattgctaca ggcatcgtgg tgtcacgctc gtcgtttggt atggcttcat tcagctccgg 7200
ttcccaacga tcaaggcgag ttacatgatc ccccatgttg tgcaaaaaag cggttagctc 7260
cttcggtcct ccgatcgttg tcagaagtaa gttggccgca gtgttatcac tcatggttat 7320
ggcagcactg cataattctc ttactgtcat gccatccgta agatgctttt ctgtgactgg 7380
tgagtactca accaagtcat tctgagaata gtgtatgcgg cgaccgagtt gctcttgccc 7440
ggcgtcaata cgggataata ccgcgccaca tagcagaact ttaaaagtgc tcatcattgg 7500
aaaacgttct tcggggcgaa aactctcaag gatcttaccg ctgttgagat ccagttcgat 7560
gtaacccact cgtgcaccca actgatcttc agcatctttt actttcacca gcgtttctgg 7620
gtgagcaaaa acaggaaggc aaaatgccgc aaaaaaggga ataagggcga cacggaaatg 7680
ttgaatactc atactcttcc tttttcaata ttattgaagc atttatcagg gttattgtct 7740
catgagcgga tacatatttg aatgtattta gaaaaataaa caaatagggg ttccgcgcac 7800
atttccccga aaagtgccac ctgacgtcga 7830

<210> SEQ ID NO 39
<211> LENGTH: 5025
<212> TYPE: DNA
<213> ORGANISM: artificial
<220> FEATURE:
<223> OTHER INFORMATION: Fab Expression Vector pMORPH-X9_MH

<400> SEQUENCE: 39
ctagataacg agggcaaaaa atgaaaaaga cagctatcgc gattgcagtg gcactggctg 60

-continued

```
gtttcgctac cgtagcgcag gccgatatcg tgctgaccca gccgccttca gtgagtggcg    120
caccaggtca gcgtgtgacc atctcgtgta gcggcagcag cagcaacatt ggtaataatt    180
atgtgtcttg gtaccagcag ttgcccggga cggcgccgaa acttctgatt tctcgtaatt    240
ctaagcgtcc ctcaggcgtg ccggatcgtt ttagcggatc caaaagcggc accagcgcga    300
gccttgcgat tacgggcctg caaagcgaag acgaagcgga ttattattgc tctacttatg    360
atactttttc tattgtgttt ggcggcggca cgaagttaac cgttcttggc cagccgaaag    420
ccgcaccgag tgtgacgctg tttccgccga gcagcgaaga attgcaggcg aacaaagcga    480
ccctggtgtg cctgattagc gacttttatc cgggagccgt gacagtggcc tggaaggcag    540
atagcagccc cgtcaaggcg ggagtggaga ccaccacacc ctccaaacaa agcaacaaca    600
agtacgcggc cagcagctat ctgagcctga cgcctgagca gtggaagtcc cacagaagct    660
acagctgcca ggtcacgcat gaggggagca ccgtggaaaa aaccgttgcg ccgactgagg    720
cctgataagc atgcgtagga gaaaataaaa tgaaacaaag cactattgca ctggcactct    780
taccgttgct cttcacccct gttaccaaag cccaggtgca attgcaacag tctggtccgg    840
gcctggtgaa accgagccaa accctgagcc tgacctgtgc gatttccgga gatagcgtga    900
gcgataattc tgctgcttgg tcttggattc gccagtctcc tgggcgtggc ctcgagtggc    960
tgggccttat ctatcttcgt agcaagtggg ataacgatta tgcggtgagc gtgaaaagcc   1020
ggattaccat caacccggat acttcgaaaa accagtttag cctgcaactg aacagcgtga   1080
ccccggaaga tacggccgtg tattattgcg cgcgtactgg tcgtgctgat gagtttgatg   1140
tttggggcca aggcaccctg gtgacggtta gctcagcgtc gaccaaaggt ccaagcgtgt   1200
ttccgctggc tccgagcagc aaaagcacca gcggcggcac ggctgccctg ggctgcctgg   1260
ttaaagatta tttcccggaa ccagtcaccg tgagctggaa cagcggggcg ctgaccagcg   1320
gcgtgcatac ctttccggcg gtgctgcaaa gcagcggcct gtatagcctg agcagcgttg   1380
tgaccgtgcc gagcagcagc ttaggcactc agacctatat ttgcaacgtg aaccataaac   1440
cgagcaacac caaagtggat aaaaaagtgg aaccgaaaag cgaattcgag cagaagctga   1500
tctctgagga ggatctgaac ggcgcgccgc accatcatca ccatcactga taagcttgac   1560
ctgtgaagtg aaaaatggcg cagattgtgc gacatttttt ttgtctgccg tttaattaaa   1620
gggggggggg ggccggcctg ggggggggtg tacatgaaat tgtaaacgtt aatattttgt   1680
taaaattcgc gttaaatttt tgttaaatca gctcattttt taaccaatag gccgaaatcg   1740
gcaaaatccc ttataaatca aaagaataga ccgagatagg gttgagtgtt gttccagttt   1800
ggaacaagag tccactatta aagaacgtgg actccaacgt caaagggcga aaaaccgtct   1860
atcagggcga tggcccacta cgagaaccat caccctaatc aagttttttg gggtcgaggt   1920
gccgtaaagc actaaatcgg aaccctaaag ggagcccccg atttagagct tgacggggaa   1980
agccggcgaa cgtggcgaga aaggaaggga agaaagcgaa aggagcgggc gctagggcgc   2040
tggcaagtgt agcggtcacg ctgcgcgtaa ccaccacacc cgccgcgctt aatgcgccgc   2100
tacagggcgc gtgctagact agtgtttaaa ccggaccggg ggggggctta agtgggctgc   2160
aaaacaaaac ggcctcctgt caggaagccg cttttatcgg gtagcctcac tgcccgcttt   2220
ccagtcggga aacctgtcgt gccagctgca tcagtgaatc ggccaacgcg cggggagagg   2280
cggtttgcgt attgggagcc agggtggttt ttcttttcac cagtgagacg ggcaacagct   2340
gattgccctt caccgcctgg ccctgagaga gttgcagcaa gcggtccacg ctggtttgcc   2400
ccagcaggcg aaaatcctgt ttgatggtgg tcagcggcgg gatataacat gagctgtcct   2460
```

-continued

```
cggtatcgtc gtatcccact accgagatgt ccgcaccaac gcgcagcccg gactcggtaa   2520
tggcacgcat tgcgcccagc gccatctgat cgttggcaac cagcatcgca gtgggaacga   2580
tgccctcatt cagcatttgc atggtttgtt gaaaaccgga catggcactc cagtcgcctt   2640
cccgttccgc tatcggctga atttgattgc gagtgagata tttatgccag ccagccagac   2700
gcagacgcgc cgagacagaa cttaatgggc cagctaacag cgcgatttgc tggtggccca   2760
atgcgaccag atgctccacg cccagtcgcg taccgtcctc atgggagaaa ataatactgt   2820
tgatgggtgt ctggtcagag acatcaagaa ataacgccgg aacattagtg caggcagctt   2880
ccacagcaat agcatcctgg tcatccagcg gatagttaat aatcagccca ctgacacgtt   2940
gcgcgagaag attgtgcacc gccgctttac aggcttcgac gccgcttcgt tctaccatcg   3000
acacgaccac gctggcaccc agttgatcgg cgcgagattt aatcgccgcg acaatttgcg   3060
acggcgcgtg cagggccaga ctggaggtgg caacgccaat cagcaacgac tgtttgcccg   3120
ccagttgttg tgccacgcgg ttaggaatgt aattcagctc cgccatcgcc gcttccactt   3180
tttcccgcgt tttcgcagaa acgtggctgg cctggttcac cacgcgggaa acggtctgat   3240
aagagacacc ggcatactct gcgacatcgt ataacgttac tggtttcaca ttcaccaccc   3300
tgaattgact ctcttccggg cgctatcatg ccataccgcg aaaggttttg cgccattcga   3360
tgctagccat gtgagcaaaa ggccagcaaa aggccaggaa ccgtaaaaag gccgcgttgc   3420
tggcgttttt ccataggctc cgcccccctg acgagcatca caaaaatcga cgctcaagtc   3480
agaggtggcg aaacccgaca ggactataaa gataccaggc gtttccccct ggaagctccc   3540
tcgtgcgctc tcctgttccg accctgccgc ttaccggata cctgtccgcc tttctccctt   3600
cgggaagcgt ggcgctttct catagctcac gctgtaggta tctcagttcg gtgtaggtcg   3660
ttcgctccaa gctgggctgt gtgcacgaac cccccgttca gcccgaccgc tgcgccttat   3720
ccggtaacta tcgtcttgag tccaacccgg taagacacga cttatcgcca ctggcagcag   3780
ccactggtaa caggattagc agagcgaggt atgtaggcgg tgctacagag ttcttgaagt   3840
ggtggcctaa ctacggctac actagaagaa cagtatttgg tatctgcgct ctgctgtagc   3900
cagttacctt cggaaaaaga gttggtagct cttgatccgg caaacaaacc accgctggta   3960
gcggtggttt ttttgtttgc aagcagcaga ttacgcgcag aaaaaaagga tctcaagaag   4020
atcctttgat cttttctacg gggtctgacg ctcagtggaa cgaaaactca cgttaaggga   4080
ttttggtcag atctagcacc aggcgtttaa gggcaccaat aactgcctta aaaaaattac   4140
gccccgccct gccactcatc gcagtactgt tgtaattcat taagcattct gccgacatgg   4200
aagccatcac aaacggcatg atgaacctga atcgccagcg gcatcagcac cttgtcgcct   4260
tgcgtataat atttgcccat agtgaaaacg ggggcgaaga agttgtccat attggctacg   4320
tttaaatcaa aactggtgaa actcacccag ggattggctg agacgaaaaa catattctca   4380
ataaaccctt tagggaaata ggccaggttt tcaccgtaac acgccacatc ttgcgaatat   4440
atgtgtagaa actgccggaa atcgtcgtgg tattcactcc agagcgatga aaacgtttca   4500
gtttgctcat ggaaaacggt gtaacaaggg tgaacactat cccatatcac cagctcaccg   4560
tctttcattg ccatacggaa ctccgggtga gcattcatca ggcgggcaag aatgtgaata   4620
aaggccggat aaaacttgtg cttatttttc tttacggtct ttaaaaaggc cgtaatatcc   4680
agctgaacgg tctggttata ggtacattga gcaactgact gaaatgcctc aaaatgttct   4740
ttacgatgcc attgggatat atcaacggtg gtatatccag tgattttttt ctccatttta   4800
gcttccttag ctcctgaaaa tctcgataac tcaaaaaata cgcccggtag tgatcttatt   4860
```

tcattatggt gaaagttgga acctcacccg acgtctaatg tgagttagct cactcattag 4920
gcaccccagg ctttacactt tatgcttccg gctcgtatgt tgtgtggaat tgtgagcgga 4980
taacaatttc acacaggaaa cagctatgac catgattacg aattt 5025

<210> SEQ ID NO 40
<211> LENGTH: 6746
<212> TYPE: DNA
<213> ORGANISM: artificial
<220> FEATURE:
<223> OTHER INFORMATION: IgG4 Expression Vector pMORPH?_h_Ig 4

<400> SEQUENCE: 40
aattgcatga agaatctgct tagggttagg cgttttgcgc tgcttcgcga tgtacgggcc 60
agatatacgc gttgacattg attattgact agttattaat agtaatcaat tacggggtca 120
ttagttcata gcccatatat ggagttccgc gttacataac ttacggtaaa tggcccgcct 180
ggctgaccgc ccaacgaccc ccgcccattg acgtcaataa tgacgtatgt tcccatagta 240
acgccaatag ggactttcca ttgacgtcaa tgggtggact atttacggta aactgcccac 300
ttggcagtac atcaagtgta tcatatgcca agtacgcccc ctattgacgt caatgacggt 360
aaatggcccg cctggcatta tgcccagtac atgaccttat gggactttcc tacttggcag 420
tacatctacg tattagtcat cgctattacc atggtgatgc ggttttggca gtacatcaat 480
gggcgtggat agcggtttga ctcacgggga tttccaagtc tccaccccat tgacgtcaat 540
gggagtttgt tttggcacca aaatcaacgg gactttccaa aatgtcgtaa caactccgcc 600
ccattgacgc aaatgggcgg taggcgtgta cggtgggagg tctatataag cagagctctc 660
tggctaacta gagaacccac tgcttactgg cttatcgaaa ttaatacgac tcactatagg 720
gagacccaag ctggctagcg ccaccatgaa acacctgtgg ttcttcctcc tgctggtggc 780
agctcccaga tgggtcctgt cccaggtgga attgcaacag tctggtccgg gcctggtgaa 840
accgagccaa accctgagcc tgacctgtgc gatttccgga gatagcgtga gcgataattc 900
tgctgcttgg tcttggattc gccagtctcc tgggcgtggc ctcgagtggc tgggccttat 960
ctatcttcgt agcaagtggg ataacgatta tgcggtgagc gtgaaaagcc ggattaccat 1020
caacccggat acttcgaaaa accagtttag cctgcaactg aacagcgtga ccccggaaga 1080
tacggccgtg tattattgcg cgcgtactgg tcgtgctgat gagtttgatg tttggggcca 1140
aggcaccctg gtgacggtta gctcagcttc caccaaggga ccatccgtct tccccctggc 1200
gccctgctcc aggagcacct ccgagagcac agccgccctg ggctgcctgg tcaaggacta 1260
cttccccgaa ccggtgacgg tgtcgtggaa ctcaggcgcc ctgaccagcg gcgtgcacac 1320
cttcccggct gtcctacagt cctcaggact ctactccctc agcagcgtgg tgaccgtgcc 1380
ctccagcagc ttgggcacga agacctacac ctgcaacgta gatcacaagc ccagcaacac 1440
caaggtggac aagagagttg agtccaaata tggtccccca tgcccatcat gcccagcacc 1500
tgagttcctg gggggaccat cagtcttcct gttcccccca aaacccaagg acactctcat 1560
gatctcccgg acccctgagg tcacgtgcgt ggtggtggac gtgagccagg aagaccccga 1620
ggtccagttc aactggtacg tggatggcgt ggaggtgcat aatgccaaga caaagccgcg 1680
ggaggagcag ttcaacagca cgtaccgtgt ggtcagcgtc ctcaccgtcc tgcaccagga 1740
ctggctgaac ggcaaggagt acaagtgcaa ggtctccaac aaaggcctcc cgtcctccat 1800
cgagaaaacc atctccaaag ccaaagggca gccccgagag ccacaggtgt acaccctgcc 1860
cccatcccag gaggagatga ccaagaacca ggtcagcctg acctgcctgg tcaaaggctt 1920

```
ctaccccagc gacatcgccg tggagtggga gagcaatggg cagccggaga acaactacaa   1980
gaccacgcct cccgtgctgg actccgacgg ctccttcttc ctctacagca ggctaaccgt   2040
ggacaagagc aggtggcagg aggggaatgt cttctcatgc tccgtgatgc atgaggctct   2100
gcacaaccac tacacacaga agagcctctc cctgtctctg ggtaaatgag ggcccgttta   2160
aacccgctga tcagcctcga ctgtgccttc tagttgccag ccatctgttg tttgcccctc   2220
ccccgtgcct tccttgaccc tggaaggtgc cactcccact gtcctttcct aataaaatga   2280
ggaaattgca tcgcattgtc tgagtaggtg tcattctatt ctggggggtg gggtggggca   2340
ggacagcaag ggggaggatt gggaagacaa tagcaggcat gctggggatg cggtgggctc   2400
tatggcttct gaggcggaaa gaaccagctg gggctctagg gggtatcccc acgcgccctg   2460
tagcggcgca ttaagcgcgg cgggtgtggt ggttacgcgc agcgtgaccg ctacacttgc   2520
cagcgcccta gcgcccgctc ctttcgcttt cttcccttcc tttctcgcca cgttcgccgg   2580
ctttccccgt caagctctaa atcggggcat ccctttaggg ttccgattta gtgctttacg   2640
gcacctcgac cccaaaaaac ttgattaggg tgatggttca cgtagtgggc catcgccctg   2700
atagacggtt tttcgccctt tgacgttgga gtccacgttc tttaatagtg gactcttgtt   2760
ccaaactgga acaacactca accctatctc ggtctattct tttgatttat aagggatttt   2820
ggggatttcg gcctattggt taaaaaatga gctgatttaa caaaaattta acgcgaatta   2880
attctgtgga atgtgtgtca gttagggtgt ggaaagtccc caggctcccc aggcaggcag   2940
aagtatgcaa agcatgcatc tcaattagtc agcaaccagg tgtggaaagt ccccaggctc   3000
cccagcaggc agaagtatgc aaagcatgca tctcaattag tcagcaacca tagtcccgcc   3060
cctaactccg cccatcccgc ccctaactcc gcccagttcc gcccattctc cgccccatgg   3120
ctgactaatt ttttttattt atgcagaggc cgaggccgcc tctgcctctg agctattcca   3180
gaagtagtga ggaggctttt ttggaggcct aggcttttgc aaaaagctcc cgggagcttg   3240
tatatccatt ttcggatctg atcaagagac aggatgagga tcgtttcgca tgattgaaca   3300
agatggattg cacgcaggtt ctccggccgc ttgggtggag aggctattcg gctatgactg   3360
ggcacaacag acaatcggct gctctgatgc cgccgtgttc cggctgtcag cgcaggggcg   3420
cccggttctt tttgtcaaga ccgacctgtc cggtgccctg aatgaactgc aggacgaggc   3480
agcgcggcta tcgtggctgg ccacgacggg cgttccttgc gcagctgtgc tcgacgttgt   3540
cactgaagcg ggaagggact ggctgctatt gggcgaagtg ccggggcagg atctcctgtc   3600
atctcacctt gctcctgccg agaaagtatc catcatggct gatgcaatgc ggcggctgca   3660
tacgcttgat ccggctacct gcccattcga ccaccaagcg aaacatcgca tcgagcgagc   3720
acgtactcgg atggaagccg gtcttgtcga tcaggatgat ctggacgaag agcatcaggg   3780
gctcgcgcca gccgaactgt tcgccaggct caaggcgcgc atgcccgacg gcgaggatct   3840
cgtcgtgacc catggcgatg cctgcttgcc gaatatcatg gtggaaaatg gccgcttttc   3900
tggattcatc gactgtggcc ggctgggtgt ggcggaccgc tatcaggaca tagcgttggc   3960
tacccgtgat attgctgaag agcttggcgg cgaatgggct gaccgcttcc tcgtgcttta   4020
cggtatcgcc gctcccgatt cgcagcgcat cgccttctat cgccttcttg acgagttctt   4080
ctgagcggga ctctggggtt cgaaatgacc gaccaagcga cgcccaacct gccatcacga   4140
gatttcgatt ccaccgccgc cttctatgaa aggttgggct tcggaatcgt tttccgggac   4200
gccggctgga tgatcctcca gcgcggggat ctcatgctgg agttcttcgc ccaccccaac   4260
ttgtttattg cagcttataa tggttacaaa taaagcaata gcatcacaaa tttcacaaat   4320
```

-continued

```
aaagcatttt tttcactgca ttctagttgt ggtttgtcca aactcatcaa tgtatcttat   4380
catgtctgta taccgtcgac ctctagctag agcttggcgt aatcatggtc atagctgttt   4440
cctgtgtgaa attgttatcc gctcacaatt ccacacaaca tacgagccgg aagcataaag   4500
tgtaaagcct ggggtgccta atgagtgagc taactcacat taattgcgtt gcgctcactg   4560
cccgctttcc agtcgggaaa cctgtcgtgc cagctgcatt aatgaatcgg ccaacgcgcg   4620
gggagaggcg gtttgcgtat tgggcgctct tccgcttcct cgctcactga ctcgctgcgc   4680
tcggtcgttc ggctgcggcg agcggtatca gctcactcaa aggcggtaat acggttatcc   4740
acagaatcag gggataacgc aggaaagaac atgtgagcaa aaggccagca aaaggccagg   4800
aaccgtaaaa aggccgcgtt gctggcgttt ttccataggc tccgcccccc tgacgagcat   4860
cacaaaaatc gacgctcaag tcagaggtgg cgaaacccga caggactata aagataccag   4920
gcgtttcccc ctggaagctc cctcgtgcgc tctcctgttc cgaccctgcc gcttaccgga   4980
tacctgtccg cctttctccc ttcgggaagc gtggcgcttt ctcaatgctc acgctgtagg   5040
tatctcagtt cggtgtaggt cgttcgctcc aagctgggct gtgtgcacga accccccgtt   5100
cagcccgacc gctgcgcctt atccggtaac tatcgtcttg agtccaaccc ggtaagacac   5160
gacttatcgc cactggcagc agccactggt aacaggatta gcagagcgag gtatgtaggc   5220
ggtgctacag agttcttgaa gtggtggcct aactacggct acactagaag gacagtattt   5280
ggtatctgcg ctctgctgaa gccagttacc ttcggaaaaa gagttggtag ctcttgatcc   5340
ggcaaacaaa ccaccgctgg tagcggtggt ttttttgttt gcaagcagca gattacgcgc   5400
agaaaaaaag gatctcaaga agatcctttg atcttttcta cggggtctga cgctcagtgg   5460
aacgaaaact cacgttaagg gattttggtc atgagattat caaaaaggat cttcacctag   5520
atccttttaa attaaaaatg aagttttaaa tcaatctaaa gtatatatga gtaaacttgg   5580
tctgacagtt accaatgctt aatcagtgag gcacctatct cagcgatctg tctatttcgt   5640
tcatccatag ttgcctgact ccccgtcgtg tagataacta cgatacggga gggcttacca   5700
tctggcccca gtgctgcaat gataccgcga gacccacgct caccggctcc agatttatca   5760
gcaataaacc agccagccgg aagggccgag cgcagaagtg gtcctgcaac tttatccgcc   5820
tccatccagt ctattaattg ttgccgggaa gctagagtaa gtagttcgcc agttaatagt   5880
ttgcgcaacg ttgttgccat tgctacaggc atcgtggtgt cacgctcgtc gtttggtatg   5940
gcttcattca gctccggttc ccaacgatca aggcgagtta catgatcccc catgttgtgc   6000
aaaaaagcgg ttagctcctt cggtcctccg atcgttgtca gaagtaagtt ggccgcagtg   6060
ttatcactca tggttatggc agcactgcat aattctctta ctgtcatgcc atccgtaaga   6120
tgcttttctg tgactggtga gtactcaacc aagtcattct gagaatagtg tatgcggcga   6180
ccgagttgct cttgcccggc gtcaatacgg gataataccg cgccacatag cagaacttta   6240
aaagtgctca tcattggaaa acgttcttcg gggcgaaaac tctcaaggat cttaccgctg   6300
ttgagatcca gttcgatgta acccactcgt gcacccaact gatcttcagc atcttttact   6360
ttcaccagcg tttctgggtg agcaaaaaca ggaaggcaaa atgccgcaaa aaagggaata   6420
agggcgacac ggaaatgttg aatactcata ctcttccttt ttcaatatta ttgaagcatt   6480
tatcagggtt attgtctcat gagcggatac atatttgaat gtatttagaa aaataaacaa   6540
ataggggttc cgcgcacatt tccccgaaaa gtgccacctg acgtcgacgg atcgggagat   6600
ctcccgatcc cctatggtcg actctcagta caatctgctc tgatgccgca tagttaagcc   6660
agtatctgct ccctgcttgt gtgttggagg tcgctgagta gtgcgcgagc aaaatttaag   6720
```

ctacaacaag gcaaggcttg accgac 6746

<210> SEQ ID NO 41
<211> LENGTH: 5627
<212> TYPE: DNA
<213> ORGANISM: artificial
<220> FEATURE:
<223> OTHER INFORMATION: IgG Lambda Chain Expression Vector pMORPH?
_h_Ig_lambda

<400> SEQUENCE: 41
aattgcatga agaatctgct tagggttagg cgttttgcgc tgcttcgcga tgtacgggcc 60
agatatacgc gttgacattg attattgact agttattaat agtaatcaat tacggggtca 120
ttagttcata gcccatatat ggagttccgc gttacataac ttacggtaaa tggcccgcct 180
ggctgaccgc ccaacgaccc ccgcccattg acgtcaataa tgacgtatgt tcccatagta 240
acgccaatag ggactttcca ttgacgtcaa tgggtggact atttacggta aactgcccac 300
ttggcagtac atcaagtgta tcatatgcca agtacgcccc ctattgacgt caatgacggt 360
aaatggcccg cctggcatta tgcccagtac atgaccttat gggactttcc tacttggcag 420
tacatctacg tattagtcat cgctattacc atggtgatgc ggttttggca gtacatcaat 480
gggcgtggat agcggtttga ctcacgggga tttccaagtc tccaccccat tgacgtcaat 540
gggagtttgt tttggcacca aaatcaacgg gactttccaa aatgtcgtaa caactccgcc 600
ccattgacgc aaatgggcgg taggcgtgta cggtgggagg tctatataag cagagctctc 660
tggctaacta gagaacccac tgcttactgg cttatcgaaa ttaatacgac tcactatagg 720
gagacccaag ctggctagcg ccaccatggc ctgggctctg ctgctcctca ccctcctcac 780
tcagggcaca ggatcctggg ctgatatcgt gctgacccag ccgccttcag tgagtggcgc 840
accaggtcag cgtgtgacca tctcgtgtag cggcagcagc agcaacattg gtaataatta 900
tgtgtcttgg taccagcagt tgcccgggac ggcgccgaaa cttctgattt ctcgtaattc 960
taagcgtccc tcaggcgtgc cggatcgttt tagcggatcc aaaagcggca ccagcgcgag 1020
ccttgcgatt acgggcctgc aaagcgaaga cgaagcggat tattattgct ctacttatga 1080
tactttttct attgtgtttg gcggcggcac gaagttaacc gtcctaggtc agcccaaggc 1140
tgccccctcg gtcactctgt tcccgccctc ctctgaggag cttcaagcca acaaggccac 1200
actggtgtgt ctcataagtg acttctaccc gggagccgtg acagtggcct ggaagggaga 1260
tagcagcccc gtcaaggcgg gagtggagac caccacaccc tccaaacaaa gcaacaacaa 1320
gtacgcggcc agcagctatc tgagcctgac gcctgagcag tggaagtccc acagaagcta 1380
cagctgccag gtcacgcatg aagggagcac cgtggagaag acagtggccc ctacagaatg 1440
ttcatagggg cccgtttaaa cccgctgatc agcctcgact gtgccttcta gttgccagcc 1500
atctgttgtt tgcccctccc ccgtgccttc cttgaccctg gaaggtgcca ctcccactgt 1560
cctttcctaa taaaatgagg aaattgcatc gcattgtctg agtaggtgtc attctattct 1620
ggggggtggg gtggggcagg acagcaaggg ggaggattgg gaagacaata gcaggcatgc 1680
tggggatgcg gtgggctcta tggcttctga ggcggaaaga accagctggg gctctagggg 1740
gtatccccac gcgccctgta gcggcgcatt aagcgcggcg ggtgtggtgg ttacgcgcag 1800
cgtgaccgct acacttgcca gcgccctagc gcccgctcct ttcgctttct tcccttcctt 1860
tctcgccacg ttcgccggct ttccccgtca agctctaaat cggggcatcc ctttagggtt 1920
ccgatttagt gctttacggc acctcgaccc caaaaaactt gattagggtg atggttcacg 1980

-continued

```
tagtgggcca tcgccctgat agacggtttt tcgccctttg acgttggagt ccacgttctt   2040

taatagtgga ctcttgttcc aaactggaac aacactcaac cctatctcgg tctattcttt   2100

tgatttataa gggattttgg ggatttcggc ctattggtta aaaaatgagc tgatttaaca   2160

aaaatttaac gcgaattaat tctgtggaat gtgtgtcagt tagggtgtgg aaagtcccca   2220

ggctccccag gcaggcagaa gtatgcaaag catgcatctc aattagtcag caaccaggtg   2280

tggaaagtcc ccaggctccc cagcaggcag aagtatgcaa agcatgcatc tcaattagtc   2340

agcaaccata gtcccgcccc taactccgcc catcccgccc ctaactccgc ccagttccgc   2400

ccattctccg ccccatggct gactaatttt ttttatttat gcagaggccg aggccgcctc   2460

tgcctctgag ctattccaga agtagtgagg aggctttttt ggaggcctag gcttttgcaa   2520

aaagctcccg ggagcttgta tatccatttt cggatctgat cagcacgtgt tgacaattaa   2580

tcatcggcat agtatatcgg catagtataa tacgacaagg tgaggaacta aaccatggcc   2640

aagttgacca gtgccgttcc ggtgctcacc gcgcgcgacg tcgccggagc ggtcgagttc   2700

tggaccgacc ggctcgggtt ctcccgggac ttcgtggagg acgacttcgc cggtgtggtc   2760

cgggacgacg tgaccctgtt catcagcgcg gtccaggacc aggtggtgcc ggacaacacc   2820

ctggcctggg tgtgggtgcg cggcctggac gagctgtacg ccgagtggtc ggaggtcgtg   2880

tccacgaact tccgggacgc ctccgggccg gccatgaccg agatcggcga gcagccgtgg   2940

gggcgggagt tcgccctgcg cgacccggcc ggcaactgcg tgcacttcgt ggccgaggag   3000

caggactgac acgtgctacg agatttcgat tccaccgccg ccttctatga aaggttgggc   3060

ttcggaatcg ttttccggga cgccggctgg atgatcctcc agcgcgggga tctcatgctg   3120

gagttcttcg cccaccccaa cttgtttatt gcagcttata atggttacaa ataaagcaat   3180

agcatcacaa atttcacaaa taaagcattt ttttcactgc attctagttg tggtttgtcc   3240

aaactcatca atgtatctta tcatgtctgt ataccgtcga cctctagcta gagcttggcg   3300

taatcatggt catagctgtt tcctgtgtga aattgttatc cgctcacaat tccacacaac   3360

atacgagccg gaagcataaa gtgtaaagcc tggggtgcct aatgagtgag ctaactcaca   3420

ttaattgcgt tgcgctcact gcccgctttc cagtcgggaa acctgtcgtg ccagctgcat   3480

taatgaatcg gccaacgcgc ggggagaggc ggtttgcgta ttgggcgctc ttccgcttcc   3540

tcgctcactg actcgctgcg ctcggtcgtt cggctgcggc gagcggtatc agctcactca   3600

aaggcggtaa tacggttatc cacagaatca ggggataacg caggaaagaa catgtgagca   3660

aaaggccagc aaaaggccag gaaccgtaaa aaggccgcgt tgctggcgtt tttccatagg   3720

ctccgccccc ctgacgagca tcacaaaaat cgacgctcaa gtcagaggtg gcgaaacccg   3780

acaggactat aaagatacca ggcgtttccc cctggaagct ccctcgtgcg ctctcctgtt   3840

ccgaccctgc cgcttaccgg atacctgtcc gcctttctcc cttcgggaag cgtggcgctt   3900

tctcaatgct cacgctgtag gtatctcagt tcggtgtagg tcgttcgctc caagctgggc   3960

tgtgtgcacg aaccccccgt tcagcccgac cgctgcgcct tatccggtaa ctatcgtctt   4020

gagtccaacc cggtaagaca cgacttatcg ccactggcag cagccactgg taacaggatt   4080

agcagagcga ggtatgtagg cggtgctaca gagttcttga agtggtggcc taactacggc   4140

tacactagaa ggacagtatt tggtatctgc gctctgctga agccagttac cttcggaaaa   4200

agagttggta gctcttgatc cggcaaacaa accaccgctg gtagcggtgg tttttttgtt   4260

tgcaagcagc agattacgcg cagaaaaaaa ggatctcaag aagatccttt gatcttttct   4320

acggggtctg acgctcagtg gaacgaaaac tcacgttaag ggattttggt catgagatta   4380
```

```
tcaaaaagga tcttcaccta gatcctttta aattaaaaat gaagttttaa atcaatctaa   4440

agtatatatg agtaaacttg gtctgacagt taccaatgct taatcagtga ggcacctatc   4500

tcagcgatct gtctatttcg ttcatccata gttgcctgac tccccgtcgt gtagataact   4560

acgatacggg agggcttacc atctggcccc agtgctgcaa tgataccgcg agacccacgc   4620

tcaccggctc cagatttatc agcaataaac cagccagccg gaagggccga gcgcagaagt   4680

ggtcctgcaa ctttatccgc ctccatccag tctattaatt gttgccggga agctagagta   4740

agtagttcgc cagttaatag tttgcgcaac gttgttgcca ttgctacagg catcgtggtg   4800

tcacgctcgt cgtttggtat ggcttcattc agctccggtt cccaacgatc aaggcgagtt   4860

acatgatccc ccatgttgtg caaaaaagcg gttagctcct tcggtcctcc gatcgttgtc   4920

agaagtaagt tggccgcagt gttatcactc atggttatgg cagcactgca taattctctt   4980

actgtcatgc catccgtaag atgcttttct gtgactggtg agtactcaac caagtcattc   5040

tgagaatagt gtatgcggcg accgagttgc tcttgcccgg cgtcaatacg ggataatacc   5100

gcgccacata gcagaacttt aaaagtgctc atcattggaa aacgttcttc ggggcgaaaa   5160

ctctcaagga tcttaccgct gttgagatcc agttcgatgt aacccactcg tgcacccaac   5220

tgatcttcag catcttttac tttcaccagc gtttctgggt gagcaaaaac aggaaggcaa   5280

aatgccgcaa aaaagggaat aagggcgaca cggaaatgtt gaatactcat actcttcctt   5340

tttcaatatt attgaagcat ttatcagggt tattgtctca tgagcggata catatttgaa   5400

tgtatttaga aaaataaaca aataggggtt ccgcgcacat ttccccgaaa agtgccacct   5460

gacgtcgacg gatcgggaga tctcccgatc ccctatggtc gactctcagt acaatctgct   5520

ctgatgccgc atagttaagc cagtatctgc tccctgcttg tgtgttggag gtcgctgagt   5580

agtgcgcgag caaaatttaa gctacaacaa ggcaaggctt gaccgac                 5627
```

```
<210> SEQ ID NO 42
<211> LENGTH: 5629
<212> TYPE: DNA
<213> ORGANISM: artificial
<220> FEATURE:
<223> OTHER INFORMATION: IgG Kappa Chain Expression Vector pMORPH?
      _h_Ig_kappa

<400> SEQUENCE: 42
```

```
aattgcatga agaatctgct tagggttagg cgttttgcgc tgcttcgcga tgtacgggcc     60

agatatacgc gttgacattg attattgact agttattaat agtaatcaat tacggggtca    120

ttagttcata gcccatatat ggagttccgc gttacataac ttacggtaaa tggcccgcct    180

ggctgaccgc ccaacgaccc ccgcccattg acgtcaataa tgacgtatgt tcccatagta    240

acgccaatag ggactttcca ttgacgtcaa tgggtggagt atttacggta aactgcccac    300

ttggcagtac atcaagtgta tcatatgcca agtacgcccc ctattgacgt caatgacggt    360

aaatggcccg cctggcatta tgcccagtac atgaccttat gggactttcc tacttggcag    420

tacatctacg tattagtcat cgctattacc atggtgatgc ggttttggca gtacatcaat    480

gggcgtggat agcggtttga ctcacgggga tttccaagtc tccaccccat tgacgtcaat    540

gggagtttgt tttggcacca aaatcaacgg gactttccaa aatgtcgtaa caactccgcc    600

ccattgacgc aaatgggcgg taggcgtgta cggtgggagg tctatataag cagagctctc    660

tggctaacta gagaacccac tgcttactgg cttatcgaaa ttaatacgac tcactatagg    720

gagacccaag ctggctagcg ccaccatggt gttgcagacc caggtcttca tttctctgtt    780

gctctggatc tctggtgcct acggggatat ccagatgacc cagagcccgt ctagcctgag    840
```

-continued

```
cgcgagcgtg ggtgatcgtg tgaccattac ctgcagagcg agccagtcta tttctaattg    900
gctgaattgg taccagcaga aaccaggtaa agcaccgaaa ctattaattt ataaggcttc    960
tactttgcaa agcggggtcc cgtcccgttt tagcggctct ggatccggca ctgattttac   1020
cctgaccatt agcagcctgc aacctgaaga ctttgcgact tattattgcc agcagtatgg   1080
taatattcct attacctttg gccagggtac gaaagttgaa attaaacgta cggtggctgc   1140
accatctgtc ttcatcttcc cgccatctga tgagcagttg aaatctggaa ctgcctctgt   1200
tgtgtgcctg ctgaataact tctatcccag agaggccaaa gtacagtgga aggtggataa   1260
cgccctccaa tcgggtaact cccaggagag tgtcacagag caggacagca aggacagcac   1320
ctacagcctc agcagcaccc tgacgctgag caaagcagac tacgagaaac acaaagtcta   1380
cgcctgcgaa gtcacccatc agggcctgag ctcgcccgtc acaaagagct tcaacagggg   1440
agagtgttag ggcccgttt aaacccgctg atcagcctcg actgtgcctt ctagttgcca    1500
gccatctgtt gtttgcccct cccccgtgcc ttccttgacc ctggaaggtg ccactcccac   1560
tgtcctttcc taataaaatg aggaaattgc atcgcattgt ctgagtaggt gtcattctat   1620
tctggggggt ggggtggggc aggacagcaa gggggaggat tgggaagaca atagcaggca   1680
tgctggggat gcggtgggct ctatggcttc tgaggcggaa agaaccagct ggggctctag   1740
ggggtatccc cacgcgccct gtagcggcgc attaagcgcg gcgggtgtgg tggttacgcg   1800
cagcgtgacc gctacacttg ccagcgccct agcgcccgct cctttcgctt tcttcccttc   1860
ctttctcgcc acgttcgccg gctttccccg tcaagctcta aatcgggggc tccctttagg   1920
gttccgattt agtgctttac ggcacctcga ccccaaaaaa cttgattagg gtgatggttc   1980
acgtagtggg ccatcgccct gatagacggt ttttcgccct ttgacgttgg agtccacgtt   2040
ctttaatagt ggactcttgt tccaaactgg aacaacactc aaccctatct cggtctattc   2100
ttttgattta taagggattt tgccgatttc ggcctattgg ttaaaaaatg agctgattta   2160
acaaaaattt aacgcgaatt aattctgtgg aatgtgtgtc agttagggtg tggaaagtcc   2220
ccaggctccc cagcaggcag aagtatgcaa agcatgcatc tcaattagtc agcaaccagg   2280
tgtggaaagt ccccaggctc cccagcaggc agaagtatgc aaagcatgca tctcaattag   2340
tcagcaacca tagtcccgcc cctaactccg cccatcccgc ccctaactcc gcccagttcc   2400
gcccattctc cgccccatgg ctgactaatt ttttttattt atgcagaggc cgaggccgcc   2460
tctgcctctg agctattcca gaagtagtga ggaggctttt ttggaggcct aggcttttgc   2520
aaaaagctcc cgggagcttg tatatccatt ttcggatctg atcagcacgt gttgacaatt   2580
aatcatcggc atagtatatc ggcatagtat aatacgacaa ggtgaggaac taaaccatgg   2640
ccaagttgac cagtgccgtt ccggtgctca ccgcgcgcga cgtcgccgga gcggtcgagt   2700
tctggaccga ccggctcggg ttctcccggg acttcgtgga ggacgacttc gccggtgtgg   2760
tccgggacga cgtgaccctg ttcatcagcg cggtccagga ccaggtggtg ccggacaaca   2820
ccctggcctg ggtgtgggtg cgcggcctgg acgagctgta cgccgagtgg tcggaggtcg   2880
tgtccacgaa cttccgggac gcctccgggc cggccatgac cgagatcggc gagcagccgt   2940
gggggcggga gttcgccctg cgcgacccgg ccggcaactg cgtgcacttc gtggccgagg   3000
agcaggactg acacgtgcta cgagatttcg attccaccgc cgccttctat gaaaggttgg   3060
gcttcggaat cgttttccgg gacgccggct ggatgatcct ccagcgcggg gatctcatgc   3120
tggagttctt cgcccacccc aacttgttta ttgcagctta taatggttac aaataaagca   3180
atagcatcac aaatttcaca aataaagcat ttttttcact gcattctagt tgtggtttgt   3240
```

-continued

```
ccaaactcat caatgtatct tatcatgtct gtataccgtc gacctctagc tagagcttgg   3300
cgtaatcatg gtcatagctg tttcctgtgt gaaattgtta tccgctcaca attccacaca   3360
acatacgagc cggaagcata aagtgtaaag cctggggtgc ctaatgagtg agctaactca   3420
cattaattgc gttgcgctca ctgcccgctt tccagtcggg aaacctgtcg tgccagctgc   3480
attaatgaat cggccaacgc gcggggagag gcggtttgcg tattgggcgc tcttccgctt   3540
cctcgctcac tgactcgctg cgctcggtcg ttcggctgcg gcgagcggta tcagctcact   3600
caaaggcggt aatacggtta tccacagaat caggggataa cgcaggaaag aacatgtgag   3660
caaaaggcca gcaaaaggcc aggaaccgta aaaaggccgc gttgctggcg tttttccata   3720
ggctccgccc ccctgacgag catcacaaaa atcgacgctc aagtcagagg tggcgaaacc   3780
cgacaggact ataaagatac caggcgtttc cccctggaag ctccctcgtg cgctctcctg   3840
ttccgaccct gccgcttacc ggatacctgt ccgcctttct cccttcggga agcgtggcgc   3900
tttctcatag ctcacgctgt aggtatctca gttcggtgta ggtcgttcgc tccaagctgg   3960
gctgtgtgca cgaacccccc gttcagcccg accgctgcgc cttatccggt aactatcgtc   4020
ttgagtccaa cccggtaaga cacgacttat cgccactggc agcagccact ggtaacagga   4080
ttagcagagc gaggtatgta ggcggtgcta cagagttctt gaagtggtgg cctaactacg   4140
gctacactag aagaacagta tttggtatct gcgctctgct gaagccagtt accttcggaa   4200
aaagagttgg tagctcttga tccggcaaac aaaccaccgc tggtagcggt ggtttttttg   4260
tttgcaagca gcagattacg cgcagaaaaa aaggatctca agaagatcct ttgatctttt   4320
ctacggggtc tgacgctcag tggaacgaaa actcacgtta agggattttg gtcatgagat   4380
tatcaaaaag gatcttcacc tagatccttt taaattaaaa atgaagtttt aaatcaatct   4440
aaagtatata tgagtaaact tggtctgaca gttaccaatg cttaatcagt gaggcaccta   4500
tctcagcgat ctgtctattt cgttcatcca tagttgcctg actccccgtc gtgtagataa   4560
ctacgatacg ggagggctta ccatctggcc ccagtgctgc aatgataccg cgagacccac   4620
gctcaccggc tccagattta tcagcaataa accagccagc cggaagggcc gagcgcagaa   4680
gtggtcctgc aactttatcc gcctccatcc agtctattaa ttgttgccgg gaagctagag   4740
taagtagttc gccagttaat agtttgcgca acgttgttgc cattgctaca ggcatcgtgg   4800
tgtcacgctc gtcgtttggt atggcttcat tcagctccgg ttcccaacga tcaaggcgag   4860
ttacatgatc ccccatgttg tgcaaaaaag cggttagctc cttcggtcct ccgatcgttg   4920
tcagaagtaa gttggccgca gtgttatcac tcatggttat ggcagcactg cataattctc   4980
ttactgtcat gccatccgta agatgctttt ctgtgactgg tgagtactca accaagtcat   5040
tctgagaata gtgtatgcgg cgaccgagtt gctcttgccc ggcgtcaata cgggataata   5100
ccgcgccaca tagcagaact ttaaaagtgc tcatcattgg aaaacgttct tcggggcgaa   5160
aactctcaag gatcttaccg ctgttgagat ccagttcgat gtaacccact cgtgcaccca   5220
actgatcttc agcatctttt actttcacca gcgtttctgg gtgagcaaaa acaggaaggc   5280
aaaatgccgc aaaaaaggga ataagggcga cacggaaatg ttgaatactc atactcttcc   5340
tttttcaata ttattgaagc atttatcagg gttattgtct catgagcgga tacatatttg   5400
aatgtattta gaaaaataaa caaatagggg ttccgcgcac atttccccga aaagtgccac   5460
ctgacgtcga cggatcggga gatctcccga tcccctatgg tgcactctca gtacaatctg   5520
ctctgatgcc gcatagttaa gccagtatct gctccctgct tgtgtgttgg aggtcgctga   5580
gtagtgcgcg agcaaaattt aagctacaac aaggcaaggc ttgaccgac                5629
```

<210> SEQ ID NO 43
<211> LENGTH: 7101
<212> TYPE: DNA
<213> ORGANISM: artificial
<220> FEATURE:
<223> OTHER INFORMATION: IgG4 Expression Vector pMORPH2?_h_Ig 4

<400> SEQUENCE: 43
taatacgact cactataggg agacccaagc tggctagcgc caccatgaaa cacctgtggt 60
tcttcctcct gctggtggca gctcccagat gggtcctgtc ccaggtgcaa ttgcaacagt 120
ctggtccggg cctggtgaaa ccgagccaaa ccctgagcct gacctgtgcg atttccggag 180
atagcgtgag cgataattct gctgcttggt cttggattcg ccagtctcct gggcgtggcc 240
tcgagtggct gggccttatc tatcttcgta gcaagtggga taacgattat gcggtgagcg 300
tgaaaagccg gattaccatc aacccggata cttcgaaaaa ccagtttagc ctgcaactga 360
acagcgtgac cccggaagat acggccgtgt attattgcgc gcgtactggt cgtgctgatg 420
agtttgatgt ttggggccaa ggcaccctgg tgacggttag ctcagcttcc accaagggac 480
catccgtctt cccctggcg ccctgctcca ggagcacctc cgagagcaca gccgccctgg 540
gctgcctggt caaggactac ttccccgaac cggtgacggt gtcgtggaac tcaggcgccc 600
tgaccagcgg cgtgcacacc ttcccggctg tcctacagtc ctcaggactc tactccctca 660
gcagcgtggt gaccgtgccc tccagcagct tgggcacgaa gacctacacc tgcaacgtag 720
atcacaagcc cagcaacacc aaggtggaca agagagttga gtccaaatat ggtcccccat 780
gcccatcatg cccagcacct gagttcctgg ggggaccatc agtcttcctg ttccccccaa 840
aacccaagga cactctcatg atctcccgga cccctgaggt cacgtgcgtg gtggtggacg 900
tgagccagga agaccccgag gtccagttca actggtacgt ggatggcgtg gaggtgcata 960
atgccaagac aaagccgcgg gaggagcagt tcaacagcac gtaccgtgtg gtcagcgtcc 1020
tcaccgtcct gcaccaggac tggctgaacg gcaaggagta caagtgcaag gtctccaaca 1080
aaggcctccc gtcctccatc gagaaaacca tctccaaagc caaagggcag ccccgagagc 1140
cacaggtgta caccctgccc ccatcccagg aggagatgac caagaaccag gtcagcctga 1200
cctgcctggt caaaggcttc taccccagcg acatcgccgt ggagtgggag agcaatgggc 1260
agccggagaa caactacaag accacgcctc ccgtgctgga ctccgacggc tccttcttcc 1320
tctacagcag gctaaccgtg gacaagagca ggtggcagga ggggaatgtc ttctcatgct 1380
ccgtgatgca tgaggctctg cacaaccact acacacagaa gagcctctcc ctgtctctgg 1440
gtaaatgagg gcccgtttaa acgggtggca tccctgtgac ccctccccag tgcctctcct 1500
ggccctggaa gttgccactc cagtgcccac cagccttgtc ctaataaaat taagttgcat 1560
cattttgtct gactaggtgt ccttctataa tattatgggg tggagggggg tggtatggag 1620
caaggggcaa gttgggaaga caacctgtag ggcctgcggg gtctattggg aaccaagctg 1680
gagtgcagtg gcacaatctt ggctcactgc aatctccgcc tcctgggttc aagcgattct 1740
cctgcctcag cctcccgagt tgttgggatt ccaggcatgc atgaccaggc tcacctaatt 1800
tttgtttttt tggtagagac ggggtttcac catattggcc aggctggtct ccaactccta 1860
atctcaggtg atctacccac cttggcctcc caaattgctg ggattacagg cgtgaaccac 1920
tgctcccttc cctgtccttc tgattttaaa ataactatac cagcaggagg acgtccagac 1980
acagcatagg ctacctggcc atgcccaacc ggtgggacat ttgagttgct tgcttggcac 2040
tgtcctctca tgcgttgggt ccactcagta gatgcctgtt gaattgggta cgcggcatcg 2100

-continued

```
attccacgcg ccctgtagcg gcgcattaag cgcggcgggt gtggtggtta cgcgcagcgt   2160
gaccgctaca cttgccagcg ccctagcgcc cgctcctttc gctttcttcc cttcctttct   2220
cgccacgttc gccggctttc cccgtcaagc tctaaatcgg gggctccctt tagggttccg   2280
atttagtgct ttacggcacc tcgaccccaa aaaacttgat tagggtgatg gttcacgtag   2340
tgggccatcg ccctgataga cggtttttcg ccctttgacg ttggagtcca cgttctttaa   2400
tagtggactc ttgttccaaa ctggaacaac actcaaccct atctcggtct attcttttga   2460
tttataaggg attttgccga tttcggccta ttggttaaaa aatgagctga tttaacaaaa   2520
atttaacgcg aattaattct gtggaatgtg tgtcagttag ggtgtggaaa gtccccaggc   2580
tccccagcag gcagaagtat gcaaagcatg catctcaatt agtcagcaac caggtgtgga   2640
aagtccccag gctccccagc aggcagaagt atgcaaagca tgcatctcaa ttagtcagca   2700
accatagtcc cgcccctaac tccgcccatc ccgcccctaa ctccgcccag ttccgcccat   2760
tctccgcccc atggctgact aatttttttt atttatgcag aggccgaggc cgcctctgcc   2820
tctgagctat tccagaagta gtgaggaggc ttttttggag gcctaggctt ttgcaaaaag   2880
ctcccgggag cttgtatatc cattttcgga tctgatcaag agacaggatg aggatcgttt   2940
cgcatgattg aacaagatgg attgcacgca ggttctccgg ccgcttgggt ggagaggcta   3000
ttcggctatg actgggcaca acagacaatc ggctgctctg atgccgccgt gttccggctg   3060
tcagcgcagg ggcgcccggt tctttttgtc aagaccgacc tgtccggtgc cctgaatgaa   3120
ctgcaggacg aggcagcgcg gctatcgtgg ctggccacga cgggcgttcc ttgcgcagct   3180
gtgctcgacg ttgtcactga agcgggaagg gactggctgc tattgggcga agtgccgggg   3240
caggatctcc tgtcatctca ccttgctcct gccgagaaag tatccatcat ggctgatgca   3300
atgcggcggc tgcatacgct tgatccggct acctgcccat tcgaccacca agcgaaacat   3360
cgcatcgagc gagcacgtac tcggatggaa gccggtcttg tcgatcagga tgatctggac   3420
gaagagcatc aggggctcgc gccagccgaa ctgttcgcca ggctcaaggc gcgcatgccc   3480
gacggcgagg atctcgtcgt gacccatggc gatgcctgct tgccgaatat catggtggaa   3540
aatggccgct tttctggatt catcgactgt ggccggctgg gtgtggcgga ccgctatcag   3600
gacatagcgt tggctacccg tgatattgct gaagagcttg gcggcgaatg ggctgaccgc   3660
ttcctcgtgc tttacggtat cgccgctccc gattcgcagc gcatcgcctt ctatcgcctt   3720
cttgacgagt tcttctgagc gggactctgg ggttcgaaat gaccgaccaa gcgacgccca   3780
acctgccatc acgagatttc gattccaccg ccgccttcta tgaaaggttg ggcttcggaa   3840
tcgttttccg ggacgccggc tggatgatcc tccagcgcgg ggatctcatg ctggagttct   3900
tcgcccaccc caacttgttt attgcagctt ataatggtta caaataaagc aatagcatca   3960
caaatttcac aaataaagca tttttttcac tgcattctag ttgtggtttg tccaaactca   4020
tcaatgtatc ttatcatgtc tgtataccgt cgacctctag ctagagcttg gcgtaatcat   4080
ggtcatagct gtttcctgtg tgaaattgtt atccgctcac aattccacac aacatacgag   4140
ccggaagcat aaagtgtaaa gcctggggtg cctaatgagt gagctaactc acattaattg   4200
cgttgcgctc actgcccgct ttccagtcgg gaaacctgtc gtgccagctg cattaatgaa   4260
tcggccaacg cgcggggaga ggcggtttgc gtattgggcg ctcttccgct tcctcgctca   4320
ctgactcgct gcgctcggtc gttcggctgc ggcgagcggt atcagctcac tcaaaggcgg   4380
taatacggtt atccacagaa tcaggggata acgcaggaaa gaacatgtga gcaaaaggcc   4440
agcaaaaggc caggaaccgt aaaaaggccg cgttgctggc gtttttccat aggctccgcc   4500
```

-continued

```
cccctgacga gcatcacaaa aatcgacgct caagtcagag gtggcgaaac ccgacaggac   4560
tataaagata ccaggcgttt ccccctggaa gctccctcgt gcgctctcct gttccgaccc   4620
tgccgcttac cggatacctg tccgcctttc tcccttcggg aagcgtggcg ctttctcata   4680
gctcacgctg taggtatctc agttcggtgt aggtcgttcg ctccaagctg ggctgtgtgc   4740
acgaaccccc cgttcagccc gaccgctgcg ccttatccgg taactatcgt cttgagtcca   4800
acccggtaag acacgactta tcgccactgg cagcagccac tggtaacagg attagcagag   4860
cgaggtatgt aggcggtgct acagagttct tgaagtggtg gcctaactac ggctacacta   4920
gaagaacagt atttggtatc tgcgctctgc tgaagccagt taccttcgga aaaagagttg   4980
gtagctcttg atccggcaaa caaaccaccg ctggtagcgg tggttttttt gtttgcaagc   5040
agcagattac gcgcagaaaa aaaggatctc aagaagatcc tttgatcttt tctacggggt   5100
ctgacgctca gtggaacgaa aactcacgtt aagggatttt ggtcatgaga ttatcaaaaa   5160
ggatcttcac ctagatcctt ttaaattaaa aatgaagttt taaatcaatc taaagtatat   5220
atgagtaaac ttggtctgac agttaccaat gcttaatcag tgaggcacct atctcagcga   5280
tctgtctatt tcgttcatcc atagttgcct gactccccgt cgtgtagata actacgatac   5340
gggagggctt accatctggc cccagtgctg caatgatacc gcgagaccca cgctcaccgg   5400
ctccagattt atcagcaata aaccagccag ccggaagggc cgagcgcaga agtggtcctg   5460
caactttatc cgcctccatc cagtctatta attgttgccg ggaagctaga gtaagtagtt   5520
cgccagttaa tagtttgcgc aacgttgttg ccattgctac aggcatcgtg gtgtcacgct   5580
cgtcgtttgg tatggcttca ttcagctccg gttcccaacg atcaaggcga gttacatgat   5640
cccccatgtt gtgcaaaaaa gcggttagct ccttcggtcc tccgatcgtt gtcagaagta   5700
agttggccgc agtgttatca ctcatggtta tggcagcact gcataattct cttactgtca   5760
tgccatccgt aagatgcttt tctgtgactg gtgagtactc aaccaagtca ttctgagaat   5820
agtgtatgcg gcgaccgagt tgctcttgcc cggcgtcaat acgggataat accgcgccac   5880
atagcagaac tttaaaagtg ctcatcattg gaaaacgttc ttcggggcga aaactctcaa   5940
ggatcttacc gctgttgaga tccagttcga tgtaacccac tcgtgcaccc aactgatctt   6000
cagcatcttt tactttcacc agcgtttctg ggtgagcaaa aacaggaagg caaaatgccg   6060
caaaaaaggg aataagggcg acacggaaat gttgaatact catactcttc ctttttcaat   6120
attattgaag catttatcag ggttattgtc tcatgagcgg atacatattt gaatgtattt   6180
agaaaaataa acaaataggg gttccgcgca catttccccg aaaagtgcca cctgacgtcg   6240
acggatcggg agatctcccg atcccctatg gtgcactctc agtacaatct gctctgatgc   6300
cgcatagtta agccagtatc tgctccctgc ttgtgtgttg gaggtcgctg agtagtgcgc   6360
gagcaaaatt taagctacaa caaggcaagg cttgaccgac atttgcatga agaatctgct   6420
tagggttagg cgttttgcgc tgcttcgcga tgtacgggcc agatatacgc gttgacattg   6480
attattgact agttattaat agtaatcaat tacggggtca ttagttcata gcccatatat   6540
ggagttccgc gttacataac ttacggtaaa tggcccgcct ggctgaccgc ccaacgaccc   6600
ccgcccattg acgtcaataa tgacgtatgt tcccatagta acgccaatag ggactttcca   6660
ttgacgtcaa tgggtggagt atttacggta aactgcccac ttggcagtac atcaagtgta   6720
tcatatgcca agtacgcccc ctattgacgt caatgacggt aaatggcccg cctggcatta   6780
tgcccagtac atgaccttat gggactttcc tacttggcag tacatctacg tattagtcat   6840
cgctattacc atggtgatgc ggttttggca gtacatcaat gggcgtggat agcggtttga   6900
```

-continued ctcacgggga tttccaagtc tccaccccat tgacgtcaat gggagtttgt tttggcacca 6960
aaatcaacgg gactttccaa aatgtcgtaa caactccgcc ccattgacgc aaatgggcgg 7020
taggcgtgta cggtgggagg tctatataag cagagctctc tggctaacta gagaacccac 7080
tgcttactgg cttatcgaaa t 7101

<210> SEQ ID NO 44
<211> LENGTH: 5983
<212> TYPE: DNA
<213> ORGANISM: artificial
<220> FEATURE:
<223> OTHER INFORMATION: IgG Lambda Chain Expression Vector pMORPH?
2_h_Ig_lambda2

<400> SEQUENCE: 44
taatacgact cactataggg agacccaagc tggctagcgc caccatggcc tgggctctgc 60
tgctcctcac cctcctcact cagggcacag gatcctgggc tgatatcgtg ctgacccagc 120
cgccttcagt gagtggcgca ccaggtcagc gtgtgaccat ctcgtgtagc ggcagcagca 180
gcaacattgg taataattat gtgtcttggt accagcagtt gcccgggacg gcgccgaaac 240
ttctgatttc tcgtaattct aagcgtccct caggcgtgcc ggatcgtttt agcggatcca 300
aaagcggcac cagcgcgagc cttgcgatta cgggcctgca aagcgaagac gaagcggatt 360
attattgctc tacttatgat actttttcta ttgtgtttgg cggcggcacg aagttaaccg 420
tcctaggtca gcccaaggct gccccctcgg tcactctgtt cccgccctcc tctgaggagc 480
ttcaagccaa caaggccaca ctggtgtgtc tcataagtga cttctacccg ggagccgtga 540
cagtggcctg gaaggcagat agcagccccg tcaaggcggg agtggagacc accacaccct 600
ccaaacaaag caacaacaag tacgcggcca gcagctatct gagcctgacg cctgagcagt 660
ggaagtccca cagaagctac agctgccagg tcacgcatga agggagcacc gtggagaaga 720
cagtggcccc tacagaatgt tcataggggc ccgtttaaac gggtggcatc cctgtgaccc 780
ctccccagtg cctctcctgg ccctggaagt tgccactcca gtgcccacca gccttgtcct 840
aataaaatta agttgcatca ttttgtctga ctaggtgtcc ttctataata ttatggggtg 900
gaggggggtg gtatggagca aggggcaagt tgggaagaca acctgtaggg cctgcggggt 960
ctattgggaa ccaagctgga gtgcagtggc acaatcttgg ctcactgcaa tctccgcctc 1020
ctgggttcaa gcgattctcc tgcctcagcc tcccgagttg ttgggattcc aggcatgcat 1080
gaccaggctc acctaatttt tgttttttttg gtagagacgg ggtttcacca tattggccag 1140
gctggtctcc aactcctaat ctcaggtgat ctacccacct tggcctccca aattgctggg 1200
attacaggcg tgaaccactg ctcccttccc tgtccttctg attttaaaat aactatacca 1260
gcaggaggac gtccagacac agcataggct acctggccat gcccaaccgg tgggacattt 1320
gagttgcttg cttggcactg tcctctcatg cgttgggtcc actcagtaga tgcctgttga 1380
attgggtacg cggcatcgat tccacgcgcc ctgtagcggc gcattaagcg cggcgggtgt 1440
ggtggttacg cgcagcgtga ccgctacact tgccagcgcc ctagcgcccg ctcctttcgc 1500
tttcttccct tcctttctcg ccacgttcgc cggctttccc cgtcaagctc taaatcgggg 1560
gctcccttta gggttccgat ttagtgcttt acggcacctc gaccccaaaa aacttgatta 1620
gggtgatggt tcacgtagtg ggccatcgcc ctgatagacg gtttttcgcc ctttgacgtt 1680
ggagtccacg ttctttaata gtggactctt gttccaaact ggaacaacac tcaaccctat 1740
ctcggtctat tcttttgatt tataagggat tttggggatt tcggcctatt ggttaaaaaa 1800

-continued

```
tgagctgatt taacaaaaat ttaacgcgaa ttaattctgt ggaatgtgtg tcagttaggg   1860
tgtggaaagt ccccaggctc cccaggcagg cagaagtatg caaagcatgc atctcaatta   1920
gtcagcaacc aggtgtggaa agtccccagg ctccccagca ggcagaagta tgcaaagcat   1980
gcatctcaat tagtcagcaa ccatagtccc gcccctaact ccgcccatcc cgcccctaac   2040
tccgcccagt tccgcccatt ctccgcccca tggctgacta attttttta tttatgcaga   2100
ggccgaggcc gcctctgcct ctgagctatt ccagaagtag tgaggaggct tttttggagg   2160
cctaggcttt tgcaaaaagc tcccgggagc ttgtatatcc attttcggat ctgatcagca   2220
cgtgttgaca attaatcatc ggcatagtat atcggcatag tataatacga caaggtgagg   2280
aactaaacca tggccaagtt gaccagtgcc gttccggtgc tcaccgcgcg cgacgtcgcc   2340
ggagcggtcg agttctggac cgaccggctc gggttctccc gggacttcgt ggaggacgac   2400
ttcgccggtg tggtccggga cgacgtgacc ctgttcatca gcgcggtcca ggaccaggtg   2460
gtgccggaca acaccctggc ctgggtgtgg gtgcgcggcc tggacgagct gtacgccgag   2520
tggtcggagg tcgtgtccac gaacttccgg gacgcctccg ggccggccat gaccgagatc   2580
ggcgagcagc cgtgggggcg ggagttcgcc ctgcgcgacc cggccggcaa ctgcgtgcac   2640
ttcgtggccg aggagcagga ctgacacgtg ctacgagatt tcgattccac cgccgccttc   2700
tatgaaaggt tgggcttcgg aatcgttttc cgggacgccg gctggatgat cctccagcgc   2760
ggggatctca tgctggagtt cttcgcccac cccaacttgt ttattgcagc ttataatggt   2820
tacaaataaa gcaatagcat cacaaatttc acaaataaag cattttttc actgcattct   2880
agttgtggtt tgtccaaact catcaatgta tcttatcatg tctgtatacc gtcgacctct   2940
agctagagct tggcgtaatc atggtcatag ctgtttcctg tgtgaaattg ttatccgctc   3000
acaattccac acaacatacg agccggaagc ataaagtgta aagcctgggg tgcctaatga   3060
gtgagctaac tcacattaat tgcgttgcgc tcactgcccg ctttccagtc gggaaacctg   3120
tcgtgccagc tgcattaatg aatcggccaa cgcgcgggga gaggcggttt gcgtattggg   3180
cgctcttccg cttcctcgct cactgactcg ctgcgctcgg tcgttcggct gcggcgagcg   3240
gtatcagctc actcaaaggc ggtaatacgg ttatccacag aatcagggga taacgcagga   3300
aagaacatgt gagcaaaagg ccagcaaaag gccaggaacc gtaaaaaggc cgcgttgctg   3360
gcgtttttcc ataggctccg cccccctgac gagcatcaca aaaatcgacg ctcaagtcag   3420
aggtggcgaa acccgacagg actataaaga taccaggcgt ttccccctgg aagctccctc   3480
gtgcgctctc ctgttccgac cctgccgctt accggatacc tgtccgcctt tctcccttcg   3540
ggaagcgtgg cgctttctca atgctcacgc tgtaggtatc tcagttcggt gtaggtcgtt   3600
cgctccaagc tgggctgtgt gcacgaaccc cccgttcagc ccgaccgctg cgccttatcc   3660
ggtaactatc gtcttgagtc caacccggta agacacgact tatcgccact ggcagcagcc   3720
actggtaaca ggattagcag agcgaggtat gtaggcggtg ctacagagtt cttgaagtgg   3780
tggcctaact acggctacac tagaaggaca gtatttggta tctgcgctct gctgaagcca   3840
gttaccttcg gaaaaagagt tggtagctct tgatccggca aacaaaccac cgctggtagc   3900
ggtggttttt ttgtttgcaa gcagcagatt acgcgcagaa aaaaaggatc tcaagaagat   3960
cctttgatct tttctacggg gtctgacgct cagtggaacg aaaactcacg ttaagggatt   4020
ttggtcatga gattatcaaa aaggatcttc acctagatcc ttttaaatta aaaatgaagt   4080
tttaaatcaa tctaaagtat atatgagtaa acttggtctg acagttacca atgcttaatc   4140
agtgaggcac ctatctcagc gatctgtcta tttcgttcat ccatagttgc ctgactcccc   4200
```

-continued

```
gtcgtgtaga taactacgat acgggagggc ttaccatctg gccccagtgc tgcaatgata   4260

ccgcgagacc cacgctcacc ggctccagat ttatcagcaa taaaccagcc agccggaagg   4320

gccgagcgca gaagtggtcc tgcaacttta tccgcctcca tccagtctat taattgttgc   4380

cgggaagcta gagtaagtag ttcgccagtt aatagtttgc gcaacgttgt tgccattgct   4440

acaggcatcg tggtgtcacg ctcgtcgttt ggtatggctt cattcagctc cggttcccaa   4500

cgatcaaggc gagttacatg atcccccatg ttgtgcaaaa aagcggttag ctccttcggt   4560

cctccgatcg ttgtcagaag taagttggcc gcagtgttat cactcatggt tatggcagca   4620

ctgcataatt ctcttactgt catgccatcc gtaagatgct tttctgtgac tggtgagtac   4680

tcaaccaagt cattctgaga atagtgtatg cggcgaccga gttgctcttg cccggcgtca   4740

atacgggata ataccgcgcc acatagcaga actttaaaag tgctcatcat tggaaaacgt   4800

tcttcggggc gaaaactctc aaggatctta ccgctgttga gatccagttc gatgtaaccc   4860

actcgtgcac ccaactgatc ttcagcatct tttactttca ccagcgtttc tgggtgagca   4920

aaaacaggaa ggcaaaatgc cgcaaaaaag ggaataaggg cgacacggaa atgttgaata   4980

ctcatactct tcctttttca atattattga agcatttatc agggttattg tctcatgagc   5040

ggatacatat ttgaatgtat ttagaaaaat aaacaaatag gggttccgcg cacatttccc   5100

cgaaaagtgc cacctgacgt cgacggatcg ggagatctcc cgatccccta tggtcgactc   5160

tcagtacaat ctgctctgat gccgcatagt taagccagta tctgctccct gcttgtgtgt   5220

tggaggtcgc tgagtagtgc gcgagcaaaa tttaagctac aacaaggcaa ggcttgaccg   5280

acaattgcat gaagaatctg cttagggtta ggcgttttgc gctgcttcgc gatgtacggg   5340

ccagatatac gcgttgacat tgattattga ctagttatta atagtaatca attacggggt   5400

cattagttca tagcccatat atggagttcc gcgttacata acttacggta aatggcccgc   5460

ctggctgacc gcccaacgac ccccgcccat tgacgtcaat aatgacgtat gttcccatag   5520

taacgccaat agggactttc cattgacgtc aatgggtgga ctatttacgg taaactgccc   5580

acttggcagt acatcaagtg tatcatatgc caagtacgcc ccctattgac gtcaatgacg   5640

gtaaatggcc cgcctggcat tatgcccagt acatgacctt atgggacttt cctacttggc   5700

agtacatcta cgtattagtc atcgctatta ccatggtgat gcggttttgg cagtacatca   5760

atgggcgtgg atagcggttt gactcacggg gatttccaag tctccacccc attgacgtca   5820

atgggagttt gttttggcac caaaatcaac gggactttcc aaaatgtcgt aacaactccg   5880

ccccattgac gcaaatgggc ggtaggcgtg tacggtggga ggtctatata agcagagctc   5940

tctggctaac tagagaaccc actgcttact ggcttatcga aat                    5983
```

<210> SEQ ID NO 45
<211> LENGTH: 5986
<212> TYPE: DNA
<213> ORGANISM: artificial
<220> FEATURE:
<223> OTHER INFORMATION: IgG kappa Chain Expression Vector pMORPH?
      2_h_Ig_kappa

<400> SEQUENCE: 45

```
taatacgact cactataggg agacccaagc tggctagcgc caccatggtg ttgcagaccc     60

aggtcttcat ttctctgttg ctctggatct ctggtgccta cggggatatc cagatgaccc    120

agagcccgtc tagcctgagc gcgagcgtgg gtgatcgtgt gaccattacc tgcagagcga    180

gccagtctat ttctaattgg ctgaattggt accagcagaa accaggtaaa gcaccgaaac    240

tattaattta taaggcttct actttgcaaa gcggggtccc gtcccgtttt agcggctctg    300
```

-continued

```
gatccggcac tgattttacc ctgaccatta gcagcctgca acctgaagac tttgcgactt    360
attattgcca gcagtatggt aatattccta ttacctttgg ccagggtacg aaagttgaaa    420
ttaaacgtac ggtggctgca ccatctgtct tcatcttccc gccatctgat gagcagttga    480
aatctggaac tgcctctgtt gtgtgcctgc tgaataactt ctatcccaga gaggccaaag    540
tacagtggaa ggtggataac gccctccaat cgggtaactc ccaggagagt gtcacagagc    600
aggacagcaa ggacagcacc tacagcctca gcagcaccct gacgctgagc aaagcagact    660
acgagaaaca caaagtctac gcctgcgaag tcacccatca gggcctgagc tcgcccgtca    720
caaagagctt caacagggga gagtgttagg ggcccgttta aacgggtggc atccctgtga    780
cccctcccca gtgcctctcc tggccctgga agttgccact ccagtgccca ccagccttgt    840
cctaataaaa ttaagttgca tcattttgtc tgactaggtg tccttctata atattatggg    900
gtggaggggg gtggtatgga gcaaggggca agttgggaag acaacctgta gggcctgcgg    960
ggtctattgg gaaccaagct ggagtgcagt ggcacaatct tggctcactg caatctccgc   1020
ctcctgggtt caagcgattc tcctgcctca gcctcccgag ttgttgggat tccaggcatg   1080
catgaccagg ctcacctaat ttttgttttt ttggtagaga cggggtttca ccatattggc   1140
caggctggtc tccaactcct aatctcaggt gatctaccca ccttggcctc ccaaattgct   1200
gggattacag gcgtgaacca ctgctccctt ccctgtcctt ctgattttaa aataactata   1260
ccagcaggag gacgtccaga cacagcatag gctacctggc catgcccaac cggtgggaca   1320
tttgagttgc ttgcttggca ctgtcctctc atgcgttggg tccactcagt agatgcctgt   1380
tgaattgggt acgcggcatc gattccacgc gccctgtagc ggcgcattaa gcgcggcggg   1440
tgtggtggtt acgcgcagcg tgaccgctac acttgccagc gccctagcgc ccgctccttt   1500
cgctttcttc ccttcctttc tcgccacgtt cgccggcttt ccccgtcaag ctctaaatcg   1560
ggggctccct ttagggttcc gatttagtgc tttacggcac ctcgacccca aaaaacttga   1620
ttagggtgat ggttcacgta gtgggccatc gccctgatag acggtttttc gccctttgac   1680
gttggagtcc acgttcttta atagtggact cttgttccaa actggaacaa cactcaaccc   1740
tatctcggtc tattcttttg atttataagg gattttgggg atttcggcct attggttaaa   1800
aaatgagctg atttaacaaa aatttaacgc gaattaattc tgtggaatgt gtgtcagtta   1860
gggtgtggaa agtccccagg ctccccaggc aggcagaagt atgcaaagca tgcatctcaa   1920
ttagtcagca accaggtgtg gaaagtcccc aggctcccca gcaggcagaa gtatgcaaag   1980
catgcatctc aattagtcag caaccatagt cccgccccta actccgccca tcccgcccct   2040
aactccgccc agttccgccc attctccgcc ccatggctga ctaatttttt ttatttatgc   2100
agaggccgag gccgcctctg cctctgagct attccagaag tagtgaggag gcttttttgg   2160
aggcctaggc ttttgcaaaa agctcccggg agcttgtata tccattttcg gatctgatca   2220
gcacgtgttg acaattaatc atcggcatag tatatcggca tagtataata cgacaaggtg   2280
aggaactaaa ccatggccaa gttgaccagt gccgttccgg tgctcaccgc gcgcgacgtc   2340
gccggagcgg tcgagttctg gaccgaccgg ctcgggttct cccgggactt cgtggaggac   2400
gacttcgccg gtgtggtccg ggacgacgtg accctgttca tcagcgcggt ccaggaccag   2460
gtggtgccgg acaacaccct ggcctgggtg tgggtgcgcg gcctggacga gctgtacgcc   2520
gagtggtcgg aggtcgtgtc cacgaacttc cgggacgcct ccgggccggc catgaccgag   2580
atcggcgagc agccgtgggg gcgggagttc gccctgcgcg acccggccgg caactgcgtg   2640
cacttcgtgg ccgaggagca ggactgacac gtgctacgag atttcgattc caccgccgcc   2700
```

-continued

```
ttctatgaaa ggttgggctt cggaatcgtt ttccgggacg ccggctggat gatcctccag   2760
cgcggggatc tcatgctgga gttcttcgcc caccccaact tgtttattgc agcttataat   2820
ggttacaaat aaagcaatag catcacaaat ttcacaaata aagcattttt ttcactgcat   2880
tctagttgtg gtttgtccaa actcatcaat gtatcttatc atgtctgtat accgtcgacc   2940
tctagctaga gcttggcgta atcatggtca tagctgtttc ctgtgtgaaa ttgttatccg   3000
ctcacaattc cacacaacat acgagccgga agcataaagt gtaaagcctg gggtgcctaa   3060
tgagtgagct aactcacatt aattgcgttg cgctcactgc ccgctttcca gtcgggaaac   3120
ctgtcgtgcc agctgcatta atgaatcggc caacgcgcgg ggagaggcgg tttgcgtatt   3180
gggcgctctt ccgcttcctc gctcactgac tcgctgcgct cggtcgttcg gctgcggcga   3240
gcggtatcag ctcactcaaa ggcggtaata cggttatcca cagaatcagg ggataacgca   3300
ggaaagaaca tgtgagcaaa aggccagcaa aaggccagga accgtaaaaa ggccgcgttg   3360
ctggcgtttt tccataggct ccgcccccct gacgagcatc acaaaaatcg acgctcaagt   3420
cagaggtggc gaaacccgac aggactataa agataccagg cgtttccccc tggaagctcc   3480
ctcgtgcgct ctcctgttcc gaccctgccg cttaccggat acctgtccgc ctttctccct   3540
tcgggaagcg tggcgctttc tcaatgctca cgctgtaggt atctcagttc ggtgtaggtc   3600
gttcgctcca agctgggctg tgtgcacgaa ccccccgttc agcccgaccg ctgcgcctta   3660
tccggtaact atcgtcttga gtccaacccg gtaagacacg acttatcgcc actggcagca   3720
gccactggta acaggattag cagagcgagg tatgtaggcg gtgctacaga gttcttgaag   3780
tggtggccta actacggcta cactagaagg acagtatttg gtatctgcgc tctgctgaag   3840
ccagttacct tcggaaaaag agttggtagc tcttgatccg gcaaacaaac caccgctggt   3900
agcggtggtt tttttgtttg caagcagcag attacgcgca gaaaaaaagg atctcaagaa   3960
gatcctttga tcttttctac ggggtctgac gctcagtgga acgaaaactc acgttaaggg   4020
attttggtca tgagattatc aaaaaggatc ttcacctaga tccttttaaa ttaaaaatga   4080
agttttaaat caatctaaag tatatatgag taaacttggt ctgacagtta ccaatgctta   4140
atcagtgagg cacctatctc agcgatctgt ctatttcgtt catccatagt tgcctgactc   4200
cccgtcgtgt agataactac gatacgggag ggcttaccat ctggccccag tgctgcaatg   4260
ataccgcgag acccacgctc accggctcca gatttatcag caataaacca gccagccgga   4320
agggccgagc gcagaagtgg tcctgcaact ttatccgcct ccatccagtc tattaattgt   4380
tgccgggaag ctagagtaag tagttcgcca gttaatagtt tgcgcaacgt tgttgccatt   4440
gctacaggca tcgtggtgtc acgctcgtcg tttggtatgg cttcattcag ctccggttcc   4500
caacgatcaa ggcgagttac atgatccccc atgttgtgca aaaaagcggt tagctccttc   4560
ggtcctccga tcgttgtcag aagtaagttg gccgcagtgt tatcactcat ggttatggca   4620
gcactgcata attctcttac tgtcatgcca tccgtaagat gcttttctgt gactggtgag   4680
tactcaacca agtcattctg agaatagtgt atgcggcgac cgagttgctc ttgcccggcg   4740
tcaatacggg ataataccgc gccacatagc agaactttaa aagtgctcat cattggaaaa   4800
cgttcttcgg ggcgaaaact ctcaaggatc ttaccgctgt tgagatccag ttcgatgtaa   4860
cccactcgtg cacccaactg atcttcagca tcttttactt tcaccagcgt ttctgggtga   4920
gcaaaaacag gaaggcaaaa tgccgcaaaa aagggaataa gggcgacacg gaaatgttga   4980
atactcatac tcttcctttt tcaatattat tgaagcattt atcagggtta ttgtctcatg   5040
agcggataca tatttgaatg tatttagaaa aataaacaaa taggggttcc gcgcacattt   5100
```

```
ccccgaaaag tgccacctga cgtcgacgga tcgggagatc tcccgatccc ctatggtcga   5160

ctctcagtac aatctgctct gatgccgcat agttaagcca gtatctgctc cctgcttgtg   5220

tgttggaggt cgctgagtag tgcgcgagca aaatttaagc tacaacaagg caaggcttga   5280

ccgacaattg catgaagaat ctgcttaggg ttaggcgttt tgcgctgctt cgcgatgtac   5340

gggccagata tacgcgttga cattgattat tgactagtta ttaatagtaa tcaattacgg   5400

ggtcattagt tcatagccca tatatggagt tccgcgttac ataacttacg gtaaatggcc   5460

cgcctggctg accgcccaac gacccccgcc cattgacgtc aataatgacg tatgttccca   5520

tagtaacgcc aatagggact ttccattgac gtcaatgggt ggactattta cggtaaactg   5580

cccacttggc agtacatcaa gtgtatcata tgccaagtac gccccctatt gacgtcaatg   5640

acggtaaatg gcccgcctgg cattatgccc agtacatgac cttatgggac tttcctactt   5700

ggcagtacat ctacgtatta gtcatcgcta ttaccatggt gatgcggttt tggcagtaca   5760

tcaatgggcg tggatagcgg tttgactcac ggggatttcc aagtctccac cccattgacg   5820

tcaatgggag tttgttttgg caccaaaatc aacgggactt tccaaaatgt cgtaacaact   5880

ccgccccatt gacgcaaatg ggcggtaggc gtgtacggtg ggaggtctat ataagcagag   5940

ctctctggct aactagagaa cccactgctt actggcttat cgaaat                  5986
```

<210> SEQ ID NO 46
<211> LENGTH: 12
<212> TYPE: PRT
<213> ORGANISM: Homo sapiens

<400> SEQUENCE: 46

```
Lys Ile Val Ile Leu Leu Asp Tyr Met Phe Gln Asp
1               5                   10
```

<210> SEQ ID NO 47
<211> LENGTH: 12
<212> TYPE: PRT
<213> ORGANISM: Homo sapiens

<400> SEQUENCE: 47

```
Ala Ile Arg Asp Tyr Ser Phe Lys Arg Leu Tyr Arg
1               5                   10
```

<210> SEQ ID NO 48
<211> LENGTH: 12
<212> TYPE: PRT
<213> ORGANISM: Homo sapiens

<400> SEQUENCE: 48

```
Leu Lys Val Leu Glu Ile Ser His Trp Pro Tyr Leu
1               5                   10
```

<210> SEQ ID NO 49
<211> LENGTH: 15
<212> TYPE: PRT
<213> ORGANISM: Homo sapiens

<400> SEQUENCE: 49

```
Asn Leu Thr Ala Val Pro Tyr Leu Ala Val Arg His Leu Val Tyr
1               5                   10                  15
```

<210> SEQ ID NO 50
<211> LENGTH: 9
<212> TYPE: PRT
<213> ORGANISM: Homo sapiens

-continued

```
<400> SEQUENCE: 50

Tyr Phe Thr Cys Arg Arg Ala Arg Ile
1               5


<210> SEQ ID NO 51
<211> LENGTH: 15
<212> TYPE: PRT
<213> ORGANISM: Homo sapiens

<400> SEQUENCE: 51

Asp Val Leu Leu Pro Asn Tyr Phe Thr Cys Arg Arg Ala Arg Ile
1               5                   10                  15
```